United States Patent [19]

Himmelsbach et al.

[11] Patent Number: 5,541,343

[45] Date of Patent: Jul. 30, 1996

[54] CYCLIC IMINO DERIVATIVES AND PHARMACEUTICAL COMPOSITIONS CONTAINING THEM

[75] Inventors: Frank Himmelsbach, Mittelbiberach; Volkhard Austel, Biberach; Helmut Pieper, Biberach; Wolfgang Eisert, Biberach; Thomas Mueller, Biberach; Johannes Weisenberger, Biberach; Guenter Linz, Mittelbiberach; Gerd Krueger, Biberach, all of Germany

[73] Assignee: Karl Thomae GmbH, Biberach an der Riss, Germany

[21] Appl. No.: 365,336

[22] Filed: Dec. 28, 1994

Related U.S. Application Data

[63] Continuation of Ser. No. 783,065, Oct. 25, 1991, abandoned.

[30] Foreign Application Priority Data

Nov. 2, 1990 [DE] Germany .......................... 40 35 961.1

[51] Int. Cl.[6] ..................... C07D 207/273; A61K 31/40
[52] U.S. Cl. .............................. 514/424; 548/550
[58] Field of Search .............................. 548/550; 514/424

[56] References Cited

U.S. PATENT DOCUMENTS 4,247,466 1/1981 Chiccarelli .......................... 260/343.6

FOREIGN PATENT DOCUMENTS 0194548 3/1986 European Pat. Off. ..
0196184 10/1986 European Pat. Off. ..
0350437 1/1990 European Pat. Off. ..

*Primary Examiner*—David B. Springer
*Attorney, Agent, or Firm*—Robert P. Raymond; Alan R. Stempel; Mary-Ellen M. Devlin

[57] ABSTRACT

The invention relates to cyclic imino compounds which have, inter alia, valuable pharmacological properties, especially inhibitory effects on cell aggregation, pharmaceutical compositions which contain these compounds and processes for preparing them.

10 Claims, No Drawings

CYCLIC IMINO DERIVATIVES AND PHARMACEUTICAL COMPOSITIONS CONTAINING THEM

This is a Continuation of application Ser. No. 07/783,065, filed Oct. 25, 1991, abandoned.

The invention relates to cyclic imino derivatives of general formula $$B\text{---}X\text{---}A\text{---}Y\text{---}E \qquad (I)$$

the stereoisomers, the mixtures and the addition salts thereof, particularly the physiologically acceptable addition salts with inorganic or organic acids or bases which have, inter alia, valuable pharmacological properties, preferably aggregation-inhibiting effects, pharmaceutical compositions which contain these compounds and processes for preparing them.

In general formula I above

A represents a 4-, 5-, 6- or 7-membered cyclic alkyleneimino group in which an ethylene group may be replaced by an ethenylene group or a methylene group may be replaced by a carbonyl group and which are optionally substituted by the groups $R_1$, $R_2$ and $R_3$, whilst $R_1$ represents an aryl group or an optionally mono- or polyunsaturated $C_{1-6}$-alkyl group which may be substituted by one or two aryl groups, by a cycloalkyl, alkylsulphenyl, alkylsulphinyl, alkylsulphonyl, alkylcarbonyl, aralkylcarbonyl, arylcarbonyl, $R_4OCO$, $(R_5)_2NCO$ or $R_6CO$ group or by a bi- or tricyclic aryl a triple bond of the unsaturated alkyl group cannot be bound directly to the cyclic nitrogen atom of the group A and a double bond can only be bound to the cyclic nitrogen atom if a carbonyl group is adjacent to the double bond, or, if $R_1$ is not linked to the nitrogen atom of the group A where A represents a lactam ring, $R_1$ may represent a carbonyl group which is substituted by an alkyl, aralkyl, aryl, $(R_5)_2N$, $R_4O\text{---}CO$, $(R_5)_2N\text{---}CO$, alkoxy, aralkoxy, alkylcarbonyl-$NR_5$-alkyl, aralkylcarbonyl-$NR_5$-alkyl, arylcarbonyl-$NR_5$-alkyl, $R_4O$-alkyl, $(R_5)_2N$-alkyl, alkyl-$SO_2$-$NR_5$-alkyl, aralkyl-$SO_2$-$NR_5$-alkyl or aryl-$SO_2$-$N_5$-alkyl group, or $R_1$ may represent a $C_{1-6}$-alkyl group which is substituted by $R_6$, by one or two hydroxy groups, by an alkoxy, aryloxy, aralkoxy, arylsulphenyl, aralkylsulphenyl, arylsulphinyl, aralkylsulphinyl, arylsulphonyl, aralkylsulphonyl, $N(R_5)_2$-sulphonyl, $R_6$-sulphonyl, $(R_5)_2N$, alkylcarbonyl-$NR_5$, arylcarbonyl-$NR_5$, aralkylcarbonyl-$NR_5$, alkylsulphonyl-$NR_5$, arylsulphonyl-$NR_5$, aralkylsulphonyl-$NR_5$, $(R_5)_2N$-CO-$NR_5$ or $(R_5)_2N$-$SO_2$-$NR_5$ group, whilst if $R_1$ is linked to the cyclic nitrogen atom of the group A, the substituents of the alkyl group can only appear at position 2 onwards, or, if the group $R_1$ is not linked to a carbon atom adjacent to the cyclic nitrogen atom and is not linked to an unsaturated carbon atom of the group A, $R_1$ may also represent a hydroxy, alkylcarbonyl-$NR_5$, arylcarbonyl-$NR_5$, aralkylcarbonyl-$NR_5$, alkylsulphonyl-$NR_5$, arylsulphonyl-$NR_5$, aralkylsulphonyl-$NR_5$, $(R_5)_2N\text{---}CO\text{---}NR_5$ or $(R_5)_2N\text{---}SO_2NR_5$ group, or, if $R_1$ is not linked to the nitrogen atom of the group A where A represents a lactam ring and is not bound to the carbon atom adjacent to the cyclic nitrogen, $R_1$ may also represent an alkylsulphonyl, arylsulphonyl, aralkylsulphonyl or $(R_5)_2N\text{---}SO_2$ group, or, if the group $R_1$ is not linked to the cyclic nitrogen atom of the group A, nor to a carbon atom of the group A adjacent to the cyclic nitrogen atom, nor to an unsaturated carbon atom of the group A, $R_1$ may also represent an alkoxy, aryloxy, aralkoxy, alkylsulphenyl, arylsulphenyl, aralkylsulphenyl, alkylsulphinyl, arylsulphinyl or aralkylsulphinyl group, or, if $R_1$ is not linked to the cyclic nitrogen atom of the group A, $R_1$ may also represent a carboxy group, whilst $R_4$ and $R_5$, which may be identical or different, may each represent a hydrogen atom, an alkyl, aralkyl, aryl or alkoxyalkyl group, but the alkoxy group cannot be located at the same carbon atom as the carbonyloxy or carbonylamino group, and $R_6$ represents a 5- to 7-membered alkyleneimino group bound via the nitrogen atom, wherein a methylene group may be replaced, in the 3- or 4-position, or, if $R_6$ is not bound to a carbonyl or sulphonyl group, also in the 2-position, by a carbonyl group or, in the 4-position, by an oxygen atom or by a sulphenyl, sulphinyl, sulphonyl, imino, alkylimino, aralkylimino, arylimino, formylimino, alkanoylimino, aralkanoylimino, arylcarbonylimino, $(R_5)_2N$-carbonylimino, alkylsulphonylimino, aralkylsulphonylimino, arylsulphonylimino or $(R_5)_2N$-sulphonylimino group, whilst $R_5$ is defined as hereinbefore and the alkanoyl moiety may contain from 1 to 4 carbon atoms, $R_2$ and $R_3$, which may be identical or different, represent alkyl, aryl or aralkyl groups, B represents a cyano or nitro group, an amino or amino($C_{1-6}$-alkyl) group optionally substituted at the nitrogen atom by one or two $C_{1-5}$-alkyl groups or by an aralkyl group; an amidino, guanidino, amidinoalkyl or guanidinoalkyl group optionally substituted by one, two or three $C_{1-5}$-alkyl groups or by an aralkyl group, wherein the alkyl moiety may contain 1 to 6 carbon atoms and each two nitrogen atoms of an amidino or guanidino group may also be linked together by a $C_{2-4}$-alkylene group, whilst additionally a nitrogen atom in the above-mentioned groups, provided that this does not form an ammonium structure, may be substituted by a cyano, hydroxy, alkoxy, amino, arylcarbonyl, aryloxycarbonyl, aralkoxycarbonyl or alkoxycarbonyl group having a total of 2 to 6 carbon atoms, or an ammonium or ammonio($C_{1-6}$-alkyl) group substituted by three $C_{1-3}$-alkyl groups, E, which is bound to a carbon atom of the group Y or the group A and the shortest distance of which, to the first nitrogen atom of group B, is at least 10 bonds, represents a vinyl, hydroxymethyl, bis(hydroxycarbonyl)methyl, bis(alkoxycarbonyl)methyl, cyano, sulpho, phosphono, O-alkyl-phosphono or 5-tetrazolyl group or a carbonyl group substituted by a $C_{1-7}$-alkoxy group or by an amino, hydroxy, aralkoxy, heteroarylalkoxy, aminoalkoxy or aminocarbonylalkoxy group, wherein the amino groups may each be mono- or disubstituted by alkyl, aryl or aralkyl groups, or an alkyleneimino-alkoxy group having 5 to 7 ring members wherein a methylene group of the 5- to 7-membered alkyleneimino ring may be replaced by a carbonyl group or, in the 4-position, by an oxygen atom or by a sulphenyl, sulphinyl, imino, alkylimino, aralkylimino or arylimino group or, in the 2- or 4-position, by a sulphonyl group, whilst, if the group B is bound via a nitrogen atom to an aryl group of group X, E cannot simultaneously be a vinyl group bound via a methylene group to the cyclic nitrogen of group A, if the latter represents a pyrrolidine ring, X represents a group of the formula $$-X_1-X_2-X_3-X_4-X_5-,$$

wherein $X_1$ is bound to the group A and $X_5$ to the group B and $X_1$ represents a bond, an optionally mono- or polyunsaturated alkylene group or an arylene group, whilst between the alkylene group and the adjacent group $X_2$ there may additionally be an oxygen or sulphur atom, an —SO—, —SO$_2$—, —NR$_7$—, —CO—, —CO—NR$_8$—, —NR$_8$—CO—, —SO$_2$—NR$_8$—, —NR$_8$—SO$_2$—, —NR$_8$—CO—NR$_8$— or —NR$_8$—SO$_2$—NR$_8$— group, or, if the group $X_1$ is not linked to the cyclic nitrogen atom of the group A, if A represents a lactam ring, $X_1$ may represent a carbonyl, alkylene-carbonyl, —CONR$_8$— or —CO—O— group or, if the group $X_1$ is not linked to a carbon atom adjacent to the cyclic nitrogen atom and is not linked to the cyclic nitrogen atom of the group A, if A represents a lactam ring, $X_1$ may represent an —SO$_2$— or —SO$_2$—NR$_8$— group or, if the group $X_1$ is not linked to a carbon atom of the group A adjacent to the cyclic nitrogen atom, it may also represent an oxygen, an —NR$_7$—, —NR$_8$—CO— or —NR$_8$—SO$_2$— group, or, if the group $X_1$ is not linked to the cyclic nitrogen atom and is not linked to a carbon atom of the group A adjacent to the cyclic nitrogen atom, it may also represent a sulphur atom or a sulphinyl group, whilst $R_7$ may represent a hydrogen atom, an alkyl, aralkyl, aryl, alkylcarbonyl, aralkylcarbonyl, arylcarbonyl, alkylsulphonyl, arylsulphonyl, aralkylsulphonyl, aminocarbonyl or aminosulphonyl group, whilst the above-mentioned amino groups may be mono- or disubstituted by an alkyl, aralkyl or aryl group and the substituents may be identical or different, and $R_8$ represents a hydrogen atom or an alkyl, aryl or aralkyl group, $X_2$ represents a fluorenylene ring, the methylene group of which may be replaced by a carbonyl or hydroxymethylene group, or an arylene ring, in which 2 adjacent carbon atoms of the arylene ring may be linked via an additional propylene, propenylene, butylene, butenylene, butadienylene, pentylene, pentenylene or pentadienylene bridge, a naphthalene ring which is wholly or partially hydrogenated in both rings or a tricyclic arylene ring which is optionally wholly or partially hydrogenated, whilst in addition, in the above mentioned cyclic systems, a methylene group may be replaced by a carbonyl or hydroxymethylene group, an optionally mono- or polyunsaturated cycloalkylene group, an optionally mono- or polyunsaturated $C_{6-12}$-bicycloalkylene group or an optionally mono- or polyunsaturated $C_{8-12}$-spiroalkylene group which may additionally each carry 1 to 3 alkyl substituents, a $C_{1-8}$-alkylene group which may be mono- or polyunsaturated, but in which a double or triple bond cannot be adjacent to a heteroatom, $X_3$ represents a bond, a $C_{1-7}$-alkylene group which may be mono- or polyunsaturated, but in which a double or triple bond cannot be adjacent to a triple bond of the group $X_2$, or a hydroxyalkylene group or, if $X_3$ is not directly followed by an optionally alkylated amino group, a trialkylammonium or nitro group or a triple bond of the group B, $X_3$ may also represent a —CO—, —CO—NR$_8$— or —NR$_8$—CO— group, whilst the latter may not be directly bound to an aliphatic double or triple bond of the group $X_2$, or, if $X_3$ is not directly followed by a heteroatom or an unsaturated carbon atom of the group B, $X_3$ may also represent an —SO$_2$— group, or, if $X_2$ does not contain an aliphatic double or triple bond at the end and $X_3$ is not directly followed by a heteroatom or an unsaturated carbon atom of the group B, $X_3$ may represent an oxygen or sulphur atom, an —SO—, —NR$_7$—, —NR$_8$SO$_2$— or —SO$_2$—NR$_8$— group, whilst $R_7$ and $R_8$ are defined as hereinbefore, $X_4$ represents a bond, an arylene ring wherein 2 adjacent carbon atoms may additionally be connected via a propylene, propenylene, butylene, butenylene, butadienylene, pentylene, pentenylene or pentadienylene bridge, or a cycloalkylene group or a $C_{6-12}$-bicycloalkylene group and $X_5$ represents a bond, an alkylene group which may be mono- or polyunsaturated, but wherein the double or triple bond is not adjacent to a heteroatom of the group B or the group $X_3$ or to a terminal triple bond of the group $X_3$, if $X_4$ represents a bond, or $X_5$ represents a —CO—alkylene group or, if $X_5$ is not directly followed by an optionally alkylated amino group, a trialkylammonium or nitro group or a triple bond of the group B, $X_5$ may represent a —CO—, —CO—NR$_8$— or —NR$_8$—CO— group, whilst the latter group does not directly follow an oxygen or sulphur atom or a carbonyl group of the group $X_3$ or a double or triple bond, or, if $X_5$ is followed by an alkylene group of the group B and $X_5$ is not directly adjacent to an oxygen atom or a sulphenyl or sulphinyl group of the group $X_3$ or a double or triple bond, $X_5$ may also represent an —NR$_7$— group or, if $X_5$ is followed by an alkylene chain of the group B and $X_5$ is not directly adjacent to an oxygen or sulphur atom or to a carbonyl group of the group $X_3$ or a double or triple bond, $X_5$ may also represent an —NR$_8$—SO$_2$—, —SO$_2$—NR$_8$— or —SO$_2$— group or, if $X_5$ is not directly adjacent to a heteroatom or a —CO— group of the group $X_3$ or a double or triple bond, it may represent an O-alkylene, S-alkylene or SO-alkylene group, whilst additionally a heteroatom of group B cannot be situated at the same carbon atom as —O—, —S— or —SO— and the above-mentioned groups $R_7$ and $R_8$ are defined as hereinbefore, and Y represents a group of the formula $$-Y_1-Y_2-Y_3-,$$

wherein $Y_1$ is bound to the group A and $Y_3$ is bound to the group E and $Y_1$ represents a bond, an alkylene group which may be mono- or polyunsaturated, but wherein a triple bond of the alkyl group cannot be bound directly to the cyclic nitrogen atom of the group A and a double bond can only be bound to the cyclic nitrogen atom if a carbonyl group follows on adjacent to said double bond, a hydroxyalkylene group which, if $Y_1$ is bound to the cyclic nitrogen atom, cannot carry the hydroxy group at the carbon atom which is bound to the cyclic nitrogen atom of the group A, a —CO— or —CO—NR$_8$— group, provided that this is not bound to the cyclic nitrogen atom of the group A, if the latter represents a lactam ring, or, if $Y_1$ is not linked to the carbon atom of group A adjacent to the cyclic nitrogen atom and is not located at the cyclic nitrogen atom of group A, and if A represents a lactam ring, $Y_1$ may also represent an —SO$_2$— or —SO$_2$NR$_8$— group or, if $Y_1$ is not linked to the cyclic nitrogen atom or to a carbon atom adjacent to the cyclic nitrogen atom or to an unsaturated carbon atom of the group A, it may also represent an oxygen or sulphur atom or an —SO—, —NR$_7$— or —NR$_8$—SO$_2$— group, wherein $R_7$ and $R_8$ are defined as hereinbefore, $Y_2$ represents a bond, an alkylene group which may be mono- or polyunsaturated, but wherein a double or triple bond cannot be adjacent to a heteroatom or to a triple bond of the group $Y_1$, or an arylene group or, if $Y_1$ does not end with an oxygen or sulphur atom or with a triple bond or a —CO— group, $Y_2$ may represent a —CO—, —$SO_2$— or —CO—$NR_8$— group or, if $Y_1$ does not end with an oxygen atom, a sulphenyl or sulphinyl group or with a double or triple bond, $Y_2$ may represent an —$NR_7$— group or, if $Y_1$ does not end with a heteroatom, a double or triple bond or a —CO— group, $Y_2$ may represent an oxygen or sulphur atom or an —SO— or —O—CO— group or, if $Y_1$ does not end with a double or triple bond or with an oxygen or sulphur atom or a —CO— group, $Y_2$ may represent an —$NR_8$—CO—, —$NR_8$—$SO_2$— or —$SO_2$—$NR_8$— group, wherein $R_7$ and $R_8$ are defined as hereinbefore, $Y_3$ represents a bond, an arylene, alkylene-arylene, alkyleneoxy-arylene, alkylenesulphenyl-arylene, alkylene-sulphinyl-arylene, alkylenesulphonyl-arylene, alkylene-$NR_8$-arylene, alkylene-N(alkylcarbonyl)-arylene, alkylene-N(aralkylcarbonyl)-arylene, alkylene-N(arylcarbonyl)-arylene, alkylene-$NR_8$-carbonyl-arylene, alkylenecarbonyl-$NR_8$-arylene, bisarylene, alkylenebisarylene or alkyleneoxy-bisarylene group, wherein $R_8$ is defined as hereinbefore, or, if $Y_1$ and $Y_2$ each represent a bond, $Y_3$ may represent a hydroxyalkylene, $N(R_5)_2$-alkylene, alkylcarbonyl-$NR_8$-alkylene, aralkylcarbonyl-$NR_8$-alkylene, arylcarbonyl-$NR_8$-alkylene, alkylsulphonyl-$NR_8$-alkylene or arylsulphonyl-$NR_8$-alkylene group, whilst if Y is bound to the cyclic nitrogen atom of the group A, a hydroxy, —$NR_8$— and —$N(R_5)_2$— group cannot be bound to the carbon atom of group A linked to the cyclic nitrogen atom, and $R_5$ and $R_8$ are defined as hereinbefore, whilst, unless otherwise stated, the above-mentioned term "an alkylene group" indicates a straight-chained or branched $C_{1-6}$-alkylene group, "an alkyl group" means a straight-chained or branched $C_{1-4}$-alkyl group, "an alkoxy group" means a $C_{1-3}$-alkoxy group, "a cycloalkyl group" or "a cycloalkylene group" means a $C_{3-7}$-cycloalkyl ring which may additionally be substituted by one or two $C_{1-3}$-alkyl groups, and "an aryl or arylene group" means a mono-, bi- or tricyclic aromatic hydrocarbon group which may be monosubstituted by an aryl, aralkyl or nitro group and/or mono-, di- or trisubstituted by fluorine, chlorine or bromine atoms or by $C_{1-5}$-alkyl groups, or by hydroxy, alkoxy, aralkoxy, trifluoromethyl, mercapto, alkylsulphenyl, alkylsulphinyl, alkylsulphonyl, amino, alkylamino, dialkylamino, alkylcarbonylamino, aralkylcarbonylamino, arylcarbonylamino, alkoxycarbonylamino, alkylsulphonylamino, arylsulphonylamino, N-alkylcarbonyl-alkylamino, N-aralkylcarbonyl-alkylamino, N-arylcarbonyl-alkylamino, N-alkoxycarbonyl-alkylamino, N-alkylsulphenyl-alkylamino, N-arylsulphonyl-alkylamino, cyano, aminocarbonyl, alkylaminocarbonyl, dialkylaminocarbonyl, aminosulphonyl, alkylaminosulphonyl, dialkylaminosulphonyl, alkylcarbonyl, aralkylcarbonyl, arylcarbonyl, carboxy, sulpho, alkoxycarbonyl, aminocarbonylamino, N-aminocarbonyl-alkylamino or aminoalkyl groups, whilst the substituents may be identical or different and the amino group in the above-mentioned aminocarbonylamino, N-aminocarbonyl-alkylamino or aminoalkyl groups may additionally be mono- or disubstituted by alkyl or aralkyl groups.

Preferred compounds of general formula I above are those wherein

A represents a pyrrolidine, pyrroline, 2-pyrrolidinone, 2-pyrrolinone, piperidine or 2-piperidinone ring optionally substituted by the groups $R_1$ and $R_2$, wherein $R_1$ represents a phenyl group which may be substituted by a carboxy, alkoxycarbonyl, aminocarbonyl, aminosulphonyl, alkylaminocarbonyl, dialkylaminocarbonyl, alkylsulphonylamino or alkanoylamino group, a $C_{2-4}$-alkenyl group wherein the double bond cannot be situated directly at the cyclic nitrogen atom of group A, a $C_{1-4}$-alkyl group which may be substituted by two phenyl groups, by a $C_{3-7}$-cycloalkyl group, by a naphthyl, alkylsulphenyl, alkylsulphinyl, alkylsulphonyl or phenyl group, whilst the latter may be substituted by a fluorine, chlorine or bromine atom, by a $C_{1-4}$-alkyl group, by a $C_{1-6}$-alkoxy group, by an alkylsulphenyl, alkylsulphinyl, alkylsulphonyl, phenyl, phenylalkyl, phenylalkoxy, hydroxy or trifluoromethyl group, by two alkoxy groups or by two chlorine or bromine atoms, a $C_{1-4}$-alkyl group which is substituted by a phenylsulphenyl, phenylsulphinyl, phenylsulphonyl, amino, alkanoylamino, benzoylamino, N-alkylalkanoylamino, alkanesulphonylamino, phenylsulphonylamino, hydroxy, alkoxy or phenoxy group, whilst, if the group $R_1$ is located at the cyclic nitrogen atom of group A, these groups cannot be situated at the same carbon atom as the cyclic nitrogen, a methyl group which is substituted by a carboxy, alkoxycarbonyl, aminocarbonyl, alkylaminocarbonyl, dialkylaminocarbonyl, benzylaminocarbonyl, bis(2-methoxyethyl)aminocarbonyl, pyrrolidinocarbonyl, piperidinocarbonyl, hexamethyleneiminocarbonyl, morpholinocarbonyl, thiomorpholinocarbonyl, 1-oxidothiomorpholinocarbonyl, 1,1-dioxido-thiomorpholinocarbonyl, piperazinocarbonyl, N-alkyl-piperazinocarbonyl, N-alkanoyl-piperazinocarbonyl, N-alkylsulphonyl-piperazinocarbonyl, N-benzoylpiperazinocarbonyl, N-phenylsulphonyl-piperazinocarbonyl or biphenylyl group, a carbonyl group which is substituted by an alkyl, phenyl, alkoxyalkyl, amino, alkylamino, aminoalkyl, dialkylamino, carboxy, alkoxycarbonyl or dialkylaminocarbonyl group, whilst this group cannot be situated at the cyclic nitrogen atom of the group A if A represents a lactam ring or, if $R_1$ is not situated at a carbon atom adjacent to the cyclic nitrogen atom of the group A, $R_1$ represents a hydroxy group or a sulphonyl group substituted by an alkyl, dialkylamino, phenyl or methoxyphenyl group, whilst this substituted sulphonyl group cannot be at the cyclic nitrogen atom of the group A either, if A represents a lactam ring, and $R_2$ represents an optionally phenyl-substituted $C_{1-4}$-alkyl group, B represents a cyano, amino, dimethylamino, trimethylammonio or imidazolin-2-yl group, an amino($C_{1-5}$alkyl) group, an amidino, guanidino or guanidino-alkyl group having 1 to 5 carbon atoms, whilst one of the nitrogen atoms in the above-mentioned groups may be substituted by a cyano, hydroxy or methoxy group or by one or two $C_{1-4}$-alkyl groups or by a benzyl, benzoyl, methoxybenzoyl, benzyloxycarbonyl, phenyloxycarbonyl or alkyloxycarbonyl group with a total of 2 to 5 carbon atoms, provided that this does not form an ammonium structure, the Y-E group represents a straight-chained or branched $C_{1-5}$-alkyl group which may be substituted by a vinyl, hydroxymethyl, 1,2-dihydroxyethyl, carboxy, 5-tetrazolyl, phosphono or O-alkyl-phosphono group, by an alkoxycarbonyl group with a total of 2 to 7 carbon atoms, by an alkylaminocarbonyl group with a total of 2 to 5 carbon atoms, by an aminocarbonyl, dialkylaminocarbonyl-alkoxycarbonyl, morpholinoalkoxycarbonyl, (2-oxo-1-pyrrolidinyl)-alkoxycarbonyl, pyridylalkoxycarbonyl or phenylalkoxycarbonyl group wherein the phenyl nucleus may additionally be substituted by one or two methoxy groups, whilst the shortest spacing between these constituents and the first nitrogen atom of group B is at least 10 bonds, or, if the Y-E group is not linked to the cyclic nitrogen atom of the group A, Y-E may also represent a carboxy, carboxy-hydroxymethyl, alkoxycarbonyl or alkoxycarbonyl-hydroxymethyl group or, if the Y-E group is not linked to the cyclic nitrogen atom and is not linked to a carbon atom of group A adjacent to the cyclic nitrogen atom, Y-E may also represent a carboxymethoxy, alkoxycarbonyl-methoxy, carboxymethylsulphenyl, alkoxycarbonylmethylsulphenyl, N-methyl-carboxymethylamino or N-methyl-alkoxycarbonylmethylamino group, a phenyloxymethyl or biphenylyloxymethyl group substituted in the aryl moiety by a carboxy, carboxymethyl or aminocarbonyl group, whilst the shortest distance between the carboxy or alkoxycarbonyl group and the first nitrogen atom of group B is at least 10 bonds, and provided that the group B is bound to an aryl group of group X via a nitrogen atom, the group Y-E cannot represent an allyl group which is bound to the cyclic nitrogen of group A if the latter represents a pyrrolidine ring, and X represents a group of the formula

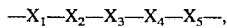

wherein $X_1$ represents a bond, a $C_{1-2}$-alkylene group in which between the alkylene group and the adjacent group $X_2$ there may additionally be a —CO— or —CONH— group or an oxygen or sulphur atom or a sulphonyl, imino, alkylimino, phenylalkylimino, —N(CO-alkyl), —N(SO$_2$-alkyl), —NH—CO—, —N(alkyl)—CO—, —NH—SO$_2$— or —NH—CO—NH— group, whilst, if the alkyl group is bound to the nitrogen atom of the ring A, these latter atoms and groups cannot be situated at the same carbon atom as the cyclic nitrogen, or $X_1$ represents a —COCH$_2$— group, $X_2$ and $X_4$, which may be identical or different, each represent a phenylene group which may be substituted by a fluorine, chlorine or bromine atom or by an alkyl, alkoxy, trifluoromethyl, alkylsulphenyl, alkylsulphinyl, alkylsulphonyl, nitro, alkanoylamino or alkanesulphonylamino group or by another alkyl group, an optionally mono- or polyunsaturated straight-chained $C_{1-3}$-alkylene group in which a double or triple bond cannot be adjacent to a heteroatom, a straight-chained $C_{4-7}$-alkylene group, a $C_{3-6}$-cycloalkylene group, a $C_{7-10}$-bicycloalkylene group or a naphthylene group, whilst $X_4$ may additionally represent a bond, $X_3$ represents a bond or a methylene group which, provided it is not followed by a heteroatom of group B, may be substituted by a hydroxy group or, if $X_3$ is not directly followed by an optionally alkylated amino group, a trialkylammonium group or a triple bond of group B, $X_3$ may represent a —CO—, —CONH— or —NHCO— group, whilst the latter may not be bound to an aliphatic double or triple bond of the group $X_2$ or, if $X_2$ does not contain an aliphatic double or triple bond at the end and $X_3$ is not immediately followed by a heteroatom or an unsaturated carbon atom of group B, $X_3$ may also represent an oxygen atom, a sulphenyl, sulphinyl, sulphonyl, imino, sulphonylimino or iminosulphonyl group or $X_2$ together with $X_3$ and $X_4$ represents a phenanthrenylene or naphthylene group which may be wholly or partially hydrogenated, a fluorenylene group in which the methylene group may be replaced by a hydroxymethylene or carbonyl group, an indanylene or indanylene-methylene group, a $C_{1-7}$-n-alkylene group, a $C_{7-11}$-bicycloalkylene group or a $C_{8-11}$-spiroalkylene group and $X_5$ represents a bond or, if $X_5$ is not immediately followed by an optionally alkylated amino group, a trimethylammonium group or a triple bond of group B, $X_5$ may represent a —CO— or —NH—CO— group, whilst the latter may not be bound by the nitrogen atom to an aliphatic double or triple bond, whilst, unless otherwise stated, the above-mentioned alkyl, alkoxy and alkanoyl moieties may each contain from 1 to 3 carbon atoms, particularly those compounds wherein $R_1$ is linked to the cyclic nitrogen atom or 3position of group A.

Another group of preferred compounds of general formula I consists of those wherein A represents a pyrrolidine, 2-pyrrolidinone or 2-pyrrolinone ring optionally substituted by the groups $R_1$ and $R_2$, wherein $R_1$ represents a phenyl group which may be substituted by a carboxy, alkoxycarbonyl, aminocarbonyl, aminosulphonyl, alkylaminocarbonyl, dialkylaminocarbonyl, alkylsulphonylamino or alkanoylamino group, a $C_{1-4}$-alkyl group which may be substituted by a hydroxy, alkoxy, phenoxy, alkylsulphenyl, alkylsulphinyl, alkylsulphonyl, phenylsulphenyl, phenylsulphinyl, phenylsulphonyl, amino, alkanoylamino, benzoylamino, N-alkyl-alkanoylamino, alkanesulphonylamino or benzenesulphonylamino group, whilst these groups are not in the 1-position if $R_1$ is bound to the cyclic nitrogen of the group A, a $C_{1-4}$-alkyl group substituted by a $C_{3-7}$-cycloalkyl group, by two phenyl groups or by a phenyl group, whilst the latter may be substituted by a fluorine, chlorine or bromine atom, by a $C_{1-4}$-alkyl group, by a $C_{1-6}$-alkoxy group, by a phenyl, phenylalkyl, phenylalkoxy, alkylsulphenyl, alkylsulphonyl, hydroxy or trifluoromethyl group or by two alkoxy groups or by two chlorine or bromine atoms, a methyl group which is substituted by a carboxy, alkoxycarbonyl, aminocarbonyl, alkylaminocarbonyl, dialkylaminocarbonyl, phenylalkylaminocarbonyl, pyrrolidinocarbonyl, piperidinocarbonyl, hexamethyleneiminocarbonyl, morpholinocarbonyl, thiomorpholinocarbonyl, 1-oxido-thiomorpholinocarbonyl, 1,1-dioxidothiomorpholinocarbonyl, piperazinocarbonyl, N-alkylpiperazinocarbonyl, N-alkanoyl-piperazinocarbonyl, N-alkylsulphonyl-piperazinocarbonyl, N-benzoyl-piperazinocarbonyl or N-benzenesulphonyl-piperazinocarbonyl group, or, if $R_1$ is not at the cyclic nitrogen atom, if A represents a 2-pyrrolidinone or 2-pyrrolinone group, $R_1$ may represent a carbonyl group which is substituted by an alkyl, phenyl, alkoxyalkyl, amino, alkylamino, aminoalkyl, dialkylamino, carboxy, alkoxycarbonyl or dialkylamino-carbonyl group, or, provided that $R_1$ is not located at a carbon atom adjacent to the cyclic nitrogen, $R_1$ may represent a sulphonyl group substituted by an alkyl, dialkylamino, phenyl or alkoxyphenyl group and R2 represents an optionally phenyl-substituted $C_{1-4}$-alkyl group, B represents an amino group, an amino($C_{1-5}$-alkyl) group, a guanidino or guanidinoalkyl group having 1 to 5 carbon atoms or an amidino group, whilst the above-mentioned groups may be substituted at one of the nitrogen atoms by a hydroxy group or by one or two $C_{1-4}$-alkyl groups or by a benzoyl, benzyloxycarbonyl, phenyloxycarbonyl or alkyloxycarbonyl group having a total of 2 to 5 carbon atoms, the Y-E group represents a straight-chained or branched $C_{1-4}$-alkyl group which is substituted by a vinyl, hydroxymethyl, carboxy, phosphono or O-alkyl-phosphono group, by an alkoxycarbonyl group having a total of 2 to 7 carbon atoms, by a dialkylaminocarbonylalkoxycarbonyl, morpholinoalkoxycarbonyl, (2-oxo-1-pyrrolidinyl)alkoxycarbonyl, pyridylalkoxycarbonyl or phenylalkoxycarbonyl group in which the phenyl nucleus may be substituted by one or two alkoxy groups, whilst the shortest distance between these substituents and the first nitrogen atom of group B is at least 10 bonds and, provided that the group B is bound to an aryl group of group X via a nitrogen atom, the group Y-E cannot represent an allyl group which is bound to the cyclic nitrogen atom of group B if the latter represents a pyrrolidine ring, and X represents a group of the formula

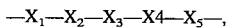

$$-X_1-X_2-X_3-X_4-X_5-,$$

wherein $X_1$ represents a bond, a methylene or ethylene group in which between the methylene or ethylene group and the adjacent group $X_2$ there may additionally be a —CONH— group, or between the ethylene group, or a methylene group which is not bound to the cyclic nitrogen atom of group A, and the adjacent group $X_2$ there may additionally be an oxygen or sulphur atom, a sulphonyl, imino, —N(CO-alkyl)—, —N(SO$_2$-alkyl)—, —N(CO-phenyl)—, —N(SO$_2$-phenyl)—, —NH—CO—, —N(alkyl)—CO—, —NH—SO$_2$— or —NH—CO—NH— group, or a —COCH$_2$— group, $X_2$ and $X_4$, which may be identical or different, may each represent a phenylene group which may be substituted by a fluorine, chlorine or bromine atom or by an alkyl, alkoxy, trifluoromethyl, alkylsulphenyl, alkylsulphinyl, alkylsulphonyl, nitro, alkanoylamino or alkanesulphonylamino group or by another alkyl group, an optionally mono- or polyunsaturated straight-chained $C_{1-3}$-alkylene group in which however a double or triple bond must not be adjacent to a heteroatom, a straight-chained $C_{4-6}$-alkylene group, a $C_{3-6}$cycloalkylene group, a $C_{7-10}$-bicycloalkylene group or a naphthylene group, whilst $X_4$ may additionally also represent a bond, $X_3$ represents a bond, a methylene group or, if $X_3$ is not directly followed by a heteroatom or a triple bond of group B, a —CO—, —CO—NH— or —NHCO— group, whilst this group may not be immediately adjacent to an aliphatic double or triple bond of the group $X_2$, or, if $X_2$ does not have an aliphatic double or triple bond at the end and $X_3$ is not directly followed by a heteroatom or a saturated carbon atom of the group B, $X_3$ may represent an oxygen atom, a sulphenyl, sulphinyl, sulphonyl, hydroxymethylene, imino, sulphonylimino or iminosulphonyl group or $X_2$ together with $X_3$ and $X_4$ represents a phenanthrenylene or naphthylene group which may be wholly or partially hydrogenated, a fluorenylene group in which the methylene group may be replaced by a hydroxymethylene or carbonyl group, an indanylene group or a spiroalkylene group having 8 to 11 carbon atoms, and $X_5$ represents a bond, particularly those compounds wherein $R_1$ is in positions 1 and 3 of group A, whilst, unless otherwise mentioned, the above-mentioned alkyl, alkoxy and alkanoyl moieties may each contain 1 to 3 carbon atoms.

Particularly preferred compounds of general formula I above are those wherein

A represents a pyrrolidine, 2-pyrrolidinone or 2-pyrrolinone ring optionally substituted by the groups $R_1$ and $R_2$, whilst $R_1$ represents a phenyl group which may be substituted by a carboxy, methoxycarbonyl, aminocarbonyl, methylaminocarbonyl, ethylaminocarbonyl, dimethylaminocarbonyl, methanesulphonylamino or acetylamino group, a $C_{1-4}$-alkyl group which may be substituted by a hydroxy, methoxy, phenoxy, methylsulphenyl, methylsulphinyl, methylsulphonyl, phenylsulphenyl, phenylsulphinyl, phenylsulphonyl, amino, acetylamino, benzoylamino, N-methyl-acetylamino, methanesulphonylamino or benzenesulphonylamino group, whilst these groups cannot be in the 1-position if $R_1$ is linked to the cyclic nitrogen atom of the group A, or a $C_{1-4}$-alkyl group which is substituted by two phenyl groups, one cyclohexyl group or one phenyl group, whilst the latter may be substituted by a fluorine, chlorine or bromine atom, by a $C_{1-4}$-alkyl group, by a $C_{1-6}$-alkoxy group, by a phenyl, phenylmethyl, hydroxy, benzyloxy, methylsulphenyl, methylsulphonyl or trifluoromethyl group, by two methoxy groups or by two chlorine atoms, a methyl group substituted by a carboxy, methoxycarbonyl, aminocarbonyl, methylaminocarbonyl, ethylaminocarbonyl, dimethylaminocarbonyl, benzylaminocarbonyl, pyrrolidinocarbonyl, piperidinocarbonyl, hexamethyleneiminocarbonyl, morpholinocarbonyl, thiomorpholinocarbonyl, 1-oxido-thiomorpholinocarbonyl, 1,1-dioxido-thiomorpholinocarbonyl, piperazinocarbonyl, N-methyl-piperazinocarbonyl, N-acetyl-piperazinocarbonyl or N-methanesulphonyl-piperazinocarbonyl group, or, if $R_1$ is not at the cyclic nitrogen atom, if A represents a 2-pyrrolidinone or 2-pyrrolinone group, $R_1$ may represent a carbonyl group substituted by a methyl, phenyl, methoxymethyl, amino, methylamino, ethylamino, aminomethyl, dimethylamino, carboxy, methoxycarbonyl or dimethylaminocarbonyl group, or, if $R_1$ is also not situated at a carbon atom adjacent to the cyclic nitrogen atom, $R_1$ may represent a sulphonyl group substituted by a methyl, dimethylamino, phenyl or methoxyphenyl group and $R_2$ represents a $C_{1-4}$-alkyl group optionally substituted by a phenyl group, B represents an amino($C_{1-5}$-alkyl) group, an amino, amidino, guanidino or guanidinoalkyl group having 1 to 5 carbon atoms, whilst the above-mentioned amino, aminoalkyl or amidino groups are substituted at one of the nitrogen atoms by a hydroxy group or by a $C_{1-4}$-alkyl group or by a methoxycarbonyl, ethoxycarbonyl, isopropyloxycarbonyl, isobutyloxycarbonyl, benzyloxycarbonyl, phenyloxy-carbonyl or benzoyl group, the Y-E group represents a straight-chained $C_{1-3}$-alkyl group substituted by a vinyl, carboxy, phosphono, O-methylphosphono or hydroxymethyl group, by an alkoxycarbonyl group having a total of 2 to 7 carbon atoms, by a dialkylaminocarbonylmethoxycarbonyl group in which each alkyl moiety may contain 1 to 3 carbon atoms, by a morpholinoethoxycarbonyl or (2-oxo-1-pyrrolidinyl)-ethoxycarbonyl group, by a phenylalkoxycarbonyl group having 1 to 3 carbon atoms in the alkoxy moiety, whilst the phenyl nucleus may be substituted by one or two methoxy groups, or by a pyridylmethyloxycarbonyl group, whilst the shortest distance between these substituents and the first nitrogen atom of group B is at least 10 bonds and, if the group B is bound to an aryl group of group X via a nitrogen atom, the group Y-E cannot represent an allyl group which is bound to the cyclic nitrogen atom of group A if the latter represents a pyrrolidine ring, and X represents a group of the formula

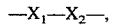

wherein $X_1$ is bound to the group A and $X_2$ to the group B and $X_1$ represents a bond, a methylene or ethylene group in which between the methylene group, provided that it is not bound to the cyclic nitrogen atom of group A, and the adjacent group $X_2$, there may additionally be an oxygen or sulphur atom or a sulphonyl, imino, —N(COCH$_3$)—, —N(SO$_2$CH$_3$)—, —CONH—, —NH—CO—, —NH—SO$_2$— or —NH—CO—NH— group or between the ethylene group and the adjacent group $X_2$ there may additionally be an imino, —NHCO— or —N(C$_2$H$_5$)CO— group, $X_2$ represents a phenylene or biphenylylene group which may be substituted by a fluorine, chlorine or bromine atom, by a methyl, methoxy, ethoxy, trifluoromethyl, methylsulphenyl, methylsulphinyl, methylsulphonyl, nitro, acetylamino or methanesulphonylamino group or by another methyl group, an optionally mono- or polyunsaturated straight-chained phenylene($C_{1-3}$-alkylene) group wherein however a double or triple bond cannot be adjacent to a heteroatom, a phenylenecycloalkylene or cycloalkylenephenylene group each having 4 to 6 carbon atoms in the cycloalkyl moiety, a phenylenenaphthylene, phenanthrenylene or dihydrophenanthrenylene group or a naphthylene group, which may be wholly or partially hydrogenated, a fluorenylene group wherein the methylene group may be replaced by a hydroxymethylene or carbonyl group, an indanylene, spiroundecylene or phenylenebicycloheptylene group or a phenylene-W-phenylene group wherein W represents an oxygen or sulphur atom or an imino, carbonyl, hydroxymethylene, sulphinyl or sulphonyl group, or, if $X_2$ is not directly followed by a heteroatom or an unsaturated carbon atom of group B, $X_2$ may also represent an oxyphenylene or carbonylaminophenylene group, particularly those compounds wherein $R_1$ is linked to the cyclic nitrogen atom or position 3 of the group A.

The most particularly preferred compounds of general formula I above are those wherein A represents a pyrrolidine or 2-pyrrolidinone ring optionally substituted by the groups $R_1$ and $R_2$, $R_1$ represents a phenyl group which may be substituted by a carboxy, methoxycarbonyl or dimethylaminocarbonyl group, a straight-chained $C_{1-4}$-alkyl group which may be terminally substituted by a phenyl group (which in turn may be substituted by a $C_{1-4}$-alkyl, a $C_{1-6}$-alkoxy, phenyl, benzyl, methylsulphenyl, methyl-sulphonyl or trifluoromethyl group, or by two methoxy groups or by two chlorine atoms), or by a cyclohexyl group or by two phenyl groups, a $C_{2-4}$-alkyl group substituted in the 2-, 3- or 4-position by a hydroxy, methoxy or phenoxy group, a methyl group substituted by a carboxy, methoxycarbonyl, aminocarbonyl, ethylaminocarbonyl, dimethylaminocarbonyl, benzylaminocarbonyl, pyrrolidinocarbonyl or morpholinocarbonyl group, or, if $R_1$ is not at the cyclic nitrogen atom, if A represents a 2-pyrrolidinone group, $R_1$ may represent a carbonyl group substituted by a methyl, phenyl, ethylamino, dimethylamino, methoxymethyl or aminomethyl group, or, if $R_1$ is also not situated at a carbon adjacent to the cyclic nitrogen, $R_1$ may represent a sulphonyl group substituted by a methyl, methoxyphenyl or dimethylamino group, and $R_2$ represents a $C_{1-4}$-alkyl group, B represents a guanidinomethyl group or an amidino which may be substituted at one of the nitrogen atoms by a $C_{1-4}$-alkyl group or by a methoxycarbonyl, ethoxycarbonyl, isopropyloxycarbonyl, isobutyloxycarbonyl, phenyloxycarbonyl, benzyloxycarbonyl or benzoyl group, the Y-E group represents a methyl group substituted by a carboxy, phosphono, O-methyl-phosphono or dimethylamino-carbonylmethoxycarbonyl group or by an alkoxycarbonyl group having a total of 2 to 7 carbon atoms, wherein a methoxy moiety may be substituted by a phenyl or pyridyl group, an ethoxy moiety may be terminally substituted by a phenyl, dimethoxyphenyl, morpholino or 2-oxo-1-pyrrolidinyl group and a n-propoxy moiety may be terminally substituted by a phenyl group, whilst the shortest distance between these substituents and the first nitrogen atom of group B is at least 10 bonds, and X represents a group of the formula

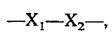

wherein $X_1$ represents a bond, a methylene group which provided that it is not bound to the cyclic nitrogen atom of group A is bound via an oxygen atom, or a sulphonyl, imino, —N(COCH$_3$)—, —NH—CO— or —NH—SO$_2$— group to the adjacent $X_2$ group, or an ethylene group bound via an —NH—CO— group to the adjacent $X_2$ group, and $X_2$ represents a biphenylylene group which may be substituted by a fluorine, chlorine or bromine atom, by a methyl, methoxy, ethoxy, trifluoromethyl, methylsulphenyl, methylsulphinyl, methylsulphonyl, nitro, acetylamino or methanesulphonylamino group or by another methyl group, a phenylenecycloalkylene group having a total of 10 to 12 carbon atoms, a phenylenesulphenylphenylene, phenylenesulphinylphenylene, dihydrophenanthrenylene, indanylene or naphthylene group or a fluorenylene group in which the methylene group may be replaced by a hydroxymethylene or carbonyl group, but particularly those compounds wherein $R_1$ is linked to the cyclic nitrogen atom or 3-position of the group A.

According to the invention, the new compounds of general formula I are obtained, for example, by the following methods which are known per se:

a) In order to prepare compounds of general formula I wherein B represents an amidino group, which may be mono-, di- or trisubstituted at a nitrogen atom by an amino, hydroxy or alkoxy group or at both nitrogen atoms by $C_{1-5}$-alkyl groups, and the two nitrogen atoms of the amidino group may be linked together by a $C_{2-4}$-alkylene group:

Reacting a compound of general formula

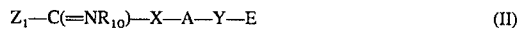

optionally formed in the reaction mixture, wherein A, E, X and Y are defined as hereinbefore, $R_{10}$ represents a hydrogen atom or a $C_{1-5}$-alkyl group and $Z_1$ represents an alkoxy or aralkoxy group such as a methoxy, ethoxy, n-propoxy, isopropoxy or benzyloxy group or an alkylthio or aralkylthio group such as a methylthio, ethylthio, n-propylthio or benzylthio group or an amino group, with an amine of general formula

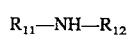

wherein $R_{11}$ represents a hydrogen atom or a $C_{1-5}$-alkyl group and $R_{12}$ represents a hydrogen atom, a $C_{1-5}$-alkyl group, a hydroxy group, a $C_{1-3}$-alkoxy group, an amino group or a straight-chained $C_{2-4}$-alkyl group terminally substituted by an amino group, or with the acid addition salts thereof.

The reaction is expediently carried out in a solvent such as methanol, ethanol, n-propanol, water, methanol/water, tetrahydrofuran or dioxane at temperatures between 0° and 150° C., preferably at temperatures between 20° and 120° C., with a corresponding free amine or with a corresponding acid addition salt such as ammonium carbonate.

A compound of general formula II is obtained for example by reacting a corresponding nitrile with a corresponding alcohol such as methanol, ethanol, n-propanol, isopropanol or benzyl alcohol in the presence of an acid such as hydrochloric acid or by reacting a corresponding amide with a trialkyloxonium salt such as triethyloxonium-tetrafluoroborate in a solvent such as methylene chloride, tetrahydrofuran or dioxane at temperatures between 0° and 50° C., but preferably at 20° C., or a corresponding nitrile with hydrogen sulphide, appropriately in a solvent such as pyridine or dimethylformamide and in the presence of a base such as triethylamine and subsequent alkylation of the thioamide formed with a corresponding alkyl or aralkyl halide.

b) In order to prepare compounds of general formula I wherein B contains an amino group:
Reduction of a compound of general formula $$NC-X-A-Y-E \qquad (IV)$$

wherein

A, E, X and Y are defined as hereinbefore.

The reduction is preferably carried out in a suitable solvent such as methanol, methanol/water, methanol/water/ammonia, methanol/hydrochloric acid, ethanol, ether, tetrahydrofuran, dioxane or glacial acetic acid in the presence of catalytically activated hydrogen, e.g. hydrogen in the presence of Raney nickel, platinum or palladium/charcoal, or in the presence of a metal hydride such as sodium borohydride, lithium borohydride or lithium aluminium hydride at temperatures between 0° and 100° C., preferably at temperatures between 20° and 80° C.

c) In order to prepare compounds of general formula I wherein B represents a guanidino group:
Reacting a compound of general formula $$H_2N-X-A-Y-E \qquad (V)$$

wherein

A, E, X and Y are defined as hereinbefore, or an acid addition salt thereof, with cyanamide.

The reaction is expediently carried out in a solvent such as dioxane, dioxane/water or tetrahydrofuran, preferably at temperatures between 80° and 120° C., e.g. at the boiling temperature of the reaction mixture.

d) In order to prepare compounds of general formula I wherein B represents a guanidino group which may be mono-, di- or trisubstituted by $C_{1-5}$-alkyl groups and wherein two nitrogen atoms may also be linked together by a $C_{2-4}$-alkylene group, and one of the nitrogen atoms may also be substituted by a cyano, hydroxy, alkoxy, amino, alkoxycarbonyl or aralkoxycarbonyl group, whilst the above-mentioned alkyl, alkoxy and aralkyl moieties are defined as hereinbefore:
Reacting a compound of general formula $$R_{13}-NH-X-A-Y-E \qquad (VI)$$

wherein

A, E, X and Y are defined as hereinbefore and $R_{13}$ represents a hydrogen atom or a $C_{1-5}$-alkyl group, with an amidine of general formula $$R_{14}-Z_2 \qquad (VII)$$

wherein $R_{14}$ represents an amidino group optionally mono-, di- or trisubstituted by $C_{1-5}$-alkyl groups, wherein two nitrogen atoms may also be linked together by a $C_{2-4}$-alkylene group, and one of the nitrogen atoms may also be substituted by a cyano, hydroxy, alkoxy, amino, alkoxycarbonyl or aralkoxycarbonyl group, whilst the above-mentioned alkyl, alkoxy and aralkyl moieties are defined as hereinbefore, and $Z_2$ represents a cleavable group such as a 3,5-dimethyl-pyrazol-1-yl, sulpho, methoxy or methylthio group.

The reaction is expediently carried out in a solvent such as dimethylformamide, water, dimethylformamide/water, dioxane, dioxane/water or tetrahydrofuran, optionally in the presence of a tertiary organic base such as triethylamine at temperatures between 0° and 100° C., preferably at temperatures between 20° and 50° C.

e) In order to prepare compounds of general formula I wherein B represents an amino group:
Reduction of a compound of general formula $$Z_3-X-A-Y-E \qquad (VIII)$$

optionally formed in the reaction mixture, wherein A, E, X and Y are defined as hereinbefore and $Z_3$ represents a nitro or azido group.

The reduction is preferably carried out in a solvent such as water, methanol, methanol/water, ethanol, ethanol/water, glacial acetic acid, ethyl acetate or dimethylformamide, expediently with hydrogen in the presence of a hydrogenation catalyst such as Raney nickel, platinum or palladium/charcoal, or with hydrazine in the presence of Raney nickel at temperatures between 0° and 100° C., but preferably at temperatures between 20° and 80° C.

The reduction of a nitro group may also be carried out with metals such as iron, tin or zinc in the presence of an acid such as zinc/acetic acid or zinc/calcium chloride or with salts such as iron(II) sulphate, tin(II)chloride, sodium sulphide, sodium hydrogen sulphite or sodium dithionite in a solvent such as glacial acetic acid, ethanol, ethanol/water, water, water/hydrochloric acid or water/sulphuric acid.

f) In order to prepare compounds of general formula I wherein E represents a carboxy or bis(hydroxycarbonyl)methyl group:
Converting a compound of general formula $$B-X-A-Y-E' \qquad (IX)$$

wherein

A, B, X and Y are defined as hereinbefore and E', which is bound to a carbon atom, represents a group which can be converted by hydrolysis, treatment with acids, thermolysis or hydrogenolysis into a carboxy or bis(hydroxycarbonyl)methyl group, optionally with subsequent decarboxylation.

For example, functional derivatives of the carboxyl group such as the unsubstituted or substituted amides, esters, thioesters, trimethylsilylesters, orthoesters, iminoesters, amidines or anhydrides, or the nitrile group may be converted by hydrolysis into a carboxyl group, esters with tertiary alcohols, e.g. the tert.-butylester, may be converted by treatment with an acid or thermolysis into a carboxyl group, esters with aralkanols, e.g. the benzylester, may be converted by hydrogenolysis into a carboxyl group, and bis(alkoxycarbonyl)methyl groups may be converted by hydrolysis or treatment with an acid into a bis(hydroxycarbonyl)methyl group.

The hydrolysis is expediently carried out either in the presence of an acid such as hydrochloric, sulphuric, phosphoric, trichloroacetic or trifluoroacetic acid, in the presence of a base such as sodium hydroxide or potassium hydroxide in a suitable solvent such as water, water/methanol, ethanol, water/ethanol, water/isopropanol or water/dioxane at temperatures between −10° C. and 120° C., e.g. at temperatures between ambient temperature and the boiling temperature of the reaction mixture. In the case of treatment with an organic acid such as trichloroacetic or trifluoroacetic acid, any alcoholic hydroxy groups present may simultaneously be converted into a corresponding acyloxy group such as the trifluoroacetoxy group.

If E' in a compound of formula IX represents a cyano or aminocarbonyl group, these groups may also be converted into the carboxyl group with a nitrite, e.g. sodium nitrite, in the presence of an acid such as sulphuric acid, which may expediently be used as solvent at the same time, at temperatures between 0° and 50° C.

If E' in a compound of formula IX represents, for example, the tert.-butyloxycarbonyl group, the tert.-butyl group may also be cleaved by treatment with an acid such as trifluoroacetic acid, formic acid, p-toluenesulphonic acid, sulphuric acid, phosphoric acid or polyphosphoric acid, optionally in an inert solvent such as methylene chloride, chloroform, benzene, toluene, tetrahydrofuran or dioxane, preferably at temperatures between −10° and 120° C., e.g. at temperatures between 0° and 60° C., or thermally, optionally in an inert solvent such as methylene chloride, chloroform, benzene, toluene, tetrahydrofuran or dioxane and preferably in the presence of a catalytic quantity of an acid such as p-toluenesulphonic acid, sulphuric acid, phosphoric acid or polyphosphoric acid, preferably at the boiling temperature of the solvent used, e.g. at temperatures between 40° C. and 100° C.

If E' in a compound of formula IX represents, for example, the benzyloxycarbonyl group, the benzyl group may also be cleaved hydrogenolytically in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0° and 50° C., e.g. at ambient temperature, under a hydrogen pressure of from 1 to 10 bar. During hydrogenolysis, other groups may be reduced at the same time, e.g. a nitro group to the amino group or a benzyloxy group to the hydroxy group.

The optional subsequent decarboxylation is preferably carried out in a solvent such as glacial acetic acid at elevated temperatures, e.g. at the boiling temperature of the reaction mixture.

g) In order to prepare compounds of general formula I wherein E represents a bis(alkoxycarbonyl)methyl group wherein the alkoxy moiety may contain 1 to 4 carbon atoms:

Reacting a compound of general formula $$B—X—A—Y—Z_4 \qquad (X)$$

wherein

A, B, X and Y are defined as hereinbefore and $Z_4$ represents a leaving group such as a halogen atom, e.g. a chlorine, bromine or iodine atom, or a substituted sulphonyloxy group, e.g. a methanesulphonyloxy, phenylsulphonyloxy or p-toluenesulphonyloxy group, with a dialkylmalonate in which the alkoxy moiety may contain 1 to 4 carbon atoms.

The reaction is preferably carried out in a solvent such as dioxane, dimethylformamide or dimethylsulphoxide in the presence of a base such as potassium carbonate or sodium hydride at temperatures between 0° and 80° C., preferably at temperatures between 20° and 70° C.

h) In order to prepare compounds of general formula I wherein E represents one of the ester or amide groups mentioned hereinbefore:

Reaction of a compound of general formula $$B—X—A—Y—COOH \qquad (XI)$$

wherein

A, B, X and Y are defined as hereinbefore, or the reactive derivatives thereof such as the esters, anhydrides or halides thereof, with a compound of general formula $$H—R_{15} \qquad (XII)$$

wherein $R_{15}$ represents a $C_{1-7}$-alkoxy group, an amino, aralkoxy, heteroarylalkoxy, aminoalkoxy, alkyleneiminoalkoxy or aminocarbonylalkoxy group, whilst the above-mentioned amino groups may each be mono- or disubstituted by alkyl, aryl or aralkyl groups and a methylene group of the 5- to 7-membered alkyleneimino ring may be replaced by a carbonyl group or in the 4-position by an oxygen atom or by a sulphenyl, sulphinyl, imino, alkylimino, aralkylimino or arylimino group or in the 2- or 4-position by a sulphonyl group.

The reaction is expediently carried out in a solvent such as tetrahydrofuran, chloroform, dimethylformamide or in a corresponding alcohol in the presence of an acid activating agent or a dehydrating agent, e.g. in the presence of isobutylchloroformate, thionylchloride, trimethylchlorosilane, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexylcarbodi-imide/N-hydroxysuccinimide or 1-hydroxy-benztriazole, N,N'-carbonyldiimidazole or N,N'-thionyldiimidazole or triphenylphosphine/carbon tetrachloride, or an agent which activates the amino group, e.g. phosphorus trichloride, and optionally in the presence of a base such as sodium carbonate, potassium carbonate, potassium tert.-butoxide or 1-hydroxy-benztriazole/triethylamine or in the presence of a tertiary organic base such as triethylamine, N-ethyldiisopropylamine, N-methyl-morpholine or pyridine, which may simultaneously serve as solvent, at temperatures between −30° and 100° C., but preferably at temperatures between −10° and 80° C. However, the reaction may also be carried out with a corresponding acid halide or acid anhydride, optionally in the presence of an acid binding agent as described above.

i) In order to prepare compounds of general formula I wherein E represents a carboxy group:

Oxidation of a compound of general formula $$B—X—A—Y—CHO \qquad (XIII)$$

wherein

A, B, X and Y are defined as hereinbefore.

The oxidation is preferably carried out in a solvent such as methylene chloride, acetonitrile, tetrahydrofuran/water, dioxane/water or acetone/water in the presence of an oxidising agent such as potassium permanganate or chromium trioxide and in the presence of an acid such as sulphuric acid, hydrochloric acid or trifluoroacetic acid at temperatures between 0° and 50° C., preferably at ambient temperature.

j) In order to prepare compounds of general formula I wherein the B—X—A group represents either a B—G$_1$—T—G$_2$—A group or a B—G$_1$—A group, whilst G$_2$ corresponds to part of X and G$_1$-T corresponds to the other part of X and additionally G$_1$ and G$_2$ or G$_1$—T may also represent a bond and G$_1$ may also represent X, and T represents an oxygen or sulphur atom or an imino, alkylimino, aralkylimino, arylimino, alkanoylimino, aroylimino, alkylsulphonylimino or arylsulphonylimino group:

Reacting a compound of general formula

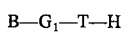    B—G$_1$—T—H    (XIV)

with a compound of general formula

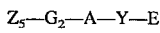    Z$_5$—G$_2$—A—Y—E    (XV)

or a compound of general formula

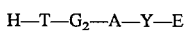    H—T—G$_2$—A—Y—E    (XVI)

with a compound of general formula

    B—G$_1$—Z$_5$    (XVII)

or a compound of general formula

    H—A—Y—E    (XVIII)

with a compound of general formula

    B—G$_1$—Z$_5$    (XVII)

wherein

A, B, E and Y are defined as hereinbefore, G$_2$ corresponds to a part of X and G$_1$—T corresponds to the other part of X, whilst additionally G$_1$ and G$_2$ or G$_1$—T may represent a bond and G$_1$ may also represent X and X is defined as hereinbefore, T represents an oxygen or sulphur atom or an imino, alkylimino, aralkylimino, arylimino, alkanoylimino, aroylimino, alkylsulphonylimino or arylsulphonylimino group and Z$_5$ represents a leaving group, and with the alkali metal or alkaline earth metal salts such as the lithium, sodium, potassium, cesium, magnesium or calcium salts or MgHal salts of a compound of general formula XIV, XVI or XVIII.

If Z$_5$ is bound to a methyl group optionally substituted by an alkyl or aryl group, the leaving group is preferably a halogen atom, e.g. a chlorine, bromine or iodine atom, or a substituted hydroxy group, e.g. a methanesulphonyloxy, ethanesulphonyloxy, benzenesulphonyloxy, p-toluenesulphonyloxy or triphenylphosphoniooxy group, or if Z$_5$ is bound to a carbonyl or sulphonyl group, the leaving group may, for example, be a halogen atom, e.g. a chlorine or bromine atom, an alkoxy, aryloxy, alkylthio, arylthio, azido, imidazolyl, alkylcarbonyloxy, arylcarbonyloxy or alkoxycarbonyloxy group, whilst the above-mentioned alkyl and aryl parts are defined as hereinbefore.

The reaction is expediently carried out in a solvent such as methanol, methylene chloride, chloroform, carbon tetrachloride, ether, tetrahydrofuran, dioxane, benzene, toluene, acetonitrile, dimethylsulphoxide, sulpholane or dimethylformamide, optionally in the presence of an inorganic or organic base, optionally in the presence of a reaction accelerator such as copper or copper(I)chloride or, if Z$_5$ represents a hydroxy group bound to the carbonyl group, optionally in the presence of an acid activating agent, optionally in the presence of a dehydrating agent or optionally in the presence of an agent which activates the amino group, at temperatures between −20° and 200° C., but preferably at temperatures between −10° and 160° C.

The alkylation is preferably carried out in a solvent such as tetrahydrofuran, acetone, dioxane, dimethylsulphoxide, sulpholane, dimethylformamide or dimethylacetamide in the presence of an inorganic base such as potassium carbonate, cesium carbonate, sodium hydroxide, potassium hydroxide, sodium hydride or potassium tert.-butoxide or in the presence of tertiary organic bases such as N-ethyl-diisopropylamine which may optionally also be used as solvent, and optionally in the presence of a phase transfer catalyst such as polyethyleneglycol-750-monomethylether on polystyrene or hexadecyl-trimethylammonium chloride at temperatures between 0° and 180° C., but preferably at temperatures between 10° and 160° C.

Reactions wherein Z$_5$ represents a leaving group bound to a carbonyl or sulphonyl group, are expediently carried out in a solvent such as tetrahydrofuran, methylene chloride, chloroform, acetonitrile, sulpholane or dimethylformamide and, if Z$_5$ represents a hydroxy group bound to a carbonyl group, in the presence of an acid activating agent or a dehydrating agent, e.g. in the presence of isobutylchloroformate, thionylchloride, phosphorus trichloride, phosphorus pentoxide, N,N'-dicyclohexylcarbodiimide, N,N'-dicyclohexylcarbodiimide/N-hydroxysuccinimide or 1-hydroxybenztriazole, N,N'-carbonyldiimidazole or N,N'-thionyldiimidazole or triphenylphosphine/carbon tetrachloride, or an agent which activates the amino group, e.g. phosphorus trichloride, and optionally in the presence of a base such as sodium carbonate, potassium carbonate or potassium tert.-butoxide or in the presence of a tertiary organic base such as 4-dimethylamino-pyridine, triethylamine, N-ethyl-diisopropylamine, N-methylmorpholine or pyridine, which may simultaneously serve as solvent, at temperatures between −50° and 100° C., but preferably at temperatures between −30° and 50° C. The acylations and sulphonations may, however, also be carried out with a corresponding acid halide or acid anhydride, optionally in the presence of an acid-binding agent as described hereinbefore.

k) In order to prepare compounds of general formula I wherein R$_1$ represents one of the alkyl groups mentioned for R$_1$ hereinbefore:

Alkylating a compound of general formula

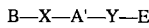    B—X—A'—Y—E    (XIX)

(wherein

B, E, X and Y are defined as hereinbefore and A' represents a 4-, 5-, 6- or 7-membered cyclic alkyleneimino group optionally substituted in the carbon skeleton by the groups R$_2$ and R$_3$, in which alkyleneimino group an ethylene group may be replaced by an ethenylene group or a methylene group by a carbonyl group, whilst R$_2$ and R$_3$ are defined as hereinbefore) with a compound of general formula

    R$_1$'—Z$_6$    (XX)

wherein

R$_1$' represents one of the alkyl groups mentioned hereinbefore for R$_1$ and

Z$_6$ represents a leaving group such as a halogen atom, e.g. a chlorine, bromine or iodine atom, or a substituted sulphonyloxy group, e.g. a methanesulphonyloxy, ethanesulphonyloxy, phenylsulphonyloxy or p-toluenesulphonyloxy group.

The alkylation is preferably carried out in a solvent such as methanol, methylene chloride, chloroform, carbon tetrachloride, ether, tetrahydrofuran, dioxane, benzene, toluene, acetonitrile, sulpholane or dimethylformamide in the presence of an inorganic base such as potassium carbonate, cesium carbonate, sodium hydroxide, potassium hydroxide, sodium hydride or potassium tert.-butoxide or in the presence of a tertiary organic base such as N-ethyldiisopropylamine which may optionally also serve as solvent, and optionally in the presence of a phase transfer catalyst such as polyethyleneglycol-750-monomethylether on polystyrene or hexadecyltrimethylammonium chloride at temperatures between 0° and 180° C., but preferably at temperatures between 10° and 160° C.

l) In order to prepare compounds of general formula I wherein R$_1$ represents one of the above-mentioned acyl or sulphonyl groups and A does not represent a lactam ring:

Acylation or sulphonation of a compound of general formula

B—X—A"—Y—E        (XXI)

(wherein

B, E, X and Y are defined as hereinbefore and A" represents a 4-, 5-, 6- or 7-membered cyclic alkyleneimino group optionally substituted in the carbon skeleton by the groups R$_2$ and R$_3$, in which alkyleneimino group an ethylene group may be replaced by an ethenylene group, wherein R$_2$ and R$_3$ are defined as hereinbefore) with a compound of general formula

R$_1$"—Z$_7$        (XXII)

wherein

R$_1$" represents one of the acyl or sulphonyl groups mentioned for R$_1$ hereinbefore and Z$_7$ represents a hydroxy group, a leaving group such as a halogen atom, e.g. a chlorine or bromine atom, an azido group or an acyloxy group, e.g. an acetoxy, methoxycarbonyloxy, ethoxycarbonyloxy or isobutoxycarbonyloxy group, or Z$_7$ together with the hydrogen atom of an imino group adjacent to the carbonyl group may represent another carbon-nitrogen bond.

The reaction is conveniently carried out in a solvent such as methanol, methylene chloride, chloroform, carbon tetrachloride, ether, tetrahydrofuran, dioxane, benzene, toluene, acetonitrile, sulpholane or dimethylformamide, optionally in the presence of an inorganic or organic base, optionally in the presence of an acid activating agent, optionally in the presence of a dehydrating agent or optionally an agent which activates the amino group, at temperatures between −20° and 200° C., but preferably at temperatures between −10° and 160° C.

If Z$_7$ represents a hydroxy group, the acylation is expediently carried out in a solvent such as tetrahydrofuran, methylene chloride, chloroform, sulpholane or dimethylformamide in the presence of an acid activating agent or a dehydrating agent, e.g. in the presence of ethyl chloroformate, thionylchloride, phosphorus trichloride, phosphorus pentoxide, N,N'-dicyclohexylcarbodiimide, N,N'-dicyclohexylcarbodiimide/N-hydroxysuccinimide or 1-hydroxybenztriazole, N,N'-carbonyldiimidazole or N,N'-thionyldiimidazole or triphenylphosphine/carbon tetrachloride, or an agent which activates the amino group, e.g. phosphorus trichloride, and optionally in the presence of a base such as sodium carbonate, potassium carbonate, potassium tert.-butoxide or 1-hydroxy-benztriazole/triethylamine or in the presence of a tertiary organic base such as 4-dimethylaminopyridine, triethylamine, N-ethyldiisopropylamine, N-methyl-morpholine or pyridine, which may simultaneously be used as solvent, at temperatures between −10° and 100° C., but preferably at temperatures between 0° and 50° C.

However, the acylation or sulphonylation is preferably carried out with a corresponding acid halide or acid anhydride, optionally in the presence of an acid binding agent as described hereinbefore.

m) In order to prepare compounds of general formula I wherein E contains a hydroxycarbonyl, alkoxycarbonyl or aralkoxycarbonyl group:

Oxidation of a compound of general formula

B—X—A—Y—E"        (XXIII)

(wherein

A, B, X and Y are defined as hereinbefore and E" represents a vinyl or 1,2-dihydroxyalkyl group) and if necessary subsequent esterification with a corresponding alcohol.

The oxidation is carried out in a solvent such as methylene chloride, acetonitrile, acetonitrile/water, methylene chloride/acetonitrile/water or carbon tetrachloride/acetonitrile/water in the presence of an oxidising agent such as potassium permanganate or ruthenium tetroxide, the ruthenium tetroxide preferably being formed in the reaction mixture by reacting a ruthenium salt such as ruthenium trichloride with an oxidising agent such as sodium periodate, at temperatures between −10° and 60° C., preferably at temperatures between 0° and 40° C.

The optional subsequent esterification is expediently carried out in a suitable solvent, e.g. in a corresponding alcohol, pyridine, toluene, methylene chloride, tetrahydrofuran or dioxane, in the presence of an acid activating and/or dehydrating agent such as hydrogen chloride, concentrated sulphuric acid, thionyl chloride, ethylchloroformate, carbonyldiimidazole or N,N'-dicyclohexylcarbodiimide or the isourea esters thereof, optionally in the presence of a reaction accelerator such as copper chloride, or by transesterification, e.g. with a corresponding carbonic acid diester, at temperatures between 0° and 100° C., but preferably at temperatures between 20° C. and the boiling temperature of the solvent in question.

n) In order to prepare compounds of general formula I wherein E represents one of the above-mentioned carbonyl groups substituted by an alkoxy, aralkoxy or heteroarylalkoxy group:

Reaction of a compound of general formula

B—X—A—Y—COOH        (XI)

wherein

A, B, X and Y are defined as hereinbefore, with a formamide acetal of general formula

(R$_{16}$)$_2$N—CH(OR$_{17}$)$_2$        (XXIV)

wherein

R$_{16}$ represents a lower alkyl group such as a methyl, ethyl, n-propyl or isopropyl group and R$_{17}$ represents a C$_{1-7}$-alkyl group, an aralkyl or heteroarylalkyl group.

The reaction is expediently carried out in a solvent such as tetrahydrofuran, dioxane or toluene at temperatures between 40° and 160° C., but preferably at temperatures between 60° and 120° C.

o) In order to prepare compounds of general formula I wherein A does not represent a lactam ring and $R_1$ represents an $(R_5)_2NCO$ group which is linked to the nitrogen atom of the group A:

Reaction of a compound of general formula

B—X—A'''—Y—E    (XXV)

wherein

B, E, X and Y are defined as hereinbefore and A''' represents a 4-, 5-, 6- or 7-membered cyclic alkyleneimino group optionally substituted by the groups $R_2$ and $R_3$, and substituted at the nitrogen atom by a halocarbonyl or N-azolylcarbonyl group, and in which at the same time an ethylene group may be replaced by an ethenylene group, with an amine of general formula

H—N($R_5$)$_2$    (XXVI)

wherein $R_5$ is defined as hereinbefore, or with the reactive derivatives thereof.

The reaction is expediently carried out in a solvent such as methylene chloride, dioxane, tetrahydrofuran or toluene, optionally in the presence of a base such as triethylamine, N-ethyldiisopropylamine, N-methyl-morpholine or pyridine, which may simultaneously be used as solvent, at temperatures between −10° and 60° C., but preferably at ambient temperature.

p) In order to prepare compounds of general formula I wherein E represents a hydroxycarbonyl, alkoxycarbonyl or aralkoxycarbonyl group, Y represents a bond and A represents one of the above-mentioned 5- to 7-membered lactam rings and the B—X group is linked to the nitrogen atom of the lactam ring:

Reaction of a compound of general formula

B—X—NH$_2$    (XXVII)

wherein

B and X are defined as hereinbefore, with a compound of general formula

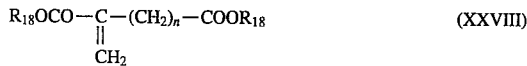

$R_{18}OCO-\underset{\underset{CH_2}{\|}}{C}-(CH_2)_n-COOR_{18}$    (XXVIII)

wherein $R_{18}$ represents a hydrogen atom, a $C_{1-7}$-alkyl group or an aralkyl group and n represents the number 1, 2 or 3.

The reaction is carried out in a solvent such as dioxane, toluene, xylene or decaline, but preferably without a solvent, at elevated temperatures, e.g. at temperatures between 60° and 200° C., but preferably at temperatures between 100° and 180° C.

If, according to the invention, a compound of general formula I is obtained which contains as substituent a nitro group, this may be converted by reduction into a corresponding amino compound of general formula I and/or if a compound of general formula I is obtained which contains an amino, alkylamino or imino group, this may be converted by acylation, sulphonylation or alkylation into a corresponding compound of general formula I and/or if a compound of general formula I is obtained which contains a hydroxy group, this may be converted by alkylation or acylation into a corresponding compound of general formula I and/or if a compound of general formula I is obtained which contains a carbonyl bridge, this may be converted by reduction into a corresponding hydroxymethylene compound of general formula I and/or if a compound of general formula I is obtained which contains a carbonyl bridge, this may be converted by reduction into a corresponding methylene compound of general formula I and/or if a compound of general formula I is obtained which contains an alkylsulphenyl or arylsulphenyl group or a thioether bridge, this may be converted by oxidation into a corresponding S-oxide compound of general formula I and/or if a compound of general formula I is obtained which contains an alkylsulphenyl, alkylsulphinyl, arylsulphenyl or arylsulphinyl group or a thioether bridge, or an S-oxide compound of general formula I, this may be converted by oxidation into a corresponding S,S-dioxide compound of general formula I and/or if a compound of general formula I is obtained which contains an aromatic group substituted by an amino group, this may be converted by Sandmeyer reaction into a corresponding cyano compound of general formula I and/or if a compound of general formula I is obtained which contains an ester group, this may be converted by reaction with an amine into a corresponding amide and/or if a compound of general formula I is obtained which contains an ester group, this may be converted by reduction into a corresponding hydroxymethyl compound of general formula I and/or if a compound of general formula I is obtained which contains an ester group, this may be converted by transesterification into a corresponding ester and/or if a compound of general formula I is obtained which contains an amidino or guanidino group, this may be converted by acylation or cyanation into a corresponding compound of general formula I.

The subsequent reduction of the nitro group is preferably carried out in a solvent such as water, water/ethanol, methanol, glacial acetic acid, ethyl acetate or dimethylformamide, expediently with hydrogen in the presence of a hydrogenation catalyst such as Raney nickel, platinum or palladium/charcoal, with metals such as iron, tin or zinc in the presence of an acid such as zinc/acetic acid or zinc/calcium chloride, with salts such as iron(II)sulphate, tin(II)chloride, sodium sulphide, sodium hydrogen sulphite or sodium dithionite, or with hydrazine in the presence of Raney nickel at temperatures between 0° and 100° C., but preferably at temperatures between 20° and 80° C.

The subsequent acylation or sulphonylation of an amino, alkylamino, imino or hydroxy group is expediently carried out in a solvent such as methylene chloride, chloroform, carbon tetrachloride, ether, tetrahydrofuran, dioxane, benzene, toluene, acetonitrile or dimethylformamide, optionally in the presence of an acid activating agent or a dehydrating agent, e.g. in the presence of ethyl chloroformate, thionylchloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole or triphenylphosphine/carbon tetrachloride, optionally in the presence of an inorganic base such as sodium carbonate or a tertiary organic base such as triethylamine, pyridine or 4-dimethylaminopyridine, which may simultaneously be used as solvent, at temperatures between −25° and 150° C., but preferably at temperatures between −10° C. and the boiling temperature of the solvent used. However, the subsequent acylation or sulphonylation is preferably carried out with a corresponding acid halide or acid anhydride, as described hereinbefore, and this may also be carried out without a solvent.

The subsequent alkylation of an amino, alkylamino or imino compound is carried out, for example, in a solvent or mixture of solvents such as methylene chloride, dimethylformamide, dimethylsulphoxide, benzene, chlorobenzene, tetrahydrofuran, benzene/tetrahydrofuran or dioxane in the presence of an alkylating agent such as methyliodide, methylbromide, ethylbromide, dimethylsulphate or benzylchloride, for example in the presence of an acid binding agent, e.g. an alkoxide such as potassium tert.-butoxide, an alkali metal hydroxide such as sodium or potassium hydroxide, an alkali metal carbonate such as potassium carbonate, an alkali metal amide such as sodium amide or an alkali metal hydride such as sodium hydride, expediently at temperatures between 0° and 150° C., preferably at temperatures between 0° and 50° C.

The subsequent alkylation of an amino or alkylamino compound may also be carried out by reductive amination in a suitable solvent such as methanol, ethanol, tetrahydrofuran, dioxane, acetonitrile or mixtures thereof with water in the presence of a suitable reducing agent such as a suitable complex metal hydride, but preferably in the presence of sodium cyanoborohydride, or with hydrogen in the presence of a hydrogenation catalyst such as palladium/charcoal at temperatures between 0° and 50° C., but preferably at ambient temperature.

The subsequent O-alkylation is expediently carried out in a solvent or mixture of solvents such as methylene chloride, dimethylformamide, dimethylsulphoxide, benzene, chlorobenzene, tetrahydrofuran, benzene/tetrahydrofuran or dioxane, in the presence of an alkylating agent such as methyliodide, methylbromide, ethylbromide, dimethylsulphate or benzylchloride, preferably in the presence of an acid binding agent, e.g. an alkoxide such as potassium tert.-butoxide, an alkali metal hydroxide such as sodium or potassium hydroxide, an alkali metal carbonate such as potassium carbonate, an alkali metal amide such as sodium amide or an alkali metal hydride such as sodium hydride, appropriately at temperatures between 0° and 150° C., preferably at temperatures between 0° and 50° C.

The subsequent O-acylation is conveniently carried out in a solvent such as methylene chloride, chloroform, carbon tetrachloride, ether, tetrahydrofuran, dioxane, benzene, toluene, acetonitrile or dimethylformamide, optionally in the presence of an acid activating agent or a dehydrating agent, e.g. in the presence of ethyl chloroformate, thionylchloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole or triphenylphosphine/carbon tetrachloride, optionally in the presence of an inorganic base such as sodium carbonate or a tertiary organic base such as pyridine, 4-dimethylaminopyridine or triethylamine, which may simultaneously be used as solvent, at temperatures between −25° and 150° C., but preferably at temperatures between −10° C. and the boiling temperature of the solvent used. However, the subsequent O-acylation is preferably carried out with a corresponding acid halide or acid anhydride, as described hereinbefore, but may also be carried out without a solvent.

The subsequent reduction of the carbonyl bridge to a hydroxymethyl bridge is carried out in a suitable solvent such as methanol, methanol/water, ethanol, ether, tetrahydrofuran, dioxane or glacial acetic acid in the presence of catalytically activated hydrogen, e.g. hydrogen in the presence of platinum or palladium/charcoal, or in the presence of a metal hydride such as sodium borohydride, lithium borohydride or lithium aluminium hydride at temperatures between 0° and 50° C., but preferably at ambient temperature.

The subsequent reduction of the carbonyl bridge to a methylene bridge is effected in a suitable solvent such as methanol, ethanol, ether, tetrahydrofuran, dioxane or glacial acetic acid in the presence of catalytically activated hydrogen, e.g. hydrogen in the presence of platinum or palladium/charcoal, or in the presence of a metal hydride such as sodium borohydride, lithium borohyride or lithium aluminium hydride at elevated temperatures, e.g. at temperatures between 30° and 150° C., preferably at temperatures between 50° and 100° C.

The subsequent oxidation of the thioether is preferably carried out in a solvent or mixture of solvents, e.g. in water, water/pyridine, acetone, glacial acetic acid, methylene chloride, glacial acetic acid/acetic anhydride, dilute sulphuric acid or trifluoroacetic acid, at temperatures between −80° and 100° C., depending on the oxidising agent used.

In order to prepare a corresponding S-oxide compound of general formula I, the oxidation is conveniently carried out with one equivalent of the oxidising agent used, e.g. with hydrogen peroxide in glacial acetic acid, trifluoroacetic acid or formic acid at 0° to 20° C. or in acetone at 0° to 60° C., with a peracid such as performic acid in glacial acetic acid or trifluoroacetic acid at 0° to 50° C. or with m-chloroperbenzoic acid in methylene chloride or chloroform at −20° to 60° C., with sodium metaperiodate in aqueous methanol or ethanol at −15° to 25° C., with bromine in glacial acetic acid or aqueous acetic acid, with N-bromosuccinimide in ethanol, with tert.butyl-hypochlorite in methanol at −80° to −30° C., with iodobenzodichloride in aqueous pyridine at 0° to 50° C., with nitric acid in glacial acetic acid at 0° to 20° C., with chromic acid in glacial acetic acid or in acetone at 0° to 20° C. and with sulphuryl chloride in methylene chloride at −70° C. and the resulting thioether-chlorine complex is expediently hydrolysed with aqueous ethanol.

In order to prepare an S,S-dioxide compound of general formula I the oxidation is conveniently carried out with one or with two or more equivalents of the oxidising agent used, e.g. with hydrogen peroxide in glacial acetic acid/acetic anhydride, trifluoroacetic acid or in formic acid at 20° to 100° C. or in acetone at 0° to 60° C., with a peracid such as performic acid or m-chloroperbenzoic acid in glacial acetic acid, trifluoroacetic acid, methylene chloride or chloroform at temperatures between 0° and 60° C., with nitric acid in glacial acetic acid at 0° to 20° C., with chromic acid or potassium permanganate in glacial acetic acid, water/sulphuric acid or in acetone at 0° to 20° C.

The subsequent reaction of a diazonium salt, e.g. the hydrogen sulphate in sulphuric acid or the chloride in aqueous hydrochloric acid is conveniently carried out in the presence of trisodium-copper(I)-tetracyanide in a solvent such as water, methanol/water or water/hydrochloric acid. The diazonium salt required for this is expediently prepared in a solvent, e.g. in water/hydrochloric acid, water/sulphuric acid, methanol/hydrochloric acid, ethanol/hydrochloric acid or dioxane/hydrochloric acid, by diazotisation of a corresponding amino compound with a nitrite, e.g. sodium nitrite or an ester of the nitrous acids, at low temperatures, e.g. at temperatures between −10° and 5° C.

The subsequent reaction of an ester with an amine is preferably carried out in a solvent such as methanol, ethanol, tetrahydrofuran, dioxane or in an excess of the amine used, at temperatures between 0° and 70° C., preferably at temperatures between 20° and 50° C.

The subsequent reduction of an ester group is preferably carried out in a solvent such as diethylether, tetrahydrofuran or dioxane with a complex metal hydride such as lithium borohydride or lithium aluminium hydride at temperatures between −20° and 80° C., but preferably with lithium borohydride or lithium aluminium hydride in tetrahydrofuran/methanol at temperatures between 0° C. and 25° C.

The subsequent reaction of an ester group with an alcohol is preferably carried out in a corresponding alcohol as solvent, optionally in the presence of another solvent such as methylene chloride or ether, preferably in the presence of an acid such as hydrochloric acid at temperatures between 0° and 100° C., preferably at temperatures between 20° and 80° C.

The subsequent acylation or cyanation of an amidino or guanidino group is conveniently carried out in a solvent such as methylene chloride, chloroform, dioxane, tetrahydrofuran or dimethylformamide, preferably with an acid halide or anhydride, more particularly with a carbonic acid ester chloride, or with a halocyanogen compound in the presence of an inorganic base such as sodium carbonate or sodium hydroxide solution or a tertiary organic base such as triethylamine, N-ethyldiisopropylamine, pyridine or 4-dimethylaminopyridine, which may simultaneously serve as solvent, at temperatures between −25° and 100° C., but preferably at temperatures between 0° and 50° C.

In reactions a) to p) described above and in the subsequent reactions, any reactive groups present such as hydroxy, carboxy, phosphono, amidino, guanidino, amino or alkylamino groups, may optionally be protected during the reaction by means of conventional protecting groups which are cleaved again after the reaction.

For example, a suitable protective group for a hydroxy group might be a trimethylsilyl, acetyl, benzoyl, tert.-butyl, trityl, benzyl or tetrahydropyranyl group, whilst protective groups for a carboxyl group might be the trimethylsilyl, methyl, ethyl, tert.-butyl, benzyl or tetrahydropyranyl group, protective groups for an amidino or guanidino group might
  be the benzyloxycarbonyl group and an additional protecting group for the guanidino group might be the 4-methoxy-2,3,6-trimethyl-phenylsulphonyl group, protecting groups for a phosphono group might be the trimethylsilyl, methyl, ethyl or benzyl group and protecting groups for an amino, alkylamino or imino group
  might be the acetyl, benzoyl, ethoxycarbonyl, tert.-butoxycarbonyl, benzyloxycarbonyl, benzyl or methoxybenzyl group and an additional protecting group for the amino group might be the phthalyl group.

The optional subsequent cleaving of a protecting group is carried out, for example, hydrolytically in an aqueous solvent, e.g. in water, methanol/water, isopropanol/water, tetrahydrofuran/water or dioxane/water, in the presence of an acid such as trifluoroacetic acid, hydrochloric acid or sulphuric acid or in the presence of an alkali metal base such as sodium hydroxide or potassium hydroxide or by ether cleavage, e.g. in the presence of iodotrimethylsilane, at temperatures between 0° and 100° C., preferably at temperatures between 10° and 50° C.

However, a benzyl, methoxybenzyl or benzyloxycarbonyl group is cleaved, for example, by hydrogenolysis, e.g. with hydrogen in the presence of a catalyst such as palladium/charcoal in a solvent such as methanol, ethanol, dioxane, ethyl acetate or glacial acetic acid, optionally with the addition of an acid such as hydrochloric acid at temperatures between 0° and 50° C., but preferably at ambient temperature, under a hydrogen pressure of from 1 to 7 bar, but preferably from 3 to 5 bar.

The cleaving of a methoxybenzyl group may also be carried out in the presence of an oxidising agent such as Ce(IV)ammonium nitrate in a solvent such as methylene chloride, acetonitrile or acetonitrile/water at temperatures between 0° and 50° C., but preferably at ambient temperature.

A tert.-butyl or tert.-butyloxycarbonyl group is preferably cleaved by treatment with an acid such as trifluoroacetic or hydrochloric acid, optionally using a solvent such as methylene chloride, dioxane, ethyl acetate or ether.

The cleaving of only one alkyl group from an O,O'-dialkylphosphono group is carried out, for example, with sodium iodide in a solvent such as acetone, ethylmethylketone, acetonitrile or dimethylformamide at temperatures between 40° and 150° C., but preferably at temperatures between 60° and 100° C.

The cleaving of both alkyl groups from an O,O'-dialkylphosphono group is carried out for example with iodotrimethylsilane, bromotrimethylsilane or chlorotrimethylsilane/sodium iodide in a solvent such as methylene chloride, chloroform or acetonitrile at temperatures between 0° C. and the boiling temperature of the reaction mixture, but preferably at temperatures between 20° and 60° C.

The cleaving of a phthalyl group is preferably carried out in the presence of hydrazine or a primary amine such as methylamine, ethylamine or n-butylamine in a solvent such as methanol, ethanol, isopropanol, toluene/water or dioxane at temperatures between 20° and 50° C.

Moreover, the compounds of general formula I obtained may, as already mentioned hereinbefore, be resolved into the enantiomers and/or diastereomers thereof. Thus, for example, cis/trans mixtures may be resolved into their cis and trans isomers and compounds having at least one optically active carbon atom may be resolved into their enantiomers.

Thus, for example, the cis/trans mixtures obtained may be separated by chromatography into their cis and trans isomers, the compounds of general formula I obtained in the form of racemates may be separated by known methods (see Allinger N. L. and Eliel E. L. in "Topics in Stereochemistry", Vol. 6, Wiley Interscience, 1971) into their optical antipodes and compounds of general formula I having at least 2 asymmetric carbon atoms can be separated on the basis of their physicalchemical differences into their diastereomers by methods known per se, e.g. by chromatography and/or fractional crystallisation, and if these diastereomers are obtained in racemic form they may subsequently be separated into the enantiomers as mentioned above.

Enantiomer separation is preferably achieved by column separation on chiral phases or by recrystallisation from an optically active solvent or by reacting with an optically active substance which forms salts with the racemic compound, more particularly acids, and separating the diastereomeric salt mixture obtained in this way, e.g. on the basis of different solubilities, whilst the free antipodes may be liberated from the pure diastereomeric salts by the action of suitable agents. Particularly common optically active acids are, for example, the D and L forms of tartaric or dibenzoyltartaric acid, di-o-tolyl-tartaric acid, malic, mandelic and camphorsulphonic acid, glutamic acid, aspartic acid or quinic acid.

Moreover, the compounds of formula I obtained may be converted into the acid addition salts thereof, more particularly for pharmaceutical use the physiologically acceptable salts thereof with inorganic or organic acids. Examples of suitable acids include hydrochloric acid, hydrobromic acid, sulphuric acid, phosphoric acid, fumaric acid, succinic acid, lactic acid, citric acid, tartaric acid and maleic acid.

In addition, the new compounds of formula I thus obtained, should they contain a carboxyl group, may if desired subsequently be converted into the addition salts thereof with inorganic or organic bases, more particularly for pharmaceutical use into the physiologically acceptable addition salts thereof. Examples of suitable bases include sodium hydroxide, potassium hydroxide, cyclohexylamine, ethanolamine, diethanolamine and triethanolamine.

The compounds of formulae II to XXVIII used as starting materials are known from the literature in some cases or may be obtained by methods known from the literature (see the Examples).

The compounds of general formula XXV used as starting materials are obtained by reacting a compound of general formula XXI with a carbonyldihalide or with an N,N'-carbonyl-bis-azole.

As already mentioned hereinbefore, the new cyclic imino derivatives of general formula I and the addition salts thereof, particularly the physiologically acceptable addition salts thereof with inorganic or organic acids or bases, have valuable properties. Thus, the compounds of general formula I wherein B contains an optionally substituted amino or imino group or a group which can optionally be converted in vivo into an optionally substituted amino or imino group, e.g. an amino or imino group substituted by an alkoxycarbonyl group, and Y-E contains a carboxyl, sulpho, phosphono, O-alkyl-phosphono or 5-tetrazolyl group or a group which can be converted in vivo into a carboxyl, sulpho, phosphono, O-alkyl-phosphono or tetrazolyl group, e.g. a carbonyl group substituted by an alkoxy group, have valuable pharmacological properties, not only an anti-inflammatory effect which inhibits the breakdown of bone but in particular antithrombotic and anti-aggregatory effects and inhibitory effects on tumours or metastases. The other compounds of general formula I are, in particular, valuable intermediate products for preparing the above-mentioned pharmacologically active compounds.

For example, the compounds of general formula I were tested for their biological effects in the following way:

1. Fibrinogen binding to human thrombocytes

Blood obtained by puncture of an antecubital vein is anticoagulated with trisodium citrate (final concentration: 13 mM) and centrifuged for 10 minutes at 170 g. The supernatant platelet-rich plasma is placed on a Sepharose 2B column (Pharmacia) and eluted with a solution of 90 mM common salt, 14 mM trisodium citrate, 5 mM glucose and 50 mM tris(hydroxymethyl)aminomethane, adjusted to pH 7.4. The gel-filtered platelets (GFP) appearing in front of the plasma proteins are used for the binding tests.

50 µl of a 60 mM calcium chloride solution, 50 µl of a 0.6 mM adenosine diphosphate solution, 100 µl of substance solution or solvent and 50 µl of fibrinogen solution (containing 3 µg 125-J-fibrinogen) are added to 750 µl of GFP and incubated for 20 minutes at ambient temperature. The non-specific binding is measured in the presence of 3 mg/ml of cold fibrinogen.

900 µl of the incubate are carefully pipetted onto 250 µl of silicon oil (AP 38: AR 20, 1:2 v/v, Wacker Chemie) in Eppendorf vessels and centrifuged for 2 minutes at 10,000 g. The aqueous supernatant and some of the oil are removed, the tip of the vessel with the platelet pellet is cut off and the quantity of bound fibrinogen is measured in a gamma-counter. The concentration of substance which inhibits fibrinogen binding by 50% is calculated from a concentration series and given as the $IC_{50}$.

2. Antithrombotic effect

Method

The thrombocyte aggregation is measured by the Born and Cross method (J. Physiol. 170: 397 (1964)) in platelet-rich plasma from healthy test subjects. To inhibit coagulation, 3.14% sodium citrate is added to the blood in a ratio by volume of 1:10.

Collagen-induced aggregation

The curve of the decrease in optical density of the platelet suspension is measured and recorded photometrically after the addition of the aggregation-inducing substance. The speed of aggregation is determined from the angle of inclination of the density curve. The point on the curve where maximum transmittance occurs is used to calculate the optical density.

The quantity of collagen is made as small as possible but sufficient to produce an irreversible reaction curve. Standard commercial collagen made by Hormonchemie of Munich is used. Before the addition of collagen, the plasma is incubated for 10 minutes with the substance at 37° C.

From the measurements obtained, an $EC_{50}$ is determined graphically relating to a 50% change in the optical density in the sense of an inhibition of aggregation.

The Table which follows contains the results found:

| Substance (Example No.) | Fibrinogen binding test $IC_{50}[\mu M]$ | Inhibition of platelet aggregation $EC_{50}[\mu m]$ |
| --- | --- | --- |
| 6(2) | 2.3 | 1.9 |
| 6(184) | 0.42 | 1.0 |
| 7 | 0.032 | 0.9 |
| 7(1) | 0.024 | 0.17 |
| 7(3) | 0.031 | 0.06 |
| 7(10) | 0.05 | 2.6 |
| 7(36) | 0.041 | 0.41 |
| 7(40) | 0.17 | 2.0 |
| 7(41) | 2.8 | 19.0 |
| 7(46) | 0.69 | 12.0 |
| 7(51) | 0.027 | 0.08 |
| 7(56) | 0.02 | 0.06 |
| 7(58) | 0.02 | 0.21 |
| 7(70) | 0.4 | 19.0 |
| 7(89) | 0.23 | 2.8 |
| 7(93) | 0.026 | 0.1 |
| 23(8) | 4.6 | 20.0 |
| 31(1) | 4.7 | 66.0 |
| 32 | 1.2 | 5.8 |
| 32(1) | 2.2 | 33.0 |
| 71 | 4.6 | 11.0 |

Moreover, the compound of Example 70(1), for example, inhibits collagen-induced thrombocyte aggregation ex vivo in rhesus monkeys following oral administration of 1 mg/kg for more than 8 hours.

The new compounds are well tolerated since the approximate $LD_{50}$ in rats is, for example, for the compound of Example (3) above 100 mg/kg after intravenous route and for the compound of Example 70(1) above 2.000 mg/kg after oral administration.

In view of their inhibitory effect on cell-cell and cell-matrix interactions, the new cyclic imino derivatives of general formula I and the physiologically acceptable addition salts thereof are suitable for combating or preventing diseases in which smaller or larger clumps of cells are produced or cell-matrix interactions are involved, e.g. in combating or preventing venous and arterial thrombosis, cerebro-vascular diseases, pulmonary embolisms, cardiac infarct, arteriosclerosis, osteoporosis and tumour metastasis and the therapy of genetically caused or acquired disorders of the interaction of cells with one another or with solid structures. They are also suitable as an accompanying therapy in thrombolysis with fibrinolytics or vascular interventions such as transluminal angioplasty or in the treatment of shock, psoriasis, diabetes and inflammation.

For combating or preventing the above-mentioned diseases, the dose is between 0.1 μg and 30 mg/kg of body weight, preferably 1 μg to 15 mg/kg of body weight, in up to 4 doses per day. For this purpose, the compounds of formula I prepared according to the invention may be formulated, optionally in conjunction with other active substances such as thromboxan receptor antagonists and thromboxan synthesis inhibitors or combinations thereof, serotonin antagonists, α-receptor antagonists, alkyl nitrates such as glycerol trinitrate, phosphodiesterase inhibitors, prostacyclin and analogues thereof, fibrinolytics such as tPA, prourokinase, urokinase, streptokinase, or anticoagulants such as heparin, dermatane sulphate, activated protein C, vitamin K antagonists, hirudin, inhibitors of thrombin or other activated clotting factors, together with one or more inert conventional carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose, cyclodextrines such as hydroxypropyl-β-cyclodextrine or fatty substances such as hard fat or suitable mixtures thereof, to produce conventional galenic preparations such as plain or coated tablets, capsules, powders, suspensions, solutions, sprays or suppositories.

The Examples which follow are intended to illustrate the invention:

Preparation of the starting compounds:

Example I (S)-1-(4-Phenylbutyl)-5-[(trityloxy)methyl]-2-pyrrolidinone

To 6 g of sodium hydride (55–60% dispersion in paraffin oil) in 50 ml of dry dimethylformamide, 40 g of (S)-5-[(trityloxy)methyl]-2-pyrrolidinone in 150 ml of dry dimethylformamide are added dropwise with stirring and cooling with ice. The mixture is then stirred for 2 hours at ambient temperature and then 32 g of 4-phenylbutylbromide in 50 ml of dry dimethylformamide are added dropwise. After 18 hours stirring at ambient temperature the mixture is poured onto ice, extracted three times with ethyl acetate, the combined organic phases are washed with water, dried over sodium sulphate and evaporated down. The crude product is purified over a silica gel column with toluene/acetone (4:1).

Yield: 51.5 g (94% of theory), $R_f$ value: 0.41 (silica gel; toluene/acetone=4:1)

The following are obtained analogously:
(1) (5S)-1-(4-methoxybenzyl)-5-[(trityloxy)methyl]-2-pyrrolidinone $R_f$ value: 0.50 (silica gel; cyclohexane/ethyl acetate=1:1) Calculated: C 80.48 H 6.54 N 2.93 Found: 80.21 6.74 2.75
(2) (S)-1-[3-(4-benzyloxyphenyl)propyl]-5-[(trityloxy)methyl]-2-pyrrolidinone $R_f$ value: 0.47 (silica gel; toluene/acetone=4:1)

Example II (S)-1-(3-Phenylpropyl)-5-[(trityloxy) methyl]-2-pyrrolidinone 203.7 g of (S)-5-[(trityloxy)methyl]-2-pyrrolidinone, 3 liters of toluene, 1.4 liters of 50% aqueous sodium hydroxide solution, 139.4 g of 3-phenylpropylbromide and 10 g of methyl-trioctyl ammonium chloride are stirred vigorously for 25 hours at ambient temperature under argon. Then 40 ml of 3-phenylpropylbromide are added and the mixture is stirred for a further 24 hours. It is distributed between toluene and water, the organic phase is separated off, dried over magnesium sulphate, then stirred for half an hour with 5 spoons of active charcoal, filtered and concentrated by rotary evaporation. The evaporation residue is chromatographed over a silica gel column with methylene chloride and then with ethyl acetate. The crystalline evaporation residue is then recrystallised from isopropanol/water 4:1.

Yield: 234.3 g (86% of theory), Melting point: 103°–104° C. $R_f$ value: 0.71 (silica gel; ethyl acetate)

The following are obtained analogously:
(1) (S)-1-(3-cyclohexylpropyl)-5-[(trityloxy)methyl]-2-pyrrolidinone $R_f$ value: 0.14 (silica gel; methylene chloride/methanol=100:1)
(2) (R)-1-(3-phenylpropyl)-5-[(trityloxy)methyl]-2-pyrrolidinone Melting point: 109° C. $R_f$ value: 0.37 (silica gel; cyclohexane/ethyl acetate=2:1) Calculated: C 83.33 H 6.99 N 2.94 Found: 83.31 7.15 2.95
(3) (R,S)-[5-(4-methoxyphenyl)-1-(3-phenylpropyl)-2-pyrrolidinone $R_f$ value: 0.09 (silica gel; cyclohexane/ethyl acetate=2:1) Calculated: C 77.64 H 7.49 N 4.53 Found: 77.33 7.58 4.53
(4) (S)-1-benzyl-5-[(trityloxy)methyl]-2-pyrrolidinone Melting point: 103°–104° C.
(5) (S)-1-[2-(2-naphthyl)ethyl]-5-[(trityloxy)methyl]-2-pyrrolidinone $R_f$ value: 0.33 (silica gel; toluene/acetone=4:1)
(6) (S)-1-[2-(1-naphthyl)ethyl]-5-[(trityloxy)methyl]-2-pyrrolidinone $R_f$ value: 0.42 (silica gel; toluene/acetone=4:1)
(7) (S)-1-isobutyl-5-[(trityloxy)methyl]-2-pyrrolidinone Melting point: 91°–93° C. $R_f$ value: 0.68 (silica gel; ethyl acetate)
(8) (S)-1-(2-phenylethyl)-5-[(trityloxy)methyl]-2-pyrrolidinone Melting point: 95°–98° C.
(9) (S)-1-(4-phenyloxybutyl)-5-[(trityloxy)methyl]-2-pyrrolidinone Melting point: 69°–72° C.
(10) (S)-1-[2-(benzyloxy)ethyl-5-[(trityloxy)methyl]-2-pyrrolidinone Melting point: 78°–80° C., $R_f$ value: 0.60 (silica gel; ethyl acetate)
(11) (S)-1-methyl-5-[(trityloxy)methyl]-2-pyrrolidinone $R_f$ value: 0.41 (silica gel; ethyl acetate)

Example III (S)-1-(3-phenylpropyl)-5-[(trityloxy)methyl]-2-pyrrolidinone 741 g of potassium tert.-butoxide are added in batches to 2255 g of (S)-5-[(trityloxy)methyl]-2-pyrrolidinone and 1005 ml of 3-phenylpropylbromide in 4.5 liters of toluene, with vigorous stirring at ambient temperature and the mixture is then stirred for 17 hours at ambient temperature. The reaction mixture is mixed with 4 liters of water and acidified with citric acid. The aqueous phase is separated off, extracted with 1 liter of toluene and the combined toluene phases are washed three times with 1.5 l of water each time. The organic phase is dried with sodium sulphate, filtered and divided into two equal portions. The solutions are separately concentrated by rotary evaporation and the evaporation residues are each mixed with 4 liters of hot cyclohexane. They are cooled with stirring and the two sets of crystals are suction filtered. The two batches are washed with cyclohexane and dried.

Yield: total 2532 g (88.7% of theory), Melting point: 103° C. $R_f$ value: 0.26 (silica gel; methylene chloride/methanol= 50:1)

Example IV (3R,5S)-3-Allyl-1-(3-phenylpropyl)-5-[(trityloxy)-methyl]-2-pyrrolidinone 225 ml of diisopropylamine are dissolved in 250 ml of tetrahydrofuran and while cooling in a bath of dry ice/methanol, 1000 ml of a 1.6 molar solution of n-butyl lithium in n-hexane are added in batches thereto. The mixture is cooled to −75° C. and a solution of (S)-1-(3 -phenylpropyl)-5-[(trityloxy)methyl]-2-pyrrolidinone in 2000 ml of tetrahydrofuran is added dropwise so that the temperature remains between −75° and −65° C. The mixture is stirred for a further 3 hours at −75° C., then within one hour a solution of 134 ml of allyl bromide in 150 ml of tetrahydrofuran is added, the temperature being maintained between −75° and −65° C., and the mixture is then stirred for a further hour at −75° C. It is allowed to return to ambient temperature and the reaction solution is poured onto 2000 ml of semisaturated common salt solution. It is extracted with ethyl acetate, the organic phases are washed with water, dried with sodium sulphate and the solvent is distilled off in vacuo. The crude product remaining is further reacted without any further purification and still contains a few percent of the (3S,5S)-isomer [$R_f$ value: 0.55 (silica gel; cyclohexane, ethyl acetate=2:1)]

Yield: 788 g (100% of theory), $R_f$ value: 0.63 (silica gel; cyclohexane/ethyl acetate=2:1)

The following are prepared analogously:
(1) (3R,5S)-3-allyl-1-phenyl-5-[(trityloxy)methyl]-2-pyrrolidinone
$R_f$ value: 0.53 (silica gel; cyclohexane/ethyl acetate=1:1)
Calculated: 83.69 H 6.60 N 2.96 Found: 83.40 7.08 2.83
(2) (3R,5S)-3-allyl-1-(3-cyclohexylpropyl)-5-[(trityloxy)methyl]-2-pyrrolidinone
$R_f$ value: 0.50 (silica gel; cyclohexane/ethyl acetate=8:2)
Calculated: 82.88 H 8.31 N 2.68 Found: 82.68 8.56 2.46
(3) (3R, 5S)-3-allyl-1-(4-methoxybenzyl)-5-[(trityloxy)-methyl]-2-pyrrolidinone
Melting point: 130°–132° C. $R_f$ value: 0.38 (silica gel; cyclohexane/ethyl acetate=8:2) Calculated: 81.21 H 6.81 N 2.71 Found: 81.16 6.85 2.53
(4) (3S,5R)-3-allyl-1-(3-phenylpropyl)-5-[(trityloxy)methyl]-2-pyrrolidinone
$R_f$ value: 0.60 (silica gel; cyclohexane/ethyl acetate=2:1)
(5) (3R,S;5S,R)-3-allyl-5-(4-methoxyphenyl)-1-(3-phenylpropyl)-2-pyrrolidinone
$R_f$ value: 0.23 (silica gel; cyclohexane/ethyl acetate=2:1)
Calculated: 79.05 H 7.79 N 4.01 Found: 78.82 7.60 4.18
(6) (3R,5S)-3-allyl-1-(4-phenylbutyl)-5-[(trityloxy)-methyl]-2-pyrrolidinone
$R_f$ value: 0.53 (silica gel; toluene/acetone=4:1)
(7) (3R,5S)-3-allyl-1-[2-(2-naphthyl)ethyl]-5-[(trityloxy)methyl]-2 -pyrrolidinone
$R_f$ value: 0.65 (silica gel; toluene/acetone=4:1)
(8) (3R,5S)-3-allyl-1-[2-(1-naphthyl)ethyl]-5-[(trityloxy)methyl]-2 -pyrrolidinone
$R_f$ value: 0.70 (silica gel; toluene/acetone=4:1)
(9) (3R,5S)-3-allyl-1-isobutyl-5-[(trityloxy)methyl]-2-pyrrolidinone
Melting point: 75°–77° C. $R_f$ value: 0.25 (silica gel; petroleum ether/tert.-butylmethylether =2:1)
(10) (6R,8S)-6-allyl-3-cyclohexyl-perhydropyrrolo-[1,2-c]-oxazol-5-one
$R_f$ value: 0.43 (silica gel; cyclohexane/ethyl acetate=2:1)
By-product: (8S)-3-cyclohexyl-6,6-diallylperhydropyrrolo [1,2-c]oxazol-5-one
$R_f$ value: 0.52 (silica gel; cyclohexane/ethyl acetate=4:1)
(11) (6R,8S)-6-allyl-3-tert.butyl-perhydropyrrolo-[1,2-c]oxazol-5-one
$R_f$ value: 0.29 (silica gel; cyclohexane/ethyl acetate=4:1)
(12) (3R,5S)-3-allyl-3-methyl-1-(3-phenylpropyl)-5-[(trityloxy)methyl]-2 -pyrrolidinone
$R_f$ value: 0.63 (silica gel; cyclohexane/ethyl acetate=2:1)
(13) (3R,5S)-3-methyl-1-(3-phenylpropyl)-5-[(trityloxy)-methyl]-2-pyrrolidinone
Alkylating agent: methyl iodide. $R_f$ value: 0.59 (silica gel; cyclohexane/ethyl acetate=2:1)
(14) (3R,5S)-3-allyl-1-benzyl-5-[(trityloxy)methyl]2-pyrrolidinone
Melting point: 113°–116° C.
(15) (3R,5S)-3-allyl-1-(2-phenylethyl)-5-[(trityloxy)-methyl]-2-pyrrolidinone
$R_f$ value: 0.47 (silica gel; toluene/acetone=8:1)
(16) (3R,5S)-3-allyl-1-(4-phenylbutyl)-5-[(trityloxy)-methyl]-2-pyrrolidinone
$R_f$ value: 0.53 (silica gel; toluene/acetone=4:1)
(17) (3R,5S)-]-allyl-1-(4-phenyloxybutyl)-5-[(trityloxy)methyl]-2-pyrrolidinone
$R_f$ value: 0.38 (silica gel; toluene/acetone=8:1)
(18) (3R,5S)-3-allyl-1,3-bis-(3-phenylpropyl)-5-[(trityloxy)-methyl]-2-pyrrolidinone
$R_f$ value: 0.66 (silica gel; cyclohexane/ethyl acetate=2:1)
(19) (3R,5S)-1,3-bis-(3-phenylpropyl)-5-[(trityloxy)-methyl]-2-pyrrolidinone
Alkylating agent: 3-phenylpropylbromide $R_f$ value: 0.66 (silica gel; cyclohexane/ethyl acetate=2:1)
(20) (3R, 5S)-3-allyl-3-(n-butyl)-1-(3-phenylpropyl)-5-[(trityloxy)methyl]-2 -pyrrolidinone
$R_f$ value: 0.70 (silica gel; cyclohexane/ethyl acetate=2:1)
(21) (3R,5S)-3-(n-butyl)-1-(3-phenylpropyl)-5-[(trityloxy)methyl]-2-pyrrolidinone
Alkylating agent: n-butyl iodide $R_f$ value: 0.69 (silica gel; cyclohexane/ethyl acetate=2:1)
(22) (3R,5S)-3-allyl-1-[3-(4-benzyloxyphenyl)propyl]-5-[(trityloxy)methyl]-2 -pyrrolidinone
$R_f$ value: 0.63 (silica gel; toluene/acetone=4:1)
(23) (3R,S;5R,S)-3-allyl-3-methyl-1-(3-phenylpropyl)-5-[(trityloxy)methyl]-2 -pyrrolidinone
Alkylating agent: methyl iodide $R_f$ value: 0.72 (silica gel; methylene chloride/ethanol=5:1)
(24) (3R,S;5S,R)-3-allyl-1-(3-phenylpropyl)-5 -[(trityloxy)methyl]-2-pyrrolidinone
$R_f$ value: 0.36 (silica gel; cyclohexane/ethyl acetate=5:1)
(25) (3R,5S)-3-(1-buten-4-yl)-1-(3-phenylpropyl)-5 -[(trityloxy)methyl]-2-pyrrolidinone
$R_f$ value: 0.60 (silica gel; methylene chloride/methanol= 19:1)
(26) (3R,S;4R,S)-3-allyl-1-(3-phenylpropyl)-4 -[(trityloxy)methyl]-2-pyrrolidinone
$R_f$ value: 0.87 (silica gel; methylene chloride/methanol= 30:1)
(27) (6S,8S)-6-allyl-3-tert.butyl-perhydropyrrolo -[1,2-c] oxazol-5-one(chromatographically separated by-product of Example IV (11))

$R_f$ value: 0.48 (silica gel; cyclohexane/ethyl acetate=4:1)

(28) (6R,8S)-6-allyl-3-cyclohexyl-6-methylperhydropyrrolo-[1,2-c]oxazol-5-one $R_f$ value: 0.53 (silica gel; cyclohexane/ethyl acetate=7:3)
Calculated: C 72.96 H 9.57 N 5.32 Found: 73.10 9.74 5.50

(29) (6R,S;8S)-3-cyclohexyl-6-methyl-perhydropyrrolo-[1,2-c]oxazol-5-one $R_f$ value: 0.33 and 0.46 (silica gel; cyclohexane/ethyl acetate=7:3)

(30) (3R,5S)-3-allyl-1-[2-(benzyloxy)ethyl]-5-[(trityloxy)methyl]-2-pyrrolidinone $R_f$ value: 0.50 (silica gel; cyclohexane/ethyl acetate=7:3)
Calculated: C 81.30 H 7.00 N 2.60 Found: 81.15 7.20 2.49

(31) (6S,8R)-6-allyl-3-cyclohexyl-perhydropyrrolo-[1,2-c]oxazol-5-one $R_f$ value: 0.29 (silica gel; cyclohexane/ethyl acetate=4:1) Calculated: C 72.25 H 9.30 N 5.62 Found: 71.96 9.46 5.44

(32) (3S,5S)-1-(benzyloxycarbonyl)-3-[(tert.butyloxycarbonyl)methyl-]-5-[(trityloxy)methyl]-2-pyrrolidinone. Lithium hexamethyldisilazide was used as base and tert.-butylbromoacetate was used as alkylating agent.

$R_f$ value: 0.66 (silica gel; cyclohexane/ethyl acetate=2:1)
Calculated: C 75.35 H 6.49 N 2.31 Found: 75.17 6.65 2.50

(33) (3R,5S)-3-(3-cyanopropyl)-1-methyl-3-[(trityloxy)methyl-]-2-pyrrolidinone

Alkylating agent: 4-iosobutyric acid nitrile $R_f$ value: 0.66 (silica gel; ethyl acetate)

(34) (3R,5S)-3-(5-cyanopentyl)-1-isobutyl-5-[(trityloxy)methyl]-2-pyrrolidinone Alkylating agent: 6-iodocaproic acid nitrile $R_f$ value: 0.53 (silica gel; toluene/acetone=4:1)

(35) (3R,5S)-3-(3-cyanopropyl)-1-isobutyl-5-[(trityloxy)methyl]-2-pyrrolidinone Alkylating agent: 4-iodobutyric acid nitrile $R_f$ value: 0.50 (silica gel; toluene/acetone=4:1)

(36) (3R,5S)-3-(1-penten-5-yl)-1-(3-phenylpropyl)-5-[(trityloxy)methyl]-2-pyrrolidinone Alkylating agent: 5-bromo-1-pentene $R_f$ value: 0.29 (silica gel; ether/hexane=1:1)

(37) (3R,5S)-3-(5-cyanopentyl)-1-(3-phenylpropyl)-5-[(trityloxy)methyl]-2-pyrrolidinone Alkylating agent: 6-iodocaproic acid nitrile $R_f$ value: 0.55 (silica gel; ethyl acetate/cyclohexane=1:1)

(38) (3R,S;4R,S)-3-allyl-1-(4-methoxybenzyl)-4-[(trityloxy)-methyl]-2-pyrrolidinone $R_f$ value: 0.22 (silica gel; cyclohexane/ethyl acetate=4:1)

(39) (3S,5S)-1-(benzyloxycarbonyl)-3-[(methoxycarbonyl)methyl]-5-[(trityloxy)methyl]-2-pyrrolidinone. Use of lithium hexamethyl disilazide as base and methyl bromoacetate as alkylating agent.

$R_f$ value: 0.54 (silica gel; cyclohexane/ethyl acetate=2:1)
Calculated: C 74.58 H 5.90 N 2.49 Found: 74.61 6.09 2.43

(40) (3R,S;4R,S)-3-allyl-1-(4-methoxybenzyl)-3-methyl-4-[(trityloxy)methyl]-2-pyrrolidinone $R_f$ value: 0.41 (silica gel; cyclohexane/ethyl acetate=3:1)

(41) (3R,S;4R,S)-1-(4-methoxybenzyl)-3-methyl-4-[(trityloxy)methyl]-2-pyrrolidinone. Use of 1,3-dimethyl-3,4,5,6-tetrahydro-2(1H)-pyrimidone as co-solvent.

$R_f$ value: 0.36 (silica gel; cyclohexane/ethyl acetate=2:1)

Example V (3R,5S)-3-Allyl-5-hydroxymethyl-1-(3-phenylpropyl)-2-pyrrolidinone

A solution of 690 g of (3R,5S)-3-allyl-1-(3-phenylpropyl)-5-[(trityloxy)methyl]-2-pyrrolidinone in 2000 ml of methanol is mixed with 650 ml of 5N hydrochloric acid, then stirred for 3 hours at 40° C. and for 2 days at ambient temperature. The precipitate formed is redissolved by heating to 50° C. and stirred for a further 16 hours at ambient temperature. The precipitate formed is filtered off and the filtrate is concentrated until crystallisation begins (to about 1500 ml). After the precipitate has been filtered off the filtrate is evaporated down, the residue is taken up in methylene chloride, the organic phase is washed with water and evaporated down.

Yield: 365 g (100% of theory), $R_f$ value: 0.12 (silica gel; methylene chloride/methanol=30:1)

The following are obtained analogously:

(1) (3R,5S)-3-allyl-1-(3-cyclohexylpropyl)-5-hydroxymethyl-2-pyrrolidinone $R_f$ value: 0.20 (silica gel; cyclohexane/ethyl acetate=1:1)

(2) (3R,5S)-3-allyl-1-(4-methoxybenzyl)-5-hydroxymethyl-2-pyrrolidinone $R_f$ value: 0.33 (silica gel; cyclohexane/ethyl acetate=1:2)

(3) (3S,5R)-3-allyl-5-hydroxymethyl-1-(3-phenylpropyl)-2-pyrrolidinone $R_f$ value: 0.43 (silica gel; methylene chloride/methanol 15:1) Calculated: C 74.69 H 8.48 N 5.12 Found: 74.85 8.56 5.00

(4) (3R,5S)-3-allyl-5-hydroxymethyl-1-(4-phenylbutyl)-2-pyrrolidinone $R_f$ value: 0.18 (silica gel; toluene/acetone=4:1)

(5) (3R, 5S)-3-allyl-5-hydroxymethyl-1-[2-(2-naphthyl)-ethyl]-2-pyrrolidinone $R_f$ value: 0.20 (silica gel; toluene/acetone=2:1)

(6) (3R,5S)-3-allyl-5-hydroxymethyl-1-[2-(1-naphthyl)ethyl]-2-pyrrolidinone $R_f$ value: 0.28 (silica gel; toluene/acetone=2:1)

(7) (3R,5S)-3-allyl-5-hydroxymethyl-1-isobutyl-2-pyrrolidinone $R_f$ value: 0.26 (silica gel; ethyl acetate)

(8) (3R, 5S)-3-allyl-5-hydroxymethyl-3-methyl-1-(3-phenylpropyl)-2-pyrrolidinone $R_f$ value: 0.16 (silica gel; cyclohexane/ethyl acetate=2:1)

(9) (3R, 5S)-3-allyl-1-benzyl-5-hydroxymethyl-2-pyrrolidinone $R_f$ value: 0.63 (silica gel; methylene chloride/methanol=10:1)

(10) (3R,5S)-3-allyl-5-hydroxymethyl-1-(2-phenylethyl)-2-pyrrolidinone $R_f$ value: 0.49 (silica gel; methylene chloride/methanol=10:1)

(11) (3R,5S)-3-allyl-5-hydroxymethyl-1-(4-phenylbutyl)-2-pyrrolidinone $R_f$ value: 0.28 (silica gel; toluene/acetone=4:1)

(12) (3R,5S)-3-allyl-5-hydroxymethyl-1-(4-phenyloxybutyl)-2-pyrrolidinone $R_f$ value: 0.36 (silica gel; methylene chloride/methanol=10:1)

(13) (3R,5S)-3-allyl-5-hydroxymethyl-1,3-bis(3-phenylpropyl)-2-pyrrolidinone $R_f$ value: 0.28 (silica gel; cyclohexane/ethyl acetate=2:1)

(14) (3R,5S)-3-allyl-3-(n-butyl)-5-hydroxymethyl-1-(3-phenylpropyl)-2-pyrrolidinone $R_f$ value: 0.25 (silica gel; cyclohexane/ethyl acetate=2:1)

(15) (3R,5S)-3-allyl-1-[3-(4-benzyloxyphenyl)propyl]-5-hydroxymethyl-2-pyrrolidinone $R_f$ value: 0.13 (silica gel; toluene/acetone=4:1)

(16) (3R,S;5R,S)-3-allyl-5-hydroxymethyl-3-methyl-1-(3-phenylpropyl)-2-pyrrolidinone $R_f$ value: 0.39 (silica gel; methylene chloride/ethanol=15:1)

(17) (3R,5S)-3-(1-buten-4-yl)-5-hydroxymethyl-1-(3-phenylpropyl)-2-pyrrolidinone $R_f$ value: 0.70 (silica gel; methylene chloride/methanol= 9:1)

(18) (3R,S;4R,S) -3-allyl-4-hydroxymethyl-1-(3phenylpropyl) -2-pyrrolidinone $R_f$ value: 0.47 (silica gel; methylene chloride/methanol= 9:1)

(19) (3R,5S)-3-allyl-1-[2-(benzyloxy)ethyl]-5 -hydroxymethyl-2-pyrrolidinone $R_f$ value: 0.47 (silica gel; ethyl acetate) Calc. x 0.5 H$_2$O: C 68.43 H 8.11 N 4.69 Found: 68.59 8.14 4.41

(20) (3R,S;4R,S)-3-allyl-4-hydroxymethyl-1-(4 -methoxybenzyl)-2-pyrrolidinone $R_f$ value: 0.31 (silica gel; cyclohexane/ethyl acetate=1:2) Calculated: C 69.80 H 7.69 N 5.09 Found: 69.84 7.84 4.96

(21) (3R,S;4R,S)-3-allyl-4-hydroxymethyl-1-(4 -methoxybenzyl)-3-methyl-2-pyrrolidinone $R_f$ value: 0.44 (silica gel; cyclohexane/ethyl acetate=1:2) Calculated: C 70.56 H 8.01 N 4.84 Found: 70.40 8.07 4.82

(22) (3R,5S)-3-(3-cyanopropyl)-5-hydroxymethyl-1-methyl -2-pyrrolidinone $R_f$ value: 0.33 (silica gel; ethyl acetate/methanol=9:1)

(23) (3R,5S)-3-(3-cyanopropyl)-5-hydroxymethyl-1 -isobutyl-2-pyrrolidinone

Melting point: 46°–48° C., $R_f$ value: 0.45 (silica gel; ethyl acetate/methanol=9:1)

Example VI (3R,5S)-3-Allyl-5-[(methanesulphonyloxy)methyl]- 1-(3-phenylpropyl)-2-pyrrolidinone A solution of 54.7 g of (3R,5S)-3-allyl-5 -hydroxymethyl-1-(3-phenylpropyl)-2-pyrrolidinone in 500 ml of methylene chloride is cooled to −10° C. and first 16 ml of methanesulphonyl chloride and then a solution of 29.4 ml of triethylamine in 50 ml of methylene chloride are added thereto with stirring, whilst the temperature is maintained at −10° C. The mixture is allowed to heat up to ambient temperature and react for a further hour. The resulting solution is washed successively with water, 0.5N aqueous ammonia and water and evaporated down.

Yield: 70 g (100% of theory), $R_f$ value: 0.61 (silica gel; methylene chloride/methanol= 0:1) (after developing twice)

The following are obtained analogously:

(1) (3S,5S)-5-[(methanesulphonyloxy)methyl]-3 -[(methoxycarbonyl)methyl]-1-phenyl-2-pyrrolidinone $R_f$ value: 0.63 (silica gel; chloroform/methanol=95:5)

(2) (3R,5S)-3-allyl-1-(3-cyclohexylpropyl)-5 -[(methanesulphonyloxy)methyl]-2-pyrrolidinone $R_f$ value: 0.26 (silica gel; cyclohexane/ethyl acetate=6:4) Calculated: C 60.47 H 8.74 N 3.92 S 8.97 Found: 60.30 8.79 3.79 8.92

(3) (3R,5S)-3-allyl-1-(4-methoxybenzyl)-5 -[(methanesulphonyloxy)methyl]-2-pyrrolidinone $R_f$ value: 0.38 (silica gel; cyclohexane/ethyl acetate=1:1) Calculated: C 57.77 H 6.56 N 3.96 S 9.07 Found: 57.89 6.76 3.75 8.93

(4) (3S,5R)-3-allyl-5-[(4-methanesulphonyloxy)methyl]-1 -(3-phenylpropyl)-2-pyrrolidinone $R_f$ value: 0.63 (silica gel; cyclohexane/ethyl acetate=1:2) Calculated: C 61.51 H 7.17 N 3.99 S 9.12 Found: 61.30 7.37 3.70 8.88

(5) (3R,5S)-3-allyl-5-[(methanesulphonyloxy)methyl]-1-(4-phenylbutyl)-2-pyrrolidinone $R_f$ value: 0.38 (silica gel; toluene/acetone=4:1)

(6) (3R,5S)-3-allyl-5-[(methanesulphonyloxy)methyl]-1-[2-(2-naphthyl)ethyl]-2-pyrrolidinone $R_f$ value: 0.79 (silica gel; ethyl acetate)

(7) (3R,5S)-3-allyl-5-[(methanesulphonyloxy)methyl]-1-[2-(1-naphthyl)ethyl]-2-pyrrolidinone $R_f$ value: 0.86 (silica gel; ethyl acetate)

(8) (3R,5S)-3-allyl-1-isobutyl-5-[(methanesulphonyloxy)methyl]-2-pyrrolidinone $R_f$ value: 0.69 (silica gel; ethyl acetate)

(9) (3R,5S)-3-allyl-5-[(methanesulphonyloxy)methyl]-2-pyrrolidinone

Melting point: 62°–63° C. $R_f$ value: 0.40 (silica gel; ethyl acetate)

(10) (3R,5S)-3-allyl-5-[(methanesulphonyloxy)methyl]-3 -methyl-1-(3-phenylpropyl)-2-pyrrolidinone $R_f$ value: 0.50 (silica gel; methylene chloride/methanol= 15:1)

(11) (3R,5S)-3-allyl-1-benzyl-5-[(methanesulphonyloxy)methyl]-2-pyrrolidinone $R_f$ value: 0.75 (silica gel; ethyl acetate)

(12) (3R,5S)-3-allyl-5-[(methanesulphonyloxy)methyl]-1-(2-phenylethyl)-2-pyrrolidinone $R_f$ value: 0.73 (silica gel; ethyl acetate)

(13) (3R,5S)-3-allyl-5-[(methanesulphonyloxy)methyl]-1-(4-phenylbutyl)-2-pyrrolidinone $R_f$ value: 0.38 (silica gel; toluene/acetone=4:1)

(14) (3R,5S)-3-allyl-5-[(methanesulphonyloxy)methyl]-1 -(4-phenyloxybutyl)-2-pyrrolidinone $R_f$ value: 0.64 (silica gel; ethyl acetate)

(15) (3R,5S)-3-allyl-5-[(methanesulphonyloxy)methyl]-1,3-bis-(3-phenylpropyl)-2-pyrrolidinone $R_f$ value: 0.53 (silica gel; methylene chloride/methanol= 40:1)

(16) (3R,5S)-3-allyl-3-(n-butyl)-5-[(methanesulphonyloxy -oxy)-methyl]-1-(3-phenylpropyl)-2-pyrrolidinone $R_f$ value: 0.53 (silica gel; methylene chloride/methanol= 40:1)

(17) (3R,5S)-3-allyl-1-[3-(4-benzyloxyphenyl)propyl]-5 -[(methanesulphonyloxy)methyl]-2-pyrrolidinone $R_f$ value: 0.47 (silica gel; toluene/acetone=2:1)

(18) (3S,5S)-5-[(methanesulphonyloxy)methyl]-3 -[(methoxycarbonyl)methyl]-1-(3-phenylpropyl)-2-pyrrolidinone $R_f$ value: 0.36 (silica gel; methylene chloride/ethanol 15:1)

(19) (3R,S;5R,S)-3-allyl-5-[(methanesulphonyloxy)-methyl]-3-methyl-1-(3-phenylpropyl)-2-pyrrolidinone. Pyridine is used as the base.

$R_f$ value: 0.58 (silica gel; methylene chloride/ethanol 15:1)

(20) 1-benzyloxy-3-[3-(methanesulphonyloxy)propyl]-benzene. Carried out in pyridine.

$R_f$ value: 0.92 (silica gel; methylene chloride)

(21) 1-benzyloxy-4-[3-(methanesulphonyloxy)propyl]-benzene. Carried out in pyridine.

$R_f$ value: 0.75 (silica gel; methylene chloride)

(22) 4-[4-(methanesulphonyloxy)butyl]anisole. Tetrahydrofuran is used as solvent and pyridine as base.

$R_f$ value: 0.81 (silica gel; methylene chloride)

(23) (3R, 5S) -3-allyl-1-(tert.butyloxycarbonyl) -5 -[(methanesulphonyloxy)methyl]-pyrrolidine $R_f$ value: 0.65 (silica gel; cyclohexane/ethyl acetate=1:1)

(24) (3S,5S)-3-allyl-5-[(methanesulphonyloxy)methyl]-2-pyrrolidinone

Melting point: 74°–76° C., $R_f$ value: 0.32 (silica gel; ethyl acetate)

(25) (3R,5S)-3-allyl-5-[(methanesulphonyloxy)methyl]-3 -methyl-2-pyrrolidinone $R_f$ value: 0.46 (silica gel; ethyl acetate)
(26) (3R,5S)-3-allyl-1-[2-(benzyloxy)ethyl]-5-[(methanesulphonyloxy)methyl]-2-pyrrolidinone
$R_f$ value: 0.59 (silica gel; chloroform/methanol=95:5)
(27) (3S,5R)-3-allyl-5-[(methanesulphonyloxy)methyl]-2-pyrrolidinone
$R_f$ value: 0.38 (silica gel; ethyl acetate)
(28) (3S,5S)-3-[(tert.butyloxycarbonyl)methyl]-5-[(methanesulphonyloxy)methyl]-2-pyrrolidinone
Melting point: 114°–116° C. $R_f$ value: 0.47 (silica gel; toluene/acetone=1:3) Calculated: C 46.89 H 6.89 N 4.56 S 10.43 Found: 46.90 6.79 4.84 10.17
(29) (3R,5S)-3-(3-cyanopropyl)-5-[(methanesulphonyloxy)methyl]-1-methyl-2-pyrrolidinone
$R_f$ value: 0.29 (silica gel; ethyl acetate)
(30) (3R,5S)-3-(5-cyanopentyl)-1-isobutyl-5-[(methanesulphonyloxy)methyl]-2-pyrrolidinone
$R_f$ value: 0.72 (silica gel; ethyl acetate/methanol=9:1)
(31) (3R,5S)-3-(3-cyanopropyl)-1-isobutyl-5-[(methanesulphonyloxy)methyl]-2-pyrrolidinone
$R_f$ value: 0.63 (silica gel; ethyl acetate/methanol=9:1)
(32) (3S,5S)-5-[2-(methanesulphonyloxy)ethyl]-3-[(methoxycarbonyl)methyl]-1-(3-phenylpropyl)-2-pyrrolidinone
$R_f$ value: 0.68 (silica gel; methylene chloride/methanol= 19:1) (after developing twice)
(33) (3R,5S)-5-[(methanesulphonyloxy)methyl]-3-[3-(methoxycarbonyl) propyl]-1-(3-phenylpropyl)-2-pyrrolidinone
$R_f$ value: 0.36 (silica gel; methylene chloride/methanol= 19:1)
(34) (3R,5S)-5-[(methanesulphonyloxy)methyl]-3-[5(methoxycarbonyl)pentyl]-1-(3-phenylpropyl)-2pyrrolidinone
$R_f$ value: 0.38 (silica gel; methylene chloride/methanol= 19:1)
(35) (S)-3,3-diallyl-5-[(methanesulphonyloxy)methyl]-2-pyrrolidinone
$R_f$ value: 0.56 (silica gel; ethyl acetate)
(36) (3R,S;4R,S)-3-allyl-4-[(methanesulphonyloxy)-methyl]-1-(4-methoxybenzyl)-2-pyrrolidinone
$R_f$ value: 0.38 (silica gel; cyclohexane/ethyl acetate=1:2) Calculated: C 57.77 H 5.56 N 3.96 S 9.07 Found: 57.60 6.40 4.02 9.31
(37) (3S,5S)-5-[(methanesulphonyloxy)methyl]-3-[(methoxycarbonyl)methyl]-2-pyrrolidinone
Melting point: 85°–87° C. $R_f$ value: 0.42 (silica gel; acetone/petroleum ether=4:1) Calculated: C 40.75 H 5.70 N 5.28 S 12.09 Found: 40.63 5.50 5.45 12.01
(38) (3R,S;4R,S)-3-allyl-4-[(methanesulphonyloxy)-methyl]-1-(4-methoxybenzyl)-3-methyl-2-pyrrolidinone
$R_f$ value: 0.53 (silica gel; cyclohexane/ethyl acetate=1:2) Calculated: C 58.83 H 6.86 N 3.81 S 8.73 Found: 58.52 6.70 3.71 8.70
(39) 1-(4'-cyano-4-biphenylyl)-4-[(methanesulphonyloxy)methyl]-2-pyrrolidinone
Melting point: 183°–186° C. $R_f$ value: 0.47 (silica gel; ethyl acetate) Calculated: C 61.61 H 4.90 N 7.56 S 8.65 Found: 61.43 4.90 7.47 8.62

Example VII (3R,5S)-3-Allyl-5-[(4-nitrophenyl)oxymethyl]-1-(3-phenylpropyl)-2-pyrrolidinone Prepared analogously to Example 2 from (3R,5S)-3-allyl-5-[(methanesulphonyloxy)methyl]-1-(3-phenylpropyl)-2-pyrrolidinone and 4-nitrophenol.

$R_f$ value: 0.50 (silica gel; cyclohexane/ethyl acetate=2:1) Calculated: C 70.03 H 6.64 N 7.10 Found: 69.88 6.72 7.04

Example VIII (3S,5S)-5-[(4'-Aminocarbonyl-3'-chloro-4-biphenylyl)-oxymethyl]-3-[(methoxycarbonyl)methyl]-1-(3-phenylpropyl)-2-pyrrolidinone Prepared analogously to Example 3 from (3S,5S)-5-[(methanesulphonyloxy)methyl]-3-[(methoxycarbonyl)-methyl]-1-(3-phenylpropyl)-2-pyrrolidinone and 4'-aminocarbonyl-3'-chloro-4-hydroxybiphenyl.

$R_f$ value: 0.40 (silica gel; ethyl acetate) Calculated: C 67.34 H 5.84 N 5.24 Cl 6.63 Found: 67.25 5.92 5.23 6.52

The following is obtained analogously:
(1) (3R,5S)-3-[4-(tert.butyloxycarbonylamino)butyl]-5-[(3-formyl-4-biphenylyl)oxymethyl]-1-methyl-2-pyrrolidinone
$R_f$ value: 0.41 (silica gel; ethyl acetate)

Example IX (3S,5S)-3-[(Methoxycarbonyl)methyl]-5-[(4-nitrophenyl)oxymethyl]-1-(3-phenylpropyl)-2-pyrrolidinone Prepared analogously to Example 5 by oxidation of (3R,5S)-3-allyl-5-[(4-nitrophenyl)oxymethyl]-1-(3-phenylpropyl)-2-pyrrolidinone and subsequent esterification with methanol.

$R_f$ value: 0.40 (silica gel; cyclohexane/ethyl acetate=1:1) Calculated: C 64.78 H 6.15 N 6.57 Found: 64.95 6.31 6.51

Intermediate product:
(3S,5S)-3-carboxymethyl-5-[(4-nitrophenyl)oxymethyl]-1-(3-phenylpropyl)-2-pyrrolidinone
$R_f$ value: 0.90 (silica gel; methylene chloride/methanol= 10:1) Calculated: C 64.07 H 5.87 N 6.79 Found: 63.88 5.91 6.63

Example X (S)-1-Phenyl-5-[(trityloxy)methyl]-2-pyrrolidinone

A 500 ml two-necked flask is fitted with a magnetic stirrer, a Soxhlet fitting containing an extraction sleeve with 10 g of potassium carbonate and 20 g of silica gel, and a reflux condenser. In this apparatus, 17 g of (S)-5-[(trityloxy)methyl]-2-pyrrolidinone, 24.3 g of iodobenzene, 1.3 g of copper powder and 11.8 g of potassium acetate are refluxed with 120 ml of dimethylformamide for 7 hours. The mixture is cooled, the extraction sleeve is changed and refluxing is continued for a further one and a half hours. After this time the dimethylformamide is rotary-evaporated off in a water jet vacuum and the residue is mixed with 400 ml of ethyl acetate and 400 ml of water and stirred for 30 minutes. It is then suction filtered and the filter residue is washed with ethyl acetate and methanol. The organic phase of the filtrate is separated off and washed with water and saturated common salt solution, then dried and evaporated down. The dark, oily residue is chromatographed over silica gel with cyclohexane/ethyl acetate (1:1). The product fractions are evaporated down, the residue is stirred with diisopropylether and suction filtered. After drying, 10.5 g (51% of theory) of crystalline product remains.

Melting point: 144°–146° C. $R_f$ value: 0.24 (silica gel; cyclohexane/ethyl acetate=1:1) Calculated: C 83.11 H 6.28 N 3.23 Found: 83.06 6.46 3.28

Example XI (3S,5S)-3-Carboxymethyl-1-phenyl-5-[(trityloxy)methyl]-2-pyrrolidinone 8 g of (3R,5S)-3-allyl-1-phenyl-5-[(trityloxy)methyl]-2-pyrrolidinone are dissolved in 40 ml of methylene chloride and 40 ml of acetonitrile and the solution is cooled to 5° C. After the addition of 0.45 g of ruthenium(III)chloride-trihydrate, 19.8 g of sodium metaperiodate in 160 ml of water are added in such a way that the temperature remains below 10° C. After 2 hours, 20 g of kieselguhr are stirred in and the mixture is suction filtered. The filter residue is washed out with water and methylene chloride and the phases of the filtrate are separated. The aqueous phase is extracted twice with methylene chloride, the combined organic phases are washed with water, dried and evaporated down. 11.7 g of crude product remain as a dark, viscous resin.

$R_f$ value: 0.60 (silica gel; ethyl acetate) $R_f$ value; 0.62 (silica gel; toluene/dioxane/ethanol/ethyl acetate= 90:10:10:6)

The following are obtained analogously:

(1) (3S,5S)-3-carboxymethyl-1-(3-phenylpropyl)-5-(N -phthalimidomethyl)-2-pyrrolidinone $R_f$ value: 0.51 (silica gel; methylene chloride/methanol= 8:1)

(2) (3S,5S)-3-carboxymethyl-1-(3-phenylpropyl)-5 -[(trityloxy)methyl]-2-pyrrolidinone $R_f$ value: 0.32 (silica gel; methylene chloride/cyclohexane/methanol/conc. aqueous ammonia=68:15:15:2)

(3) (3S,5S)-3-carboxymethyl-1-(3-phenylpropyl)-5-[[[2 -(N-phthalimidomethyl)-5-indanyl]sulphonylamino]methyl]-2-pyrrolidinone $R_f$ value: 0.15 (silica gel; methylene chloride/cyclohexane/methanol/conc. aqueous ammonia=68:15:15:2)

(4) (3S,5S)-3-carboxymethyl-1-(3-phenylpropyl)-5-[[[2 -(N-phthalimido)-5-indanyl]sulphonylamino]methyl]-2-pyrrolidinone $R_f$ value: 0.25 (silica gel; methylene chloride/cyclohexane/methanol/conc. aqueous ammonia=68:15:15:2)

(5) (3R,S;4R,S)-3-carboxymethyl-1-(3-phenylpropyl)-4-(N -phthalimidomethyl)-2-pyrrolidinone $R_f$ value: 0.48 (silica gel; methylene chloride/methanol= 9:1)

(6) (3R,5S)-3-(3-carboxypropyl)-1-(3-phenylpropyl)-5 -[(trityloxy)methyl]-2-pyrrolidinone $R_f$ value: 0.33 (silica gel; methylene chloride/methanol= 19:1)

(7) (3S,5S)-5-aminocarbonylmethyl-3-carboxymethyl-1-(3 -phenylpropyl)-2-pyrrolidinone $R_f$ value: 0.18 (silica gel; methylene chloride/methanol/ conc. aqueous ammonia=4:1:0.25)

(8) (3S, 5S) -3-carboxymethyl-5-cyanomethyl-1- (3-phenylpropyl) -2-pyrrolidinone $R_f$ value: 0.30 (silica gel; methylene chloride/methanol 19:1)

Example XII (3S,5S)-5-Hydroxymethyl-3-[(methoxycarbonyl)methyl]-1-phenyl-2-pyrrolidinone 11.7 g (3S,5S)-3-carboxymethyl-1-phenyl-5-[(trityloxy)methyl]-2-pyrrolidinone are mixed with 50 ml of methanol. Hydrogen chloride is introduced for 5 minutes, with stirring, whereupon a dark solution is formed. After a further 30 minutes stirring, the solution is concentrated by evaporation and the resin remaining is extracted three times with ethyl acetate under heating. The ethyl acetate filtrates are evaporated down and the residue is chromatographed with cyclohexane/ethyl acetate (1:1), cyclohexane/ethyl acetate (4:6) and ethyl acetate over silica gel. 1.2 g (25% of theory) of an oil are obtained which slowly crystallises out.

$R_f$ value: 0.16 (silica gel; cyclohexane/ethyl acetate=1:1) Calculated: C 63.86 H 6.51 N 5.32 Found: 63.60 6.56 5.06

The following are obtained analogously:

(1) (3S,5S)-5-hydroxymethyl-3-[(methoxycarbonyl)methyl] -1-(3-phenylpropyl)-2-pyrrolidinone $R_f$ value: 0.27 (silica gel; methylene chloride/ethanol= 15:1) Reaction in methanolic hydrochloric acid/conc. aqueous hydrochloric acid (2) (3R, 5S) -5-hydroxymethyl-3- [3- (methoxycarbonyl)-propyl]-1-(3-phenylpropyl)-2-pyrrolidinone $R_f$ value: 0.45 (silica gel; methylene chloride/methanol= 9:1)

Example XIII (3R,5S)-3-Allyl-1-(3-phenylpropyl)-5-(N-phthalimidomethyl)-2-pyrrolidinone 34 g of diethyl azodicarboxylate are slowly added dropwise, whilst cooling with ice, to 28.7 g of phthalimide, 50 g of (3R,5S)-3-allyl-5-hydroxymethyl-1 -(3-phenylpropyl)-2-pyrrolidinone and 51.15 g of triphenylphosphine in 900 ml of dry tetrahydrofuran. The mixture is then stirred for 18 hours at ambient temperature. The solution is evaporated down and the residue is taken up in a little toluene. The undissolved material is suction filtered, washed with toluene and the filtrate is evaporated down. The residue obtained is purified by chromatography over silica gel with toluene/acetone (4:1). 76 g (100% of theory) of the product are obtained, to which some toluene is still adhering.

$R_f$ value: 0.57 (silica gel; toluene/acetone=4:1)

The following are obtained analogously:

(1) (3R,5S)-3-allyl-1-(4-phenoxybutyl)-5 -(N-phthalimidomethyl)-2-pyrrolidinone $R_f$ value: 0.56 (silica gel; toluene/acetone=4:1)

(2) (3R,5S)-3-allyl-1-(2-phenylethyl)-5 -(N-phthalimidomethyl)-2-pyrrolidinone $R_f$ value: 0.87 (silica gel; methylene chloride/methanol 10:1)

(3) (3R,5S)-3-allyl-1-benzyl-5-(N-phthalimidomethyl)-2-pyrrolidinone $R_f$ value: 0.69 (silica gel; toluene/acetone=2:1)

(4) (3R,5S)-3-allyl-1-[2-(1-naphthyl)ethyl]-5 -(N-phthalimidomethyl)-2-pyrrolidinone $R_f$ value: 0.60 (silica gel; toluene/acetone=2:1)

(5) (3R,5S)-3-allyl-1-[2-(2-naphthyl)ethyl]-5 -(N-phthalimidomethyl)-2-pyrrolidinone $R_f$ value: 0.63 (silica gel; toluene/acetone=2:1)

(6) (3R,5S)-3-allyl-1-isobutyl-5-(N-phthalimidomethyl)-2-pyrrolidinone

Melting point: 75°–87° C. $R_f$ value: 0.78 (silica gel; tert.butyl-methylether)

(7) (3R,5S)-3-(1-buten-4-yl)-1-(3-phenylpropyl)-5 -(N-phthalimidomethyl)-2-pyrrolidinone $R_f$ value: 0. 70 (silica gel; methylene chloride/methanol= 9:1)

(8) (3R,S;4R,S) -3-allyl-1-(3-phenylpropyl)-4 -(N-phthalimidomethyl)-2-pyrrolidinone R$_f$ value: 0. 45 (silica gel; methylene chloride/methanol= 30:1)

(9) (3R,S;4R,S)-3-allyl-1-(4-methoxybenzyl)-4 -(N-phthalimidomethyl)-2-pyrrolidinone R$_f$ value: 0.63 (silica gel; cyclohexane/ethyl acetate=1:2)

Example XIV (3S,5S)-3-[(Methoxycarbonyl)methyl]-5-[[(3'-nitro-3biphenylyl)carbonyl]aminomethyl]-1-(3-phenylpropyl)-2-pyrrolidinone Prepared analogously to Example 16 from 3'-nitrobiphenyl-3-carboxylic acid, (3S,5S)-5-aminomethyl -3-[(methoxycarbonyl)methyl]-1-(3-phenylpropyl)-2 -pyrrolidinone-hydrochloride and triethylamine.

R$_f$ value: 0.47 (silica gel; methylene chloride/ethyl acetate=1:1) Calculated: C 68.04 H 5.90 N 7.93 Found: 67.84 6.00 7.66

Example XV (3R, S;5S,R)-3-Allyl-5-(4-hydroxyphenyl)-1-(3-phenylpropyl)-2-pyrrolidinone 62.6 g of boron tribromide are added dropwise, with vigorous stirring, to a solution of 39 g of (3R,S;5S,R) -3-allyl-5-(4-methoxyphenyl)-1-(3-phenylpropyl)-2-pyrrolidinone in 1 liter of dry 1,2-dichloroethane, cooled to −50° C. After 2 hours at −50° C. the mixture is allowed to come up to ambient temperature and stirred for a further 3 hours. The clear solution is added in batches to 1 liter of 50% aqueous ethanol and the mixture is concentrated by evaporation in vacuo down to about 600 ml. The concentrate is poured onto 1.5 kg of ice and the mixture is left to stand overnight. The precipitate formed is suction filtered, taken up in ethylene chloride and the solution is dried with magnesium sulphate, filtered and concentrated by evaporation. The oil remaining hardens when left to stand overnight. The crystal cake is digested with diethylether, suction filtered and dried.

Yield: 35.6 g (95% of theory), Melting point: 108°–111° C. R$_f$ value: 0.18 (silica gel; cyclohexane/ethyl acetate=2:1) Calculated: C 78.77 H 7.52 N 4.18 Found: 78.55 7.31 4.32

The following are obtained analogously:

(1) 4'-cyano-3-fluoro-4-hydroxybiphenyl×0.2 water
 Melting point: 203°–204° C. R$_f$ value: 0.50 (silica gel; methylene chloride) Calculated: C 72.02 H 3.90 N 6.57 Found: 72.19 3.91 6.39

(2) 4'-cyano-4-hydroxy-3-trifluoromethylbiphenyl
 Melting point: 201°–203° C. R$_f$ value: 0.67 (silica gel; methylene chloride/ethyl acetate=9:1)

(3) 4'-aminocarbonyl-3'-chloro-4-hydroxybiphenyl
 Melting point: 215°–216° C. R$_f$ value: 0.67 (silica gel; methylene chloride/methanol=9:1)

(4) 4'-cyano-4-hydroxy-2'-methylbiphenyl
 R$_f$ value: 0.12 (silica gel; methylene chloride/petroleum ether=1:1)

(5) 4'-cyano-2,3-dimethyl-4-hydroxybiphenyl
 Melting point: 174°–176° C. R$_f$ value: 0.72 (silica gel; methylene chloride)

(6) 6-cyano-2-hydroxynaphthalene
 Melting point: 160°–164° C. R$_f$ value: 0.40 (silica gel; cyclohexane/ethyl acetate=2:1)

(7) 4-(4-hydroxyphenyl)butyronitrile
 Melting point: 52°–54° C.

(8) 2-cyano-7-hydroxy-fluorenone
 Melting point: 275°–277° C.

(9) 4-(4-cyanobenzoylamino)phenol
 Melting point: 190°–192° C. Calculated: C 70.58 H 4.53 N 11.76 Found: 70.73 4.38 11.50

(10) 4-(4-hydroxybenzoylamino)benzonitrile
 Melting point: 228°–231° C.

(11) 4-[(4-hydroxyphenyl)sulphonylamino]benzonitrile
 Melting point: 230°–233° C. Calculated: C 56.88 H 3.67 N 10.21 S 11.69 Found: 56.88 3.75 10.03 11.87

(12) 3-cyano-4'-hydroxy-diphenylsulphide
 Melting point: 120°–124° C.

(13) 3-cyano-4'-hydroxy-benzophenone
 Melting point: 165°–168° C. Calculated: C 75.33 H 4.06 N 6.28 Found: 75.25 4.04 6.42

(14) 4'-cyano-4-hydroxy-3-methylsulphenyl-biphenyl
 R$_f$ value: 0.39 (silica gel; cyclohexane/ethyl acetate=2:1)

(15) 2-cyano-7-hydroxy-9,10-dihydrophenanthrene
 R$_f$ value: 0.42 (aluminium oxide; methylene chloride/methanol=30:1)

(16) 4'-cyano-3'-fluoro-4-hydroxybiphenyl
 Melting point: 200°–202° C. R$_f$ value: 0.45 (silica gel; cyclohexane/ethyl acetate=7:3) Calculated: C 73.23 H 3.78 N 6.57 Found: 72.97 3.83 6.54

Example XVI (8S)-3-Cyclohexyl-perhydro-pyrrolo[1,2-c]oxazol-5-one 150 g of (S)-5-hydroxymethyl-2-pyrrolidinone and 209 ml of cyclohexanealdehyde are boiled, with stirring, with 5 g of p-toluenesulphonic acid and 1.5 liters of toluene for 3 hours using a water separator. After cooling, a viscous residue is decanted off, the toluene solution is washed with saturated sodium hydrogen sulphite solution, water and saturated bicarbonate solution, then dried with sodium sulphate and concentrated by evaporation. After vacuum distillation, 197 g (71% of theory) are obtained.

Boiling point: 105°–111° C. (0.05 mbar) Melting point: 42°–43° C. R$_f$ value: 0.30 (silica gel; cyclohexane/ethyl acetate=15:1)

The following are obtained analogously:

(1) (8S)-3-tert.butyl-perhydro-pyrrolo[1,2-c]oxazol-5-one
 Boiling point: 90°–94° C. (0.2 mbar) R$_f$ value: 0.40 (silica gel; cyclohexane/ethyl acetate=1:1) Calculated: C 65.54 H 9.35 N 7.64 Found: 65.36 9.64 7.64

(2) (8R)-3-cyclohexyl-perhydro-pyrrolo[1,2-c]oxazol-5-one
 R$_f$ value: 0.42 (silica gel; cyclohexane/ethyl acetate=1:1) Calculated: C 68.87 H 9.15 N 6.69 Found: 68.73 9.30 6.55

Example XVII (3R,5S)-3-Allyl-5-hydroxymethyl-2-pyrrolidinone 800 ml of semi-concentrated hydrochloric acid are added to 94.7 g of (6R,8S)-6-allyl-3-cyclohexyl -perhydro-pyrrolo[1,2-c]oxazol-5-one in 900 ml of acetone and the mixture is stirred for 18 hours at ambient temperature. The acetone is then drawn off, the aqueous phase is washed with ethyl acetate, the ethyl acetate phase is extracted with water and the combined aqueous phases are evaporated to dryness. The residue is taken up in 750 ml of methylene chloride, then neutralised with potassium hydrogen carbonate and a little water. Then the salts are removed by suction filtering, the organic phase is dried with sodium sulphate, filtered over activated charcoal and evaporated down. 58.9 g (100% of theory) of an oil remain, which slowly crystallises out.

Melting point: 53°–55° C. $R_f$ value: 0.51 (silica gel; ethyl acetate/methanol=4:1)

The cleaving of (6R,8S)-6-allyl-3-tert.butylperhydropyrrolo[1,2-c]oxazol-5-one with semiconcentrated hydrochloric acid and a little dioxane proceeds in a similar way and yields the same product.

The following are obtained analogously:
(1) (3S,5S)-3-allyl-5-hydroxymethyl-2-pyrrolidinone
  $R_f$ value: 0.15 (silica gel; ethyl acetate)
(2) (3R,5S)-3-allyl-5-hydroxymethyl-3-methyl-2-pyrrolidinone
  $R_f$ value: 0.22 (silica gel; ethyl acetate)
(3) (3S,5R)-3-allyl-5-hydroxymethyl-2-pyrrolidinone
  $R_f$ value: 0.12 (silica gel; ethyl acetate)
(4) (S)-3,3-diallyl-5-hydroxymethyl-2-pyrrolidinone
  $R_f$ value: 0.35 (silica gel; ethyl acetate)

Example XVIII (3R,5S)-3-Allyl-1-(3-phenylpropyl)-5-[(p-toluenesulphonyloxy)-methyl]-2-pyrrolidinone 76.4 g of 4-toluenesulphochloride are added in batches, at −20° C., to a mixture of 54.6 g of (3R,5S)-3-allyl-5-hydroxymethyl-1-(3-phenylpropyl)-2-pyrrolidinone, 500 ml of methylene chloride, 32 ml of pyridine and 0.2 g of 4-dimethylaminopyridine. The mixture is kept for a further 2 hours at −20° C. and left to stand for 64 hours at ambient temperature. The methylene chloride is evaporated off in vacuo, the residue is taken up in ether and washed with 1N hydrochloric acid. The crude product obtained after evaporation is purified by chromatography over silica gel (eluant: ether/petroleum ether=10:1)

Yield: 56.6 g (66% of theory), $R_f$ value: 0.68 (silica gel; ether)

Example XIX (3R,5S)-3-Allyl-1-(3-phenylpropyl)-5-[[2-(N-phthalimidomethyl)-5-indanyl]sulphonylaminomethyl]-2-pyrrolidinone 6.8 g of (3R,5S)-3-allyl-5-aminomethyl-1-(3-phenylpropyl)-2-pyrrolidinone are dissolved in a mixture of 150 ml of tetrahydrofuran and 7.5 ml of triethylamine, cooled to 0° C. and mixed with 9.4 g of 2-(N-phthalimidomethyl)indan-5-sulphochloride. The mixture is stirred for 4 hours at ambient temperature, poured into dilute hydrochloric acid and extracted with ethyl acetate. The ethyl acetate phase is evaporated down and the residue is purified by column chromatography over silica gel (eluant: methylene chloride/ethanol=15:1).

Yield: 11.7 g (81% of theory), $R_f$ value: 0.86 (silica gel; methylene chloride/ethanol=15:1)

The following are obtained analogously:
(1) (3R,5S)-3-allyl-1-(3-phenylpropyl)-5-[[2-(N-phthalimido)-5-indanyl)sulphonylaminomethyl]-2-pyrrolidinone
  $R_f$ value: 0.69 (silica gel; methylene chloride/ethanol=15:1)
(2) 4-[(4-methoxyphenyl)sulphonylamino]benzonitrile
  Solvent: pyridine Melting point: 187°–189° C. Calculated: C 58.32 H 4.20 N 9.72 S 11.12 Found: 58.11 4.27 9.44 11.07

Example XX 1-(3-phenylpropyl)-4-[(trityloxy)methyl]-2-pyrrolidinone

A mixture of 74.1 g of 4-hydroxymethyl-1-(3-phenylpropyl)-2-pyrrolidinone, 81 ml of triethylamine, 1.8 g of 4-dimethylaminopyridine, 97.1 g of triphenylchloromethane and 1100 ml of dimethylformamide is stirred for 16 hours at ambient temperature. The reaction mixture is evaporated down, the residue is poured onto 2500 ml of ice water and extracted with methylene chloride. The organic phase is washed with saturated ammonium chloride solution, treated with activated charcoal, concentrated by evaporation, and the residue is purified over silica gel (eluant; methylene chloride/methanol=50:1).

Yield: 109.9 g (73% of theory), $R_f$ value: 0.69 (silica gel; methylene chloride/methanol=9:1)

The following is obtained analogously:
(1) 1-(4-methoxybenzyl)-4-[(trityloxy)methyl]-2-pyrrolidinone
  Melting point: 171°–173° C. $R_f$ value: 0.80 (silica gel; ethyl acetate)

Example XXI

4-Hydroxymethyl-1-(3-phenylpropyl)-2-pyrrolidinone 88.5 g of 1-(3-phenylpropyl)-2-pyrrolidinone-4-carboxylic acid and 36.2 g of triethylamine are dissolved in 1400 ml of tetrahydrofuran. The mixture is cooled to −20° C., 38.8 g of ethyl chloroformate are added dropwise, the mixture is stirred for a further 30 minutes and the precipitate formed is filtered. The filtrate is added dropwise at −10° C. to a solution of 33.8 g of sodium borohydride in 700 ml of water. The mixture is stirred for a further 2 hours, the mixture is allowed to return to ambient temperature, adjusted to pH 4 with concentrated hydrochloric acid and left to stand for 16 hours at ambient temperature. The solution is made alkaline with sodium hydrogen carbonate and extracted with methylene chloride. The residue remaining after evaporation of the methylene chloride phase is reacted without further purification.

Yield: 57.7 g (69% of theory), $R_f$ value: 0.53 (silica gel; methylene chloride/methanol=9:1)

Example XXII 1-(3-Phenylpropyl)-2-pyrrolidinone-4-carboxylic acid

A mixture of 48 g of itaconic acid and 50 g of 3-phenylpropylamine is heated to 160° C. for one hour. After cooling, it is taken up with 500 ml of 2N sodium hydroxide solution, washed with ethyl acetate and acidified with hydrochloric acid. Extraction with ethyl acetate is carried out and the organic phase is evaporated down.

Yield: 88.5 g (97% of theory), $R_f$ value: 0.86 (silica gel; methylene chloride/methanol=5:1)

The following is obtained analogously:
(1) methyl 1-(4-methoxybenzyl)-2-pyrrolidinone-4-carboxylate The crude 1-(4-methoxybenzyl)-2-pyrrolidinone-4-carboxylic acid is converted directly with methanol/thionyl chloride into the methyl ester.
  $R_f$ value: 0.54 (silica gel; ethyl acetate) Calculated: C 63.86 H 6.51 N 5.32 Found: 63.65 6.46 5.20

Example XXIII

4-Amino-4'-cyano-biphenyl

Prepared analogously to Example 11 by reduction of 4'-cyano-4-nitrobiphenyl.

Melting point: 171°–173° C.

The following are obtained analogously:
(1) 3-amino-4'-cyano-biphenyl
  Melting point: 120°–121° C.
(2) 2-amino-7-methoxy-9,10-dihydro-phenanthrene
  $R_f$ value: 0.63 (silica gel; methylene chloride/methanol/conc. aqueous ammonia=19:1:0.1)

Example XXIV

Methyl 3-[4-(aminomethyl)phenyl]propionate hydrochloride 3.7 g of 4-(aminomethyl)cinnamic acid are dissolved in 200 ml of methanol and 10 ml of ethereal hydrochloric acid. 0.3 g of 10% palladium charcoal are added and the mixture is hydrogenated for 4 hours at ambient temperature under a hydrogen pressure of 3 bar. After the catalyst has been filtered off the solution is evaporated down and the residue is purified by chromatography on silica gel (eluant: methylene chloride/methanol 9:1).

Yield: 2.1 g (50% of theory), $R_f$ value: 0.28 (silica gel; methylene chloride/methanol=9:1)

Example XXV

4-(4-Cyanobenzoylamino) anisole

Prepared analogously to Example 18 from 4-cyanobenzoylchloride and 4-aminoanisole.

Melting point: 178°–181° C. Calculated: C 71.42 H 4.79 N 11.11 Found: 71.44 4.89 11.00

The following are obtained analogously:
(1) 4-(4-methoxybenzoylamino)benzonitrile
  Solvent: pyridine Melting point: 152°–155° C. Calculated: C 71.42 H 4.79 N 11.11 Found: 71.23 4.67 11.19
(2) (3S,5S)-3-[(methoxycarbonyl)methyl]-5-[2-[[(3'-nitro-4-biphenylyl)carbonyl]amino]ethyl]-1-(3-phenylpropyl)-2-pyrrolidinone
  $R_f$ value: 0.46 (silica gel; methylene chloride/methanol/conc. aqueous ammonia=19:1:0.1)
(3) (3S,5S)-3-[(methoxycarbonyl)methyl]-5-[[(3'-nitro-4-biphenylyl) carbonyl]aminomethyl]-1-(3-phenylpropyl)-2-pyrrolidinone
  $R_f$ value: 0.53 (silica gel; methylene chloride/methanol=9:1)

Example XXVI

4-(5-Aminopentyl)phenol-hydrochloride 20.8 g of 4-(5-aminopentyl)anisole are heated with 350 ml of semiconcentrated hydrochloric acid in a glass bomb for 10 hours to 180° C. The solution is concentrated by evaporation in vacuo, the residue is dissolved in ethanol and treated with activated charcoal. The residue remaining after evaporation is used further as a crude product.

Yield: 23 g (99% of theory).

Example XXVII

3-(4-Aminobutyl)-1-benzyloxy-benzene

Prepared analogously to Example 23 by reduction of 1-benzyloxy-3-(3-cyanopropyl)benzene.

$R_f$ value: 0.50 (silica gel; methylene chloride/cyclohexane/methanol/conc. aqueous ammonia=68:15:15:2)

The following are obtained analogously:
(1) 4-(4-aminobutyl)-1-benzyloxy-benzene Carried out in methanolic ammonia
  $R_f$ value: 0.18 (silica gel; methylene chloride/methanol=8:1)
(2) 2-aminomethyl-indane
  $R_f$ value: 0.44 (silica gel; methylene chloride/cyclohexane/methanol/conc. aqueous ammonia=68:15:15:2)
(3) 4-(5-aminopentyl)anisole
  $R_f$ value: 0.59 (silica gel; methylene chloride/cyclohexane/methanol/conc. aqueous ammonia=68:15:15:2)
(4) 4-aminomethyl-cinnamic acid
  $R_f$ value: 0.22 (silica gel; ethanol/water=9:1)
(5) (3R,5S)-3-(4-aminobutyl)-5-[(methanesulphonyloxy)methyl]-1-methyl-2-pyrrolidinone
  $R_f$ value: 0.13 (silica gel; methylene chloride/methanol=4:1)
(6) (3S,5S)-5-(2-aminoethyl)-3-carboxymethyl-1-(3-phenylpropyl)-2-pyrrolidinone
  $R_f$ value: 0.23 (silica gel; methylene chloride/methanol/glacial acetic acid=1:1:0.1)

EXAMPLE XXVIII

Methyl 6-carboxy-5,6,7,8-tetrahydronaphthalene-2-carboxylate

Prepared analogously to Example 25 by hydrolysis of methyl 6-methoxycarbonyl-5,6,7,8-tetrahydronaphthalene-2-carboxylate.

Melting point: 187°–189° C. $R_f$ value: 0.68 (silica gel; toluene/dioxane/ethanol/glacial acetic acid=90:10:10:6)

EXAMPLE XXIX

6-Cyano-2-naphthylcarbonylchloride 2.8 g of naphthalene-2,6-dicarboxylic acid monoamide, 10 ml of thionylchloride and 1 drop of dimethylformamide are refluxed for 5 hours. The clear yellow solution is evaporated down in vacuo and the solid evaporation residue is mixed with 20 ml of diethylether and 20 ml of petroleum ether, then stirred and suction filtered. The filter cake is washed with petroleum ether and diethylether and dried in vacuo.

Yield: 2.5 g (89% of theory), Melting point: 150°–155° C.

EXAMPLE XXX

Napthalene-2,6-dicarboxylic acid monoamide 3.5 g of methyl naphthalene-2,6-dicarboxylate monoamide, 40 ml of ethanol and 2 ml of 15N sodium hydroxide solution are refluxed for 1 hour. The reaction mixture is evaporated down, the residue is dissolved in 100 ml of water and extracted twice with 50 ml of methylene chloride/methanol (4:1). The aqueous phase is filtered and the filtrate is acidified with hydrochloric acid under warming. The precipitate is suction filtered, washed with water and dried at 100° C.

Yield: 2.9 (88.6% of theory), Melting point: >260° C. $R_f$ value: 0.35 (silica gel; toluene/dioxane/ethanol/glacial acetic acid=90:10:10:6) Calculated: C, 66.97; H, 4.21; N, 6.51; Found: C, 66.46; H, 4.16; N, 6.25;

The following are obtained analogously:

(1) 7-cyano-2-naphthalenecarboxylic acid

Melting point: 294°–297° C. $R_f$ value: 0.62 (silica gel; 1,2-dichloroethane/ethyl acetate/glacial acetic acid= 100:30:5)

(2) 6-cyano-5,6,7,8-tetrahydronaphthalene-2-carboxylic acid

Melting point: 231°–236° C. $R_f$ value: 0.58 (silica gel; cyclohexane/ethyl acetate=1:1)

(3) 6-aminocarbonyl-5,6,7,8-tetrahydronaphthalene-2-carboxylic acid

Melting point: >260° C. (decomp.) $R_f$ value: 0.34 (silica gel; toluene/dioxane/ethanol/glacial acetic acid=90:10:10:6)

(4) 3'-nitro-3-biphenylcarboxylic acid

Melting point: 271°–272° C. $R_f$ value: 0.51 (silica gel; cyclohexane/ethyl acetate=1:2) Calculated: C, 64.20; H, 3.73; N, 5.76; Found: C, 63.96; H, 3.78; N, 5.98.

EXAMPLE XXXI

Methyl Napthalene-2,6-dicarboxylic acid-monoamide-monomethyl ester 3.7 g of napthalene-2,6-dicarboxylic acid-monomethyl ester, 15 ml of thionylchloride and 1 drop of dimethylformamide are refluxed for 1.5 hours. Then the excess thionyl chloride is distilled off in vacuo and the solid residue is suspended in 120 ml of dioxane. Ammonia is introduced into this suspension at ambient temperature, with stirring, for 15 minutes and then stirred for a further 18 hours at ambient temperature. Then the solvent is evaporated off, the residue is mixed with water and the suspension is suction filtered. After washing with a little water/methanol and drying, 3.66 g (99.8% of theory) remain.

Melting point: 226°–228° C. $R_f$ value: 0.45 (silica gel; toluene/dioxane/ethanol/glacial acetic acid=90:10:10:6 Calculated: C, 68.11; H, 4.84; N, 6.11; Found: C, 67.98; H, 4.87; N, 6.28;

The following is obtained analogously:

(1) methyl 6-aminocarbonyl-5,6,7,8-tetrahydro-naphtha-lene-2-carboxylate

Melting point: 162°–164° C. $R_f$ value: 0.44 (silica gel; toluene/dioxane/ethanol/glacial acetic acid=90:10:10:6)

EXAMPLE XXXII

Naphthalene-2,6-dicarboxylic acid-monomethyl ester

A suspension of 1.96 g of sodium n-propylmercaptide (prepared from n-propylmercaptane and sodium hydride) in 20 ml of dimethylformamide is quickly added to a solution at 70°–75° C. of 5 g of dimethylnapthalene-2,6-dicarboxylate in 80 ml of dimethylformamide. After 2 hours stirring at ambient temperature, the reaction mixture is cooled off somewhat and mixed with ice water and hydrogen peroxide solution. The reaction mixture is acidified with hydrochloric acid, the precipitate is suction filtered and washed with water/methanol (3:1) and then dried. After recrystallisation from dioxane, 3.2 g remain (69% of theory).

Melting point: 277°–280° C. (decomp.) $R_f$ value: 0.59 (silica gel; toluene/dioxane/ethanol/glacial acetic acid= 90:10:10:6) Calculated: C, 67.82; H, 4.38; Found: C, 67.64; H, 4.17;

EXAMPLE XXXIII

Methyl 7-cyano-2-naphthalene-carboxylate 8.4 g of methyl 7-bromo-2-naphthalenecarboxylate and 3.0 g of copper(I)-cyanide are refluxed for 20 hours in 30 ml of dimethylformamide. After cooling, water is added, the mixture is acidified with hydrochloric acid and stirred with ethyl acetate. The undissolved fractions are filtered off, the phases are separated and the aqueous phase is extracted four times with ethyl acetate. The combined organic phases are washed with water, dried over magnesium sulphate and evaporated down. The residue is chromatographed over a silica gel column with cyclohexane/ethyl acetate.

Yield: 1.4 g (21% of theory), Melting point: 137°–139° C. $R_f$ value: 0.52 (silica gel; cyclohexane/ethyl acetate=8:2) Calculated: C, 73.92; H, 4.30; N, 6.63; Found: C, 73.94; H, 4.39; N, 6.65;

The following are obtained analogously:

(1) 3-(4-cyanophenyl)cyclobutane carboxylic acid $R_f$ value: 0.48 (silica gel; cyclohexane/ethyl acetate/glacial acetic acid=40:20:1) Calculated: C, 71.63; H, 5.51; N, 6.96; Found: C, 71.97; H, 5.51; N, 7.04;

(2) 4-(4-cyanophenyl)cyclohexanone-ethylene ketal

Melting point: 132°–133° C. $R_f$ value: 0.40 (silica gel; petroleum ether/ethyl acetate=3:1) Calculated: C, 74.04; H, 7.04; N, 5.76; Found: C, 73.84; H, 7.10; N, 5.58;

(3) Methyl 4'-cyano-3-biphenylylcarboxylate $R_f$ value: 0.39 (silica gel; cyclohexane/ethyl acetate=4:1)

EXAMPLE XXXIV

Methyl 7-bromo-2-naphthalene-carboxylate 15.7 g of 2,7-dibromonaphthalene in 160 ml of dry tetrahydrofuran are slowly mixed at −70° C. with 22 ml of 2.5M n-butyllithium solution in hexane. After 1 hours stirring at −70° C. a weak current of dry carbon dioxide is introduced whilst the temperature is maintained at below −60° C. After the exothermic reaction has died away the introduction of carbon dioxide is ended. The reaction mixture is mixed with diethylether and the precipitate is suction filtered and washed with ether. The precipitate is suspended in water, acidified with conc. hydrochloric acid, stirred for 20 minutes, suction filtered, washed with water and dried. The intermediate product is then refluxed for 3 hours with 400 ml of methanol and 7 ml of thionylchloride. After cooling, the insoluble matter is removed by suction filtering and the filtrate is evaporated down. After chromatography over a silica gel column with cyclohexane/ethyl acetate (98:2) 7.6 g of product (52% of theory) are isolated.

Melting point: 120°–122° C. $R_f$ value: 0.47 (silica gel; cyclohexane/ethyl acetate=95:5)

EXAMPLE XXXV

Methyl 6-cyano-5,6,7,8-tetrahydronaphthalene-2-carboxylate 6.8 g of methyl 6-aminocarbonyl-5,6,7,8-tetrahydro-naphthalene-2-carboxylate, 9.65 g of triphenylphosphine, 4.7 g of carbon tetrachloride, 3.1 g of triethylamine and 40 ml of chloroform are combined and stirred for 4 hours at 60° C. After the addition of another 2.7 g of triphenylphosphine the mixture is stirred for one more hour at 60° C. After cooling the reaction solution is concentrated by evaporation, the residue is stirred with ethyl acetate and then suction filtered to remove insoluble matter. The filtrate is concentrated by evaporation and then chromatographed over a silica gel column with cyclohexane/ethyl acetate (85:15) and then (1:1).

Yield: 5.4 g (86% of theory) Melting point: 79°–81° C. $R_f$ value: 0.70 (silica gel; cyclohexane/ethyl acetate=1:1) Calculated: C, 72.53; H, 6.09; N, 6.51; Found: C, 72.66; H, 6.18; N, 6.57;

EXAMPLE XXXVI

N-[4-(4-Benzyloxyphenyl)butyl]-N-tert.butyloxycarbonylamine 16.8 g of 4-(4-benzyloxyphenyl)butylamine are dissolved in 200 ml of methanol. The solution is cooled to saturation point and then a solution of 17 g of di-tert.butylpyrocarbonate is added dropwise. The mixture is stirred for 2 hours at ambient temperature, concentrated by evaporation, mixed with saturated common salt solution and extracted with methylene chloride. The methylene chloride phase is concentrated by evaporation and the remaining product is re-used without any further purification.

$R_f$ value: 0.57 (silica gel; cyclohexane/ethyl acetate=5:2)

The following are obtained analogously:

(1) 4-[(tert.butyloxycarbonylamino)methyl]phenol

Solvent: methanol/tetrahydrofuran $R_f$ value: 0.54 (silica gel; methylene chloride/methanol/conc. aqueous ammonia=90:10:1)

(2) 4-[2-(tert.butyloxycarbonylamino)ethyl]phenol

Solvent: methanol/tetrahydrofuran $R_f$ value: 0.61 (silica gel; methylene chloride/methanol/conc. aqueous ammonia=90:10:1)

(3) 1-benzyloxy-3-[4-(tert.butyloxycarbonylamino)butyl]benzene

Solvent: tetrahydrofuran $R_f$ value: 0.69 (silica gel; methylene chloride)

(4) 1-benzyloxy-4-[4-(tert.butyloxycarbonylamino)butyl]benzene

Reduction in tetrahydrofuran/methanol $R_f$ value: 0.57 (silica gel; cyclohexane/ethyl acetate)

(5) (3R, 5S)-3-[4-(tert.butyloxycarbonylamino)butyl]-5-(methanesulphonyloxy)methyl]-1-methyl-2-pyrrolidinone $R_f$ value: 0.30 (silica gel; ethyl acetate/methanol=20:1)

EXAMPLE XXXVII

6-(tert.Butyloxycarbonylamino)-5,6,7,8-tetrahydronaphthalene-2-carboxylic acid 180 mg of 6-amino-5,6,7,8-tetrahydronaphthalene-2-carboxylic acid are combined with 6 ml of dioxane, 2 ml of water and 0.9 ml of 1N sodium hydroxide solution. 220 mg of di-tert.butylpyrocarbonate are added thereto, whilst cooling with ice. After 2 hours stirring at ambient temperature, the dioxane is eliminated in vacuo and the residue is diluted with a little ice water. The product is precipitated by adding 200 mg of citric acid in 2 ml of water and then dried.

Yield: 210 mg (81% of theory), Melting point: 185°–187° C. $R_f$ value: 0.71 (silica gel; toluene/dioxane/ethanol/glacial acetic acid=90:10:10:6) Calculated: C, 65.96; H, 7.26; N, 4.81; Found: C, 65.95; H, 7.48; N, 4.83;

The following are obtained analogously:

(1) 4-[3-(tert.butyloxycarbonylamino)cyclobutyl]benzoic acid $R_f$ value: 0.52 (silica gel; cyclohexane/ethyl acetate=1:1)

(2) 4-[3-(tert.butyloxycarbonylamino)phenyl]butyric acid $R_f$ value: 0.20 (silica gel; methylene chloride/methanol=19:1)

(3) 2-(tert.butyloxycarbonylamino)indane-5-carboxylic acid $R_f$ value: 0.44 (silica gel; methylene chloride/ethanol=15:1)

(4) 2-[(tert.butyloxycarbonylamino)methyl]indane-5-acetic acid

Melting point: 123°–124° C. $R_f$ value: 0.56 (silica gel; methylene chloride/ethanol=10:1)

(5) 3-[3-(tert.butoxycarbonylamino)propyl]phenol $R_f$ value: 0.45 (silica gel; methylene chloride/ethanol=15:1)

(6) 4-[5-(tert.butyloxycarbonylamino)pentyl]phenol $R_f$ value: 0.70 (silica gel; methylene chloride/cyclohexane/methanol/conc. aqueous ammonia=68:15:15:2)

(7) 3-[3-(tert.butyloxycarbonylamino)phenyl]propionic acid $R_f$ value: 0.40 (silica gel; methylene chloride/methanol=9:1)

(8) 3-[4-(tert.butyloxycarbonylamino)phenyl]propionic acid $R_f$ value: 0.54 (silica gel; methylene chloride/methanol=9:1)

(9) 4-[4-(tert.butyloxycarbonylamino)phenyl]butyric acid $R_f$ value: 0.54 (silica gel; methylene chloride/methanol=9:1)

(10) 8-(tert.butyloxycarbonylamino)octane carboxylic acid $R_f$ value: 0.63 (silica gel; methylene chloride/methanol=9:1)

(11) cis-4-[4-(tert.butyloxycarbonylamino)cyclohexyl]phenol

By reacting the cis/trans mixture and precipitating the cis compound with 2N hydrochloric acid.

Melting point: 210°–213° C. $R_f$ value: 0.53 (silica gel; methylene chloride/methanol=20:1)

(12) trans-4-[4-(tert.butyloxycarbonylamino)cyclohexyl]phenol

By reacting the cis/trans mixture, precipitating the cis compound with 2N hydrochloric acid and working up the filtrate.

Melting point: 211°–214° C. (ethanol) $R_f$ value: 0.53 (silica gel; methylene chloride/methanol=20:1)

(13) 4-[cis/trans-4-(tert.butyloxycarbonylamino)cyclohexyl]benzoic acid $R_f$ value: 0.52 (silica gel; methylene chloride/methanol/conc. aqueous ammonia=4:1:0.25)

(14) 4-[cis-4-[(tert.butyloxycarbonyl)aminomethyl])cyclohexyl]phenol $R_f$ value: 0.47 (silica gel; cyclohexane/ethyl acetate=2:1)

(15) 4-[trans-4-[(tert.butyloxycarbonyl)aminomethyl]cyclohexyl]phenol $R_f$ value: 0.46 (silica gel; cyclohexane/ethyl acetate=2:1)

(16) 4-(tert.butyloxycarbonylamino)cinnamic acid $R_f$ value: 0.38 (silica gel; methylene chloride/methanol=15:1)

EXAMPLE XXXVIII

2-[(tert.Butyloxycarbonylamino)methyl]indane-5-carboxylic acid 4.5 g of 2-aminomethylindane-5-carboxylic acid hydrochloride are dissolved in a mixture of 75 ml of tetrahydrofuran, 75 ml of water and 5.6 ml of triethylamine and 5.2 g of di-tert.butylpyrocarbonate are added with stirring. The mixture is stirred for a further 64 hours at ambient temperature, the tetrahydrofuran is evaporated off in vacuo, the aqueous phase is extracted with ether and acidified with citric acid. It is extracted with ether and the organic phase obtained is evaporated down.

Yield: 5.0 g (86% of theory), $R_f$ value: 0.58 (silica gel; methylene chloride/methanol/glacial acetic acid=9:1:0.1)

The following are obtained analogously:

(1) 3-[(tert.butyloxycarbonylamino)methyl]phenol

Solvent: methanol/tetrahydrofuran $R_f$ value: 0.43 (silica gel; methylene chloride/methanol/conc. aqueous ammonia=30:10:1)

(2) 3-[2-(tert.butyloxycarbonylamino)methyl]phenol

Solvent: methanol/tetrahydrofuran $R_f$ value: 0.49 (silica gel; methylene chloride/methanol=12:1)

(3) 3-[2-(tert.butyloxycarbonylamino)ethyl]benzoic acid

Solvent: methanol/tetrahydrofuran

Melting point: 115°–120° C. $R_f$ value: 0.51 (silica gel; methylene chloride/methanol=10:1)

(4) 4-[2-(tert.butyloxycarbonylamino)ethyl]benzoic acid

Solvent: methanol/tetrahydrofuran

Melting point: 152°–155° C. $R_f$ value: 0.42 (silica gel; methylene chloride/methanol=10:1)

(5) 2-(tert.butyloxycarbonylamino)indane-5-acetic acid

Solvent: methanol $R_f$ value: 0.38 (silica gel; methylene chloride/methanol=10:1)

(6) (3R,5S)-3-allyl-1-(tert.butyloxycarbonyl)-5-hydroxymethylpyrrolidine $R_f$ value: 0.60 (silica gel; cyclohexane/ethyl acetate=1:1)

EXAMPLE XXXIX

3-[4-[(tert.Butyloxycarbonylamino)methyl]-phenyl]propionic acid 2 g of methyl 3-[4-(aminomethyl)phenyl]propionate are dissolved in 80 ml of methanol, mixed with 8.7 ml of 2N sodium hydroxide solution and stirred for 30 minutes at ambient temperature. The mixture is evaporated down in vacuo, the residue is taken up in 30 ml of a 2:1 mixture of dioxane and water, 2.1 g of di-tert.butylpyrocarbonate are added and the resulting mixture is left to stand for 16 hours at ambient temperature. It is evaporated down to about 10 ml, adjusted to pH 2 to 3 with citric acid and extracted with ethyl acetate. The ethyl acetate phase is washed with water, treated with activated charcoal and evaporated down.

Yield: 1.7 g (71% of theory), $R_f$ value: 0.63 (silica gel; methylene chloride/methanol=9:1)

EXAMPLE XL

6-Amino-5,6,7,8-tetrahydronaphthalene-2-carboxylic acid 500 mg of 6-aminocarbonyl-5,6,7,8-tetrahydro-naphthalene-2-carboxylic acid, 1.42 g of [bis(trifluoroacetoxy)iodo] benzene, 3 ml of water and 10 ml of acetonitrile are stirred for 38 hours at ambient temperature. The acetonitrile is evaporated off, the residue is diluted with water and the mixture is extracted twice with ethyl acetate. The aqueous phase is concentrated somewhat and then adjusted to pH 4 to 5 with 2N sodium hydroxide solution. The precipitate is suction filtered, washed with water and dried.

Yield: 250 mg (54% of theory), Melting point: >260° C. $R_f$ value: 0.04 (silica gel; toluene/dioxane/ethanol/glacial acetic acid=90:10:10:6)

The following is obtained analogously:

(1) 4-(3-aminocyclobutyl)benzonitrile $R_f$ value: 0.27 (silica gel; ethyl acetate/methanol=3:1) Calculated: C, 76.71; H, 7.02; N, 16.26; Found: C, 76.40; H, 7.18; N, 15.95;

EXAMPLE XLI 3-(4-Bromophenyl)cyclobutane carboxylic acid 2 g of 3-(4-bromophenyl)cyclobutane dicarboxylic acid are heated to 210° C. under nitrogen for 15 minutes. After cooling to ambient temperature the residue is taken up in 20 ml of 2N sodium hydroxide solution and extracted three times with methylene chloride. The aqueous phase is mixed with 20 ml of 2N hydrochloric acid, with formation of ice, and extracted with methylene chloride. The organic phase is dried with sodium sulphate and evaporated down.

Yield: 1.6 g (90% of theory), Melting point: 85°–90° C. $R_f$ value: 0.51 (silica gel; cyclohexane/ethyl acetate=2:1) Calculated: C, 51.79; H, 4.35; Br, 31.32; Found: C, 51.60; H, 4.30; Br, 31.37;

EXAMPLE XLII 3-(4-Bromophenyl)cyclobutane dicarboxylic acid 17.5 g of 1,3-[bis(p-tosyloxy)]-2-(4-bromophenyl)propane, 5.2 ml of diethylmalonate and 100 ml of dry dioxane are heated to 90° C. under nitrogen. 2.83 g of sodium hydride (55% in oil) are carefully added (vigorous foaming!) in batches and the mixture is then refluxed for 18 hours. After cooling the solvent is evaporated off, the residue is mixed with 25 ml of ethanol/water (1:1) and 4 g of potassium hydroxide and refluxed for 3 hours. It is then evaporated to dryness, the residue is taken up in water and extracted twice with tert.butylmethylether. The aqueous phase is acidified with conc. hydrochloric acid, whilst cooling with ice, and the precipitate is suction filtered and dried.

Yield: 7.58 g (78% of theory), $R_f$ value: 0.27 (silica gel; cyclohexane/ethyl acetate=1:1) Calculated: C, 48.19; H, 3.71; Br, 26.71; Found: C, 48.10; H, 3.84; Br, 26.96;

EXAMPLE XLIII

4-(3-Aminocyclobutyl)benzoic acid-hydrochloride 1.8 g of 4-(3-aminocyclobutyl)benzonitrile are refluxed with 20 ml of conc. hydrochloric acid. After cooling the precipitate is suction filtered, washed with 10 ml of ice water and dried at 60° C.

Yield: 2.4 g (100% of theory), Melting point: >200° C. Calculated: C, 58.03; H, 6.20; N, 6.15; Cl, 15.57; Found: C, 57.85; H, 6.36; N, 6.25; Cl, 15.59;

The following is obtained analogously:

(1) 3'-nitro-biphenyl-4-carboxylic acid

75% sulphuric acid is used and heating is carried out for 16 hours at 150° C.

Melting point: 311°–314° C. (decomp.)

EXAMPLE XLIV

4-[3-(Aminocarbonyl)cyclobutyl]benzonitrile 6.22 g of 3-(4-cyanophenyl)cyclobutane carboxylic acid are dissolved in 20 ml of dry tetrahydrofuran, 5.01 g of carbonyldiimidazole are added and the mixture is stirred for 2 hours at 50° C. The reaction mixture is then added to a mixture of 15 ml of conc. aqueous ammonia and 50 g of ice. The precipitate is suction filtered, washed with ice water and dried.

Yield: 5.39 g (87% of theory), Melting point: >200° C. $R_f$ value: 0.34 (silica gel; ethyl acetate) Calculated: C, 71.98; H, 6.04; N, 13.99; Found: C, 72.00; H, 6.15; N, 14.00;

EXAMPLE XLV

3-Bromo-4'-cyano-4-hydroxybiphenyl 3.9 g of 4'-cyano-4-hydroxybiphenyl are dissolved in 250 ml of chloroform at boiling temperature. 1 ml of bromine in 20 ml of chloroform are added dropwise to this solution with further refluxing. The colourless solution is cooled and evaporated down.

Yield: 5.48 g (100% of theory), Melting point: 186°–189° C. $R_f$ value: 0.66 (silica gel; 1,2-dichloroethane/ethyl acetate=9:1) Calculated: C, 56.96; H, 2.94; N, 5.11; Br, 29.15; Found: C, 57.07; H, 3.15; N, 5.03; Br, 29.14;

EXAMPLE XLVI

4'-Cyano-4-hydroxy-3-nitrobiphenyl

A mixture of 5.3 ml of 65% nitric acid and 5.3 ml of water is slowly added dropwise to 15.3 g of 4'-cyano-4-hydroxybiphenyl in 900 ml of glacial acetic acid. Then the mixture is stirred for 1.5 hours at 100° C. After cooling, the mixture is left to stand for 18 hours at ambient temperature. The reaction mixture is added to 3 liters of water, the precipitate is suction filtered, washed with water and dissolved in methylene chloride. After drying over sodium sulphate and removal of the solvent, 17.8 g (100% of theory) remain.

Melting point: 179°–180° C. $R_f$ value: 0.83 (silica gel; 1,2-dichloroethane/ethyl acetate=9:1) Calculated: C, 64.99; H, 3.36; N, 11.66; Found: C, 64.89; H, 3.47; N, 11.69;

The following is obtained analogously:

(1) 4-cyano-4'-nitro-biphenyl

Carried out in fuming nitric acid at a maximum of 30° C.

Melting point: 187°–190° C.

EXAMPLE XLVII

4'-Cyano-3-fluoro-4-methoxybiphenyl 6.7 g of 3-fluoro-4-methoxyphenylboric acid/3-fluoro-4-methoxyphenylboric acid anhydride, 4.9 g of 4-bromobenzonitrile, 11.3 ml of triethylamine, 0.5 g of tri-o-tolylphosphine and 0.2 g of palladium(II)-acetate are stirred in 110 ml of dimethylformamide for 3 days at 100° C. The mixture is then distributed between ice cold dilute hydrochloric acid and ethyl acetate, the organic phase is separated off and the aqueous phase is re-extracted with ethyl acetate. The organic phases are combined, dried with sodium sulphate and evaporated down. The residue is triturated with methylene chloride and filtered. The filtrate is evaporated down and purified over a silica gel column with methylene chloride/petroleum ether (1:1).

Yield: 2.75 g (45% of theory), Melting point: 103°–104° C. $R_f$ value: 0.55 (silica gel; methylene chloride/petroleum ether=1:1)

The following are obtained analogously:

(1) 4'-cyano-4-methoxy-3-trifluoromethylbiphenyl

Melting point: 126°–127° C. $R_f$ value: 0.51 (silica gel; methylene chloride/petroleum ether=1:1) Calculated: C, 64.98; H, 3.64; N, 5.05; Found: C, 64.75; H, 3.79; N, 4.97;

(2) 4'-aminocarbonyl-3'-chloro-4-methoxybiphenyl

Melting point: 207°–208° C. $R_f$ value: 0.78 (silica gel; methylene chloride/methanol=9:1)

(3) 4'-cyano-4-methoxy-2'-methylbiphenyl

Melting point: 77°–78° C. $R_f$ value: 0.50 (silica gel; methylene chloride/petroleum ether=1:1) Calculated: C, 80.69; H, 5.87; N, 6.27; Found: C, 80.48; H, 5.94; N, 5.99;

(4) 4'-cyano-2,3-dimethyl-4-methoxybiphenyl

Melting point: 114°–115° C. $R_f$ value: 0.65 (silica gel; methylene chloride/petroleum ether=1:1) Calculated: C, 80.97; H, 6.37; N, 5.30; Found: C, 81.17; H, 6.56; N, 5.86;

(5) Methyl 3'-nitro-3-biphenylcarboxylate

Melting point: 88°–89° C. $R_f$ value: 0.61 (silica gel; methylene chloride)

(6) 4'-cyano-3-nitro-biphenyl

Melting point: 164°–165° C.

(7) 3-nitro-3'-(N-phthalimido)biphenyl

Melting point: 222° C. (decomp.)

(8) Methyl 4'-bromo-3-biphenylylcarboxylate $R_f$ value: 0.59 (silica gel; cyclohexane/ethyl acetate=4:1)

(9) 4'-cyano-3'-fluoro-4-methoxybiphenyl

Carried out at ambient temperature

Melting point: 154°–156° C. Calculated: C, 74.00; H, 4.44; N, 6.16; Found: C, 73.93; H, 4.55; N, 6.20;

EXAMPLE XLVIII

3-Fluoro-4-methoxyphenylboric acid/3-fluoro-4-methoxyphenylboric acid-anhydride A few drops of 4-bromo-2-fluoroanisole are added to 1.8 g of magnesium chips in 15 ml of toluene/tetrahydrofuran (8:2). After the reaction has started, 15 g of 4-bromo-2-fluoroanisole in 85 ml of toluene/tetrahydrofuran (8:2) are added dropwise. The temperature is maintained at 35°–40° C. Stirring is continued for half an hour at 40° C., then the solution is cooled and added dropwise, with vigorous stirring, to a solution, cooled to −70° C., of 33.5 ml of triisopropylborate in 100 ml of toluene/tetrahydrofuran (1:1). After 2 hours stirring at −70° C. the mixture is heated overnight to ambient temperature. It is added to ice water and the mixture is extracted three times with ethyl acetate. The combined organic phases are dried and evaporated down. The residue is triturated with tert.butylmethylether and the majority of the product (5.15 g) is suction filtered. A further 1.5 g are obtained from the mother liquor by reprecipitation and then by column chromatography over silica gel with ethyl acetate/methylene chloride (1:1).

Total yield: 6.75 g (69% of theory), Melting point: 216°–218° C. $R_f$ value: 0.68 (silica gel; methylene chloride/ethyl acetate=1:1)

The following are prepared analogously:

(1) 4-methoxy-3-trifluoromethylphenylboric acid/4-methoxy-3-trifluoromethylphenylboric acid-anhydride Melting point: 217°–218° C. $R_f$ value: 0.70 (silica gel; methylene chloride/ethyl acetate=1:1)

(2) 2,3-dimethyl-4-methoxyphenylboric acid/2,3-dimethyl-4-methoxyphenylboric acid-anhydride Melting point: 251°–253° C., sinters above 239° C. $R_f$ value: 0.65 (silica gel; methylene chloride/ethyl acetate=1:1)

EXAMPLE XLIX trans-4-(4-Cyanophenyl)cyclohexanol 0.8 g of sodium borohydride are added in batches to 1 g of 4-(4-cyanophenyl)cyclohexanone in 40 ml of methanol, with stirring and whilst cooling with ice. After 4 hours further stirring without cooling, the mixture is evaporated down, the residue is mixed with ice water, 5 ml of 2N sodium hydroxide solution are added and the mixture is stirred for 15 minutes. The mixture is extracted with tert.butylmethyl-ether, the organic phase is dried and evaporated down. After chromatography over a silica gel column with ethyl acetate/petroleum ether (3:1) 0.8 g (80% of theory) are obtained.

$R_f$ value: 0.61 (silica gel; ethyl acetate)

EXAMPLE L 4-(4-Cyanophenyl)cyclohexanone 4 g of 4-(4-cyanophenyl)cyclohexanone-ethylene ketal, 120 ml of acetone, 12 ml of water and 0.5 g of pyridinium salt of toluenesulphonic acid are refluxed for 24 hours. The mixture is evaporated down and taken up in tert.butylmethyl-ether. The solution is washed with saturated saline solution and water, dried with magnesium sulphate and evaporated down. By column chromatography on silica gel with petroleum ether/ethyl acetate (3:1) 2.4 g of starting material and 1.1 g (33.5% of theory) of end product are obtained.

Melting point: 127°–128° C. $R_f$ value: 0.33 (silica gel; petroleum ether/ethyl acetate=2:1)

EXAMPLE LI 4-(4-Bromophenyl)cyclohexanone-ethylene ketal 8 g of 4-(4-bromophenyl)cyclohex-3-enone-ethylene ketal are hydrogenated for 8 minutes in 80 ml of ethanol with 0.8 g of platinum dioxide at ambient temperature under a hydrogen pressure of 3 bar. The solution is mixed with solid potassium hydrogen carbonate and evaporated down. The residue is distributed between ethyl acetate and water, the organic phase is separated off, dried and evaporated down. After column chromatography on silica gel with petroleum ether/ethyl acetate (9:1), 1.6 g (20% of theory) are obtained.

Melting point: 70°–71° C. $R_f$ value: 0.44 (silica gel; petroleum ether/ethyl acetate=9:1) Calculated: C, 56.58; H, 5.76; Br, 26.89; Found: C, 56.84; H, 5.94; Br, 26.72;

EXAMPLE LII 4-(4-Bromophenyl)cyclohex-3-enon-ethylene ketal 34.2 g of 4-(4-bromophenyl)-4-hydroxycyclohexanone-ethylene ketal, 0.4 g of p-toluenesulphonic acid, 40 ml of ethyleneglycol and 350 ml of toluene are boiled for 3 hours using a water separator. After cooling, the mixture is diluted with ethyl acetate and washed with saturated aqueous potassium carbonate solution and saturated aqueous common salt solution. The organic phase is dried, concentrated by evaporation and chromatographed over a short silica gel column with methylene chloride.

Yield: 25 g (77% of theory), Melting point: 108°–109° C. $R_f$ value: 0.52 (silica gel; methylene chloride)

EXAMPLE LIII 4-(4-Bromophenyl)-4-hydroxycyclohexanone-ethylene ketal

At 0°–5° C. 64.8 ml of a 2.5M n-butyllithium solution in hexane are added dropwise to 38.1 g of 1,4-dibromobenzene in 220 ml of dry ether and the mixture is then stirred for 20 minutes at 0° C. Then at −10° to +5° C. 25.2 g of 1,4-cyclohexanedione-monoethylene ketal in 100 ml of dry tetrahydrofuran are added thereto dropwise and the mixture is stirred overnight at ambient temperature. It is poured onto ice and extracted with ethyl acetate. The organic phase is washed with saturated aqueous saline solution, dried, evaporated down to 80 ml and mixed with 700 ml of petroleum ether. The crystals (34.4 g) are suction filtered. A further 4.3 g of product are obtained by evaporation from the mother liquor.

Total yield: 38.7 g (76% of theory), Melting point: 156°–158° C. $R_f$ value: 0.50 (silica gel; ethyl acetate/petroleum ether=2:3)

The following are obtained analogously:

(1) 1-benzyloxy-4-[cis/trans-4-(dibenzylamino)-1-hydroxycyclohexyl]benzene $R_f$ value: 0.52 and 0.36 (silica gel; cyclohexane/ethyl acetate=4:1)

(2) 2-[4-[4-(dibenzylamino)-1-hydroxy-cyclohexyl]phenyl]-4,4-dimethyl-oxazoline trans-product: $R_f$ value: 0.30 (silica gel; cyclohexane/ethyl acetate=2:1) cis-product: $R_f$ value: 0.16 (silica gel; cyclohexane/ethyl acetate=2:1)

(3) 1-benzyloxy-4-[cis/trans-4-(dibenzylaminomethyl)-1-hydroxy-cyclohexyl]benzene $R_f$ value: 0.45 (silica gel; cyclohexane/ethyl acetate=4:1)

EXAMPLE LIV

4'-(N-Benzyloxycarbonylamidino)-4-hydroxybiphenyl×0.25 water 3.6 g of benzyl chloroformate are added to 2.5 g of 4'-amidino-4-hydroxybiphenyl-hemicarbonate suspended in 30 ml of dioxane. Then 3.05 g of triethylamine in 5 ml of dioxane are added dropwise at ambient temperature. After one hours stirring at ambient temperature, the temperature is increased to 80° C. for a further 30 minutes. After cooling, the reaction mixture is concentrated using a rotary evaporator and the evaporation residue is taken up in 50 ml of ethyl acetate. When it is extracted with ice water to which some dilute hydrochloric acid has been added, the diacylated intermediate product starts to crystallise out. The crystals are suction filtered, taken up in methanol, mixed with 1.5 ml of 15N sodium hydroxide solution and then heated for 10 minutes over a steam bath. The reaction mixture is then acidified with glacial acetic acid and concentrated by evaporation. The evaporation residue is dissolved in ethyl acetate/methanol, washed with water and aqueous saline solution, to which a little methanol is added, and the organic phase is dried and evaporated down. This residue is stirred with a little ethyl acetate, the suspension is cooled and the solids are suction filtered and washed with ethyl acetate/petroleum ether. The crude product is then decocted with acetone, filtered and the acetone filtrate is evaporated down.

Yield: 1.45 g (46% of theory), Melting point: 178°–180° C. (decomp.) $R_f$ value: 0.38 (silica gel; cyclohexane/ethyl acetate=1:1) Calculated: C, 71.89; H, 5.32; N, 7.98; Found: C, 71.82; H, 5.25; N, 7.88;

EXAMPLE LV 1,3-[Bis-(p-tosyloxy)]-2-(4-bromophenyl)propane

At 5° C., 153.9 g of p-toluenesulphonic acid chloride are added in batches to 89.7 g of 2-(4-bromophenyl)-1,3-dihydroxypropane in 300 ml of pyridine and the mixture is then stirred for 18 hours at ambient temperature. Then 200 ml of ice water are added dropwise thereto, the reaction mixture is adjusted to pH 3 with hydrochloric acid and stirred for one hour in an ice bath. The precipitate is suction filtered, washed with ice water/2N hydrochloric acid (1:1), dried and recrystallised from ethanol.

Yield: 61.1 g (30% of theory), Melting point: 128°–130° C. $R_f$ value: 0.45 (silica gel; cyclohexane/ethyl acetate=3:1) Calculated: C, 51.21; H, 4.30; Br, 14.81; S, 11.88; Found: C, 51.46; H, 4.35; Br, 14.52; S, 12.10;

EXAMPLE LVI 2-(4-Bromophenyl)-1,3-dihydroxypropane 111.5 g of dimethyl (4-bromophenyl)malonate in 200 ml of tetrahydrofuran are added dropwise, within 1¾ hours, to 17.7 g of lithium aluminium hydride in diethylether at a temperature of 25° C. After a further 3 hours stirring at ambient temperature, 50 ml of water are cautiously added dropwise whilst cooling with ice. Then 1 liter of 15% sulphuric acid is added to the mixture, it is extracted with ethyl acetate and the organic phase is dried with magnesium sulphate. After the solvent has been evaporated off, 90.9 g (100% of theory) of crude product remain.

$R_f$ value: 0.39 (silica gel; ethyl acetate)

The following are obtained analogously:

(1) 3-(4-benzyloxyphenyl)propanol

Solvent: tetrahydrofuran with refluxing

Melting point: 52°–56° C. $R_f$ value: 0.15 (silica gel; methylene chloride)

(2) 3-(3-benzyloxyphenyl)propanol

Solvent: tetrahydrofuran with refluxing $R_f$ value: 0.23 (silica gel; methylene chloride)

EXAMPLE LVII

Dimethyl (4-bromophenyl)malonate 3.8 g of sodium hydride (55% in paraffin oil) are washed in dry toluene and then suspended in 100 ml of dry toluene. At 60° C., a solution of 10 g of methyl (4-bromophenyl)acetate and 11 ml of dimethylcarbonate in 10 ml of toluene are added dropwise within 30 minutes. The reaction mixture is stirred for a further 3½ hours at 60° C. and the precipitate formed is suction filtered. After the precipitate has been washed with toluene it is added in batches to a mixture of 100 ml of saturated aqueous common salt solution and 25 ml of glacial acetic acid. The mixture is extracted with diethylether, the ether phase is dried and evaporated down. The residue is triturated with petroleum ether, suction filtered and dried.

Yield: 7 g (56% of theory), Melting point: 77°–79° C. $R_f$ value: 0.41 (silica gel; cyclohexane/ethyl acetate=3:1) Calculated: C, 46.02; H, 3.86; Br, 27.83; Found: C, 45.99; H, 3.86; Br, 27.88;

EXAMPLE LVIII

2-Aminoindane-5-acetic acid hydrochloride 3.6 g of methyl 2-aminoindane-5-acetate-hydrochloride are refluxed for 3 hours in 160 ml of semiconcentrated hydrochloric acid. The hydrochloric acid is distilled off and the remaining product is triturated with a little ethanol, suction filtered and dried in vacuo.

Yield: 2.5 g (73.5% of theory), Melting point: 225°–230° C.

EXAMPLE LIX

3-[4-(tert.Butyloxycarbonylamino)butyl]phenol 13.5 g of 1-benzyloxy-3-[4-(tert.butyloxycarbonylamino)butyl]-benzene are shaken with 6 g of palladium (10% on activated charcoal) in 200 ml of ethyl acetate at 40° C. under a hydrogen pressure of 3 bar. After 5 minutes the theoretical hydrogen uptake has ended. The mixture is cooled and filtered and the filtrate is evaporated down.

Yield: 9.6 g (95% of theory), $R_f$ value: 0.51 (silica gel; methylene chloride/ethanol=15:1)

The following is obtained analogously:

(1) 4-[4-(tert.butyloxycarbonylamino)butyl]phenol $R_f$ value: 0.33 (silica gel; cyclohexane/ethyl acetate=5:2)

EXAMPLE LX

Benzyl 3-(3-benzyloxyphenyl)propionate 16.6 g of 3-(3-hydroxyphenyl)propionic acid, 27.7 g of potassium carbonate and 36 ml of benzyl bromide in 150 ml of dimethylformamide are stirred at ambient temperature for 17 hours. Then another 10 g of potassium carbonate and 10 ml of benzyl bromide are added and the mixture is stirred for 7 hours at ambient temperature, then for one day at 50° C. and later for one day at 100° C. After cooling, the mixture is added to 1 liter of water, extracted with ethyl acetate and the organic phase is dried over sodium sulphate and evaporated down. After chromatography over a silica gel column with cyclohexane/methylene chloride (5:1), 17.7 g (51% of theory) are obtained.

$R_f$ value: 0.76 (silica gel; methylene chloride)

59

The following is obtained analogously:
(1) Benzyl 3-(4-benzyloxyphenyl)propionate
$R_f$ value: 0.63 (silica gel; methylene chloride)

EXAMPLE LXI

4-[3-(Benzyloxycarbonylamino)propyl]phenol 2.5 g of 4-(3-aminopropyl)phenol are dissolved in 8.3 ml of 2N sodium hydroxide solution and at 0° to 5° C., 5 ml of 4N sodium hydroxide solution and 3.2 g of benzyl chloroformate in 3 ml of toluene are added in batches thereto, with stirring. The mixture is stirred for 18 hours at ambient temperature, then acidified with dilute hydrochloric acid, extracted with ethyl acetate and the organic phase is dried over sodium sulphate, filtered over activated charcoal and evaporated down. The crude product is purified over a silica gel column with methylene chloride/methanol (100:1).

Yield: 3.1 g (66% of theory), $R_f$ value: 0.51 (silica gel; methylene chloride/methanol=15:1)

EXAMPLE LXII 4-(4-Methoxyphenyl)butyronitrile 12.4 g of sodium cyanide are dissolved in 60 ml of dimethylsulphoxide with heating to 100° C. and 57.3 g of 3-(4-methoxyphenyl)propyliodide are added dropwise so that the temperature remains between 100°–120° C. The mixture is left to stand for 16 hours at ambient temperature, stirred into 200 ml of water, extracted with ether and the organic phases are evaporated down.

Yield: 97 g (100% of theory), $R_f$ value: 0.22 (silica gel; cyclohexane/ethyl acetate=5:1)

EXAMPLE LXIII 4-(4-Benzyloxyphenyl)butyronitrile 29.4 g of 3-(4-benzyloxyphenyl)-1-methanesulphonyloxy-propane are dissolved in 300 ml of dimethylformamide, 6 g of sodium cyanide are added and the mixture is heated for 2 days to 100° C. The solvent is distilled off under a high vacuum, the residue is stirred with water and extracted with ethyl acetate. The residue remaining after evaporation of the ethyl acetate is purified by chromatography over silica gel (eluant: methylene chloride).

Yield: 16.6 g (72% of theory), $R_f$ value: 0.72 (silica gel; methylene chloride)

The following is obtained analogously:
(1) 4-(3-benzyloxyphenyl)butyronitrile
$R_f$ value: 0.69 (silica gel; methylene chloride/cyclohexane=1:1)

EXAMPLE LXIV (3R,5S)-3-Allyl-5-cyanomethyl-1-(3-phenylpropyl)-2-pyrrolidinone 56.6 g of (3R,5S)-3-allyl-1-(3-phenylpropyl)-5-[(p-toluenesulphonyloxy)methyl]- 2-pyrrolidinone are dissolved in 60 ml of dimethylformamide, mixed with 7.8 g of sodium cyanide and stirred for 45 minutes at 90° C. 500 ml of ice water are added to the mixture, which is then extracted with ether. After the ether has been evaporated down the product is left as an oil.

60

Yield: 36.6 g (98% of theory), $R_f$ value: 0.41 (silica gel; ether/petroleum ether=10:1 (after developing twice)

The following is obtained analogously:
(1) 5-(4-methoxyphenyl)valeric acid nitrile
Prepared from 4-[4-(methanesulphonyloxy)butyl]-anisole and sodium cyanide.
$R_f$ value: 0.44 (silica gel; cyclohexane/ethyl acetate=5:1)

EXAMPLE LXV

2-Cyano-5-hydroxyindane 19.6 g of 5-acetoxy-2-cyanoindane are dissolved in 200 ml of methanol, 20 g of potash are added and the mixture is refluxed for one hour. The solids are filtered off, the filtrate is evaporated down, mixed with dilute hydrochloric acid and extracted with ethyl acetate. The ethyl acetate phase is treated with activated charcoal, filtered over silica gel and concentrated by evaporation.

$R_f$ value: 0.47 (silica gel; methylene chloride/methanol=15:1)

EXAMPLE LXVI

5-Acetyl-2-cyanoindane 40 g of aluminium chloride are suspended in 180 ml of 1,2-dichloroethane and 13.2 ml of acetyl chloride are added with stirring. Then 17.2 g of 2-cyanoindane are added in batches, whilst the temperature is kept below 40° C. The mixture is stirred for a further 3 hours at ambient temperature, poured onto ice, made strongly acidic with hydrochloric acid and extracted with methylene chloride to which methanol has been added. The organic phases are washed with saturated saline solution and water and concentrated after drying with sodium sulphate. On trituration with diisopropylether, the product crystallises out.

Yield: 19.3 g (87% of theory), $R_f$ value: 0.34 (silica gel; cyclohexane/ethyl acetate=2:1)

The following is obtained analogously:
(1) 5-acetyl-2-(acetylaminomethyl)indane
Melting point: 90°–92° C.

EXAMPLE LXVII

5-Acetoxy-2-cyanoindane

A mixture of 18.4 g of 5-acetyl-2-cyanoindane, 34 g of m-chloroperoxybenzoic acid and 300 ml of chloroform is stirred for one week at ambient temperature, with the exclusion of light. The solid constituents are filtered off, the filtrate is diluted with 300 ml of methylene chloride and extracted successively with sodium sulphite solution, sodium bicarbonate solution and saturated saline solution. The crude product left behind when the organic phase is concentrated is further processed in this form.

Yield: 19.6 g (98% of theory), $R_f$ value: 0.44 (silica gel; cyclohexane/ethyl acetate=2:1)

EXAMPLE LXVIII 4-(3-Cyanophenyl)butyric acid 12.7 g of 4-(3-aminophenyl)butyric acid-hydrochloride are dissolved in 50 ml of water and 5 ml of concentrated hydrochloric acid. At 0° to –5° C. a solution of 4.07 g of sodium nitrite in 20 ml of water is added dropwise to this solution over a period of 30 minutes. This solution is added dropwise at 70° C. to a mixture of 40 ml of water, 17.3 g of potassium cyanide and 5.9 g of copper(I)-cyanide. It is maintained at this temperature for a further 15 minutes, cooled to ambient temperature and is adjusted to a pH of 5 to 6 with glacial acetic acid. The mixture is extracted with ethyl acetate and the crude product remaining after evaporation is purified by chromatography over silica gel (eluant: methylene chloride/methanol=50:1).

Yield: 4.5 g (40% of theory), $R_f$ value: 0.27 (silica gel; methylene chloride/methanol=19:1)

The following is obtained analogously:

(1) 2-cyano-7-methoxy-9,10-dihydrophenanthrene $R_f$ value: 0.52 (silica gel; methylene chloride/cyclohexane 3:1)

EXAMPLE LXIX 2-(Aminomethyl)indane-5-carboxylic acid-hydrochloride 7.5 g of 2-(acetylaminomethyl)indane-5-carboxylic acid are refluxed for 2 days in 180 ml of semi-concentrated hydrochloric acid. The product remaining on evaporation is used directly.

Yield: 6.6 g (90% of theory), $R_f$ value: 0.34 (silica gel; methanol with 2% aqueous ammonia)

The following is obtained analogously:

(1) 2-aminoindane-5-carboxylic acid-hydrochloride $R_f$ value: 0.67 (silica gel; methanol/conc. aqueous ammonia=1:0.02)

EXAMPLE LXX 2-(Acetylaminomethyl)indane-5-carboxylic acid 18 g of 5-acetyl-2-(acetylaminomethyl)indane are stirred together with a solution of 47 g of sodium hydroxide in 500 ml of water and 15 ml of bromine for 64 hours at ambient temperature. 7.5 ml of 40% sodium bisulphite solution are added and the mixture is extracted with ether. The aqueous phase is adjusted to pH 4 with sulphuric acid and evaporated down to 250 ml in vacuo. The precipitate formed is filtered off and the filtrate is extracted with methylene chloride. The organic phase is concentrated by evaporation and the residue is triturated in crystalline form with ethyl acetate.

Yield: 7.5 g (41% of theory), Melting point: 184°–185° C.

The following is obtained analogously:

(1) 2-acetylaminoindane-5-carboxylic acid $R_f$ value: 0.31 (silica gel; methylene chloride/ethanol= 15:1)

EXAMPLE LXXI 2-(Acetylaminomethyl)indane 29.6 g of 2-aminomethylindane are dissolved in 200 ml of ethyl acetate, 35 ml of triethylamine are added and 14.3 ml of acetylchloride are added dropwise thereto, whilst cooling with ice. The mixture is stirred for one hour at ambient temperature, filtered to remove the precipitate, the filtrate is washed with dilute hydrochloric acid and evaporated down.

Yield: 35.5 g (96% of theory), $R_f$ value: 0.56 (silica gel; methylene chloride/cyclohexane/methanol/conc. aqueous ammonia=68:15:15:2)

EXAMPLE LXXII 2-(N-Phthalimidomethyl)indane-5-sulphochloride 7.4 g of 2-(N-phthalimidomethyl)indane are stirred in batches into 15 ml of chlorosulphonic acid cooled to 0° C. The mixture is stirred for a further 30 minutes at ambient temperature, poured onto 200 ml of ice water and the solid product precipitated is filtered off.

Yield: 9.4 g (94% of theory), $R_f$ value: 0.39 (silica gel; cyclohexane/ethyl acetate=2:1)

The following is obtained analogously:

(1) 2-(N-phthalimido)indane-5-sulphochloride $R_f$ value: 0.41 (silica gel; cyclohexane/ethyl acetate=2:1)

EXAMPLE LXXIII 2-(N-Phthalimidomethyl)indane

A mixture of 7.4 g of 2-aminomethylindane, 8.9 g of phthalic acid anhydride and 40 ml of dioxane is refluxed for 4 hours. After cooling it is poured into water, the precipitate is filtered off and triturated with methylene chloride. The methylene chloride phase is dried with sodium sulphate and evaporated down.

Yield: 7.4 g (53% of theory), $R_f$ value: 0.91 (silica gel; methylene chloride/cyclohexane/methanol/conc. aqueous ammonia=68:15:15:2)

EXAMPLE LXXIV

2-Aminomethylindane-5-acetic acid

A mixture of 25.5 g of the reaction product obtained in Example LXXV (containing about 17 g of 2-(acetylaminomethyl)-indane-5-thioacetic acid-morpholide), 20 g of potassium hydroxide dissolved in 30 ml of water, and 20 ml of ethanol is refluxed for one day. The mixture is substantially evaporated in vacuo, 200 ml of ice water are added to the residue and it is extracted with methylene chloride. The aqueous phase is neutralised with hydrochloric acid, whereupon the product is precipitated. Another fraction is obtained by evaporating the mother liquor.

Yield: 7.0 g (64% of theory), Melting point: 249° C. (decomp.)

EXAMPLE LXXV 2-(Acetylaminomethyl)indane-5-thioacetic acid-morpholide

A mixture of 12.3 g of 5-acetyl-2-(acetylaminomethyl)indane, 2.6 g of sulphur and 10.8 ml of morpholine is heated to 140° C. for one day. The reaction mixture obtained is used directly in Example LXXIV.

EXAMPLE LXXVI 4-(4-Hydroxybutyl)anisole 100 g of 4-(4-methoxyphenyl)-butyric acid, dissolved in 500 ml of tetrahydrofuran, are added dropwise to a boiling solution of 30.3 g of lithium alanate in 1000 ml of tetrahydrofuran. The mixture is refluxed for a further 4 hours, then after cooling, 30 ml of water, 30 ml of 20% sodium hydroxide solution and finally a further 90 ml of water are added dropwise thereto, the precipitate is filtered off and evaporated down.

Yield: 89.8 g (97% of theory), $R_f$ value: 0.71 (silica gel; methylene chloride/cyclohexane/methanol/conc. aqueous ammonia=68:15:15:2)

EXAMPLE LXXVII

3-Cyano-4'-methoxy-diphenylsulphide

At 0° C. and with stirring, a solution of 1.6 g of sodium nitrite in 10 ml of water is slowly added dropwise to a solution of 5 g of 4-amino-3-cyano-4'-methoxy-diphenylsulphide in 5 ml of water and 15 ml of conc. hydrochloric acid. After it has all been added, the mixture is stirred for a further 15 minutes at 0° C., then 40 ml of ethanol are added and the mixture is heated to 40° C. It is slowly heated to 80° C. and the temperature is maintained until no further nitrogen development can be detected. Then it is poured onto ice and extracted with ethyl acetate. The combined extracts are dried and evaporated to dryness. The residue is purified over a silica gel column, using dichloromethane as eluant. The 3-cyano-4'-methoxy-diphenylsulphide thus obtained is triturated with petroleum ether and suction filtered.

Yield: 2.7 g (58% of theory), $R_f$ value: 0.65 (silica gel; dichloromethane)

EXAMPLE LXXVIII

4-Amino-3-cyano-4'-methoxy-diphenylsulphide 13.2 g of tin dichloride-monohydrate are added in batches and with stirring to a solution of 5 g of 3-cyano-4'-methoxy-4-nitrodiphenylsulphide in 25 ml of conc. hydrochloric acid. After 2 hours stirring, it is poured onto a mixture of ice and 10N sodium hydroxide solution and extracted with dichloromethane. The combined extracts are dried, shaken with activated charcoal and evaporated to dryness in vacuo. The residue is crystallised with ether/petroleum ether.

Yield: 3.7 g (82% of theory), Melting point: 95°–98° C. Calculated: C, 65.38; H, 5.76; N, 11.44; Found: C, 65.20; H, 5.80; N, 11.54;

EXAMPLE LXXIX

3-Cyano-4'-methoxy-4-nitro-diphenylsulphide

At ambient temperature and with stirring, a hot solution of 34 g of 5-chloro-2-nitro-benzonitrile in ethanol is added dropwise to a solution of 23 ml of 4-methoxythiophenol and 20.2 g of sodium carbonate in 250 ml of water. After it has all been added, the mixture is refluxed for 4 hours. The yellow precipitate is suction filtered and dissolved in dichloromethane. This solution is dried and evaporated to dryness in vacuo. The residue is crystallised from toluene/petroleum ether.

Yield: 45.2 g (85% of theory), Melting point: 99°–101° C.

EXAMPLE LXXX (3R,5S)-3-Allyl-5-aminomethyl-1-(3-phenylpropyl)-2-pyrrolidinone 73 g of (3R,5S)-3-allyl-1-(3-phenylpropyl)-5-(N-phthalimidomethyl)-2-pyrrolidinone, 600 ml of 40% aqueous methylamine solution and 1000 ml of toluene are stirred vigorously for 4½ days at ambient temperature. The toluene phase is separated off and the aqueous phase is extracted once more with toluene. The combined toluene phases are evaporated down and the residue is purified over a silica gel column with methylene chloride/methanol (10:1). 41.6 g (89% of theory) of an oil are obtained.

$R_f$ value: 0.40 (silica gel; methylene chloride/methanol= 10:1)

The following are obtained analogously:

(1) (3R,S;4S,R)-3-allyl-4-aminomethyl-1-(4-methoxybenzyl)-2-pyrrolidinone $R_f$ value: 0.28 (silica gel; ethyl acetate/methanol=9:1) Calculated: C, 70.04; H, 8.08; N, 10.21; Found: C, 69.98; H, 8.25; N, 10.00;

(2) (3S,5S)-5-aminomethyl-3-carboxymethyl-1-(3-phenylpropyl)-2-pyrrolidinone

By working up and chromatographic purification of the aqueous phase.

Melting point: 188°–192° C. $R_f$ value: 0.44 (silica gel; methanol/water=95:5)

(3) (3R,5S)-3-allyl-5-aminomethyl-1-(4-phenoxybutyl)-2-pyrrolidinone $R_f$ value: 0.46 (silica gel; methylene chloride/methanol= 10:1)

(4) (3R,5S)-3-allyl-5-aminomethyl-1-(2-phenylethyl)-2-pyrrolidinone $R_f$ value: 0.37 (silica gel; methylene chloride/methanol= 10:1)

(5) (3R,5S)-3-allyl-5-aminomethyl-1-benzyl-2-pyrrolidinone $R_f$ value: 0.43 (silica gel; methylene chloride/methanol= 10:1)

(6) (3R,5S )-3 -allyl-5-aminomethyl-1-[2-(1-naphthyl)-ethyl]-2-pyrrolidinone $R_f$ value: 0.28 (silica gel; methylene chloride/methanol= 12:1)

(7) (3R, 5S)-3-allyl-5-aminomethyl-1-[2-(2-naphthyl)-ethyl]-2-pyrrolidinone $R_f$ value: 0.27 (silica gel; methylene chloride/methanol= 12:1)

(8) (3R,5S)-3-allyl-5-aminomethyl-1-isobutyl-2-pyrrolidinone $R_f$ value: 0.62 (silica gel; methylene chloride/methanol= 4:1)

(9) (3R,5S)-5-aminomethyl-3-(1-buten-4-yl)-1-(3-phenylpropyl)-2-pyrrolidinone $R_f$ value: 0.40 (silica gel; methylene chloride/methanol= 9:1)

(10) (3R,S;4S,R)-4-aminomethyl-3-carboxymethyl-1-(3-phenylpropyl)-2-pyrrolidinone By working up and chromatographic purification of the aqueous phase.

$R_f$ value: 0.38 (silica gel; ethanol/water=10:1)

(11) 3-amino-3'-nitro-biphenyl $R_f$ value: 0.35 (silica gel; methylene chloride/cyclohexane=2.5:1) after developing twice)

EXAMPLE LXXXI (3R,5S)-3-Allyl-5-hydroxymethyl-pyrrolidine 40 g of (3R,5S)-3-allyl-5-hydroxymethyl-2-pyrrolidinone dissolved in 500 ml of dry tetrahydrofuran are added dropwise at ambient temperature to 13.3 g of lithium aluminium hydride in 600 ml of dry tetrahydrofuran. Then the mixture is stirred for 2 hours at ambient temperature and 4 hours at 60° C. and then left to stand for 18 hours at ambient temperature. After the addition of another 5.7 g of lithium aluminium hydride, the mixture is stirred for a further 4 hours at 60° C. and left to stand for 18 hours at ambient temperature. The mixture is cooled with ice water and water is carefully added dropwise thereto, with stirring. The precipitate is suction filtered, washed with ether and the combined filtrates are evaporated down in vacuo.

Yield: 35.4 g (97.2% of theory), $R_f$ value: 0.22 (silica gel; methylene chloride/methanol=3:1)

EXAMPLE LXXXII (S)-1-(Benzyloxycarbonyl)-5-[(trityloxy)methyl]-2-pyrrolidinone A solution of 160 g of (S)-5-[(trityloxy)methyl]-2-pyrrolidinone in 1600 ml of dry tetrahydrofuran is mixed within 35 minutes at −65° C. with 179 ml of a 2.5M solution of butyl lithium in hexane. After 10 minutes at −65° C. a solution of 66.8 ml of benzyl chloroformate in 100 ml of dry tetrahydrofuran is added dropwise and the resulting mixture is stirred for one hour. Then 200 ml of saturated saline solution are added and tetrahydrofuran is evaporated off. The residue is distributed between 3.5 liters of ethyl acetate and 200 ml of water, the organic phase is separated off and washed twice each with water and saline solution. The organic phase is separated off, dried and evaporated down. The crude product is recrystallised from a little ethanol.

Yield: 181 g (82% of theory), Melting point: 103°–105° C. $R_f$ value: 0.53 (silica gel; cyclohexane/ethyl acetate=2:1) Calculated: C, 78.19; H, 5.95; N, 2.85; Found: C, 78.34; H, 6.00; N, 3.10;

EXAMPLE LXXXIII (3S,5S)-3-[(tert.Butyloxycarbonyl)methyl]-5-hydroxymethyl-2-pyrrolidinone 246 g of (3S,5S)-1-(benzyloxycarbonyl)-3-[(tert.butyloxycarbonyl)methyl]-5 -[(trityloxy)methyl]-2-pyrrolidinone in 1.6 liters of tert.butanol are hydrogenated for 1½ days at 50° C. under a hydrogen pressure of 5 bar with 50 g of palladium (10% on activated charcoal). The mixture is then diluted with acetone, the catalyst is filtered off and the filtrate is evaporated down. The residue is stirred with a total of 2 liters of petroleum ether in 3 batches. The remaining oil is dried in vacuo.

Yield: 77.8 g (84% of theory), $R_f$ value: 0.43 (silica gel; ethyl acetate/methanol=15:1)

The following is obtained analogously:

(1) (3S,5S)-5-hydroxymethyl-3-[(methoxycarbonyl)methyl]-2-pyrrolidinone $R_f$ value: 0.36 (silica gel; methylene chloride/methanol=10:1)

EXAMPLE LXXXIV (3R,5S)-3-(3-Cyanopropyl)-1-isobutyl-5-iodomethyl-2-pyrrolidinone 2.5 g of (3R,5S)-3-(3-cyanopropyl)-1-isobutyl-5-[(methanesulphonyloxy)methyl]-2 -pyrrolidinone, 2 g of sodium iodide and 80 ml of dry acetone are refluxed for one day. After cooling, the mixture is filtered and the filtrate is evaporated down, taken up in methylene chloride and washed with water, sodium disulphite solution and water again. The organic phase is dried, filtered and evaporated down. The residue is purified by silica gel chromatography with toluene/acetone=4:1.

Yield: 1.95 g (71% of theory), Melting point: 45°–50° C. $R_f$ value: 0.35 (silica gel; toluene/acetone=4:1)

The following is obtained analogously:

(1) 1-(4'-cyano-4-biphenylyl)-4-iodomethyl-2-pyrrolidinone

Melting point: 178°–179° C. $R_f$ value: 0.75 (silica gel; ethyl acetate)

EXAMPLE LXXXV (3S,5S)-5-(2-Hydroxyethyl)-3-[(methoxycarbonyl)methyl]-1-(3-phenylpropyl)- 2-pyrrolidinone 36.5 g (3S,5S)-5-(2-aminoethyl)-3-[(methoxycarbonyl)methyl]-1-(3 -phenylpropyl)-2-pyrrolidinone are dissolved in 750 ml of water with the addition of 13 ml of glacial acetic acid and at 0° C. a solution of 15.8 g of sodium nitrite in 50 ml of water is added over a period of 10 minutes. The mixture is stirred for 30 minutes and heated for 3 hours over a steam bath. It is extracted with methylene chloride and the residue remaining after concentration of the organic phase is purified by chromatography on silica gel (eluant: acetone/methanol=40:3).

Yield: 19 g (52% of theory), $R_f$ value: 0.70 (silica gel; acetone/methanol=7.5:1)

EXAMPLE LXXXVI (3S,5S)-5-[2-[N-(3'-Nitro-3-biphenylyl)benzylamino]-ethyl-]3-[(methoxycarbonyl)methyl]-1-(3-phenylpropyl)-2-pyrrolidinone 3.2 g of (3S,5S)-3-[(methoxycarbonyl)methyl]-5-[2-[( 3'-nitro-3-biphenylyl)amino]ethyl]-1-(3-phenylpropyl)-2-pyrrolidinone are heated with 1.5 ml of ethyl-diisopropylamine and 0.75 ml of benzylchloride for 7 hours, with stirring, over a steam bath. The reaction mixture is stirred with ether and water, the ether phase is concentrated by evaporation and the residue remaining is purified by chromatography on silica gel (eluant: ether).

Yield: 3.1 g (83% of theory), $R_f$ value: 0.43 (silica gel; ethyl acetate/cyclohexane=1:1)

EXAMPLE LXXXVII

4-[cis/trans-4-Aminocyclohexyl]benzoic acid

A solution of 23.5 g of 4-[4-(dibenzylamino)cyclohex-1-enyl]-benzoic acid-hydrochloride in 1.2 liters of glacial acetic acid and 23.5 g of palladium dihydroxide on charcoal is hydrogenated under a hydrogen pressure of 5 bar at 50° C. After the reaction has ended the catalyst is filtered off and washed several times with glacial acetic acid. The filtrate is evaporated down, the solid residue is triturated with ethanol, suction filtered and dried in vacuo.

Yield: 9.8 g (86% of theory), $R_f$ value: 0.19 (silica gel; methylene chloride/methanol/conc. aqueous ammonia= 4:1:0.25)

The following are obtained analogously:

(1) 4-[cis-4-(aminomethyl)cyclohexyl]phenol

Prepared by hydrogenation of the cis/trans mixture, triturating the crude product with ethanol and isolating the undissolved matter.

$R_f$ value: 0.59 (silica gel; methylene chloride/methanol/ conc. aqueous ammonia=4:1:0.25)

(2) 4-[trans-4-(aminomethyl)cyclohexyl]phenol

Prepared by hydrogenating the cis/trans mixture and working up the ethanol mother liquor.

$R_f$ value: 0.59 (silica gel; methylene chloride/methanol/ conc. aqueous ammonia=4:1:0.25)

(3) cis/trans-4-(4-aminocyclohexyl)phenol $R_f$ value: 0.52 (silica gel; methylene chloride/methanol/ conc. aqueous ammonia=4:1:0.25)

EXAMPLE LXXXVIII

4-[4-(Dibenzylamino)cyclohex-1-enyl]benzoic acid-hydrochloride

A solution of 1.0 g of 2-[4-[4-(dibenzylamino)-1-hydroxycyclohexyl]phenyl]- 4,4-dimethyl-oxazoline in 40 ml of 3N hydrochloric acid is refluxed for 30 minutes. The solution is allowed to cool and the crystalline precipitate is suction filtered. The solid matter is dissolved in 40 ml of methanol, 10 ml of 10N sodium hydroxide solution are added and the suspension is again refluxed for 30 minutes. It is left to cool, suction filtered and the filtrate is evaporated using a rotary evaporator. The aqueous phase remaining is acidified with 32% hydrochloric acid, with cooling, the precipitate is suction filtered and washed with water. The solids are then recrystallised from methanol.

Yield: 0.65 g (68% of theory), $R_f$ value: 0.71 (silica gel; methylene chloride/methanol=8:2)

EXAMPLE LXXXIX 4-(Dibenzylamino)cyclohexanone 9.4 g of absolute dimethylsulphoxide are slowly added dropwise to a solution of 7.4 g of oxalylchloride in 150 ml of absolute methylene chloride, under inert gas at −78° C. The mixture is stirred for 10 minutes and then a solution of 15.0 g of trans-4-(dibenzylamino)cyclohexanol in 60 ml of absolute methylene chloride is added dropwise. The mixture is stirred for one hour at −78° C. and then 25.3 g of absolute triethylamine are added. The cooling bath is allowed to come up to ambient temperature overnight with stirring and the reaction solution is poured onto a 500 ml ice/water mixture. The aqueous phase is extracted three times with methylene chloride, the combined organic phases are washed once with water, the organic phase is dried over sodium sulphate and evaporated down. The residue obtained is purified by chromatography on silica gel with cyclohexane/ethyl acetate=4:1.

Yield: 13.9 g (95% of theory), $R_f$ value: 0.45 (silica gel; cyclohexane/ethyl acetate=4:1)

The following is obtained analogously:

(1) 4-(dibenzylaminomethyl)cyclohexanone $R_f$ value: 0.45 (silica gel; cyclohexane/ethyl acetate=4:1)

EXAMPLE XC trans-4-(Dibenzylamino)cyclohexanol 154 g of benzylbromide are added dropwise to a well stirred solution of 60.65 g of trans-4-amino-cyclohexanol-hydrochloride and 110.6 g of potassium carbonate in 700 ml of water/methanol=1:1 and the resulting mixture is stirred for 16 hours at ambient temperature. It is then refluxed for one hour, cooled and mixed with a little water. The solid precipitate is suction filtered, washed with water, dried and recrystallised from about 1.5 liters of cyclohexane.

Yield: 109 g (92% of theory), $R_f$ value: 0.57 (silica gel; methylene chloride/methanol=9:1)

The following is obtained analogously:

(1) cis/trans-4-(dibenzylaminomethyl)cyclohexanol $R_f$ value of trans product: 0.30 (silica gel; cyclohexane/ethyl acetate=6:1) $R_f$ value of cis product: 0.25 (silica gel; cyclohexane/ethyl acetate=6:1)

EXAMPLE XCI

4'-Cyano-4-methoxy-3-methylsulphenyl-biphenyl

A solution of 17 g of crude 4'-aminocarbonyl-4-methoxy-3-methylsulphenyl-biphenyl in 70 ml of phosphorus oxychloride is heated over a steam bath for 1 hour. The reaction solution is cooled and mixed with water and extracted with ethyl acetate. The organic phase is washed with water, dried, filtered over activated charcoal and evaporated down. The crude product obtained is purified by chromatography over silica gel with cyclohexane/ethyl acetate=2:1.

Yield: 4.6 g (29% of theory), $R_f$ value: 0.63 (silica gel; cyclohexane/ethyl acetate=2:1)

EXAMPLE XCII

4'-Aminocarbonyl-4-methoxy-3-methylsulphenyl-biphenyl

A suspension of 18 g of crude 4'-aminocarbonyl-4-methoxy-3-mercapto-biphenyl in 200 ml of 5% methanolic potassium hydroxide solution is stirred for 3 hours at ambient temperature. 10 ml of dimethylsulphate are added and the mixture is stirred for 30 minutes at ambient temperature. It is then diluted with water, the precipitate is suction filtered and dried in vacuo.

Yield: 17 g (90% of theory), $R_f$ value: 0.50 (silica gel; methylene chloride/cyclohexane/methanol/conc. aqueous ammonia=7:1.5:1.5:0.2)

EXAMPLE XCIII

4'-Aminocarbonyl-4-methoxy-3-mercapto-biphenyl 8.3 g of red phosphorus and 0.4 g of iodine in 35 ml of glacial acetic acid are refluxed and 30.8 g of 4'-cyano-3-chlorosulphonyl-4-methoxy-biphenyl are added in batches thereto. The mixture is refluxed for 5 hours, then water is added and the mixture is refluxed for a further 30 minutes. It is left to cool, the reaction solution is transferred into water and the precipitate is removed by suction filtering. The precipitate is dissolved in ethyl acetate, dried over sodium sulphate, filtered over activated charcoal and evaporated down.

Yield: 42.5 g crude product, $R_f$ value: 0.16 (silica gel; cyclohexane/ethyl acetate=2:1)

The following is obtained analogously:

(1) 4'-cyano-4-mercapto-biphenyl

The reaction solution is not heated any more after the addition of water.

$R_f$ value: 0.61 (silica gel; cyclohexane/ethyl acetate=2:1)

EXAMPLE XCIV

4'-Cyano-3-chlorosulphonyl-4-methoxy-biphenyl 31 g of 4'-cyano-4-methoxy-biphenyl-3-sodium sulphonate are refluxed for 3½ hours in 150 ml of phosphorus oxychloride. The mixture is left to cool and the reaction solution is transferred into water. The precipitate is suction filtered and dried in vacuo.

Yield: 30.8 g (100% of theory), $R_f$ value: 0.28 (silica gel; cyclohexane/ethyl acetate=2:1)

The following is obtained analogously:

(1) 4-chlorosulphonyl-4'-cyano-biphenyl $R_f$ value: 0.61 (silica gel; cyclohexane/ethyl acetate=2:1)

EXAMPLE XCV

4'-Cyano-biphenyl-4-sodium sulphonate

At –10° C. 75 ml of chlorosulphonic acid are added dropwise to a solution of 50 g of 4-cyanobiphenyl in 400 ml of absolute methylene chloride. The mixture is stirred for 15 minutes at –10° C., then for a further 2 hours at ambient temperature. The reaction solution is transferred into 1.5 liters of water and the methylene chloride is evaporated off. After the addition of 60 g of sodium hydroxide the fine precipitate is suction filtered and dried in vacuo.

Yield: 78.6 g (100% of theory), $R_f$ value: 0.33 (silica gel; methylene chloride/methanol/conc. aqueous ammonia= 4:1:0.25)

The following is obtained analogously:

(1) 4'-cyano-4-methoxy-biphenyl-3-sodium sulphonate $R_f$ value: 0.31 (silica gel; methylene chloride/methanol/ conc. aqueous ammonia=4:1:0.25)

EXAMPLE XCVI (3R,5S)-5-Hydroxymethyl-3-[5-(methoxycarbonyl)-pentyl]-1-(3-phenylpropyl)- 2-pyrrolidinone Prepared analogously to Example 29 by esterification of (3R,5S)-3-(5-carboxypentyl)-5-hydroxymethyl-1-(3-phenylpropyl)-2 -pyrrolidinone with methanol.

$R_f$ value; 0.67 (silica gel; methylene chloride/methanol= 9:1)

The following is obtained analogously:

(1) (3S, 5S) -5-aminocarbonylmethyl-3-[(methoxycarbonyl)methyl]-1-(3-phenylpropyl)-2 -pyrrolidinone $R_f$ value: 0.58 (silica gel; methylene chloride/methanol= 9:1)

EXAMPLE XCVII (3R,5S)-3-Allyl-5-aminocarbonylmethyl-1-(3-phenylpropyl)-2-pyrrolidinone Hydrogen chloride gas is introduced into a solution of 9 g of (3R,5S)-3-allyl-5-cyanomethyl-1-(3-phenylpropyl)-2-pyrrolidinone in 5 ml of formic acid for 2½ hours and the mixture is stirred overnight. Then a further 5 ml of formic acid are added and the mixture is stirred for 2 hours at 50° C., for 2½ days at ambient temperature and then a further 2 hours at 50° C. The reaction solution is poured onto water, extracted twice with ethyl acetate, washed with water, dried and evaporated down. The residue is purified by chromatography over a silica gel column.

Yield: 6.1 g (64% of theory), $R_f$ value: 0.16 (silica gel; ethyl acetate/methanol=40:1)

EXAMPLE XCVIII (3R,5S)-3-(5-Carboxypentyl)-5-hydroxymethyl-1-(3-phenylpropyl)-2-pyrrolidinone A solution of 17.0 g of (3R,5S)-3-(5-cyanopentyl)- 1-(3-phenylpropyl)-5-[(trityloxy)methyl]-2-pyrrolidinone in 100 ml of acetic acid and 150 ml of conc. hydrochloric acid is heated for 15 hours over a steam bath. The solution is then evaporated down and the residue is dissolved in water and ether. The ether phase is separated off and extracted with sodium hydroxide solution. The aqueous phase is extracted with ether, then the aqueous phase is acidified with 2N hydrochloric acid and extracted with ether/tetrahydrofuran mixture. The organic phase is dried and evaporated down.

Yield: 8.8 g (84% of theory), $R_f$ value: 0.20 (silica gel; methylene chloride/ethanol=19:1)

EXAMPLE XCIX

4'-Cyano-3-biphenylyl carboxylic acid

A solution of 1.7 g of methyl 4'-cyano-3-biphenylylcarboxylate and 1.28 g of lithium hydroxide hydrate in 12.5 ml of tetrahydrofuran and 10 ml of water is stirred for 16 hours at ambient temperature. Then the solvent is evaporated off, the residue is acidified with 1N hydrochloric acid and the precipitate is suction filtered.

Yield: 1.0 g (59% of theory), $R_f$ value: 0.23 (silica gel; methylene chloride/methanol/conc. aqueous ammonia= 4:1:0.25)

EXAMPLE C

3-Chloro-1-(4-cyanophenyl)-1-propene

At –10° C., 8.6 g of mesylchloride are added dropwise to a well stirred solution of 7.5 g of 1-(4-cyanophenyl)-3-hydroxy-1-propene and 6.4 g of pyridine in 50 ml of absolute methylene chloride. Then the cooling bath is removed and the mixture is stirred for 2 days at ambient temperature. The reaction solution is transferred into 200 ml of 1N hydrochloric acid and extracted with methylene chloride. The organic phase is dried, concentrated by evaporation and the oil obtained is chromatographed with cyclohexane/ethyl acetate=4:1 on silica gel.

Yield: 4.8 g (58% of theory), $R_f$ value: 0.48 (silica gel; cyclohexane/ethyl acetate=4:1)

EXAMPLE CI

4-Hydroxymethyl-1-(4-methoxybenzyl)-2-pyrrolidinone 47.7 g of sodium borohydride are added in batches to 151 g of 1-(4-methoxybenzyl)-4-[(methoxycarbonyl)methyl]-2-pyrrolidinone in 1 liter of methanol. After 1 hour, a further 9.3 g of sodium borohydride and later 9.3 g and 5.2 g of sodium borohydride are added and the mixture is then stirred for 2½ days at ambient temperature. After evaporation, the residue obtained is divided between ethyl acetate and water, the organic phase is separated, dried, filtered and evaporated down.

Yield: 118.8 g (94% of theory), $R_f$ value: 0.25 (silica gel; ethyl acetate)

EXAMPLE CII

2-Methoxy-7-nitro-9,10-dihydro-phenanthrene 8 g of 2-hydroxy-7-nitro-9,10-dihydro-phenanthrene are taken up in 250 ml of acetone and 35 ml of 1N sodium hydroxide solution and at ambient temperature 3.3 ml of dimethylsulphate are added dropwise thereto. After 30 minutes a further 3.5 ml of 1N sodium hydroxide solution and 0.35 ml of dimethylsulphate are added. The mixture is then heated for 45 minutes over a steam bath and after cooling extracted with 300 ml of ethyl acetate. After washing with 1N sodium hydroxide solution and water, the ethyl acetate phase is evaporated down and the residue is purified by chromatography on silica gel (eluant: methylene chloride/cyclohexane=1:2).

Yield: 7.4 g (88% of theory), $R_f$ value: 0.96 (silica gel; methylene chloride)

EXAMPLE CIII

2-Hydroxy-7-nitro-9,10-dihydro-phenanthrene 5.6 g of sodium nitrite are added to a solution of 16 g of 2-amino-7-nitro-9,10-dihydro-phenanthrene in 50 ml of concentrated sulphuric acid, with stirring, at −5° C., in the course of 30 minutes. The mixture is stirred for a further one and a half hours at −5° C. to 0° C., poured onto 500 ml of ice and heated for 45 minutes at 75° C. The mixture is extracted with ethyl acetate and the product obtained after evaporation of the ethyl acetate phase is purified by chromatography over silica gel (eluant: methylene chloride/methanol/conc. aqueous ammonia=75:1:0.1)

Yield: 8.1 g (50% of theory), $R_f$ value: 0.39 (silica gel; methylene chloride/methanol/conc. aqueous ammonia=30:1:0.1)

EXAMPLE CIV exo-5-(4-Cyanophenyl)bicyclo[2.2.1]heptan-exo-2-carboxylic acid

Under an inert gas atmosphere and with vigorous stirring, a solution of 3.38 g of exo-2-bicyclo[2.2.1]-heptene-carboxylic acid, 5.5 g of 4-iodobenzonitrile, 6.8 g of piperidine and 1.0 g of bis(triphenylphosphine)palladium-(II)-acetate in 30 ml of dimethylformamide is mixed with 2.8 g of formic acid. The reaction solution is heated to 60° C. for 4 hours, then cooled, mixed with water and extracted several times with ethyl acetate. The organic phase is dried over sodium sulphate and evaporated down. An oil is obtained which is chromatographed over silica gel with methylene chloride/methanol (20:1). The fractions obtained with an $R_f$ value of 0.58 (silica gel; methylene chloride/methanol=9:1) are evaporated down and the solids obtained are recrystallised from ethyl acetate.

Yield: 470 mg (8% of theory), Melting point: 210°–220° C. $R_f$ value: 0.58 (silica gel; methylene chloride/methanol=9:1)

EXAMPLE CV

1-(4'-Cyano-4-biphenylyl)-4-(O,O'-dimethylphosphonomethyl)-2-pyrrolidinone 2.2 g of dimethylphosphate in 100 ml of dimethylformamide are mixed with 830 mg of sodium hydride (55% in paraffin oil). After 15 minutes stirring at ambient temperature, 7.5 g of 1-(4'-cyano-4-biphenylyl)-4-iodomethyl-2-pyrrolidinone are added and the mixture is stirred for 3 hours at ambient temperature and a further hour at 40° C. After cooling, the mixture is slightly acidified with glacial acetic acid, ice water is added and the mixture is extracted with ethyl acetate. The organic phase is washed with water and saline solution, then dried and evaporated down. After purification over a silica gel column with methylene chloride/methanol (97.5:2.5 and 96:4) 1.5 g (21% of theory) are obtained.

Melting point: 154°–157° C. $R_f$ value: 0.30 (silica gel; toluene/dioxane/ethanol/glacial acetic acid=90:10:10:6) Calculated: C, 62.50; H, 5.51; N, 7.29; Found: C, 62.68; H, 5.61; N, 7.13;

EXAMPLE CVI

(3S,5S)-5-Aminomethyl-3-[(methoxycarbonyl)methyl]-1-(3-phenylpropyl)-2-pyrrolidinone-hydrochloride A mixture of 77 g of (3S,5S)-5-[(methanesulphonyloxy)methyl]-3-[(methoxycarbonyl)-methyl]-1-(3-phenylpropyl)-2-pyrrolidinone, 17 g of sodium azide, 500 ml of methanol and 50 ml of water is shaken for 6 hours at 100° C. in a pressurised container. After cooling, 10 g of 10% palladium charcoal are added and the mixture is hydrogenated for 3 hours at ambient temperature under 5 bar of hydrogen pressure. After the catalyst has been filtered off, the mixture is evaporated down in vacuo, the residue is taken up with ethyl acetate, the organic phase is washed with sodium bicarbonate solution, treated with activated charcoal and evaporated down. The residue is taken up with methanol, mixed with ethereal hydrochloric acid and the solvent is distilled off.

Yield: 53.2 g (78% of theory), $R_f$ value: 0.25 (silica gel; methylene chloride/ethanol=15:1)

EXAMPLE CVII

(3S,5S)-5-(2-Aminoethyl)-3-[(methoxycarbonyl)-methyl]-1-(3-phenylpropyl)-2-pyrrolidinone-hydrochloride Prepared analogously to Example 42 by reacting (3S,5S)-5-(2-aminoethyl)-3-carboxymethyl-1-(3-phenylpropyl)-2-pyrrolidinone with methanolic hydrochloric acid $R_f$ value: 0.42 (silica gel; toluene/dioxane/methanol/conc. aqueous ammonia (20:50:20:5)

Preparation of the end products:

EXAMPLE 1

(3R,5S)-3-Allyl-5-[(4'-cyano-4-biphenylyl)oxymethyl]-1-methyl-2-pyrrolidinone Prepared analogously to Example I from (3R,5S)-3-allyl-5-[(4'-cyano-4-biphenylyl)oxymethyl]-2-pyrrolidinone and methyliodide.

$R_f$ value: 0.31 (silica gel; cyclohexane/ethyl acetate=4:6) Calculated: C, 76.28; H, 6.40; N, 8.08; Found: C, 75.99; H, 6.77; N, 7.87;

The following are obtained analogously:

(1) (3R,5S)-3-allyl-1-[(aminocarbonyl)methyl]-5-[(4'-cyano-4-biphenylyl)oxymethyl]-2-pyrrolidinone $R_f$ value: 0.60 (silica gel; ethyl acetate/methanol=9:1) Calculated: C, 70.93; H, 5.95; N, 10.79; Found: C, 70.96; H, 5.90; N, 10.64;

(2) (3R,5S)-3-allyl-5-[(4'-cyano-4-biphenylyl)oxymethyl]-1-[(methoxycarbonyl)methyl]-2-pyrrolidinone $R_f$ value: 0.70 (silica gel; ethyl acetate/cyclohexane=4:1) Calculated: C, 71.27; H, 5.98; N, 6.93; Found: C, 71.19; H, 6.18; N, 6.81;

(3) (3S,5S)-5-[(4'-cyano-4-biphenylyl)oxymethyl]-1-[3-(3,4-dimethoxyphenyl)propyl]-3-[(methoxycarbonyl)methyl]-2-pyrrolidinone $R_f$ value: 0.47 (silica gel; ethyl acetate/cyclohexane=4:1)

(4) (3S,5S)-5-[(4'-cyano-4-biphenylyl)oxymethyl]-3-[(methoxycarbonyl)methyl]-1-[3-(4-hexyloxyphenyl)-propyl]-2-pyrrolidinone $R_f$ value: 0.83 (silica gel; ethyl acetate)

(5) (3S,5S)-1-[3-(4-tert.butylphenyl)propyl]-5-[(4'-cyano-4-biphenylyl)oxymethyl]-3-[(methoxycarbonyl)methyl]-2-pyrrolidinone $R_f$ value: 0.78 (silica gel; ethyl acetate)

(6) (3S,5S)-5-[(4'-cyano-4-biphenylyl)oxymethyl]-3-[(methoxycarbonyl)methyl]-1-[3-(3-trifluoromethylphenyl)propyl]-2-pyrrolidinone $R_f$ value: 0.78 (silica gel; ethyl acetate)

(7) (3S,5S)-5-[(4'-cyano-4-biphenylyl)oxymethyl]-1-[3-(2,4-dichlorophenyl)propyl]-3-[(methoxycarbonyl)methyl]-2-pyrrolidinone $R_f$ value: 0.71 (silica gel; ethyl acetate)

(8) (3S,5S)-5-[(4'-cyano-4-biphenylyl)oxymethyl]-3-[(methoxycarbonyl)methyl]-1-[3-(3-benzylphenyl)propyl]-2-pyrrolidinone $R_f$ value: 0.81 (silica gel; ethyl acetate)

(9) (3S,5S)-5-[(4'-cyano-4-biphenylyl)oxymethyl]-1-(4,4-diphenylbutyl)-3-[(methoxycarbonyl)methyl]-2-pyrrolidinone $R_f$ value: 0.81 (silica gel; ethyl acetate)

(10) (3S,5S)-5-[(4'-cyano-4-biphenylyl)oxymethyl]-3-[(methoxycarbonyl)methyl]-1-[3-(4-methylsulphenyl)propyl]-2-pyrrolidinone $R_f$ value: 0.78 (silica gel; ethyl acetate)

(11) (3S,5S)-1-(4-biphenylylmethyl)-5-[(4'-cyano-4-biphenylyl)-oxymethyl]-3-[(methoxycarbonyl)methyl]-2-pyrrolidinone $R_f$ value: 0.81 (silica gel; ethyl acetate)

(12) (3S,5S)-3-[(tert.butyloxycarbonyl)methyl]-5-[(4'-cyano-4-biphenylyl)oxymethyl]-1-[(pyrrolidin-N-carbonyl)methyl]-2-pyrrolidinone $R_f$ value: 0.35 (silica gel; ethyl acetate)

(13) (3S,5S)-3-[(tert.butyloxycarbonyl)methyl]-5-[(4'-cyano-4-biphenylyl)oxymethyl]-1-[(morpholin-N-carbonyl)methyl]-2-pyrrolidinone $R_f$ value: 0.44 (silica gel; ethyl acetate)

EXAMPLE 2

(3R,5S)-3-Allyl-5-[(4'-cyano-4-biphenylyl)oxymethyl]-1-(3-phenylpropyl)-2-pyrrolidinone To a mixture of 132 g of 4-cyano-4'-hydroxybiphenyl, 500 ml of dimethylformamide and 112.2 g of potash, a solution of 246 g of (3R,5S)-3-allyl-5-[(methanesulphonyloxy)methyl]-1-(3-phenylpropyl)-2-pyrrolidinone is added with stirring. The mixture is stirred for a further 20 hours at 60° C. and then the dimethylformamide is largely evaporated off in vacuo. The residue is stirred with 750 ml of ethyl acetate and 500 ml of water. The ethyl acetate phase is washed with dilute saline solution and the aqueous phases are extracted again with ethyl acetate. The organic phases are evaporated down and stirred with 1000 ml of ether and seed crystals. The crude product obtained is filtered off and washed with ether. From the mother liquors, another fraction is obtained by chromatography on silica gel (eluant: ether/concentrated aqueous ammonia 10:0.05). The crude products are recrystallised from methylene chloride/ether.

Yield: 257 g (85% of theory), Melting point: 74°–76° C.

The following are obtained analogously:

(1) (3S,5S)-5-[[4'-(Benzyloxycarbonylamidino)-4-biphenylyl]oxymethyl]-3-[(methoxycarbonyl)methyl]-1-phenyl-2-pyrrolidinone Melting point: 157°–159° C. $R_f$ value: 0.50 (silica gel; chloroform/methanol=95:5) Calculated: C, 71.05; H, 5.62; N, 7.10; Found: C, 70.98; H, 5.66; N, 7.07;

(2) (3R,5S)-3-allyl-5-[(4'-cyano-4-biphenylyl)oxymethyl]-1-(3-cyclohexylpropyl)-2-pyrrolidinone Melting point: 157°–159° C. $R_f$ value: 0.37 (silica gel; cyclohexane/ethyl acetate=7:3) Calculated: C, 78.91; H, 7.99; N, 6.13; Found: C, 79.00; H, 8.11; N, 5.94;

(3) (3R,5S)-3-allyl-5-[(4'-cyano-4-biphenylyl)oxymethyl]-1-(4-methoxybenzyl)-2-pyrrolidinone Melting point: 120°–122° C. $R_f$ value: 0.56 (silica gel; cyclohexane/ethyl acetate=1:1) Calculated: C, 76.97; H, 6.24; N, 6.19; Found: C, 76.95; H, 6.38; N, 6.26;

(4) (3S,5R)-3-allyl-5-[(4'-cyano-4-biphenylyl)oxymethyl]-1-(3-phenylpropyl)-2-pyrrolidinone $R_f$ value: 0.60 (silica gel; cyclohexane/ethyl acetate=1:1) Calculated: C, 79.97; H, 6.71; N, 6.22; Found: C, 80.10; H, 7.00; N, 6.00;

(5) (3R,5S)-3-allyl-5-[(4'-cyano-4-biphenylyl)oxymethyl]-2-pyrrolidinone

Melting point: 99°–101° C. $R_f$ value: 0.38 (silica gel; cyclohexane/ethyl acetate=1:4) Calculated: C, 75.88; H, 6.06; N, 8.43; Found: C, 75.86; H, 6.26; N, 8.36;

(6) (3R,5S)-3-allyl-5-[[4-[(4-cyanophenyl)aminocarbonyl]phenyl]oxymethyl]-1-(3-phenylpropyl)-2-pyrrolidinone $R_f$ value: 0.65 (silica gel; methylene chloride/ethanol=9:1)

(7) (3S,5S)-3-allyl-5-[(4'-cyano-4-biphenylyl)oxymethyl]-2-pyrrolidinone

Melting point: 169°–171° C. $R_f$ value: 0.27 (silica gel; ethyl acetate/cyclohexane=8:2) Calculated: C, 75.88; H, 6.06; N, 8.43; Found: C, 75.72; H, 6.14; N, 8.50;

(8) (3R,5S)-3-allyl-1-[2-(benzyloxy)ethyl]-5-[(4'-cyano-4-biphenylyl)oxymethyl]-2-pyrrolidinone $R_f$ value: 0.39 (silica gel; cyclohexane/ethyl acetate=1:1) Calculated: C, 77.23; H, 6.48; N, 6.00; Found: C, 76.97; H, 6.57; N, 5.97;

(9) (3S,5R)-3-allyl-5-[(4'-cyano-4-biphenylyl)oxymethyl]-2-pyrrolidinone

Melting point: 99°–101° C., $R_f$ value: 0.42 (silica gel; cyclohexane/ethyl acetate=1:4) Calculated: C, 75.88; H, 6.06; N, 8.43; Found: C, 75.75; H, 6.09; N, 8.17;

(10) (3S,5S)-3-[(tert.butyloxycarbonyl)methyl]-5-[(4'-cyano-4-biphenylyl)oxymethyl]-2-pyrrolidinone Potassium tert.butoxide was used as base.

Melting point: 158°–159° C., $R_f$ value: 0.50 (silica gel; ethyl acetate/cyclohexane=1:9) Calculated: C, 70.91; H, 6.45; N, 6.89; Found: C, 71.00; H, 6.69; N, 7.04;

(11) (S)-5-[(4'-cyano-4-biphenylyl)oxymethyl]-3,3-diallyl-2-pyrrolidinone $R_f$ value: 0.44 (silica gel; cyclohexane/ethyl acetate=1:1)

(12) (3R,S;4R,S)-3-allyl-4-[(4'-cyano-4-biphenylyl)oxymethyl]- 1-(4-methoxybenzyl)-2-pyrrolidinone $R_f$ value: 0.22 (silica gel; cyclohexane/ethyl acetate=2:1) Calculated: C, 76.97; H, 6.24; N, 6.19; Found: C, 77.10; H, 6.47; N, 5.98;

(13) (3S,5S)-5-[[4'-(N-benzyloxycarbonylamidino)-4-biphenylyl]oxymethyl]- 3-[(tert.butyloxycarbonyl)methyl]-2-pyrrolidinone Melting point: 136°–140° C. $R_f$ value: 0.39 (silica gel; ethyl acetate)

(14) (3S,5S)-5-[[4'-(N-benzyloxycarbonylamidino)-4-biphenylyl]oxymethyl]- 3-[(methoxycarbonyl)methyl]-2-pyrrolidinone Melting point: 160°–164° C. $R_f$ value: 0.43 (silica gel; ethyl acetate) Calculated: C, 67.56; H, 5.67; N, 8.15; Found: C, 67.31; H, 5.63; N, 8.09;

(15) (3S,5S)-5-[(7-cyano-9,10-dihydro-2-phenanthrenyl)oxymethyl]- 3-[(methoxycarbonyl)methyl]-2-pyrrolidinone $R_f$ value: 0.52 (silica gel; methylene chloride/methanol/conc. aqueous ammonia=30:1:0.1)

(16) (3R,S;4R,S)-3-allyl-4-[(4'-cyano-4-biphenylyl)oxymethyl]- 1-(4-methoxybenzyl)-3-methyl-2-pyrrolidinone $R_f$ value: 0.32 (silica gel; cyclohexane/ethyl acetate=2:1)

EXAMPLE 3

(3R,5S)-3-Allyl-5-[(4'-cyano-4-biphenylyl)oxymethyl]- 1-(3-phenylpropyl)-2-pyrrolidinone 3.9 g of 4-cyano-4'-hydroxybiphenyl in 30 ml of dry dimethylformamide are mixed with 9.8 g of cesium carbonate and vigorously stirred for 2 hours at ambient temperature. Then 7.03 g of (3R,5S)-3-allyl-5 -[(methanesulphonyloxy)methyl]-1-(3-phenylpropyl)-2-pyrrolidinone in 20 ml of dimethylformamide are added and the mixture is stirred for 18 hours at 55°–60° C. It is then cooled, poured into 200 ml of water and extracted three times with ethyl acetate. The combined organic phases are washed with water, dried over sodium sulphate and evaporated down. After purification over a silica gel column with cyclohexane/ethyl acetate=1:1 6.9 g (76% of theory) are obtained.

Melting point: 74°–76° C., $R_f$ value: 0.47 (silica gel; cyclohexane/ethyl acetate=1:1)

The following are obtained analogously:

(1) (3R,5S)-3-allyl-5-[(3-bromo-4'-cyano-4-biphenylyl)oxymethyl]- 1-(3-phenylpropyl)-2-pyrrolidinone $R_f$ value: 0.55 (silica gel; 1,2-dichloroethane/ethyl acetate=3:1) Calculated: C, 68.05; H, 5.52; N, 5.29; Br, 15.09; Found: C, 68.18; H, 5.61; N, 5.34; Br, 15.38;

(2) (3R,5S)-3-allyl-5-[(4'-cyano-3-nitro-4-biphenylyl)oxymethyl]- 1-(3-phenylpropyl)-2-pyrrolidinone $R_f$ value: 0.54 (silica gel; 1,2-dichloroethane/ethyl acetate=3:1) Calculated: C, 72.71; H, 5.90; N, 8.48; Found: C, 72.45; H, 5.79; N, 8.24;

(3) (3R,5S)-3-allyl-5-[(4'-cyano-3-trifluoromethyl-4-biphenylyl)-oxymethyl]- 1-(3-phenylpropyl)-2-pyrrolidinone $R_f$ value: 0.49 (silica gel; cyclohexane/ethyl acetate=1:1) Calculated: C, 71.80; H, 5.64; N, 5.40; Found: C, 71.51; H, 5.79; N, 5.06;

(4) (3R,5S)-3-allyl-5-[(4'-cyano-3-fluoro-4-biphenylyl)oxymethyl]- 1-(3-phenylpropyl)-2-pyrrolidinone $R_f$ value: 0.51 (silica gel; cyclohexane/ethyl acetate=1:1) Calculated: C, 76.90; H, 6.24; N, 5.98; Found: C, 77.10; H, 6.59; N, 5.94;

(5) (3R,5S)-3-allyl-5-[(4'-cyano-2,3-dimethyl-4-biphenylyl)-oxymethyl]- 1-(3-phenylpropyl)-2-pyrrolidinone $R_f$ value: 0.65 (silica gel; cyclohexane/ethyl acetate=2:1) Calculated: C, 80.30; H, 7.16; N, 5.85; Found: C, 79.98; H, 7.32; N, 5.59;

(6) (3S,5S)-5-[(4'-cyano-2'-methyl-4-biphenylyl)oxymethyl]- 3-[(methoxycarbonyl)methyl]-1-(3-phenylpropyl)-2-pyrrolidinone $R_f$ value: 0.39 (silica gel; cyclohexane/ethyl acetate=1:1) Calculated: C, 74.97; H, 6.50; N, 5.64; Found: C, 74.70; H, 6.51; N, 5.64;

(7) (3R,3S)-3-allyl-5-[[4-[4-(tert.butyloxycarbonylamino)butyl]phenyl]oxymethyl]- 1-(4-phenylbutyl)-2-pyrrolidinone $R_f$ value: 0.58 (silica gel; cyclohexane/ethyl acetate=1:1)

(8) (3R,5S)-3-allyl-5-[(6-cyano-2-naphthyl)oxymethyl]- 1-( 3-phenylpropyl)-2-pyrrolidinone $R_f$ value: 0.55 (silica gel; cyclohexane/ethyl acetate=1:1)

(9) (3R,5S)-3-allyl-5-[[4-[4-(tert.butyloxycarbonylamino)butyl]phenyl]oxymethyl]- 1-[2-(2-naphthyl)ethyl]-2-pyrrolidinone Melting point: 79°–83° C. $R_f$ value: 0.35 (silica gel; cyclohexane/ethyl acetate=2:1)

(10) (3R,5S)-3-allyl-5-[[4-[4-(tert.butyloxycarbonylamino)butyl]phenyl]oxymethyl]- 1-[2-(1-naphthyl)ethyl]-2-pyrrolidinone $R_f$ value: 0.43 (silica gel; cyclohexane/ethyl acetate=2:1)

(11) (3R,5S)-3-allyl-1-benzyl-5-[ [4-[4 -(tert.butyloxycarbonylamino)butyl]phenyl]oxymethyl]-2-pyrrolidinone $R_f$ value: 0.35 (silica gel; cyclohexane/ethyl acetate=2:1)

(12) (3R,5S)-3-allyl-5-[[4-[4-(tert.-butyloxycarbonylamino)butyl]phenyl]oxymethyl]-1-(4-phenoxybutyl)-2-pyrrolidinone $R_f$ value: 0.86 (silica gel; ethyl acetate)

(13) (3R,5S)-3-allyl-5-[[4-[4-(tert.butyloxycarbonylamino)butyl]phenyl]oxymethyl]-1-(2-phenylethyl)-2-pyrrolidinone $R_f$ value: 0.26 (silica gel; cyclohexane/ethyl acetate=2:1)

(14) (3R,5S)-3-allyl-5-[[4-3-(benzyloxycarbonylamino)propyl]phenyl]oxymethyl]- 1-(3-phenylpropyl)-2-pyrrolidinone $R_f$ value: 0.54 (silica gel; tert.butylmethylether/petroleum ether=4:1)

(15) (3R,5S)-3-allyl-5-[[4-[(tert.butyloxycarbonylamino)methyl]phenyl)oxymethyl]- 1-(3-phenylpropyl)-2-pyrrolidinone $R_f$ value: 0.37 (silica gel; methylene chloride/methanol=20:1)

(16) (3R, 5S)-3-allyl-5-[[3-[(tert.butyloxycarbonylamino)methyl]phenyl)oxymethyl]- 1-(3-phenylpropyl)-2-pyrrolidinone $R_f$ value: 0.34 (silica gel; methylene chloride/methanol=20:1)

(17) (3R,5S)-3-allyl-5-[[3-[4-(tert.butyloxycarbonylamino)butyl]phenyl]oxymethyl]- 1-(3-phenylpropyl)-2-pyrrolidinone $R_f$ value: 0.45 (silica gel; methylene chloride/methanol=20:1)

(18) (3R,5S)-3-allyl-5-[[3-[2-(tert.butyloxycarbonylamino)ethyl]phenyl]oxymethyl]-1-(3-phenylpropyl)-2-pyrrolidinone $R_f$ value: 0.39 (silica gel; methylene chloride/methanol=20:1)

(19) (3R,5S)-3-allyl-5-[[4-[2-(tert.butyloxycarbonylamino)ethyl]phenyl]oxymethyl]-1-(3-phenylpropyl)-2-pyrrolidinone $R_f$ value: 0.22 (silica gel; methylene chloride/methanol=50:1)

(20) (3R,5S)-3-allyl-5-[[4-[2-(tert.butyloxycarbonylamino)ethyl]phenyl]oxymethyl]-1-isobutyl-2-pyrrolidinone $R_f$ value: 0.33 (silica gel; methylene chloride/methanol=20:1)

(21) (3R,5S)-3-allyl-5-[[4-[cis-4-(tert.butyloxycarbonylamino)cyclohexyl]phenyl]oxymethyl]-1-(3-phenylpropyl)-2-pyrrolidinone $R_f$ value: 0.77 (silica gel; methylene chloride/methanol=9:1)

(22) (3R,5S)-3-allyl-5-[[4-[trans-4-(tert.butyloxycarbonylamino)cyclohexyl]phenyl]oxymethyl]-1-(3-phenylpropyl)-2-pyrrolidinone $R_f$ value: 0.79 (silica gel; methylene chloride/methanol=9:1)

(23) (3R,5S)-3-allyl-5-[(4'-cyano-4-biphenylyl)oxymethyl]-3-methyl-1-(3-phenylpropyl)-2-pyrrolidinone $R_f$ value: 0.38 (silica gel; cyclohexane/ethyl acetate=2:1)

(24) (3R,5S)-3-allyl-1-benzyl-5-[(4'-cyano-4-biphenylyl)-oxymethyl]-2-pyrrolidinone $R_f$ value: 0.41 (silica gel; cyclohexane/ethyl acetate=2:1)

(25) (3R,5S)-3-allyl-5-[(4'-cyano-4-biphenylyl)oxymethyl]-1-(2-phenylethyl)-2-pyrrolidinone $R_f$ value: 0.39 (silica gel; cyclohexane/ethyl acetate=2:1)

(26) (3R,5S)-3-allyl-5-[(4'-cyano-4-biphenylyl)oxymethyl]-1-(4-phenylbutyl)-2-pyrrolidinone $R_f$ value: 0.35 (silica gel; cyclohexane/ethyl acetate=2:1)

(27) (3R,5S)-3-allyl-5-[(4'-cyano-4-biphenylyl)oxymethyl]-1-(4-phenyloxybutyl)-2-pyrrolidinone $R_f$ value: 0.38 (silica gel; cyclohexane/ethyl acetate=2:1)

(28) (3R,5S)-3-allyl-5-[(4'-cyano-4-biphenylyl)oxymethyl]-1,3-bis-(3-phenylpropyl)-2-pyrrolidinone $R_f$ value: 0.60 (silica gel; cyclohexane/ethyl acetate=2:1)

(29) (3R,5S)-3-allyl-3-(n-butyl)-5-[(4'-cyano-4-biphenylyl)oxymethyl]-1-(3-phenylpropyl)-2-pyrrolidinone $R_f$ value: 0.66 (silica gel; cyclohexane/ethyl acetate=2:1)

(30) (3R,5S)-3-allyl-5-[[4-(3-cyanopropyl)phenyl]oxymethyl]-3-methyl-1-(3-phenylpropyl)-2-pyrrolidinone $R_f$ value: 0.36 (silica gel; cyclohexane/ethyl acetate=2:1)

(31) (3R,5S)-3-allyl-5-[[4-(3-cyanopropyl)phenyl]oxymethyl]-1-(3-phenylpropyl)-2-pyrrolidinone $R_f$ value: 0.39 (silica gel; cyclohexane/ethyl acetate=2:1)

(32) (3R,5S)-3-allyl-1-[3-(4-benzyloxyphenyl)propyl]-5-[[4-[4-(tert.butyloxycarbonylamino)butyl]phenyl]oxymethyl]-2-pyrrolidinone $R_f$ value: 0.55 (silica gel; toluene/acetone=2:1)

(33) (3R,5S)-3-allyl-5-[(2-cyano-5-indanyl)oxymethyl]-1-(3-phenylpropyl)-2-pyrrolidinone $R_f$ value: 0.32 (silica gel; cyclohexane/ethyl acetate=2:1)

(34) (3S,5S)-5-[(7-cyano-9-keto-2-fluorenyl)oxymethyl]-3-[(methoxycarbonyl)methyl]-1-(3-phenylpropyl)-2-pyrrolidinone $R_f$ value: 0.55 (silica gel; ethyl acetate/cyclohexane=1:1) (after two runs)

(35) (3S,5S)-3-allyl-5-[(4'-cyano-4-biphenylyl)oxymethyl]-1-(3-phenylpropyl)-2-pyrrolidinone Prepared from the mother liquors of the preparation of the (3R,5S) isomer.

$R_f$ value: 0.55 (silica gel; ether/conc. aqueous ammonia=10:0.1)

(36) (3R,5S)-3-allyl-5-[[3-[3-(tert.butyloxycarbonylamino)propyl]phenyl]oxymethyl]-1-(3-phenylpropyl)-2-pyrrolidinone $R_f$ value: 0.36 (silica gel; cyclohexane/ethyl acetate=2:1)

(37) (3R,5S)-3-allyl-5-[[4-[5-(tert.butyloxycarbonylamino)pentyl]phenyl]oxymethyl]-3-(phenylpropyl)-2-pyrrolidinone $R_f$ value: 0.50 (silica gel; cyclohexane/ethyl acetate=2:1)

(38) (3R,S;5R,S)-3-allyl-5-[[4-[(tert.butyloxycarbonylamino)-methyl]phenyl]oxymethyl]-3-methyl-1-(3-phenylpropyl)-2-pyrrolidinone $R_f$ value: 0.44 (silica gel; cyclohexane/ethyl acetate=2:1)

(39) (3R,S;5R,S)-3-allyl-5-[[4-[2-(tert.butyloxycarbonylamino)ethyl]phenyl]oxymethyl]-3-methyl-1-(3-phenylpropyl)-2-pyrrolidinone $R_f$ value: 0.39 (silica gel; cyclohexane/ethyl acetate=2:1)

(40) (3R,S;5R,S)-3-allyl-5-[[4-[4-(tert.butyloxycarbonylamino)butyl]phenyl]oxymethyl]-3-methyl-1-(3-phenylpropyl)-2-pyrrolidinone $R_f$ value: 0.35 (silica gel; cyclohexane/ethyl acetate=2:1)

(41) (3R,5S)-3-allyl-5-[[4-[(4-cyanophenyl)carbonylamino]phenyl]oxymethyl]-1-(3-phenylpropyl)-2-pyrrolidinone $R_f$ value: 0.63 (silica gel; ethyl acetate/cyclohexane=3:1)

(42) (3R,5S)-3-allyl-5-[[4-[(4-cyanophenyl)aminosulphonyl]phenyl]oxymethyl]-1-(3-phenylpropyl)-2-pyrrolidinone $R_f$ value: 0.84 (silica gel; ethyl acetate/cyclohexane=4:1)

(43) (3S,5S)-5-[[4-[(3-cyanophenyl)sulphenyl]phenyl]oxymethyl]-3-[(methoxycarbonyl)methyl]-1-(3-phenylpropyl)-2-pyrrolidinone $R_f$ value: 0.53 (silica gel; ethyl acetate/cyclohexane=1:1)

(44) (3S,5S)-5-[[4-[(3-cyanophenyl)carbonyl]phenyl]oxymethyl]-3-[(methoxycarbonyl)methyl]-1-(3-phenylpropyl)-2-pyrrolidinone $R_f$ value: 0.36 (silica gel; ethyl acetate/cyclohexane=1:1)

(45) (3R,5S)-3-[4-(tert.butyloxycarbonylamino)butyl]-5-[[4'-[(methoxycarbonyl)methyl]-4-biphenylyl]oxymethyl]-1-methyl-2-pyrrolidinone $R_f$ value: 0.28 (silica gel; cyclohexane/ethyl acetate=1:4)

(46) (3S,5S)-5-[[4-[cis-4-(tert.butyloxycarbonylaminomethyl)cyclohexyl]phenyl]oxymethyl]-3-[(methoxycarbonyl)-methyl]-1-(3-phenylpropyl)-2-pyrrolidinone $R_f$ value: 0.45 (silica gel; cyclohexane/ethyl acetate=1:1)

(47) (3S,5S)-5-[[4-[trans-4-(tert.butyloxycarbonylaminomethyl)cyclohexyl]phenyl]oxymethyl]-3-[(methoxycarbonyl)methyl]-1-(3-phenylpropyl)-2-pyrrolidinone $R_f$ value: 0.45 (silica gel; cyclohexane/ethyl acetate=1:1)

(48) (3S,5S)-5-[(4'-cyano-3-methylsulphenyl-4-biphenylyl)-oxymethyl]-3-[(methoxycarbonyl)methyl]-1-(3-phenylpropyl)-2-pyrrolidinone $R_f$ value: 0.75 (silica gel; methylene chloride/methanol=15:1)

(49) (3R,5S)-5-[(4'-cyano-4-biphenylyl) oxymethyl]-3-[(methoxycarbonyl)propyl]-1-(3-phenylpropyl)-2-pyrrolidinone $R_f$ value: 0.40 (silica gel; methylene chloride/methanol=19:1)

(50) (3R,5S)-5-[(4'-cyano-4-biphenylyl)oxymethyl]-3-[5-(methoxycarbonyl)pentyl]-1-(3-phenylpropyl)-2-pyrrolidinone $R_f$ value: 0.33 (silica gel; ether/petroleum ether=9:1)

(51) (3S,5S)-3-[(tert.butyloxycarbonyl)methyl]-5-[(4'-cyano- 3'-fluoro-4-biphenylyl)oxymethyl]-2-pyrrolidinone Melting point: 142°–144° C. $R_f$ value: 0.29 (silica gel; methylene chloride/ethyl acetate=8:2) Calculated: C, 67.91; H, 5.94; N, 6.60; Found: C, 67.79; H, 5.94; N, 6.64;

(52) (3S,5S)-3-[(tert.butyloxycarbonyl)methyl]-5-[(3'-chloro- 4'-cyano-4-biphenylyl)oxymethyl]-2-pyrrolidinone Melting point: 140°–142 ° C. $R_f$ value: 0.36 (silica gel; cyclohexane/ethyl acetate=3:7) Calculated: C, 65.38; H, 5.72; N, 6.35; Cl, 8.04; Found: C, 65.32; H, 5.75; N, 6.41; Cl, 8.11;

(53) (3S,5S)-5-[(3-bromo-4'-cyano-4-biphenylyl)oxymethyl]- 3-[(methoxycarbonyl)methyl]-2-pyrrolidinone $R_f$ value: 0.52 (silica gel; methylene chloride/methanol=15:1) Calculated: C, 56.90; H, 4.32; N, 6.32; Br, 18.03; Found: C, 56.78; H, 4.41; N, 6.17; Br, 17.92

(54) (3S,5S)-5-[(6-guanidinocarbonyl-2-naphthyl)oxymethyl]- 3-[(methoxycarbonyl)methyl]-2-pyrrolidinone

EXAMPLE 4

(3R,S;5S,R)-3-Allyl-5-[4-[(4-cyanobutyl)oxy]phenyl]-1-(3-phenylpropyl)-2-pyrrolidinone A mixture of 3.6 g of (3R,S;5S,R)-3-allyl-5-(4-hydroxyphenyl)- 1-(3-phenylpropyl)-2-pyrrolidinone, 1.8 g of 5-bromovaleric acid nitrile, 7.6 g of potassium carbonate and 100 ml of acetone is refluxed for 24 hours. After cooling, the mixture is filtered and the filtrate is evaporated down in vacuo. The oily residue is chromatographed over a silica gel column with chloroform.

Yield: 3.9 g (88.3% of theory), $R_f$ value: 0.10 (silica gel; chloroform) Calculated: C, 77.85; H, 7.74; N, 6.73; Found: C, 77.56; H, 7.84; N, 6.66;

EXAMPLE 5

(3S,5S)-5-[(4'-Cyano-4-biphenylyl)oxymethyl]-3-[(methoxycarbonyl)methyl]-1-(3-phenylpropyl)-2-pyrrolidinone To a mixture of 203 g of (3R,5S)-3-allyl-5-[(4'-cyano-4-biphenylyl)oxymethyl]-1-(3-phenylpropyl)-2-pyrrolidinone, 1800 ml of methylene chloride, 1800 ml of acetonitrile and 2 g of ruthenium trichloride-trihydrate, a solution of 580 g of sodium metaperiodate in 3200 ml of water is added dropwise within 1.75 hours, with vigorous stirring, whilst the temperature is maintained between 25° and 31° C. The mixture is then stirred for 4 hours and another 1800 ml of methylene chloride are added. The organic phase is separated off and washed successively with 1000 ml of water, 1000 ml of 10% sodium disulphite solution and 1000 ml of water. The aqueous phases are extracted twice more with 350 ml of methylene chloride. The combined methylene chloride phases are dried with magnesium sulphate, treated with activated charcoal and evaporated down. The foamy residue of (3S,5S)-3-carboxymethyl-5-[(4'-cyano-4-biphenylyl)oxymethyl]-1-(3-phenylpropyl)-2-pyrrolidinone which remains is used further in this form.

Yield: 208 g (84% of theory), $R_f$ value: 0.66 (silica gel; methylene chloride/methanol=15:1) (after developing twice).

The crude product obtained above is dissolved in 1200 ml of methanol, mixed with 10 ml of saturated methanolic hydrochloric acid and stirred for 16 hours at ambient temperature. It is evaporated down and the residue is purified by chromatography on silica gel (eluant: cyclohexane/ethyl acetate=1.5:1). The oily product remaining after evaporation of the eluant is stirred with 750 ml of ether and seed crystals. The crystalline product obtained is filtered off and washed twice with 150 ml of ether. Another fraction is obtained from the mother liquors.

Yield: 147 g (67% of theory over both stages), Melting point: 75°–76° C.

The following are obtained analogously:

(1) (3S,5S)-5-[(4'-cyano-4-biphenylyl)oxymethyl]-1-(3-cyclohexylpropyl)- 3-[(methoxycarbonyl)methyl]-2-pyrrolidinone $R_f$ value: 0.59 (silica gel; cyclohexane/ethyl acetate=4:6) Calculated: C, 73.74; H, 7.43; N, 5.73; Found: C, 73.52; H, 7.60; N, 5.46;

Intermediate product:

(3S,5S)-3-carboxymethyl-5-[(4'-cyano-4-biphenylyl)oxymethyl]- 1-(3-cyclohexylpropyl)-2-pyrrolidinone $R_f$ value: 0.24 (silica gel; cyclohexane/ethyl acetate=4:6)

(2) (3S,5S)-5-[(4'-cyano-4-biphenylyl)oxymethyl]-3-[(methoxycarbonyl)methyl]- 2-pyrrolidinone Melting point: 140°–142° C. $R_f$ value: 0.42 (silica gel; methylene chloride/methanol=100:2) Calculated: C, 69.22; H, 5.53; N, 7.69; Found: C, 68.95; H, 5.59; N, 7.50;

Intermediate product:

(3S,5S)-3-carboxymethyl-5-[(4'-cyano-4-biphenylyl)oxymethyl]- 2-pyrrolidinone $R_f$ value: 0.35 (silica gel; 1,2-dichloroethane/ethyl acetate/glacial acetic acid=100:30:5)

(3) (3S,5S)-5-[(4'-cyano-4-biphenylyl)oxymethyl]-3-[(methoxycarbonyl)methyl]- 1-methyl-2-pyrrolidinone $R_f$ value: 0.41 (silica gel; methylene chloride/methanol=100:2) Calculated: C, 69.83; H, 5.86; N, 7.40; Found: C, 69.60; H, 6.10; N, 7.20;

(4) (3S,5S)-5-[(3-bromo-4'-cyano-4-biphenylyl)oxymethyl]- 3-[(methoxycarbonyl)methyl]-1-(3-phenylpropyl)-2-pyrrolidinone $R_f$ value: 0.62 (silica gel; methylene chloride/ethyl acetate=4:1) Calculated: C, 64.17; H, 5.21; N, 4.99; Found: C, 64.20; H, 5.43; N, 5.06;

Intermediate product:

(3S,5S)-5-[(3-bromo-4'-cyano-4-biphenylyl)-oxymethyl] -3-carboxymethyl- 1-(3-phenylpropyl)-2-pyrrolidinone $R_f$ value: 0.75 (silica gel; ethyl acetate/methanol=9:1)

(5) (3S,5S)-5-[(4'-cyano-3-nitro-4-biphenylyl)oxymethyl]- 3-[(methoxycarbonyl)methyl]-1-(3-phenylpropyl)-2-pyrrolidinone $R_f$ value: 0.53 (silica gel; 1,2-dichloroethane/ethyl acetate=3:1) Calculated: C, 68.30; H, 5.54; N, 7.97; Found: C, 68.28; H, 5.34; N, 7.75;

Intermediate product:

(3S,5S)-3-carboxymethyl-5-[(4'-cyano-3-nitro-4-biphenylyl)-oxymethyl]- 1-(3-phenylpropyl)-2-pyrrolidinone $R_f$ value: 0.51 (silica gel; ethyl acetate/methanol=10:1)

(6) (3R,5R)-5-[(4'-cyano-4-biphenylyl)oxymethyl]-3-[(methoxycarbonyl)methyl]- 1-(3-phenylpropyl)-2-pyrrolidinone $R_f$ value: 0.70 (silica gel; cyclohexane/ethyl acetate=2:3)
Calculated: C, 74.66; H, 6.27; N, 5.81; Found: C, 74.51; H, 6.47; N, 5.63;

(7) (3S,5S)-5-[(4'-cyano-3-trifluoromethyl-4-biphenylyl)oxymethyl]-3-[(methoxycarbonyl)methyl]1-(3-phenylpropyl)-2-pyrrolidinone $R_f$ value: 0.45 (silica gel; cyclohexane/ethyl acetate=1:1)
Calculated: C, 67.62; H, 5.31; N, 5.09; Found: C, 67.73; H, 5.48; N, 5.08;

Intermediate product:
(3S,5S)-3-carboxymethyl-5-[(4'-cyano-3-trifluoromethyl-4-biphenylyl)-oxymethyl]-1-(3-phenylpropyl)-2-pyrrolidinone $R_f$ value: 0.58 (silica gel; ethyl acetate/methanol=20:1)

(8) (3S,5S)-5-[(4'-cyano-3-fluoro-4-biphenylyl)oxymethyl]-3-[(methoxycarbonyl)methyl]-1-(3-phenylpropyl)-2-pyrrolidinone $R_f$ value: 0.34 (silica gel; cyclohexane/ethyl acetate=1:1)

Intermediate product:
(3S,5S)-3-carboxymethyl-5-[(4'-cyano-3-fluoro-4-biphenylyl)-oxymethyl]- 1-(3-phenylpropyl)-2-pyrrolidinone $R_f$ value: 0.61 (silica gel; ethyl acetate/methanol=0:1)

(9) (3S,5S)-5-[(4'-cyano-2,3-dimethyl-4-biphenylyl)oxymethyl]-3-[(methoxycarbonyl)methyl]-1-(3-phenylpropyl)-2-pyrrolidinone $R_f$ value: 0.50 ( silica gel; cyclohexane/ethyl acetate=4:1)
Calculated: C, 75.27; H, 6.71; N, 5.49; Found: C, 74.96; H, 7.00; N, 5.37;

Intermediate product:
(3S,5S)-3-carboxymethyl-5-[(4'-cyano-2,3-dimethyl-4-biphenylyl)-oxymethyl]- 1-(3-phenylpropyl)-2-pyrrolidinone $R_f$ value: 0.73 (silica gel; ethyl acetate/methanol=19:1)

(10) (3S,5S)-5-[[trans-4-(4-cyanophenyl)cyclohexyl]oxymethyl]-3-[(methoxycarbonyl)methyl]-1-(3-phenylpropyl)-2-pyrrolidinone-semihydrate $R_f$ value: 0.52 (silica gel; cyclohexane/ethyl acetate=1:1)
Calculated: C, 72.41; H, 7.50; N, 5.63; Found: C, 72.35; H, 7.61; N, 5.62;

(11) (3S,5S)-5-[(4'-cyano-4-biphenylyl)oxymethyl]-3-[(methoxycarbonyl)methyl]- 3-methyl-1-(3-phenylpropyl)-2-pyrrolidinone $R_f$ value: 0.74 (silica gel; methylene chloride/methanol=15:1)

Intermediate product:
(3S,5S)-3-carboxymethyl-5-[(4'-cyano-4-biphenylyl)oxymethyl]-3-methyl-1-(3-phenylpropyl)-2-pyrrolidinone $R_f$ value: 0.40 (silica gel; methylene chloride/cyclohexane/methanol/conc. aqueous ammonia=68:15:15:2)

(12) (3S,5S)-1-benzyl-5-[(4'-cyano-4-biphenylyl)oxymethyl]- 3-[(methoxycarbonyl)methyl]-2-pyrrolidinone $R_f$ value: 0.69 (silica gel; methylene chloride/methanol=15:1)

Intermediate product:
(3S,5S)-1-benzyl-3-carboxymethyl-5-[(4'-cyano-4-biphenylyl)oxymethyl]-2-pyrrolidinone $R_f$ value: 0.38 (silica gel; methylene chloride/cyclohexane/methanol/conc. aqueous ammonia=68:15:15:2)

(13) (3S,5S)-5-[(4'-cyano-4-biphenylyl)oxymethyl]-3-[(methoxycarbonyl)methyl]- 1-(2-phenylethyl)-2-pyrrolidinone $R_f$ value: 0.44 (silica gel; cyclohexane/ethyl acetate/methanol=64:32:4)

Intermediate product:
(3S,5S)-3-carboxymethyl-5-[(4'-cyano-4-biphenylyl)oxymethyl]-1-(2-phenylethyl)-2-pyrrolidinone $R_f$ value: 0.41 (silica gel; methylene chloride/cyclohexane/methanol/conc. aqueous ammonia=68:15:15:2)

(14) (3S,5S)-5-[(4'-cyano-4-biphenylyl)oxymethyl]-3-[(methoxycarbonyl)methyl]- 1-(4-phenylbutyl)-2-pyrrolidinone $R_f$ value: 0.41 (silica gel; cyclohexane/ethyl acetate/methanol=64:32:4)

Intermediate product:
(3S,5S)-3-carboxymethyl-5-[(4'-cyano-4-biphenylyl)oxymethyl]-1-(4-phenylbutyl)-2-pyrrolidinone $R_f$ value: 0.38 (silica gel; methylene chloride/cyclohexane/methanol/conc. aqueous ammonia=68:15:15:2)

(15) (3S,5S)-5-[(4'-cyano-4-biphenylyl)oxymethyl]-3-[(methoxycarbonyl)methyl]- 1-(4-phenyloxybutyl)-2-pyrrolidinone $R_f$ value: 0.41 (silica gel; cyclohexane/ethyl acetate/methanol=64:32:4)

Intermediate product:
(3S,5S)-3-carboxymethyl-5-[(4'-cyano-4-biphenylyl)oxymethyl]-1-(4-phenyloxybutyl)-2-pyrrolidinone $R_f$ value: 0.34 (silica gel; methylene chloride/cyclohexane/methanol/conc. aqueous ammonia=68:15:15:2)

(16) (3S,5S)-5-[(4'-cyano-4-biphenylyl)oxymethyl]-3-[(methoxycarbonyl)methyl]- 1,3-bis-(3-phenylpropyl)-2-pyrrolidinone $R_f$ value: 0.41 (silica gel; cyclohexane/ethyl acetate=2:1)

Intermediate product:
(3S,5S)-3-carboxymethyl-5-[(4'-cyano-4-biphenylyl)oxymethyl]-1,3-bis-(3-phenylpropyl)-2-pyrrolidinone $R_f$ value: 0.41 (silica gel; methylene chloride/cyclohexane/methanol/conc. aqueous ammonia=68:15:15:2)

(17) (3S,5S)-3-(n-butyl)-5-[(4'-cyano-4-biphenylyl)oxymethyl]- 3-[(methoxycarbonyl)methyl]-1-(3-phenylpropyl)-2-pyrrolidinone $R_f$ value: 0.42 (silica gel; cyclohexane/ethyl acetate=2:1)

Intermediate product:
(3S,5S)-3-(n-butyl)-3-carboxymethyl-5-[(4'-cyano-4biphenylyl)oxymethyl]-1-(3-phenylpropyl)-2-pyrrolidinone $R_f$ value: 0.41 (silica gel; methylene chloride/cyclohexane/methanol/conc. aqueous ammonia=68:15:15:2)

(18) (3R,5S)-5-[(4'-cyano-4-biphenylyl)oxymethyl]-3-[(methoxycarbonyl)methyl]- 1-(3-phenylpropyl)-2-pyrrolidinone $R_f$ value: 0.59 (silica gel; methylene chloride/methanol 19:1)

Intermediate product:
(3R,5S)-3-carboxymethyl-5-[(4'-cyano-4-biphenylyl)oxymethyl]-1-(3-phenylpropyl)-2-pyrrolidinone $R_f$ value: 0.52 (silica gel; methylene chloride/methanol/conc. aqueous ammonia=8:2:0.1)

(19) (3S,5S)-5-[[4-[(4-cyanophenyl)carbonylamino]phenyl]oxymethyl]- 3-[(methoxycarbonyl)methyl]-1-(3-phenylpropyl)-2-pyrrolidinone $R_f$ value: 0.35 (silica gel; ethyl acetate/cyclohexane=1:1)

(20) (3S,5S)-5-[[4-[(4-cyanophenyl)aminosulphonyl]phenyl]oxymethyl]- 3-[(methoxycarbonyl)methyl]-1-(3-phenylpropyl)-2-pyrrolidinone $R_f$ value: 0.28 (silica gel; ethyl acetate/cyclohexane=3:1)

(21) (3S,5S)-5-[(4'-cyano-4-biphenylyl)oxymethyl]-3-[(methoxycarbonyl)methyl]- 3-methyl-2-pyrrolidinone Melting point: 105°–107.5° C., $R_f$ value: 0.27 (silica gel; cyclohexane/ethyl acetate=1:4) Calculated: C, 69.83; H, 5.86; N, 7.40; Found: C, 69.64; H, 5.73; N, 7.70;

Intermediate product:

(3S,5S)-3-carboxymethyl-5-[(4'-cyano-4-biphenylyl)oxymethyl]- 3-methyl-2-pyrrolidinone Melting point: 178°–181° C. $R_f$ value: 0.41 (silica gel; toluene/dioxane/ethanol/glacial acetic acid=90:10:10:6)

(22) (3S,5S)-5-[(4'-cyano-4-biphenylyl)oxymethyl]-3-[(methoxycarbonyl)methyl]- 1-(2-methoxyethyl)-2-pyrrolidinone $R_f$ value: 0.55 (silica gel; toluene/dioxane/ethanol/glacial acetic acid=90:10:10:6) Calculated: C, 68.23; H, 6.20; N, 6.63; Found: C, 68.02; H, 6.22; N, 6.55;

Intermediate product:

(3S,5S)-3-carboxymethyl-5-[(4'-cyano-4-biphenylyl)-oxymethyl]-1-(2-methoxyethyl)-2-pyrrolidinone $R_f$ value: 0.43 (silica gel; toluene/dioxane/ethanol/glacial acetic acid=90:10:10:6)

(23) (3S,5S)-1-(2-acetoxyethyl)-5-[(4'-cyano-4-biphenylyl)oxymethyl]-3-[(methoxycarbonyl)methyl]-2-pyrrolidinone $R_f$ value: 0.26 (silica gel; ethyl acetate)

(24) (3R,5R)-5-[(4'-cyano-4-biphenylyl)oxymethyl]-3-[(methoxycarbonyl)methyl]- 2-pyrrolidinone Melting point: 138°–140° C. $R_f$ value: 0.51 (silica gel; methylene chloride/methanol=100:2) Calculated: C, 69.22; H, 5.53; N, 7.69; Found: C, 68.98; H, 5.51; N, 7.62;

(25) (3R,S;4R,S)-4-[(4'-cyano-4-biphenylyl)oxymethyl]-3-[(methoxycarbonyl)methyl]- 2-pyrrolidinone $R_f$ value: 0.29 (silica gel; methylene chloride/methanol=98:2)

(26) (3R,S;4R,S)-4-[(4'-cyano-4-biphenylyl)carbonylamino]methyl]- 3-[(methoxycarbonyl)methyl]-2-pyrrolidinone $R_f$ value: 0.16 (silica gel; ethyl acetate/methanol=97:3)

(27) (3R,S;4R,S)-4-[(4'-cyano-4-biphenylyl)oxymethyl]-3-[(methoxycarbonyl)methyl]- 3-methyl-2-pyrrolidinone Melting point: 163°–164° C. $R_f$ value: 0.39 (silica gel; ethyl acetate) Calculated: C, 69.82; H, 5.86; N, 7.40; Found: C, 70.00; H, 6.10; N, 7.55;

EXAMPLE 6

(3S,5S)-5-[(4'-Amidino-4-biphenylyl)oxymethyl]-3-[(methoxycarbonyl)methyl]-1-(3-phenylpropyl)-2-pyrrolidinone-hydrochloride-semihydrate 140 g of (3S,5S)-5-[(4'-cyano-4-biphenylyl)oxymethyl]-3-[(methoxycarbonyl)methyl]-1-(3-phenylpropyl)-2-pyrrolidinone are dissolved in 1100 ml of methanol and cooled to −20° C. At this temperature, hydrogen chloride gas is piped in for 4 hours with stirring and the mixture is stirred for a further 16 hours at ambient temperature. The solvent is evaporated off in vacuo, leaving the crude iminoester hydrochloride as a viscous oily residue (172 g). This crude product is dissolved in 1500 ml of methanol and after the addition of 144 g of ammonium carbonate stirred for 2 hours at ambient temperature. Then a further 48 g of ammonium carbonate are added and the mixture is stirred for another 1½ hours. The reaction mixture is adjusted to pH 3.5, with stirring, with methanolic hydrochloric acid. It is then concentrated down to about 800 ml in vacuo and the ammonium chloride precipitate is filtered off. The filtrate is then evaporated further until crystallisation begins (at about 350 ml). After crystallisation has ended the precipitate is filtered off and washed with 75 ml of ice cold methanol and finally with acetone and ether. Another fraction is obtained by evaporating the filtrates. The two lots of crystals are combined and recrystallised from methanol.

Yield: 128.7 g (83% of theory), Melting point: 184°–187° C. (decomp.) Calculated: C, 66.11; H, 6.47; N, 7.71; Cl, 6.50; Found: C, 65.98; H, 6.41; N, 7.67; Cl, 6.67;

The following is obtained as a by-product:

(3S,5S)-5-[(4'-aminocarbonyl-4-biphenylyl)oxymethyl]-3-[(aminocarbonyl)methyl]- 1-(3-phenylpropyl)-2-pyrrolidinone Melting point: 197°–198° C.

The following are obtained analogously:

(1) (3S,5S)-5-[(4'-amidino-4-biphenylyl)oxymethyl]-1-(3-cyclohexylpropyl)- 3-[(methoxycarbonyl)methyl]-2-pyrrolidinone-hydrochloride $R_f$ value: 0.36 (silica gel; methylene chloride/methanol/conc. aqueous ammonia=80:20:5)

(2) (3S,5S)-5-[(4'-amidino-4-biphenylyl)oxymethyl]-3-[(methoxycarbonyl)methyl]- 2-pyrrolidinone×1.25 HCl Melting point: from 141° C. (decomp.) $R_f$ value: 0.30 (silica gel; methylene chloride/methanol=85:15) Calculated: C, 59.07; H, 5.72; N, 9.84; Cl, 10.38; Found: C, 58.96; H, 5.96; N, 9.68; Cl, 10.10;

(3) (3S,5S)-5-[(4'-amidino-4-biphenylyl)oxymethyl]-3-[(methoxycarbonyl)methyl]- 1-methyl-2-pyrrolidinone-hydrochloride Melting point: from 138° C. (decomp.) $R_f$ value: 0.31 (silica gel; methylene chloride/methanol/conc. aqueous ammonia=80:20:5)

(4) (3S,5S)-5-[(4'-amidino-3-bromo-4-biphenylyl)oxymethyl]- 3-[(methoxycarbonyl)methyl]-1-(3-phenylpropyl)-2-pyrrolidinone-hydrochloride Melting point: 104°–106° C. (decomp.) $R_f$ value: 0.46 (silica gel; methylene chloride/methanol/conc. aqueous ammonia=40:10:2) Calculated: C, 58.59; H, 5.41; N, 6.83; Found: C, 58.70; H, 5.66; N, 6.64;

(5) (3S,5S)-5-[(4'-amidino-3-nitro-4-biphenylyl)oxymethyl]- 3-[(methoxycarbonyl)methyl]-1-(3-phenylpropyl)-2-pyrrolidinone-hydrochloride $R_f$ value: 0.63 (silica gel; methylene chloride/methanol/conc. aqueous ammonia=80:20:5)

(6) (3R,5R)-5-[(4'-amidino-4-biphenylyl)oxymethyl]-3-[(methoxycarbonyl)methyl]- 1-(3-phenylpropyl)-2-pyrrolidinone-semihydrochloride $R_f$ value: 0.43 (silica gel; methylene chloride/methanol/conc. aqueous ammonia=80:20:5) Calculated: C, 69.58; H, 6.52; N, 8.11; Cl, 3.42; Found: C, 69.69; H, 6.73; N, 7.97; Cl, 2.86;

(7) (3S,5S)-5-[(4'-amidino-3-trifluoromethyl-4-biphenylyl)oxymethyl]- 3-[(methoxycarbonyl)methyl]-1-(3-phenylpropyl)-2-pyrrolidinone-hydrochloride $R_f$ value: 0.37 (silica gel; methylene chloride/methanol/conc. aqueous ammonia=80:20:5)

(8) (3S,5S)-5-[(4'-amidino-3-fluoro-4-biphenylyl)oxymethyl]- 3-[(methoxycarbonyl)methyl]-1-(3-phenylpropyl)-2-pyrrolidinone-hydrochloride (9) (3S,5S)-5-[(4'-amidino-2,3-dimethyl-4-biphenylyl)oxymethyl]-3-[(methoxycarbonyl)methyl]-1-(3-phenylpropyl)-2-pyrrolidinone-hydrochloride $R_f$ value: 0.42 (silica gel; methylene chloride/methanol/conc. aqueous ammonia=80:20:5)

(10) (3S,5S)-5-[(3-acetylamino-4'-amidino-4-biphenylyl)oxymethyl]-3-[(methoxycarbonyl)methyl]-1-(3-phenylpropyl)-2-pyrrolidinone-hydrochloride $R_f$ value: 0.38 (silica gel; methylene chloride/methanol/conc. aqueous ammonia=80:20:5)

(11) (3S,5S)-5-[(4'-amidino-3-methanesulphonylamino-4-biphenylyl)oxymethyl]-3-[(methoxycarbonyl)methyl]-1-(3-phenylpropyl)-2-pyrrolidinone-hydrochloride $R_f$ value: 0.42 (silica gel; methylene chloride/methanol/conc. aqueous ammonia=80:20:5)

(12) (3S,5S)-5-[(4'-amidino-2'-methyl-4-biphenylyl)oxymethyl]-3-[(methoxycarbonyl)methyl]-1-(3-phenylpropyl)-2-pyrrolidinone-hydrochloride $R_f$ value: 0.44 (silica gel; methylene chloride/methanol/conc. aqueous ammonia=80:20:5)

(13) (3S,5S)-5-[[(4'-amidino-4-biphenylyl)carbonyl]aminomethyl]-3-[(methoxycarbonyl)methyl]-1-(3-phenylpropyl)-2-pyrrolidinone-hydrochloride $R_f$ value: 0.34 (silica gel; methylene chloride/methanol/conc. aqueous ammonia=40:10:2)

(14) (3S,5S)-5-[[trans-4-(4-amidinophenyl)cyclohexyl]oxymethyl]-3-[(methoxycarbonyl)methyl]-1-(3-phenylpropyl)-2-pyrrolidinone-hydrochloride $R_f$ value: 0.25 (silica gel; methylene chloride/methanol/conc. aqueous ammonia=80:20:5)

(15) (3S,5S)-5-[2-[(6-amidino-2-naphthylcarbonyl)amino]ethyl]-3-[(methoxycarbonyl)methyl]-1-(3-phenylpropyl)-2-pyrrolidinone-hydrochloride $R_f$ value: 0.26 (silica gel; methylene chloride/methanol/conc. aqueous ammonia=80:20:3)

(16) (3S,5S)-5-[(6-amidino-2-naphthylcarbonyl)aminomethyl]-3-[(methoxycarbonyl)methyl]-1-(3-phenylpropyl)-2-pyrrolidinone-hydrochloride $R_f$ value: 0.26 (silica gel; methylene chloride/methanol/conc. aqueous ammonia=80:20:3)

(17) (3S,5S)-5-[(7-amidino-2-naphthylcarbonyl)aminomethyl]-3-[(methoxycarbonyl)methyl]-1-(3-phenylpropyl)-2-pyrrolidinone-hydrochloride $R_f$ value: 0.19 (silica gel; methylene chloride/methanol=9:1)

(18) (3S,5S)-5-[2-[(7-amidino-2-naphthylcarbonyl)amino]ethyl]-3-[(methoxycarbonyl)methyl]-1-(3-phenylpropyl)-2-pyrrolidinone-hydrochloride $R_f$ value: 0.25 (silica gel; methylene chloride/methanol=9:1)

(19) (3S,5S)-5-[[trans-3-(4-amidinophenyl)cyclobutyl]carbonylaminomethyl]-3-[(methoxycarbonyl)methyl]-1-(3-phenylpropyl)-2-pyrrolidinone-hydrochloride×1.5 water $R_f$ value: 0.42 (silica gel; methylene chloride/methanol/conc. aqueous ammonia=35:15:4) Calculated: C, 61.31; H, 7.10; N, 9.86; Found: C, 61.45; H, 7.18; N, 9.64;

(20) (3S,5S)-5-[[cis-3-(4-amidinophenyl)cyclobutyl]carbonylaminomethyl]- 3-[(methoxycarbonyl)methyl]-1-(3-phenylpropyl)-2-pyrrolidinone-hydrochloride×1.5 water $R_f$ value: 0.42 (silica gel; methylene chloride/methanol/conc. aqueous ammonia=35:15:4) Calculated: C, 61.31; H, 7.10; N, 9.86; Found: C, 61.67; H, 6.98; N, 9.80;

(21) (3S,5S)-5-[2-[[cis-3-(4-amidinophenyl)cyclobutyl]carbonylamino]ethyl]- 3-[(methoxycarbonyl)methyl]-1-(3-phenylpropyl)-2-pyrrolidinone-hydrochloride $R_f$ value: 0.48 (silica gel; methylene chloride/methanol/conc. aqueous ammonia=35:15:4)

(22) (3S,5S)-5-[2-[[trans-3-(4-amidinophenyl)cyclobutyl]carbonylamino]ethyl]- 3-[(methoxycarbonyl)methyl]-1-(3-phenylpropyl)-2-pyrrolidinone-hydrochloride $R_f$ value: 0.48 (silica gel; methylene chloride/methanol/conc. aqueous ammonia=35:15:4)

(23) (3S,5S)-5-[(4'-amidino-4-biphenylyl)oxymethyl]-3(aminocarbonyl)methyl]-1-(3-phenylpropyl)-2-pyrrolidinone-hydrochloride The iminoester was stirred with methanolic ammonia for six days at ambient temperature. Purification was carried out by chromatography on silica gel (eluant: methylene chloride/methanol/aqueous ammonia=4:1:0.25) $R_f$ value: 0.35 (silica gel; methylene chloride/methanol/conc. aqueous ammonia=4:1:0.25)

(24) (3R,5S)-3-allyl-5-[[3-(3-amidinophenyl)propyl]carbonylaminomethyl]-1-(3-phenylpropyl)-2-pyrrolidinone-hydrochloride $R_f$ value: 0.30 (silica gel; methylene chloride/methanol/conc. aqueous ammonia=4:1:0.1)

(25) (3S,5S)-5-[[3-(4-amidinophenyl)propyl]carbonylaminomethyl]-3-[(methoxycarbonyl)methyl]-1-(3-phenylpropyl)-2-pyrrolidinone-hydrochloride $R_f$ value: 0.50 (silica gel; methylene chloride/methanol=4:1)

(26) (3S,5S)-5-[(4'-amidino-4-biphenylyl)oxymethyl]-3-[(methoxycarbonyl)methyl]- 3-methyl-1-(3-phenylpropyl)-2-pyrrolidinone-hydrochloride $R_f$ value: 0.25 (silica gel; methylene chloride/cyclohexane/methanol/conc. aqueous ammonia=68:15:15:2)

(27) (3S,5S)-5-[(4'-amidino-4-biphenylyl)oxymethyl]-1-benzyl- 3-[(methoxycarbonyl)methyl]-2-pyrrolidinone-hydrochloride $R_f$ value: 0.19 (silica gel; methylene chloride/cyclohexane/methanol/conc. aqueous ammonia=68:15:15:2)

(28) (3S,5S)-5-[(4'-amidino-4-biphenylyl)oxymethyl]-3-[(methoxycarbonyl)methyl]- 1-(2-phenylethyl)-2-pyrrolidinone-hydrochloride $R_f$ value: 0.22 (silica gel; methylene chloride/cyclohexane/methanol/conc. aqueous ammonia=68:15:15:2)

(29) (3S,5S)-5-[(4'-amidino-4-biphenylyl)oxymethyl]-3-[(methoxycarbonyl)methyl]- 1-(4-phenylbutyl)-2-pyrrolidinone-hydrochloride $R_f$ value: 0.41 (silica gel; methylene chloride/cyclohexane/methanol/conc. aqueous ammonia=68:15:15:2)

(30) (3S,5S)-5-[(4'-amidino-4-biphenylyl)oxymethyl]-3-[(methoxycarbonyl)methyl]- 1-(4-phenyloxybutyl)-2-pyrrolidinone-hydrochloride $R_f$ value: 0.38 (silica gel; methylene chloride/cyclohexane/methanol/conc. aqueous ammonia=68:15:15:2)

(31) (3S,5S)-5-[[4'-(n-butylamidino)-4-biphenylyl]oxymethyl]- 3-[(methoxycarbonyl)methyl]-1-(3-phenylpropyl)-2-pyrrolidinone-hydrochloride The iminoester is taken up in absolute methanol and 20 times the molar amount of n-butylamine is added to the solution.

$R_f$ value: 0.38 (silica gel; methylene chloride/cyclohexane/methanol/conc. aqueous ammonia=68:15:15:2) (3S,5S)-5-[[4'-(n-butylamidino)-4-biphenylyl]oxymethyl]- 3-[(n-butylaminocarbonyl)methyl]-1-(3-phenylpropyl)-2-pyrrolidinone-hydrochloride is obtained as by-product. $R_f$ value: 0.60 (silica gel; methylene chloride/methanol/conc. aqueous ammonia=4:1:0.2)

(32) (3S,5S)-3-[(methoxycarbonyl)methyl]-5-[(4'-methylamidino- 4-biphenylyl)oxymethyl]-1-(3-phenylpropyl)-2-pyrrolidinone-hydrochloride The reaction is carried out analogously to Example 6 (31).

$R_f$ value: 0.22 (silica gel; methylene chloride/cyclohexane/methanol/conc. aqueous ammonia=68:15:15:2) (3S,5S)-5-[(4'-methylamidino-4-biphenylyl)oxymethyl]-3-[(methylaminocarbonyl)methyl]- 1-(3-phenylpropyl)-2-pyrrolidinone-hydrochloride is obtained as by-product.

Calculated: C, 67.80; H, 6.79; N, 10.20; Cl, 6.46; Found: C, 67.35; H, 6.68; N, 10.23; Cl, 6.43;

(33) (3S,5S)-5-[(4'-isopropylamidino-4-biphenylyl)oxymethyl]-3-[(methoxycarbonyl)methyl]-1-(3-phenylpropyl)-2-pyrrolidinone-hydrochloride The reaction is carried out analogously to Example 6 (31).

$R_f$ value: 0.47 (silica gel; methylene chloride/cyclohexane/methanol/conc. aqueous ammonia=68:15:15:2)

(34) (3S,5S)-5-[(4'-amidino-4-biphenylyl)oxymethyl]-3-[(methoxycarbonyl)methyl]- 1,3-bis-(3-phenylpropyl)-2-pyrrolidinone-hydrochloride $R_f$ value: 0.31 (silica gel; methylene chloride/cyclohexane/methanol/conc. aqueous ammonia=68:15:15:2)

(35) (3S,5S)-5-[(4'-amidino-4-biphenylyl)oxymethyl]-3-(n-butyl)- 3-[(methoxycarbonyl)methyl]-1-(3-phenylpropyl)-2-pyrrolidinone-hydrochloride $R_f$ value: 0.22 (silica gel; methylene chloride/cyclohexane/methanol/conc. aqueous ammonia=68:15:15:2)

(36) (3R,5S)-3-allyl-5-[(4'-amidino-4-biphenylyl)oxymethyl]-1-(3-phenylpropyl)-2-pyrrolidinone-hydrochloride Melting point: sinters above 100° C. $R_f$ value: 0.26 (silica gel; methylene chloride/methanol/conc. aqueous ammonia=8:1:0.25)

(37) (3R,5S)-3-allyl-5-[(6-amidino-2-naphthyl)oxymethyl]-1-(3-phenylpropyl)-2-pyrrolidinone-hydrochloride $R_f$ value: 0.27 (silica gel; methylene chloride/methanol/conc. aqueous ammonia=4:1:0.25)

(38) (3S,5S)-5-[(7-amidino-9-keto-2-fluorenyl)oxymethyl]-3-[(methoxycarbonyl)methyl]-1-(3-phenylpropyl)-2-pyrrolidinone-hydrochloride-hydrate Calculated: C, 64.13; H, 5.69; N, 7.24; Cl, 6.12; Found: C, 64.90; H, 5.86; N, 7.39; Cl, 6.76;

(39) (3R,5S)-5-[(4'-amidino-4-biphenylyl)oxymethyl]-3-[(methoxycarbonyl)methyl]- 1-(3-phenylpropyl)-2-pyrrolidinone-hydrochloride $R_f$ value: 0.33 (silica gel; methylene chloride/methanol/methanolic hydrochloric acid=9:1:0.05)

(40) (3S,5S)-5-[(4'-amidino-4-biphenylyl)aminomethyl]-3-[(methoxycarbonyl)methyl]- 1-(3-phenylpropyl)-2-pyrrolidinone×1.25 HCl Calculated: C, 66.15; H, 6.48; N, 10.29; Cl, 8.15; Found: C, 65.96; H, 6.66; N, 10.38; Cl, 7.96;

(41) (3S,5S)-5-[[N-(4'-amidino-4-biphenylyl)-N-methanesulphonyl]aminomethyl]- 3-[(methoxycarbonyl)methyl]-1-(3-phenylpropyl)-2-pyrrolidinone-hydrochloride Calculated: C, 60.62; H, 6.25; N, 9.12; Cl, 5.77; Found: C, 60.87; H, 6.14; N, 8.93; Cl, 5.66;

(42) (3S,5S)-5-[[N-(4'-amidino-4-biphenylyl)-N-acetyl] aminomethyl]- 3-[(methoxycarbonyl)methyl]-1-(3-phenylpropyl)-2-pyrrolidinone-hydrochloride Calculated: C, 66.59; H, 6.47; N, 9.71; Cl, 6.14; Found: C, 66.61; H, 6.85; N, 9.52; Cl, 5.94;

(43) (3S,5S)-5-[[2-[(4-amidinophenyl)amino]phenyl]carbonylaminomethyl]-3-[(methoxycarbonyl)methyl]-1-(3-phenylpropyl)-2-pyrrolidinone-hydrochloride Melting point: above 1 05° C. (decomp.) $R_f$ value: 0.27 (silica gel; cyclohexane/ethyl acetate/methanol=2:1:0.6)

(44) (3S,5S)-5-[[4-[(4-amidinophenyl)aminocarbonyl] phenyl]oxymethyl]- 3-[(methoxycarbonyl)methyl]-1-(3-phenylpropyl)-2-pyrrolidinone-hydrochloride $R_f$ value: 0.63 (silica gel; methylene chloride/ethanol= 4:1)

Mass spectrum: $(M+H)^+=543$

(45) (3S,5S)-5-[[4-[(4-amidinophenyl)carbonylamino] phenyl]oxymethyl]- 3-[(methoxycarbonyl)methyl]-1-(3-phenylpropyl)-2-pyrrolidinone-hydrochloride $R_f$ value: 0.30 (silica gel; methylene chloride/methanol/conc. aqueous ammonia=16:4:1)

(46) (3S,5S)-5-[[4-[(4-amidinophenyl)aminosulphonyl] phenyl]oxymethyl]- 3-[(methoxycarbonyl)methyl]-1-(3-phenylpropyl)-2-pyrrolidinone-hydrochloride $R_f$ value: 0.33 (silica gel; methylene chloride/methanol/conc. aqueous ammonia=16:2:1)

Mass spectrum: $(M+H)^+=579$

(47) (3S,5S)-5-[[4-[(3-amidinophenyl)sulphenyl]phenyl] oxymethyl]- 3-[(methoxycarbonyl)methyl]-1-(3-phenylpropyl)-2-pyrrolidinone-hydrochloride $R_f$ value: 0.42 (silica gel; ethyl acetate/cyclohexane=3:2)

(48) (3S,5S)-5-[[4-[(3-amidinophenyl)carbonyl]phenyl] oxymethyl]-3-[(methoxycarbonyl)methyl]-1-(3-phenylpropyl)-2-pyrrolidinone-hydrochloride $R_f$ value: 0.21 (silica gel; methylene chloride/methanol/conc. aqueous ammonia=16:4:1)

(49) (3S,5S)-5-[[4-[(3-amidinophenyl)sulphonyl]phenyl] oxymethyl]-3-[(methoxycarbonyl)methyl]-1-(3-phenylpropyl)-2-pyrrolidinone-hydrochloride $R_f$ value: 0.37 (silica gel; methylene chloride/ethanol/conc. aqueous ammonia=16:4:1) Mass spectrum: $(M+H)^+=564$

(50) (3S,5S)-5-[(4'-amidino-4-biphenylyl)oxymethyl]-1,3 -bis-[(methoxycarbonyl)methyl]-2-pyrrolidinone-hydrochloride-semihydrate $R_f$ value: 0.40 (silica gel; methylene chloride/methanol/conc. aqueous ammonia=15:5:1) Calculated: C, 57.77; H, 5.86; N, 8.42; Cl, 7.11; Found: C, 57.97; H, 5.95; N, 8.38; Cl, 7.37; Mass spectrum: $(M+H)^+=454$

(51) (3S,5S)-5-[(4'-amidino-4-biphenylyl)oxymethyl]-1-[(ethylaminocarbonyl)methyl]- 3-[(methoxycarbonyl)methyl]-2-pyrrolidinone-hydrochloride×0.25 water $R_f$ value: 0.27 (silica gel; methylene chloride/methanol/conc. aqueous ammonia=30:10:2) Calculated: C, 59.17; H, 6.26; N, 11.04; Cl, 6.99; Found: C, 59.13; H, 6.47; N, 10.91; Cl, 6.78;

(52) (3S,5S)-5-[(4'-amidino-4-biphenylyl)oxymethyl]-1-[(dimethylaminocarbonyl)methyl]-3-[(methoxycarbonyl)methyl]-2-pyrrolidinone-hydrochloride-semihydrate $R_f$ value: 0.33 (silica gel; methylene chloride/methanol/conc. aqueous ammonia=30:10:2) Calculated: C, 58.65; H, 6.30; N, 10.94; Cl, 6.92; Found: C, 58.50; H, 6.55; N, 10.79; Cl, 6.80;

(53) (3S,5S)-5-[(4'-amidino-4-biphenylyl)oxymethyl]-1-[(benzylaminocarbonyl)methyl]-3-[(methoxycarbonyl)methyl]-2-pyrrolidinone-hydrochloride $R_f$ value: 0.50 (silica gel; methylene chloride/methanol/ conc. aqueous ammonia=30:10:2) Calculated: C, 63.88; H, 5.72; N, 9.93; Cl, 6.29; Found: C, 64.06; H, 6.00; N, 9.92; Cl, 6.31;

(54) (3S,5S)-5-[(4'-amidino-4-biphenylyl)oxymethyl]-1-benzoyl- 3-[(methoxycarbonyl)methyl]-pyrrolidine-hydrochloride-semihydrate $R_f$ value: 0.18 (silica gel; methylene chloride/methanol= 0:1) Calculated: C, 65.05; H, 6.04; N, 8.13; Cl, 6.86; Found: C, 65.00; H, 6.30; N, 7.99; Cl, 6.61;

(55) (3S,5S)-5-[(4'-amidino-4-biphenylyl)oxymethyl]-1-methanesulphonyl- 3-[(methoxycarbonyl)methyl]-pyrrolidine-hydrochloride $R_f$ value: 0.24 (silica gel; methylene chloride/methanol= 10:1) Calculated: C, 54.82; H, 5.85; N, 8.72; Cl, 7.36; Found: C, 54.68; H, 5.82; N, 8.47; Cl, 7.20;

(56) (3S,5S)-1-acetyl-5-[(4'-amidino-4-biphenylyl)oxymethyl]-3-[(methoxycarbonyl)methyl]pyrrolidine-hydrochloride $R_f$ value: 0.16 (silica gel; methylene chloride/methanol= 10:1) Calculated: C, 61.95; H, 6.33; N, 9.42; Cl, 7.95; Found: C, 61.76; H, 6.31; N, 9.11; Cl, 7.84;

(57) (3S,5S)-5-[(4'-amidino-4-biphenylyl) oxymethyl]-1-(ethylaminocarbonyl)-3-[(methoxycarbonyl)methyl]-pyrrolidine×1.25 HCl $R_f$ value: 0.13 (silica gel; methylene chloride/methanol= 10:1) Calculated: C, 59.58; H, 6.51; N, 11.58; Cl, 9.16; Found: C, 59.73; H, 6.56; N, 11.33; Cl, 9.07;

(58) (3S,5S)-5-[(4'-amidino-4-biphenylyl)oxymethyl]-1-(dimethylaminosulphonyl- 3-[(methoxycarbonyl)methyl] pyrrolidine-hydrochloride Melting point: 196°–198° C. $R_f$ value: 0.18 (silica gel; methylene chloride/methanol=10:1) Calculated: C, 54.06; H, 6.11; N, 10.96; Cl, 6.94; S, 6.27; Found: C, 53.92; H, 6.14; N, 10.77; Cl, 7.02; S, 6.32;

(59) (3S,5S)-5-[(4'-amidino-4-biphenylyl)oxymethyl]-3-[(methoxycarbonyl)methyl]- 1-methyl-pyrrolidine-hydrochloride $R_f$ value: 0.18 (silica gel; methylene chloride/methanol= 10:1) Mass spectrum: (M+H)⁺=382

(60) (3R,5S)-5-[(4'-amidino-4-biphenylyl)oxymethyl]-3-[(methoxycarbonyl)methyl]- 2-pyrrolidinone-hydrochloride $R_f$ value: 0.20 (silica gel; methylene chloride/methanol= 9:1) Calculated: C, 57.86; H, 6.01; N, 9.64; Cl, 8.13; Found: C, 58.06; H, 5.93; N, 9.66; Cl, 8.25;

(61) (3S,5S)-5-[(4'-amidino-4-biphenylyl)oxymethyl]-3-[(methoxycarbonyl)methyl]- 3-methyl-2-pyrrolidinone-hydrochloride-semihydrate $R_f$ value: 0.28 (silica gel; methylene chloride/methanol/ conc. aqueous ammonia=80:20:2) Calculated: C, 59.93; H, 6.17; N, 9.53; Cl, 8.04; Found: C, 59.70; H, 6.08; N, 9.37; Cl, 8.21;

(62) (3S,5S)-5-[(4'-amidino-4-biphenylyl)oxymethyl]-3-[(methoxycarbonyl)methyl]- 1-(2-methoxyethyl)-2-pyrrolidinone-hydrochloride Conc. aqueous ammonia was used as base.

$R_f$ value: 0.39 (reversed phase silica gel (RP8); methanol/ 10% aqueous saline solution=6:4)

(63) (3S,5S)-5-[(4'-amidino-4-biphenylyl)oxymethyl]-1-(2-hydroxyethyl)-3-[(methoxycarbonyl)methyl]-2-pyrrolidinone-hydrochloride Conc. aqueous ammonia was used as base.

$R_f$ value: 0.55 (reversed phase silica gel (RP8); methanol/ 10% aqueous saline solution=6:4) and (3S,5S)-5-[(4'-amidino-4-biphenylyl)oxymethyl]-3-carboxymethyl- 1-(2-hydroxyethyl)-2-pyrrolidinone $R_f$ value: 0.70 (reversed phase silica gel (RP8); methanol/ 10% aqueous saline solution=6:4)

(64) (3S,5S)-5-[(4'-amidino-4-biphenylyl)oxymethyl]-3-[(ethoxycarbonyl)methyl]- 2-pyrrolidinone-hydrochloride Ethanolic hydrochloric acid was used as the acid.

$R_f$ value: 0.44 (reversed phase silica gel (RP8); methanol/ 10% aqueous saline solution=6:4) Calc.×0.25 H₂O: C, 60.55; H, 6.12; N, 9.63; Cl, 8.12; Found: C, 60.49; H, 6.23; N, 9.65; Cl, 8.21;

(65) (3R,5R)-5-[(4'-amidino-4-biphenylyl)oxymethyl]-3-[(methoxycarbonyl)methyl]- 2-pyrrolidinone-hydrochloride-semihydrate Melting point: 138° C. (decomp.) $R_f$ value: 0.52 (reversed phase silica gel (RP8); methanol/10% aqueous saline solution=6:4) Calculated: C, 59.08; H, 5.90; N, 9.84; Cl, 8.31; Found: C, 58.96; H, 6.19; N, 9.68; Cl, 8.93;

(66) (3S,5S)-5-[2-[(4'-amidino-3-biphenylyl)amino] ethyl]-3-[(methoxycarbonyl)methyl]-1-(3-phenylpropyl)-2-pyrrolidinone-hydrochloride $R_f$ value: 0.39 (silica gel; chloroform/methanol=3:1)

(67) (3S,5S)-5-[2-[[(3'-amidino-4-biphenylyl)carbonyl] amino]ethyl]- 3-[(methoxycarbonyl)methyl]-1-(3-phenylpropyl)-2-pyrrolidinone-hydrochloride $R_f$ value: 0.39 (silica gel; methylene chloride/methanol= 3:1)

(68) (3S,5S)-5-[(4'-amidino-3-methylsulphonyl-4-biphenylyl)oxymethyl]-3-[(methoxycarbonyl)methyl]-1-(3-phenylpropyl)-2-pyrrolidinone-hydrochloride $R_f$ value: 0.24 (silica gel; methylene chloride/cyclohexane/methanol/aqueous ammonia=7:1.5:1.5:0.2) Mass spectrum: (M+H)⁺=578

(69) (3S,5S)-5-[(4'-amidino-3-methylsulphenyl-4-biphenylyl)oxymethyl]-3-[(methoxycarbonyl)methyl]-1-(3-phenylpropyl)-2-pyrrolidinone-hydrochloride $R_f$ value: 0.25 (silica gel; methylene chloride/cyclohexane/methanol/aqueous ammonia=7:1.5:1.5:0.2) Calculated: C, 63.96; H, 6.23; N, 7.22; S, 5.51; Cl, 6.09; Found: C, 64.12; H, 6.50; N, 7.03; S, 5.36; Cl, 5.88;

(70) (3S,5S)-5-[[4'-amidino-4-biphenylyl)sulphonyl]aminomethyl]-3-[(methoxycarbonyl)methyl]-1-(3-phenyl-propyl)-2-pyrrolidinone-hydrochloride $R_f$ value: 0.19 (silica gel; methylene chloride/cyclohexane/methanol/conc. aqueous ammonia=7:1.5:1.5:0.2)

(71) (3S,5S)-5-[2-[(4-amidinocinnamoyl)amino]ethyl]-3-[(methoxycarbonyl)methyl]- 1-(3-phenylpropyl )-2pyrrolidinone-hydrochloride $R_f$ value: 0.29 (silica gel; methylene chloride/methanol/ cyclohexane/conc. aqueous ammonia=68:15:15:2)

(72) (3S,5S)-5-[(4'-amidino-4-biphenylyl)oxymethyl]-1-[3-(3,4-dimethoxyphenyl)propyl]-3-[(methoxycarbonyl)methyl]-2-pyrrolidinone-semihydrochloride $R_f$ value: 0.24 (silica gel; methylene chloride/methanol/ conc. aqueous ammonia=4:1:0.25) Calculated: C, 66.51; H, 6.54; N, 7.27; Cl, 3.07; Found: C, 66.34; H, 6.31; N, 7.07; Cl, 2.92;

(73) (3S,5S)-5-[(4'-amidino-4-biphenylyl)oxymethyl]-3-[(methoxycarbonyl)methyl]- 1-[3-(4-hexyloxyphenyl)propyl]-2-pyrrolidinone-hydrochloride $R_f$ value: 0.23 (silica gel; methylene chloride/methanol/ conc. aqueous ammonia=4:1:0.25)

(74) (3S,5S)-5-[(4'-amidino-4-biphenylyl)oxymethyl]-1-[3-(4-tert.butylphenyl)propyl]-3-[(methoxycarbonyl)methyl]-2-pyrrolidinone-hydrochloride $R_f$ value: 0.22 (silica gel; methylene chloride/methanol/conc. aqueous ammonia=4:1:0.25)

(75) (3S,5S)-5-[(4'-amidino-4-biphenylyl)oxymethyl]-3-[(methoxycarbonyl)methyl]-1-[3-(3-trifluoromethylphenyl)-propyl]-2-pyrrolidinone-hydrochloride $R_f$ value: 0.22 (silica gel; methylene chloride/methanol/conc. aqueous ammonia=4:1:0.25)

(76) (3S,5S)-5-[(4'-amidino-4-biphenylyl)oxymethyl]-1-[3-(2,4-dichlorophenyl)propyl]-3-[(methoxycarbonyl)methyl]-2-pyrrolidinone-hydrochloride $R_f$ value: 0.28 (silica gel; methylene chloride/methanol/conc. aqueous ammonia=4:1:0.25)

(77) (3S,5S)-5-[(4'-amidino-4-biphenylyl)oxymethyl]-3-[(methoxycarbonyl)methyl]- 1-[3-(3-benzylphenyl)-propyl]-2-pyrrolidinone-hydrochloride $R_f$ value: 0.34 (silica gel; methylene chloride/methanol/conc. aqueous ammonia=4:1:0.25)

(78) (3S,5S)-5-[(4'-amidino-4-biphenylyl)oxymethyl]-1-(4,4-diphenylbutyl)-3-[(methoxycarbonyl)methyl]-2-pyrrolidinone-hydrochloride $R_f$ value: 0.29 (silica gel; methylene chloride/methanol/conc. aqueous ammonia=4:1:0.25)

(79) (3S,5S)-5-[(4'-amidino-4-biphenylyl)oxymethyl]-3-[(methoxycarbonyl)methyl]- 1-[3-(4-methylsulphenylphenyl)propyl]-2-pyrrolidinone-hydrochloride $R_f$ value: 0.23 (silica gel; methylene chloride/methanol/conc. aqueous ammonia=4:1:0.25)

(80) (3S,5S)-5-[(4'-amidino-4-biphenylyl)oxymethyl]-3-[(methoxycarbonyl)methyl]- 1-[3-(4-methylsulphonylphenyl)propyl]-2-pyrrolidinone-hydrochloride $R_f$ value: 0.25 (silica gel; methylene chloride/methanol/conc. aqueous ammonia=4:2:0.25)

(81) (3S,5S)-5-[(4'-amidino-4-biphenylyl)oxymethyl]-1-(4-biphenylylmethyl)-3-[(methoxycarbonyl)methyl]-2-pyrrolidinone-hydrochloride $R_f$ value: 0.28 (silica gel; methylene chloride/methanol/conc. aqueous ammonia=4:2:0.25) Calculated: C, 69.91; H, 5.87; N, 7.19; Cl, 6.07; Found: C, 69.82; H, 5.86; N, 7.39; Cl, 6.17;

(82) (3R,5S)-5-[(4'-amidino-4-biphenylyl)oxymethyl]-3-[3-(methoxycarbonyl)propyl]-1-(3-phenylpropyl)-2-pyrrolidinone-hydrochloride $R_f$ value: 0.51 (silica gel; methylene chloride/methanol/water=8:2:0.10) Calculated: C, 68.13; H, 6.79; N, 7.45; Found: C, 67.94; H, 7.03; N, 7.26;

(83) (3R,5S)-5-[(4'-amidino-4-biphenylyl)oxymethyl]-3-[5-(methoxycarbonyl)pentyl]-1-(3-phenylpropyl)-2-pyrrolidinone-hydrochloride $R_f$ value: 0.65 (silica gel; methylene chloride/methanol/water=8:2:0.10) Calculated: C, 68.96; H, 7.15; N, 7.10; Found: C, 68.82; H, 7.22; N, 6.97;

(84) (3S,5S)-5-[[(3'-amidino-4-biphenylyl)carbonyl]aminomethyl]-3-[(methoxycarbonyl)methyl]-1-(3-phenylpropyl)-2-pyrrolidinone-hydrochloride $R_f$ value: 0.37 (silica gel; methylene chloride/methanol/conc. aqueous ammonia=4:1:0.25) Mass spectrum: (M+H)$^+$=527

(85) (3S,5S)-5-[[(4'-amidino-3-biphenylyl)carbonyl]aminomethyl]-3-[(methoxycarbonyl)methyl]-1-(3-phenylpropyl)-2-pyrrolidinone-hydrochloride $R_f$ value: 0.25 (silica gel; methylene chloride/methanol/conc. aqueous ammonia=4:1:0.25) Mass spectrum: (M+H)$^+$=527

(86) (3S,5S)-5-[(4'-amidino-4-biphenylyl)sulphonylmethyl]-3-[(methoxycarbonyl)methyl]-1-(3-phenylpropyl)-2-pyrrolidinone-hydrochloride $R_f$ value: 0.16 (silica gel; methylene chloride/methanol/cyclohexane/conc. aqueous ammonia=68:15:15:2)

(87) (3S,5S)-5-[(4'-amidino-4-biphenylyl)sulphenylmethyl]-3-[(methoxycarbonyl)methyl]-1-(3-phenylpropyl)-2-pyrrolidinone-hydrochloride $R_f$ value: 0.81 (silica gel; methylene chloride/methanol/conc. aqueous ammonia=4:1:0.25)

(88) (3S,5S)-5-[[[1-(4-amidinophenyl)-1-propen-3-yl]-aminocarbonyl]methyl]- 3-[(methoxycarbonyl)methyl]-1-(3-phenylpropyl)-2-pyrrolidinone-hydrochloride $R_f$ value: 0.15 (silica gel; methylene chloride/methanol/conc. aqueous ammonia=4:1:0.25)

The following is obtained as a by-product:

(3S,5S)-5-[[[1-(4-amidinophenyl)-1-propen-3-yl]-aminocarbonyl]methyl]- 3-[(aminocarbonyl)methyl]-1-(3-phenylpropyl)-2-pyrrolidinone-hydrochloride $R_f$ value: 0.13 (silica gel; methylene chloride/methanol/conc. aqueous ammonia=4:1:0.25) Mass spectrum: (M+H)$^+$=476

(89) (S)-5-[(4'-amidino-4-biphenylyl)oxymethyl]-3,3-diallyl- 2-pyrrolidinone-hydrochloride-semihydrate $R_f$ value: 0.50 (silica gel; methylene chloride/methanol/conc. aqueous ammonia=80:20:5) Calculated: C, 66.27; H, 6.72; N, 9.66; Cl, 8.15; Found: C, 66.32; H, 6.90; N, 9.65; Cl, 7.90;

(90) (3R,5S)-3-allyl-5-[(4'-amidino-4-biphenylyl)oxymethyl]-2-pyrrolidinone-hydrochloride $R_f$ value: 0.68 (silica gel; methylene chloride/methanol= 4:1) Calc. (x0.5 H$_2$O): C, 63.87; H, 6.38; N, 10.64; Cl, 8.98; Found: C, 63.60; H, 6.39; N, 10.45; Cl, 9.25;

(91) (3R,S;4R,S)-4-[(4'-amidino-4-biphenylyl)oxymethyl]- 3-[(methoxycarbonyl)methyl]-2-pyrrolidinone-hydrochloride $R_f$ value: 0.30 (silica gel; methylene chloride/methanol/aqueous ammonia=80:20:5)

(92) (3S,5S)-5-[(4'-amidino-4-biphenylyl)oxymethyl]-3-(2-hydroxyethyl)-2-pyrrolidinonex1.25 HClx1 water $R_f$ value: 0.29 (silica gel; methylene chloride/methanol= 85:15) Calculated: C, 57.61; H, 6.34; N, 10.07; Cl, 10.63; Found: C, 57.89; H, 6.22; N, 9.94; Cl, 10.46;

(93) (3S,5S)-5-[(7-amidino-9,10-dihydro-2-phenanthrenyl)oxymethyl]-3-[(methoxycarbonyl)methyl]-2-pyrrolidinone-hydrochloride $R_f$ value: 0.39 (silica gel; methylene chloride/methanol/water=8:2:0.1)

(94) (3S,5S)-5-[(3-amidinobenzoyl)aminomethyl]-3-[(methoxycarbonyl)methyl]- 1-(3-phenylpropyl)-2-pyrrolidinone-hydrochloride $R_f$ value: 0.27 (silica gel; methylene chloride/methanol/conc. aqueous ammonia=4:1:0.25) Mass spectrum: (M+H)$^+$=451

(95) (3S,5S)-5-[[exo-5-(4-amidinophenyl)bicyclo[2.2.1]-heptyl-exo- 2-carbonyl]aminomethyl]-3-[(methoxycarbonyl)methyl]-1-(3-phenylpropyl)-2-pyrrolidinone-hydrochloride $R_f$ value: 0.27 (silica gel; methylene chloride/methanol/conc. aqueous ammonia=4:1:0.25)

(96) (3S,5S)-5-[(4'-amidino-3'-fluoro-4-biphenylyl)oxymethyl]-3-[(methoxycarbonyl)methyl]-2-pyrrolidinone-hydrochloride-semihydrate $R_f$ value: 0.56 (reversed phase silica gel; methanol/10% aqueous saline solution=6:4) Calculated: C, 56.70; H, 5.43; N, 9.45; Cl, 7.97; Found: C, 56.61; H, 5.45; N, 9.49; Cl, 8.01;

(97) (3S,5S)-5-[[4'-(N-benzylamidino)-4-biphenylyl]oxymethyl]-3-[(methoxycarbonyl)methyl]-2-pyrrolidinone×1.5 hydrochloride The reaction is carried out analogously to Example 6(31).

Melting point 206°–208° C. $R_f$ value: 0.44 (silica gel; methylene chloride/methanol=9:1) Calculated: C, 63.78; H, 6.02; N, 7.97; Cl, 10.09; Found: C, 63.99; H, 6.00; N, 8.09; Cl, 9.97;

(98) (3S,5S)-5-[(4'-amidino-4-biphenylyl)oxymethyl]-3-[(methoxycarbonyl)methyl]- 1-[(4-methoxyphenyl)sulphonyl]-2-pyrrolidine-hydrochloride $R_f$ value: 0.55 (silica gel; methylene chloride/methanol= 9:1)

(99) (3S,5S)-5-[(4'-amidino-3'-chloro-4-biphenylyl)oxymethyl]-3-[(methoxycarbonyl)methyl]-2-pyrrolidinone-hydrochloride $R_f$ value: 0.33 (silica gel; methylene chloride/methanol= 4:1) Mass spectrum: (M+H)$^+$=416 and 418

(100) (3R,S;4R,S)-4-[(4'-amidino-4-biphenylyl)oxymethyl]- 3-[(methoxycarbonyl)methyl]-3-methyl-2-pyrrolidinone-hydrochloride $R_f$ value: 0.53 (reversed phase silica gel; methanol/10% aqueous saline solution=6:4)

(101) (3R,S;4R,S)-4-[[(4'-amidino-4-biphenylyl)carbonylamino]methyl]- 3-[(methoxycarbonyl)methyl]-2-pyrrolidinone-hydrochloride $R_f$ value: 0.23 (silica gel; methylene chloride/methanol/ glacial acetic acid=80:20:2)

(102) (3R,S;4R,S)-4-[[(4'-amidino-4-biphenylyl)carbonylamino]methyl]- 3-[(methoxycarbonyl)methyl]-3-methyl-2-pyrrolidinone-hydrochloride (103) (3S,5S)-5-[(4'-amidino-4-biphenylyl)oxymethyl]-3-[(methoxycarbonyl)methyl]- 1-[2-(methoxycarbonyl)phenyl]-2-pyrrolidinone-hydrochloride (104) (3S,5S)-5-[(4'-amidino-4-biphenylyl)oxymethyl]-1-[2-(aminocarbonyl)phenyl]-3-[(methoxycarbonyl)methyl]-2-pyrrolidinone-hydrochloride (105) (3S,5S)-5-[(4'-amidino-4-biphenylyl)oxymethyl]-1-[2-(ethylaminocarbonyl)phenyl]-3-[(methoxycarbonyl)methyl]-2-pyrrolidinone-hydrochloride (106) (3S,5S)-5-[(4'-amidino-4-biphenylyl)oxymethyl]-1-[2-(dimethylaminocarbonyl)phenyl]-3-[(methoxycarbonyl)methyl]-2-pyrrolidinone-hydrochloride (107) (3S,5S)-5-[(4'-amidino-4-biphenylyl)oxymethyl]-3-[(methoxycarbonyl)methyl]- 1-[3-(methoxycarbonyl)phenyl]-2-pyrrolidinone-hydrochloride (108) (3S,5S)-5-[(4'-amidino-4-biphenylyl)oxymethyl]-1-[3-(aminocarbonyl)phenyl]-3-[(methoxycarbonyl)methyl]-2-pyrrolidinone-hydrochloride (109) (3S,5S)-5-[(4'-amidino-4-biphenylyl)oxymethyl]-1-[3-(ethylaminocarbonyl)phenyl]-3-[(methoxycarbonyl)methyl]-2-pyrrolidinone-hydrochloride (110) (3S,5S)-5-[(4'-amidino-4-biphenylyl)oxymethyl]-1-[3-(dimethylaminocarbonyl)phenyl]-3-[(methoxycarbonyl)methyl]-2-pyrrolidinone-hydrochloride (111) (3S,5S)-5-[(4'-amidino-4-biphenylyl)oxymethyl]-3-[(methoxycarbonyl)methyl]- 1-[4-(methoxycarbonyl)phenyl]-2-pyrrolidinone-hydrochloride (112) (3S,5S)-5-[(4'-amidino-4-biphenylyl)oxymethyl]-1-[4-(aminocarbonyl)phenyl]-3-[(methoxycarbonyl)methyl]-2-pyrrolidinone-hydrochloride (113) (3S,5S)-5-[(4'-amidino-4-biphenylyl)oxymethyl]-1-[4-(ethylaminocarbonyl)phenyl]-3-[(methoxycarbonyl)methyl]-2-pyrrolidinone-hydrochloride (114) (3S,5S)-5-[(4'-amidino-4-biphenynyl)oxymethyl]-1-[4-(dimethylaminocarbonyl)phenyl]-3-[(methoxycarbonyl)methyl]-2-pyrrolidinone-hydrochloride (115) (3S,5S)-5-[(4'-amidino-4-biphenylyl)oxymethyl]-3-[(methoxycarbonyl)methyl]-1-[3-(methanesulphonylamino)phenyl]-2-pyrrolidinone-hydrochloride (116) (3S,5S)-1-[3-acetaminophenyl]-5-[(4'-amidino-4-biphenylyl)oxymethyl]-3-[(methoxycarbonyl)methyl]-2-pyrrolidinone-hydrochloride (117) (3S,5S)-5-[[(6-amidino-1,2,3,4-tetrahydro-2-naphthyl)-aminocarbonyl]aminomethyl]-3-[(methoxycarbonyl)methyl]-2-pyrrolidinone-hydrochloride (118) (3S,5S)-5-[[N-acetyl-N-[trans-4-(4-amidinophenyl)cyclohexyl]]aminomethyl]-3-[(methoxycarbonyl)methyl]-2-pyrrolidinone-hydrochloride (119) (3S,5S)-5-[[N-[trans-4-(4-amidinophenyl)cyclohexyl]-N-methanesulphonyl]aminomethyl]-3-[(methoxycarbonyl)methyl]-2-pyrrolidinone-hydrochloride (120) (3S,5S)-5-[ [trans-4-(4-amidinophenyl)cyclohexyl]oxymethyl] -3-[(methoxycarbonyl)methyl]-2-pyrrolidinone-hydrochloride (121) (3S,6S)-6-[ (4 '-amidino-4-biphenylyl)oxymethyl]-3-[(methoxycarbonyl)methyl]-2-piperidinone-hydrochloride (122) (4R, 6S) -6-[(4'-amidino-4-biphenylyl) oxymethyl]-4-methoxycarbonyl- 2-piperidinone-hydrochloride (123) (3S,5S)-5-[(4'-amidino-3-ethoxy-4-biphenylyl)oxymethyl]-3-[(methoxycarbonyl)methyl]-2-pyrrolidinone-hydrochloride (124) (3S,5S)-5-[(4'-amidino-3-bromo-4-biphenylyl)oxymethyl]-3-[(methoxycarbonyl)methyl]-2-pyrrolidinone-hydrochloride $R_f$ value: 0.25 (silica gel; methylene chloride/methanol/ conc. aqueous ammonia=4:1:0.25)

(125) (3S,5S)-5-[(4'-amidino-4-biphenylyl)oxymethyl]-3-[(methoxycarbonyl)methyl]-1-[2-(phenylsulphonyl)ethyl]- 2-pyrrolidinone-hydrochloride (126) (3S,5S)-5-[(4'-amidino-4-biphenylyl)oxymethyl]-3-[(methoxycarbonyl)methyl]-1-[2-(phenylsulphenyl)ethyl]- 2-pyrrolidinone-hydrochloride (127) (3R,5S)-5-[(4'-amidino-4-biphenylyl)oxymethyl]-3-[(methoxycarbonyl)methyloxy]-1-(3-phenylpropyl)-2-pyrrolidinone-hydrochloride (128) (3R,5S)-5-[(4'-amidino-4-biphenylyl)oxymethyl]-3-[(methoxycarbonyl)methylsulphenyl]-1-(3-phenylpropyl)-2-pyrrolidinone-hydrochloride (129) (3R,5S)-5-[(4'-amidino-4-biphenylyl)oxymethyl]-3-[[N-[(methoxycarbonyl)methyl]-N-methyl]amino]-1-(3-phenylpropyl)- 2-pyrrolidinone-hydrochloride (130) (3S,5S)-5-[[[1-(4-amidinophenyl)-1-propyn-3-yl]-aminocarbonyl]methyl]-3-[(methoxycarbonyl)methyl]-2-pyrrolidinone-hydrochloride (131) (3S,5S)-5-[(7-amidino-2-phenanthrenyl)oxymethyl]-3-[(methoxycarbonyl)methyl]-2-pyrrolidinone-hydrochloride (132) (3R,5S)-3-[(4'-amidino-4-biphenylyl)methyl]-5-[(methoxycarbonyl)methyl]-2-pyrrolidinone-hydrochloride (133) (3S, 5S)-3-[(4'-amidino-4-biphenylyl) oxymethyl]-5-(methoxycarbonyl) methyl]-2-pyrrolidinone-hydrochloride (134) 3-[(4'-amidino-4-biphenylyl)methyl]-1-[2-(methoxycarbonyl)ethyl]- 2-pyrrolidinone-hydrochloride (135) 1-[2-(4'-amidino-4-biphenylyl)ethyl]-3-[(methoxycarbonyl) methyl]-2-pyrrolidinone-hydrochloride (136) (3R,5S)-3-[2-(4'-amidino-4-biphenylyl)ethyl]-5-[(methoxycarbonyl)methyl]-2-pyrrolidinone-hydrochloride
(137) (2S,5S)-5-[(4'-amidino-4-biphenylyl)oxymethyl]-2-[(methoxycarbonyl)methyl]-1-methanesulphonyl-pyrrolidine-hydrochloride
(138) (2S,5S)-1-acetyl-5-[(4'-amidino-4-biphenylyl)oxymethyl]-2-[(methoxycarbonyl)methyl]-pyrrolidinehydrochloride
(139) (3S,5S)-5-[[(4'-amidino-3-biphenylyl)sulphonylamino]methyl]-3-[(methoxycarbonyl)methyl]-2-pyrrolidinone-hydrochloride
(140) (3S,5S)-5-[[(3'-amidino-4-biphenylyl)carbonylamino]methyl]-3-[(methoxycarbonyl)methyl]-2-pyrrolidinone-hydrochloride
(141) (3S, 5S) -5-[ (4'-amidino-4-biphenylyl)oxymethyl]-1-( 2-aminoethyl)-3-[(methoxycarbonyl)methyl]-2pyrrolidinone-dihydrochloride
(142) (3S,5S)-1-[2-(acetylamino)ethyl]-5-[(4'-amidino-4-biphenylyl)oxymethyl]-3-[(methoxycarbonyl)methyl]-2-pyrrolidinone-hydrochloride
(143) (3S,5S)-5-[(4'-amidino-4-biphenylyl)oxymethyl]-1-[2-(methanesulphonylamino)ethyl]-3-[(methoxycarbonyl)methyl]-2-pyrrolidinone-hydrochloride
(144) (3S,5S)-5-[(4'-amidino-4-biphenylyl)oxymethyl]-1-[2-(benzoylamino)ethyl]-3-[(methoxycarbonyl)methyl]-2-pyrrolidinone-hydrochloride
(145) (3S,5S)-5-[(4'-amidino-4-biphenylyl)oxymethyl]-3-[(methoxycarbonyl)methyl]-1-[2-(phenylsulphonylamino)ethyl]-2-pyrrolidinone-hydrochloride
(146) (3S,5S)-1-[2-(N-acetyl-methylamino)ethyl]-5-(4'-amidino- 4-biphenylyl)oxymethyl]-3-[(methoxycarbonyl)methyl]-2-pyrrolidinone-hydrochloride
(147) (3S,5S)-5-[[4-(4-amidinophenyl)naphthyl]oxymethyl]-3-[(methoxycarbonyl)methyl]-2-pyrrolidinone-hydrochloride
(148) (3S,5S)-5-[[[2-[ (4-amidinophenyl)oxy]phenyl]carbonylamino ]methyl]-3-[(methoxycarbonyl)methyl]-2-pyrrolidinone-hydrochloride
(149) (3S,5S)-5-[(4'-amidino-4-biphenylyl)oxymethyl]-3-[1-(methoxycarbonyl)-1-ethyl]-2-pyrrolidinone-hydrochloride
(150) (3S,5S)-5-[2-[[2-(4-amidinophenyl)cyclopropyl]carbonylamino]ethyl]-3-[(methoxycarbonyl)methyl]-2-pyrrolidinone-hydrochloride
(151) (3S,5S)-5-[ (4'-amidino-4-biphenylyl)oxymethyl]-1-[(N,N-dimethylamino)carbonyl]-3-[(methoxycarbonyl)methyl]-pyrrolidine-hydrochloride
$R_f$ value: 0.42 (silica gel; methylene chloride/methanol=4:1)
(152) (3S,5S)-5-[(4,-amidino-4-biphenylyl)oxymethyl]-1-(dimethylaminooxalyl)- 3-[(methoxycarbonyl)methyl]-pyrrolidine-hydrochloride
(153) (3S,5S)-5-[(4,-amidino-4-biphenylyl)oxymethyl]-3-(methoxycarbonyl)methyl]-1-methoxyoxalyl-pyrrolidine-hydrochloride
(154) (3S,5S)-5-[(4,-amidino-4-biphenylyl)oxymethyl]-1-aminoacetyl- 3-[(methoxycarbonyl)methyl]-pyrrolidine-dihydrochloride
(155) (3S,5S)-5-[2-[[N-(6-amidino-2-naphthylcarbonyl)-N-ethyl]amino]ethyl]-3-[(methoxycarbonyl)methyl]-2-pyrrolidinone-hydrochloride
(156) (3S,5S)-5-[(4,-amidino-4-biphenylyl)oxymethyl]-3-[(methoxycarbonyl)methyl]-1-[(4-methoxyphenyl)sulphonyl]pyrrolidine-hydrochloride
(157) (3S,5S)-5-[(4'-amidino-4-biphenylyl)oxymethyl]-1-aminocarbonyl- 3-[(methoxycarbonyl)methyl]pyrrolidine-hydrochloride
(158) (3S,5S)-5-[[4'-(2-imidazolinyl)-4-biphenylyl]oxymethyl]-3-[(methoxycarbonyl)methyl]-2-pyrrolidinone-hydrochloride
Carried out with ethylenediamine
(159) 1-[(4'-amidino-4-biphenylyl)acetyl]-3-[(methoxycarbonyl)methyl]pyrrolidine-hydrochloride
(160) (2S,4R)-4-[(4'-amidino-4-biphenylyl)oxymethyl]-1-methanesulphonyl- 2-[(methoxycarbonyl)methyl]-pyrrolidine-hydrochloride
(161) 5-[(4'-amidino-4-biphenylyl)oxymethyl]-3-[2-(methoxycarbonyl)ethyl]-1-(3-phenylpropyl)-5H-2-pyrrolidinone
(162) (3R,5S)-5-[(4'-amidino-4-biphenylyl)oxymethyl]-3-[(methanesulphonyl)methyl]-3-[(methoxycarbonyl)methyl]- 1-(3-phenylpropyl)-2-pyrrolidinone-hydrochloride
(163) (3S,5S)-5-[[cis-5-(4-amidinophenyl)-2-octahydropentalenyl]aminomethyl]-3-[(methoxycarbonyl)methyl]-2-pyrrolidinone-hydrochloride
(164) (3S,5S)-5-[(4'-amidino-4-biphenylyl)oxymethyl]-3-[(methoxycarbonyl)methyl]-1-[(pyrrolidine-N-carbonyl)-methyl]-2-pyrrolidinone-hydrochloride
$R_f$ value: 0.46 (silica gel; methylene chloride/methanol/conc. aqueous ammonia = 30:10:2)
(165) (3S,5S)-5-[(4'-amidino-4-biphenylyl)oxymethyl]-3-[(methoxycarbonyl)methyl]-1-[(piperidine-N-carbonyl)-methyl]-2-pyrrolidinone-hydrochloride
(166) (3S,5S)-5-[(4'-amidino-4-biphenylyl)oxymethyl]-1-[(azepin-N-carbonyl)methyl]-3-[(methoxycarbonyl)methyl]- 2-pyrrolidinone-hydrochloride
(167) (3S,5S)-5-[(4'-amidino-4-biphenylyl)oxymethyl]-3-[(methoxycarbonyl)methyl]-1-[(morpholine-N-carbonyl)-methyl]-2-pyrrolidinone-hydrochloride
$R_f$ value: 0.46 (silica gel; methylene chloride/methanol/conc. aqueous ammonia=30:10:2)
(168) (3S,5S)-5-[(4'-amidino-4-biphenylyl)oxymethyl]-3-[(methoxycarbonyl)methyl]-1-[(N-methylpiperazine-N'-carbonyl)-methyl]-2-pyrrolidinone-hydrochloride
(169) (3S,5S)-1-[(N-acetylpiperazine-N'-carbonyl)methyl]-5-[(4'-amidino-4-biphenylyl)oxymethyl]-3-(methoxycarbonyl)methyl]-2-pyrrolidinone-hydrochloride
(170) (3S,5S)-5-[(4,-amidino-4-biphenylyl)oxymethyl]-1-(N-methanesulphonylpiperazine-N'-carbonyl)methyl]-3-[(methoxycarbonyl)methyl]-2-pyrrolidinone-hydrochloride
(171) (3S,5S)-5-[(4,-amidino-4-biphenylyl)oxymethyl]-3-[(methoxycarbonyl)methyl]-1-[(thiomorpholine-N-carbonyl)methyl]-2-pyrrolidinone-hydrochloride
(172) (3S,5S)-5-[(4,-amidino-4-biphenylyl)oxymethyl]-3-[(methoxycarbonyl)methyl]-1-[[(thiomorpholine-S-dioxide)-N-carbonyl]methyl]-2-pyrrolidinone-hydrochloride
(173) (3S,5S)-5-[(4,-amidino-4-biphenylyl)oxymethyl]-3-[(methoxycarbonyl)methyl]-1-[(piperazinylcarbonyl)-methyl]-2-pyrrolidinone-hydrochloride
(174) (3S,5S)-5-[(4'-amidino-4-biphenylyl)oxymethyl]-1-( 4-bromobenzyl)-3-[(methoxycarbonyl)methyl]-2-pyrrolidinone-hydrochloride
(175) (3S,5S)-5-[(4,-amidino-4-biphenylyl)oxymethyl]-3-[(methoxycarbonyl)methyl]-1-(4-methylbenzyl)-2-pyrrolidinone-hydrochloride
(176) (3S,5S)-5-[(4'-amidino-4-biphenylyl)oxymethyl]-3-[(methoxycarbonyl)methyl]-1-(4-methylbenzyl)-2-pyrrolidinone-hydrochloride
(177) (3S,5S)-5-[(4'-amidino-4-biphenylyl)oxymethyl]-3-[(methoxycarbonyl)methyl]-1-[3-(methylsulphenyl)propyl]- 2-pyrrolidinone-hydrochloride
(178) (3S,5S)-5-[(4'-amidino-4-biphenylyl)oxymethyl]-3-[(methoxycarbonyl)methyl]-1-[3-(methylsulphonyl)propyl]- 2-pyrrolidinone-hydrochloride (179) (3S,5S)-5-[(4'-amidino-4-biphenylyl)oxymethyl]-3-[(methoxycarbonyl)methyl]-1-phenylsulphonyl-pyrrolidinehydrochloride (180) (3S,5S)-5-[(4'-amidino-3-methoxy-4-biphenylyl)oxymethyl]-3-[(methoxycarbonyl)methyl]-2-pyrrolidinone-hydrochloride (181) (3S,5S)-5-[(4'-amidino-4-biphenylyl)oxymethyl]-1-[[bis-(2-methoxyethyl)-aminocarbonyl]methyl]-3-[(methoxycarbonyl)methyl]-2-pyrrolidinone-hydrochloride (182) (3S,5S)-5-[(4'-amidino-4-biphenylyl)oxymethyl]-1-methoxyacetyl- 3-[(methoxycarbonyl)methyl]-pyrrolidinehydrochloride $R_f$ value: 0.10 (silica gel; methylene chloride/methanol 10:1)

(183) 1-(4'-amidino-4-biphenylyl)-4-[(methoxycarbonyl)methyl]-2-pyrrolidinone-hydrochloride (184) 1-(4'-amidino-4-biphenylyl)-4-phosphonomethyl-2-pyrrolidinone $R_f$ value: 0.73 (reversed phase silica gel; methanol/10% aqueous saline solution=1:1)

(185) 1-(4'-amidino-4-biphenylyl)-4-(O-methyl-phosphonomethyl)- 2-pyrrolidinone $R_f$ value: 0.55 (reversed phase silica gel; methanol/10% aqueous saline solution=1:1)

EXAMPLE 7

(3S,5S)-5-[(4'-Amidino-4-biphenylyl)oxymethyl)-3-carboxymethyl- 1-(3-phenylpropyl)-2-pyrrolidinone-hydrate 125.7 g of (3S,5S)-5-[(4'-amidino-4-biphenylyl)oxymethyl]-3-[(methoxycarbonyl)methyl]-1-(3-phenylpropyl)-2-pyrrolidinone-hydrochloride are dissolved in 1000 ml of methanol with heating. The solution is cooled to 20° C. and 355 ml of 1N sodium hydroxide solution are added with stirring. After one hour, 120 ml and after a further 3 hours a further 40 ml of 1N sodium hydroxide solution are added and the mixture is stirred for 16 hours more at ambient temperature. A solution of 32 g of ammonium chloride in 200 ml of water is added to the reaction mixture, after which the product begins to crystallise out. When crystallisation is complete, the product is filtered off, washed twice more with 100 ml of a mixture of 4 parts methanol and one part water and finally digested twice with 250 ml of acetone. The crude product obtained is recrystallised twice from 400 ml of a mixture of methanol, water and concentrated aqueous ammonia (40:1:1.5).

Yield: 74.7 g (63% of theory), Melting point: 168° C. (decomp.) Calculated: C 69.17 H 6.61 N 8.48 Found: 69.45 6.47 8.48

After evaporation and chromatography on silica gel (eluant: methylene chloride/methanol/concentrated aqueous ammonia=3:1:0.2) (3S,5S)-5-[(4'-aminocarbonyl- 4-biphenylyl)oxymethyl]-3-carboxymethyl-1-(3-phenyl-propyl)-2-pyrrolidinone is obtained from the mother liquors produced in the purification of the crude product.

Yield: 10.5 g (9% of theory), Melting point: 183°–186° C.

The following are obtained analogously:

(1) (3S,5S)-5-[(4'-amidino-4-biphenylyl)oxymethyl]-3-carboxymethyl- 1-phenyl-2-pyrrolidinone-dihydrate Melting point: above 215° C. (decomp.) $R_f$ value: 0.45 (reversed-phase silica gel (RP8); methanol/10% aqueous saline solution=6:4) Calculated: C 65.12 H 6.09 N 8.76 Found: 65.32 5.94 8.75

(2) (3S,5S)-5-[(4'-amidino-4-biphenylyl)oxymethyl]-1-(3-cyclohexylpropyl)- 3-carboxymethyl-2-pyrrolidinonehydrate Melting point: 182-190° C. (decomp.) $R_f$ value: 0.13 (reversed-phase silica gel (RP8); methanol/10% aqueous saline solution=6:4) Calculated: C 68.34 H 7.71 N 8.24 Found: 68.24 7.87 8.13

(3) (3S,5S)-5-[(4'-amidino-4-biphenylyl)oxymethyl]-3-carboxymethyl- 2-pyrrolidinone Melting point: 292-294° C. (decomp.) $R_f$ value: 0.63 (reversed-phase silica gel (RP8); methanol/10% aqueous saline solution=6:4) Calculated: C 65.38 H 5.76 N 11.44 Found: 65.20 5.80 11.54

(4) (3S,5S)-5-[(4'-amidino-4-biphenylyl)oxymethyl]-3-carboxymethyl- 1-methyl-2-pyrrolidinone×0.25 water Melting point: 278°–281° C. (decomp.) $R_f$ value: 0.20 (silica gel; methylene chloride/methanol/conc. aqueous ammonia=80:20:5) Calculated: C 65.36 H 6.14 N 10.89 Found: 65.32 5.97 10.84

(5) (3S,5S)-5-[(4'-amidino-B-bromo-4-biphenylyl)oxymethyl]-3-carboxymethyl-1-(3-phenylpropyl)-2-pyrrolidinone-hydrate Melting point: 236°–238° C. (decomp.) $R_f$ value: 0.45 (silica gel; methene chloride/methanol/conc. aqueous ammonia=40:40:5) Calculated: C 59.80 H 5.54 N 7.21 Br 13.72 Found: 60.00 5.73 6.97 13.56

(6) (3S, 5S) -5-[ (4 '-amidino-3-nitro-4-biphenylyl)oxymethyl]-3-carboxymethyl-1-(3-phenylpropyl)-2-pyrrolidinone-hydrate Melting point: above 192° C. (decomp.), above 180° C. sinters $R_f$ value: 0.18 (silica gel; methylene chloride/methanol/conc. aqueous ammonia=80:30:5) Calculated: C 63.49 H 5.88 N 10.21 Found: 63.64 5.93 10.33

(7) (3R,5R)-5-[(4'-amidino-4-biphenylyl)oxymethyl]-3-carboxymethyl- 1-(3-phenylpropyl)-2-pyrrolidinonesemihydrate Melting point: 183-185° C. (decomp.) $R_f$ value: 0.23 (silica gel; methylene chloride/methanol/conc. aqueous ammonia=80:20:5) Calculated: C 70.43 H 6.52 N 8.50 Found: 70.82 6.78 8.54 $[\alpha]_D^{20}$=–39.8 c=1, glacial acetic acid (8) (3S,5S)-5-[(4'-amidino-3-trifluoromethyl-4-biphenylyl)oxymethyl]-3-carboxymethyl-1-(3-phenyl-propyl)-2-pyrrolidinone-hydrate Melting point: 238-240° C. (decomp.) $R_f$ value: 0.33 (silica gel; methylene chloride/methanol/conc. aqueous ammonia=80:20:6) Calculated: C 63.00 H 5.64 N 7.35 Found: 63.16 5.98 7.37

(9) (3S,5S)-5-[(4'-amidino-B-fluoro-4-biphenylyl)-oxymethyl]-3-carboxymethyl-1-(B-phenylpropyl)-2-pyrrolidinone-hydrate Melting point: 195°–197° C. (decomp.) $R_f$ value: 0.33 (silica gel; methylene chloride/methanol/conc. aqueous ammonia=80:20:5) Calculated: C 66.78 H 6.19 N 8.06 Found: 66.90 6.20 8.06

(10) (3S,5S)-5-[(4'-amidino-2,3-dimethyl-4-biphenylyl)oxymethyl]-3-carboxymethyl-1-(3-phenylpropyl)-2-pyrrolidinone-hydrate Melting point: 211°–213° C. (decomp.) $R_f$ value: 0.14 (silica gel; methylene chloride/methanol/conc. aqueous ammonia=14:5:1) Calculated: C 70.04 H 7.02 N 7.90 Found: 70.22 6.79 8.06

(11) (3S,5S)-5-[(3-acetylamino-4'-amidino-4-biphenylyl)oxymethyl]-3-carboxymethyl-1-(3-phenylpropyl)-2-pyrrolidinone-hydrochloride-semihydrate Melting point: 183°–185° C. (decomp.) $R_f$ value: 0.17 (silica gel; methylene chloride/methanol/conc. aqueous ammonia= 40:10:3) Calculated: C 63.31 H 6.17 N 9.53 Found: 63.59 6.31 9.65

(12) (3S,5S)-5-[(4'-amidino-3-methanesulphonylamino-4-biphenylyl)oxymethyl]-3-carboxymethyl-1-(3-phenylpropyl)- 2-pyrrolidinone×0.25 water Melting point: 219°–220° C. (decomp.) $R_f$ value: 0.23 (silica gel; methylene chloride/methanol/conc. aqueous ammonia= 80:20:5) Calculated: C 61.78 H 5.96 N 9.61 Found: 61.82 6.22 9.48

(13) (3S,5S)-5-[(4'-amidino-2'-methyl-4-biphenylyl)oxymethyl]-3-carboxymethyl-1-(3-phenylpropyl)-2-pyrrolidinone-semihydrate Melting point: above 187° C. (decomp.) $R_f$ value: 0.27 (silica gel; methylene chloride/methanol/conc. aqueous ammonia=12:6:1) Calculated: C 70.85 H 6.74 N 8.26 Found: 71.08 6.77 8.20

(14) (3S,5S)-5-[(4'-amidino-3'-chloro-4-biphenylyl)oxymethyl]-3-carboxymethyl-1-(3-phenylpropyl)-2-pyrrolidinone Melting point: above 166° C. (decomp.) R$_f$ value: 0.13 (silica gel; methylene chloride/methanol/conc. aqueous ammonia=35:15:2) Calculated: C 66.98 H 5.82 N 8.08 Found: 66.63 5.87 8.07

(15) (3S,5S)-5-[[(4'-amidino-4-biphenylyl)carbonyl]aminomethyl]-3-carboxymethyl-1-(3-phenylpropyl)-2-pyrrolidinone-dihydrate Melting point: 208°–214° C. R$_f$ value: 0.40 (silica gel; methylene chloride/methanol/conc. aqueous ammonia=6:3:1) Calculated: C 65.68 H 6.61 N 10.21 Found: 65.48 6.20 9.99

(16) (3S,5S)-5-[[trans-4-(4-amidinophenyl)cyclohexyl]oxymethyl]-3-carboxymethyl-1-(3-phenylpropyl)-2-pyrrolidinone-semihydrate Melting point: 186°–198° C. R$_f$ value: 0.25 (silica gel; methylene chloride/methanol/conc. aqueous ammonia=30:15:3) Calculated: C 69.57 H 7.65 N 8.39 Found: 69.60 7.58 8.38

(17) (3S,5S)-5-[2-[(6-amidino-2-naphthylcarbonyl)-amino]ethyl]-3-carboxymethyl-1-(3-phenylpropyl)-2-pyrrolidinone×2.5 water Melting point: sinters above 166° C., 205° C. (decomp.) R$_f$ value: 0.09 (silica gel; methylene chloride/methanol/conc. aqueous ammonia=70:30:2) Calculated: C 63.84 H 6.84 N 10.27 Found: 64.00 6.77 10.13

(18) (3S,5S)-5-[(6-amidino-2-naphthylcarbonyl)aminomethyl]-3-carboxymethyl-1-(3-phenylpropyl)-2-pyrrolidinone-dihydrate Melting point: 189-202° C. (decomp.) R$_f$ value: 0.10 (silica gel; methylene chloride/methanol/conc. aqueous ammonia=70:30:2) Calculated: C 64.35 H 6.56 N 10.72 Found: 64.55 6.53 10.55

(19) (3S,5S)-5-[(7-amidino-2-naphthylcarbonyl)aminomethyl]-3-carboxymethyl-1-(3-phenylpropyl)-2-pyrrolidinone-trihydrate Melting point: 195-207° C. (decomp.) R$_f$ value: 0.38 (reversed phase silica gel (RPS); methanol/10% aqueous saline solution=6:4) Calculated: C 62.21 H 6.71 N 10.36 Found: 61.98 6.75 10.55

(20) (3S,5S)-5-[2-[(7-amidino-2-naphthylcarbonyl)-amino]ethyl]-3-carboxymethyl-1-(3-phenylpropyl)-2-pyrrolidinone×2.5 water Melting point: 185°–200° C. (decomp.) R$_f$ value: 0.41 (reversed phase silica gel (RP8); methanol/10% aqueous saline solution=6:4) Calculated: C 63.84 H 6.83 N 10.27 Found: 63.73 6.51 10.18

(21) (3S,5S)-5-[[trans-3-(4-amidinophenyl)cyclobutyl]carbonylaminomethyl]-3-carboxymethyl-1-(3-phenylpropyl)-2-pyrrolidinone×1.5 water R$_f$ value: 0.31 (silica gel; methylene chloride/methanol/conc. aqueous ammonia=35:15:4) Calculated: C 65.35 H 7.25 N 10.89 Found: 65.60 7.26 10.61

(22) (3S,5S)-5-[[cis-3-(4-amidinophenyl)cyclobutyl]carbonylaminomethyl]-3-carboxymethyl-1-(3-phenylpropyl)-2-pyrrolidinone R$_f$ value: 0.38 (silica gel; methylene chloride/methanol/conc. aqueous ammonia=35:15:4)

(23) (3S,5S)-5-[2-[[cis-3-(4-amidinophenyl)cyclobutyl]carbonylamino]ethyl]-3-carboxymethyl-1-(3-phenylpropyl)-2-pyrrolidinone×1.5 water R$_f$ value: 0.34 (silica gel; methylene chloride/methanol/conc. aqueous ammonia=35:15:4) Calculated: C 65.51 H 7.39 N 10.54 Found: 65.04 7.24 10.26

(24) (3S,5S)-5-[2-[ [trans-3-(4-amidinophenyl)cyclobutyl]carbonylamino]ethyl]-3-carboxymethyl-1-(3-phenylpropyl)-2-pyrrolidinone-dihydrate R$_f$ value: 0.30 (silica gel; methylene chloride/methanol/conc. aqueous ammonia=35:15:4) Calculated: C 64.43 H 7.45 N 10.36 Found: 64.24 7.28 9.98

(25) (3S,5S)-5-[[3-(4-amidinophenyl)propyl]carbonylaminomethyl]-3-carboxymethyl-1-(3-phenylpropyl)-2-pyrrolidinone R$_f$ value: 0.16 (silica gel; methylene chloride/methanol/aqueous ammonia=4:1:0.2)

(26) (3S,5S)-5-[(4'-amidino-4-biphenylyl)oxymethyl]-3-carboxymethyl-3-methyl-1-(3-phenylpropyl)-2-pyrrolidinone-dihydrate Calculated: C 67.27 H 6.96 N 7.85 Found: 67.46 6.85 8.13

(3S,5S)-5-[(4'-aminocarbonyl-4-biphenylyl)oxymethyl]-3-carboxymethyl-3-methyl-1-(3-phenylpropyl)-2-pyrrolidinone is obtained as a by-product and separated by chromatography on silica gel (eluant: methylene chloride/methanol/conc. aqueous ammonia=4:1:0.25). R$_f$ value: 0.81 (silica gel; methylene chloride/methanol/aqueous ammonia=4:1:0.25)

(27) (3S,5S)-5-[(4'-amidino-4-biphenylyl)oxymethyl]-1-benzyl-3-carboxymethyl-2-pyrrolidinone-dihydrate Calculated: C 65.71 H 6.33 N 8.51 Found: 66.08 6.13 8.48

(28) (3S,5S)-5-[(4'-amidino-4-biphenylyl)oxymethyl]-3-carboxymethyl-1-(2-phenylethyl)-2-pyrrolidinone-hydrate Calculated: C 68.69 H 6.38 N 8.58 Found: 68.43 6.08 8.41

(29) (3S,5S)-5-[(4'-amidino-4-biphenylyl)oxymethyl]-3-carboxymethyl-1-((4-phenylbutyl)-2-pyrrolidinone-hydrate Calculated: C 69.61 H 6.81 N 8.12 Found: 69.29 6.57 8.35

(30) (3S,5S)-5-[(4'-amidino-4-biphenylyl)oxymethyl]-3-carboxymethyl-1-(4-phenyloxybutyl)-2-pyrrolidinonedihydrate Calculated: C 65.32 H 6.76 N 7.62 Found: 65.67 6.48 8.17

(31) (3S,5S)-5-[[4'-(n-butylamidino)-4-biphenylyl]oxymethyl]-3-carboxymethyl-1-(3-phenylpropyl)-2-pyrrolidinone ×1.5 water Calculated: C 69.69 H 7.44 N 7.39 Found: 69.42 7.37 7.35

(32) (3S,5S)-3-carboxymethyl-5-[(4'-methylamidino-4-biphenylyl)oxymethyl]-1-(3-phenylpropyl)-2-pyrrolidinone-hydrate Calculated: C 69.61 H 6.81 N 8.12 Found: 69.22 6.88 7.98

(33) (3S,5S)-3-carboxymethyl-5-[(4'-isopropylamidino-4-biphenylyl)oxymethyl]-1-(3-phenylpropyl)-2-pyrrolidinone-dihydrate Calculated: C 68.18 H 7.33 N 7.45 Found: 67.87 7.47 7.91

(34) (3S,5S)-5-[(4'-amidino-4-biphenylyl)oxymethyl]-3-carboxymethyl-1,3-bis-(3-phenylpropyl)-2-pyrrolidinonesemihydrate Calculated: C 74.48 H 6.91 N 6.86 Found: 74.67 7.02 6.78

(35) (3S,5S)-5-[(4'-amidino-4-biphenylyl)oxymethyl]-3-(n-butyl)-3-carboxymethyl-1-(3-phenylpropyl)-2-pyrrolidinone-hydrate Calculated: C 70.81 H 7.38 N 7.51 Found: 70.54 7.33 7.47

(36) (3S,5S)-5-[(7-amidino-9-keto-2-fluorenyl)oxymethyl]-3-carboxymethyl-1-(3-phenylpropyl)-2-pyrrolidinone Melting point: 226° C. (decomp.)

(37) (3R,5S)-5-[(4'-amidino-4-biphenylyl)oxymethyl]-3-carboxymethyl-1-(3-phenylpropyl)-2-pyrrolidinone Melting point: 225-227° C. (decomp.)

(38) (3S,5S)-5-[(4'-amidino-4-biphenylyl)aminomethyl]-3-carboxymethyl-1-(3-phenylpropyl)-2-pyrrolidinone Melting point: 208° C. (decomp.)

(39) (3S,5S)-5-[[N-(4'-amidino-4-biphenylyl)-N-methanesulphonyl]aminomethyl]-3-carboxymethyl-1-(3-phenylpropyl)-2-pyrrolidinone Melting point: over 200° C. Calculated: C 64.03 H 6.10 N 9.96 S 5.70 Found: 63.96 5.91 9.73 5.60

(40) (3S,5S)-5-[[N-(4'-amidino-4-biphenylyl)-N-acetyl]aminomethyl]-3-carboxymethyl-1-(3-phenylpropyl)-2-pyrrolidinonehydrate Calculated: C 68.29 H 6.61 N 10.28 Found: 68.57 6.62 10.15

(41) (3S,5S)-5-[[2-[(4-amidinophenyl)amino]phenyl]carbonylaminomethyl]-3-carboxymethyl-1-(3-phenylpropyl)-2-pyrrolidinone Melting point: from 172° C. (decomp.) R$_f$ value: 0.30 (silica gel; cyclohexane/ethyl acetate/methanol=2:1:0.6)

(42) (3S,5S)-5-[[4-[(4-amidinophenyl)aminocarbonyl]phenyl]oxymethyl]-3-carboxymethyl-1-(3-phenylpropyl)-2-pyrrolidinone R$_f$ value: 0.45 (silica gel; methylene chloride/methanol/conc. aqueous ammonia=4:2:1) Calculated: C 68.16 H 6.10 N 10.60 Found: 68.46 6.19 10.44 Mass spectrum: (M+H)$^+$=529

(43) (3S,5S)-5-[[4-[(4-amidinophenyl)carbonylamino]phenyl]oxymethyl]-3-carboxymethyl-1-(3-phenylpropyl)-2-pyrrolidinone Melting point: >250° C. R$_f$ value: 0.43 (silica gel; methylene chloride/methanol/conc. aqueous ammonia=4:2:1) Mass spectrum: (M+H)$^+$=529

(44) (3S,5S)-5-[[4-[(4-amidinophenyl)aminosulphonyl]phenyl]oxymethyl]-3-carboxymethyl-1-(3-phenylpropyl)-2-pyrrolidinone Melting point: >250° C. R$_f$ value: 0.40 (silica gel; methylene chloride/methanol/conc. aqueous ammonia=4:2:1) Mass spectrum: (M+H)$^+$=565

(45) (3S,5S)-5-[[4-[(3-amidinophenyl)sulphenyl]phenyl]oxymethyl]-3-carboxymethyl-1-(3-phenylpropyl)-2-pyrrolidinone R$_f$ value: 0.14 (silica gel; methylene chloride/methanol/conc. aqueous ammonia=16:4:1) Mass spectrum: (M+H)$^+$=518

(46) (3S,5S)-5-[[4-[(3-amidinophenyl)carbonyl]phenyl]oxymethyl]-3-carboxymethyl-1-(3-phenylpropyl)-2-pyrrolidinone R$_f$ value: 0.21 (silica gel; methylene chloride/ethanol/conc. aqueous ammonia=8:2:1) Mass spectrum: (M+H)$^+$=514

(47) (3S,5S)-5-[[4-[(3-amidinophenyl)sulphonyl]phenyl]oxymethyl]-3-carboxymethyl-1-(3-phenylpropyl)-2-pyrrolidinone Melting point: 205°–207° C. R$_f$ value: 0.20 (silica gel; methylene chloride/ethanol/conc. aqueous ammonia=4:4:1) Calculated: C 63.37 H 5.69 N 7.63 S 5.83 Found: 63.10 5.90 7.59 5.92 Mass spectrum: (M+H)$^+$=550

(48) (3S,5S)-5-[[4-[(3-amidinophenyl)sulphinyl]phenyl]oxymethyl]-3-carboxymethyl-1-(3-phenylpropyl)-2-pyrrolidinone R$_f$ value: 0.25 (silica gel; methylene chloride/ethanol/conc. aqueous ammonia=4:4:1) Mass spectrum: (M+H)$^+$=534

(49) (3S,5S)-5-[(4'-amidino-4-biphenylyl)oxymethyl]-1,3-bis-(carboxymethyl)- 2-pyrrolidinone×0.25 water R$_f$ value: 0.56 (silica gel; methanol/conc. aqueous ammonia=25:1) Calculated: C 61.46 H 5.51 N 9.77 Found: 61.46 5.55 9.57 Mass spectrum: (M+H)$^+$=426

(50) (3S,5S)-5-[(4'-amidino-4-biphenylyl)oxymethyl]-3-carboxymethyl- 1-[(ethylaminocarbonyl)methyl]-2-pyrrolidinone hydrochloride-hydrate R$_f$ value: 0.36 (silica gel; methanol/conc. aqueous ammonia=50:3) Calculated: C 56.86 H 6.16 N 11.05 Cl 6.99 Found: 56.87 6.39 11.26 6.95 Mass spectrum: (M+H)$^+$=426

(51) (3S,5S)-5-[(4'-amidino-4-biphenylyl)oxymethyl]-3-carboxymethyl- 1-[(dimethylaminocarbonyl)methyl]-2-pyrrolidinone hydrochloride-semihydrate R$_f$ value: 0.24 (silica gel; methanol/conc. aqueous ammonia=50:3) Calculated: C 57.89 H 6.07 N 11.25 Cl 7.11 Found: 57.76 6.08 11.34 7.23

(52) (3S,5S)-5-[(4'-amidino-4-biphenylyl)oxymethyl]-1-[(benzylaminocarbonyl)methyl]-3-carboxymethyl-2-pyrrolidinone Melting point: >200° C., R$_f$ value: 0.37 (silica gel; methanol/conc. aqueous ammonia=50:2) Mass spectrum: (M+H)$^+$=515

(53) (3S,5S)-5-[(4'-amidino-4-biphenylyl)oxymethyl]-1-(aminocarbonyl)methyl]-3-carboxymethyl-2-pyrroidinone-hydrochloride-hydrate Melting point: >200° C., R$_f$ value: 0.30 (silica gel; methanol/conc. aqueous ammonia=50:2) Calculated: C 55.17 H 5.68 N 11.70 Cl 7.40 Found: 57.35 5.68 11.88 7.20 Mass spectrum: (M+H)$^+$=425

(54) (3S,5S)-5-[(4'-amidino-4-biphenylyl)oxymethyl]-1-benzoyl- 3-carboxymethyl-pyrrolidine-semihydrate Melting point: 234°–237° C. (decomp.), R$_f$ value: 0.51 (silica gel; methylene chloride/methanol/conc. aqueous ammonia=70:30:8) Calculated: C 69.51 H 6.05 N 9.01 Found: 69.34 6.22 8.90

(55) (3S,5S)-5-[(4'-amidino-4-biphenylyl)oxymethyl]-3-carboxymethyl- 1-methanesulphonyl-pyrrolidine-hydrate Melting point: 266°–268° C. R$_f$ value: 0.31 (silica gel; methylene chloride/methanol/conc. aqueous ammonia=100:10:4) Calculated: C 56.23 H 5.84 N 9.37 S 7.15 Found: 56.41 5.78 9.16 7.64

(56) (3S,5S)-1-acetyl-5-[(4'-amidino-4-biphenylyl)oxymethyl]-3-carboxymethyl-pyrrolidine-semihydrate Melting point: 265°–268° C. (decomp.), R$_f$ value: 0.05 (silica gel; methylene chloride/methanol/conc. aqueous ammonia=100:30:4) Calculated: C 65.33 H 6.48 N 10.39 Found: 65.58 6.55 10.20

(57) (3S,5S)-5-[(4'-amidino-4-biphenylyl)oxymethyl]-3-carboxymethyl- 1-(ethylaminocarbonyl)-pyrrolidinedihydrate Melting point: 195°–200° C. (decomp.), R$_f$ value: 0.30 (silica gel; methylene chloride/methanol/conc. aqueous ammonia=100:30:4) Calculated: C 60.00 H 7.00 N 12.17 Found: 60.18 6.98 12.34

(58) (3S,5S)-5-[(4'-amidino-4-biphenylyl)oxymethyl]-3-carboxymethyl- 1-(dimethylaminosulphonyl)-pyrrolidine×0.25 water Melting point: 278° C. (decomp.), R$_f$ value: 0.37 (silica gel; methylene chloride/methanol/conc. aqueous ammonia=100:30:4) Calculated: C 56.81 H 6.18 N 12.05 S 6.89 Found: 56.69 6.16 11.76 7.17

(59) (3S,5S)-5-[(4'-amidino-4-biphenylyl)oxymethyl]-3-carboxymethyl- 1-methyl-pyrrolidine R$_f$ value: 0.57 (reversed phase silica gel; methanol/10% aqueous saline solution=6:4) Mass spectrum: (M+H)$^+$=368

(60) (3R,5S)-5- [(4'-amidino-4-biphenylyl)oxymethyl]-3-carboxymethyl- 2-pyrrolidinone-hydrate Melting point: 288° C. (decomp.), R$_f$ value: 0.80 (reversed phase silica gel; methanol/10% aqueous saline solution=6:4) Calculated: C 62.33 H 6.01 N 10.90 Found: 62.53 5.90 11.03

(61) (3S,5S)-5-[(4'-amidino-4-biphenylyl)oxymethyl]-3-carboxymethyl- 3-methyl-2-pyrrolidinone-hydrate Melting point: 204° C. (decomp.), R$_f$ value: 0.74 (reversed phase silica gel; methanol/10% aqueous saline solution=6:4) Calculated: C 63.14 H 6.31 N 10.52 Found: 63.31 6.53 10.41

(62) (3S,5S)-5-[(4'-amidino-4-biphenylyl)oxymethyl]-3-carboxymethyl- 1-(2-methoxyethyl)-2-pyrrolidinone Melting point: 230° C. (decomp.), R$_f$ value: 0.75 (reversed phase silica gel; methanol/10% aqueous saline solution=6:4)

(63) (3R,5R)-5- [(4'-amidino-4-biphenylyl)oxymethyl]-3-carboxymethyl- 2-pyrrolidinone-semihydrate Melting point: 286°–288° C. (decomp.) R$_f$ value: 0.63 (reversed phase silica gel; methanol/10% aqueous saline solution=6:4) Calculated: C 63.82 H 5.89 N 11.16 Found: 64.04 5.82 10.89

(64) (3S,5S)-5-[2-[ (4'-amidino-3-biphenylyl)amino]ethyl] -3-carboxymethyl-1- (3-phenylpropyl)-2-pyrrolidinone-semihydrate Calculated: C 70.98 H 6.90 N 11.04 Found: 70.72 6.99 10.86

(65) (3S,5S)-3-carboxymethyl-5-[2-[(3'-guanidino-3-biphenylyl)amino]ethyl]-1-(3-phenylpropyl)-2-pyrrolidinone ×NH$_3$×2 H$_2$O×0.75 HCl R$_f$ value: 0.43 (silica gel; methylene chloride/methanol/conc. aqueous ammonia=8:2:0.1) Calculated: C 60.65 H 7.25 N 14.15 Cl 4.48 Found: 60.49 7.60 14.07 4.29

(66) (3S,5S)-5-[2-[[(3'-amidino-4-biphenylyl)carbonyl]amino]ethyl]-3-carboxymethyl-1-(3-phenylpropyl)-2-pyrrolidinone-semihydrochloride-hydrate Melting point: 214° C. (decomp.), Calculated: C 66.20 H 6.54 N 9.96 C13.15 Found: 66.41 6.53 9.91 3.22

(67) (3S,5S)-5-[(4'-amidino-3-methylsulphonyl-4-biphenylyl)oxymethyl]-3-carboxymethyl-1-(3-phenylpropyl)-2-pyrrolidinone $R_f$ value: 0.28 (silica gel; methylene chloride/methanol/aqueous ammonia=2:1:0.25) Mass spectrum: $(M+H)^+$=564

(68) (3S,5S)-5-[(4'-amidino-3-methylsulphenyl-4-biphenylyl)oxymethyl]-3-carboxymethyl-1-(3-phenylpropyl)-2-pyrrolidinone-hydrate $R_f$ value: 0.28 (silica gel; methylene chloride/methanol/aqueous ammonia=2:1:0.25) Calculated: C 65.55 H 6.42 N 7.64 S 5.83 Found: 65.70 6.58 7.64 5.50

(69) (3S,5S)-5-[(4'-amidino-3-methylsulphinyl-4-biphenylyl)oxymethyl]-3-carboxymethyl-1-(3-phenylpropyl)-2-pyrrolidinone-hydrate $R_f$ value: 0.31 (silica gel; methylene chloride/methanol/conc. aqueous ammonia=2:1:0.25) Calculated: C 63.70 H 6.07 N 7.43 S 5.67 Found: 63.55 6.31 7.34 5.69

(70) (3S,5S)-5-[(4'-amidino-4-biphenylyl)sulphonyl]aminomethyl]-3-carboxymethyl-1-(3-phenylpropyl)-2-pyrrolidinone-semihydrochloride $R_f$ value: 0.22 (silica gel; methylene chloride/methanol/conc. aqueous ammonia=2:1:0.25) Calculated: C 61.44 H 5.78 N 9.88 S 5.66 C13.13 Found: 61.27 5.98 9.65 5.58 2.92

(71) (3S,5S)-5-[2-[(4-amidinocinnamoyl)amino]ethyl]-3-carboxymethyl-1-(3-phenylpropyl)-2-pyrrolidinone $R_f$ value: 0.29 (silica gel; methylene chloride/methanol/conc. aqueous ammonia=2:1:0.25) Mass spectrum: $(M+H)^+$=477

(72) (3S,5S)-5-[(4'-amidino-4-biphenylyl)oxymethyl]-3-carboxymethyl-1-[3-(3,4-dimethoxyphenyl)propyl]-2-pyrrolidinone ×1.5 water $R_f$ value: 0.38 (silica gel; methylene chloride/methanol/conc. aqueous ammonia= 2:1:0.25) Calculated: C 65.02 H 6.69 N 7.34 Found: 65.20 6.73 7.42

(73) (3S,5S)-5-[(4'-amidino-4-biphenylyl)oxymethyl]-3-carboxymethyl-1-[3-(4-hexyloxyphenyl)propyl]-2-pyrrolidinone-hydrate $R_f$ value: 0.31 (silica gel; methylene chloride/methanol/conc. aqueous ammonia=2:1:0.25) Calculated: C 69.63 H 7.51 N 6.96 Found: 69.54 7.67 6.92

(74) (3S,5S)-5-[(4'-amidino-4-biphenylyl)oxymethyl]-1-[3-(4-tert.butylphenyl)propyl]-3-carboxymethyl-2-pyrrolidinone-semihydrate $R_f$ value: 0.25 (silica gel; methylene chloride/methanol/conc. aqueous ammonia=2:1:0.25) Calculated: C 71.97 H 7.32 N 7.63 Found: 72.22 7.24 7.70

(75) (3S,5S)-5-[(4'-amidino-4-biphenylyl)oxymethyl]-3-carboxymethyl-1-[3-(3-trifluoromethylphenyl)propyl]-2-pyrrolidinone-hydrate $R_f$ value: 0.31 (silica gel; methylene chloride/methanol/conc. aqueous ammonia=2:1:0.25) Calculated: C 63.03 H 5.64 N 7.35 Found: 63.16 5.53 7.41

(76) (3S,5S)-5-[(4'-amidino-4-biphenylyl)oxymethyl]-3-carboxymethyl-1-[3-(2,4-dichlorophenyl)propyl]-2-pyrrolidinone-hydrate $R_f$ value: 0.41 (silica gel; methylene chloride/methanol/conc. aqueous ammonia=2:1:0.25) Calculated: C 60.84 H 5.46 N 7.34 Cl 12.39 Found: 61.09 5.59 7.26 12.71

(77) (3S,5S)-5-[(4'-amidino-4-biphenylyl)oxymethyl]-3-carboxymethyl-1-[3-(3-benzylphenyl)propyl]-2-pyrrolidinone-semihydrate $R_f$ value: 0.50 (silica gel; methylene chloride/methanol/conc. aqueous ammonia=2:1:0.25) Calculated: C 73.95 H 6.55 N 7.19 Found: 73.85 6.79 6.90

(78) (3S,5S)-5-[(4'-amidino-4-biphenylyl)oxymethyl]-1-(4,4-diphenylbutyl)-3-carboxymethyl-2-pyrrolidinonehydrate $R_f$ value: 0.22 (silica gel; methylene chloride/methanol/conc. aqueous ammonia=2:1:0.25) Calculated: C 72.51 H 6.43 N 7.25 Found: 72.73 6.61 7.29

(79) (3S,5S)-5-[(4'-amidino-4-biphenylyl)oxymethyl]-3-carboxymethyl-1-[3-(4-methylsulphenylphenyl)propyl]-2-pyrrolidinone ×1.5 water $R_f$ value: 0.28 (silica gel; methylene chloride/methanol/conc. aqueous ammonia= 2:1:0.25) Calculated: C 64.49 H 6.50 N 7.52 S 5.74 Found: 64.62 6.34 7.35 5.84

(80) (3S,5S)-5-[(4'-amidino-4-biphenylyl)oxymethyl]-3-carboxymethyl-1-[3-(4-methylsulphenylphenyl)propyl]-2-pyrrolidinone $R_f$ value: 0.30 (silica gel; methylene chloride/methanol/conc. aqueous ammonia=2:1:0.25) Mass spectrum: $(M+H)^+$=564

(81) (3S,5S)-5-[(4'-amidino-4-biphenylyl)oxymethyl]-1-(4-biphenylylmethyl)-3-carboxymethyl-2-pyrrolidinone× 1.5 water $R_f$ value: 0.33 (silica gel; methylene chloride/methanol/conc. aqueous ammonia=2:1:0.25) Calculated: C 70.70 H 6.11 N 7.50 Found: 70.58 6.09 7.39

(82) (3R,5S)-5-[(4'-amidino-4-biphenylyl)oxymethyl]-3-(3-carboxypropyl)-1-(3-phenylpropyl)-2-pyrrolidinone $R_f$ value: 0.26 (silica gel; methylene chloride/methanol/conc. aqueous ammonia=8:2:0.10) Calculated: C 72.49 H 6.87 N 8.18 Found: 72.29 7.02 8.34

(83) (3R,5S)-5-[(4'-amidino-4-biphenylyl)oxymethyl]-3-(5-carboxypentyl)-1-(3-phenylpropyl)-2-pyrrolidinone $R_f$ value: 0.31 (silica gel; methylene chloride/methanol/water=8:2:0.10) Calculated: C 73.17 H 7.26 N 7.76 Found: 73.16 6.95 7.70

(84) (3S,5S)-5-[[(3'-amidino-4-biphenylyl)carbonyl]aminomethyl]-3-carboxymethyl-1-(3-phenylpropyl)-2-pyrrolidinone-hydrochloride-hydrate Carried out with lithium hydroxide and worked up with hydrochloric acid. $R_f$ value: 0.14 (silica gel; methylene chloride/methanol/conc. aqueous ammonia=4:1:0.25) Calculated: C 63.54 H 6.22 N 9.88 C16.25 Found: 63.79 6.08 9.61 6.40

(85) (3S,5S)-5-[[(4'-amidino-3-biphenylyl)carbonyl]aminomethyl]-3-carboxymethyl-1-(3-phenylpropyl)-2-pyrrolidinone $R_f$ value: 0.13 (silica gel; methylene chloride/ methanol/ conc. aqueous ammonia=4:1:0.25) Mass spectrum: $(M+H)^+$=513

(86) (3S,5S)-5-[(4'-amidino-4-biphenylyl)sulphonylmethyl]-3-carboxymethyl-1-(3-phenylpropyl)-2-pyrrolidinone $R_f$ value: 0.25 (silica gel; methylene chloride/methanol/conc. aqueous ammonia=2:1:0.25) Mass spectrum: $(M+H)^+$=534

(87) (3S,5S)-5-[(4'-amidino-4-biphenylyl)sulphenylmethyl]-3-carboxymethyl-1-(3-phenylpropyl)-2-pyrrolidinone $R_f$ value: 0.41 (silica gel; methylene chloride/methanol/conc. aqueous ammonia=4:1:0.25) Mass spectrum: $(M+H)^+$=502

(88) (3S,5S)-5-[[[1-(4-amidinophenyl)-1-propen-3-yl]aminocarbonyl]methyl]-3-carboxymethyl-1-(3-phenylpropyl)-2-pyrrolidinone $R_f$ value: 0.14 (silica gel; methylene chloride/methanol/conc. aqueous ammonia=4:1:0.25) Mass spectrum: $(M+H)^+$=477

(89) (3R,S;4R,S)-4-[(4'-amidino-4-biphenylyl)oxymethyl]-3-carboxymethyl-2-pyrrolidinone Melting point: >260° C. $R_f$ value: 0.67 (reversed phase silica gel RP 18; methanol/10% aqueous saline solution=6:4)

(90) (3S,5S)-5-[(7-amidino-9,10-dihydro-2-phenanthrenyl)oxymethyl]-3-carboxymethyl-2-pyrrolidinone ×1.25 $H_2O$×0.2 HCl $R_f$ value: 0.57 (silica gel/methylene chloride/methanol/conc. aqueous ammonia=1:1:0.2) Calculated: C 62.43 H 6.12 N 9.93 Cl1.68 Found: 62.46 6.13 9.96 1.64

(91) (3S,5S)-5-[(3-amidinobenzoyl)aminomethyl]-3-carboxymethyl-1-(3-phenylpropyl)-2-pyrrolidinone $R_f$ value: 0.13 (silica gel; methylene chloride/methanol/conc. aqueous ammonia=4:1:0.25) Mass spectrum: $(M+H)^+$=437

(92) (3S,5S)-5-[[exo-5-(4-amidinophenyl)bicyclo[2.2.1]-heptyl-exo- 2-carbonyl]aminomethyl]-3-carboxymethyl-1-(3-phenylpropyl)-2-pyrrolidinone $R_f$ value: 0.45 (silica gel; methylene chloride/methanol/conc. aqueous ammonia=4:1:0.25) Mass spectrum: $(M+H)^+=531$

(93) (3S,5S)-5-[(4'-amidino-3'-fluoro-4-biphenylyl)oxymethyl]-3-carboxymethyl-2-pyrrolidinone Melting point: 265°–267° C. (decomp.) $R_f$ value: 0.47 (reversed phase silica gel; methanol/10% aqueous saline solution 6:4)

(94) (3R,S;4R,S)-4-[(4'-amidino-4-biphenylyl)oxymethyl]-3-carboxymethyl-3-methyl-2-pyrrolidinone Melting point: 278° C. (decomp.) $R_f$ value: 0.59 (reversed phase silica gel; methanol/10% aqueous saline solution 6:4)

(95) (3R,S;4R,S)-4-[[(4'-amidino-4-biphenylyl)carbonylamino]methyl]-3-carboxymethyl-2-pyrrolidinone Melting point: 278°–280° C. (decomp.) $R_f$ value: 0.64 (reversed phase silica gel; methanol/10% aqueous saline solution 6:4)

(96) (3R,S;4R,S)-4-[[(4'-amidino-4-biphenylyl)carbonylamino]methyl]-3-carboxymethyl-3-methyl-2-pyrrolidinone

(97) (3S,5S)-5-[(4'-amidino-4-biphenylyl)oxymethyl]-3-carboxymethyl- 1-(2-carboxyphenyl)-2-pyrrolidinone

(98) (3S, 5S)-5-[(4'-amidino-4-biphenylyl) oxymethyl]-1-[(2-aminocarbonyl)phenyl]-3-carboxymethyl-2-pyrrolidinone

(99) (3S,5S)-5-[(4'-amidino-4-biphenylyl)oxymethyl]-3-carboxymethyl- 1-[2-(ethylaminocarbonyl)phenyl]-2-pyrrolidinone (100) (3S,5S)-5-[(4'-amidino-4-biphenylyl)oxymethyl]-3-carboxymethyl- 1-[2-(dimethylaminocarbonyl)Phenyl]-2-pyrrolidinone (101) (3S,5S)-5-[(4'-amidino-4-biphenylyl)oxymethyl]-3-carboxymethyl- 1-(3-carboxyphenyl)-2-pyrrolidinone (102) (3S,5S)-5-[(4'-amidino-4-biphenylyl)oxymethyl]-1-[3-(aminocarbonyl)phenyl]-3-carboxymethyl-2-pyrrolidinone (103) (3S,5S)-5-[(4'-amidino-4-biphenylyl)oxymethyl]-3-carboxymethyl- 1-[3-(ethylaminocarbonyl)Phenyl]-2-pyrrolidinone (104) (3S,5S)-5-[(4'-amidino-4-biphenylyl)oxymethyl]-3-carboxymethyl- 1-[3-(dimethylaminocarbonyl)phenyl]-2-pyrrolidinone (105) (3S,5S)-5-[(4'-amidino-4-biphenylyl)oxymethyl]-3-carboxymethyl- 1-(4-carboxyphenyl)-2-pyrrolidinone (106) (3S,5S)-5-[(4'-amidino-4-biphenylyl)oxymethyl]-1-[4-(aminocarbonyl)phenyl]-3-carboxymethyl-2-pyrrolidinone (107) (3S,5S)-5-[(4'-amidino-4-biphenylyl)oxymethyl]-3-carboxymethyl- 1-[4-(ethylaminocarbonyl)phenyl]-2-pyrrolidinone (108) (3S,5S)-5-[(4'-amidino-4-biphenylyl)oxymethyl]-3-carboxymethyl- 1-[4-(dimethylaminocarbonyl)phenyl]-2-pyrrolidinone (109) (3S,5S)-5-[(4'-amidino-4-biphenylyl)oxymethyl]-3-carboxymethyl- 1-[3-(methanesulphonylamino)phenyl]-2-pyrrolidinone (110) (3S, 5S) -1-[3-(acetamino)phenyl]-5-[ (4'-amidino-4-biphenylyl)oxymethyl]-3-carboxymethyl-2-pyrrolidinone (111) (3S,5S)-5-[[(6-amidino-1,2,3,4-tetrahydro-2-naphthyl)-aminocarbonyl]aminomethyl]-3-carboxymethyl-2-pyrrolidinone (112) (3S,5S)-5-[[N-acetyl-N-[trans-4-(4-amidinophenyl)cyclohexyl)]aminomethyl]-3-carboxymethyl-2-pyrrolidinone (113) (3S,5S)-5-[[N-[trans-4-(4-amidinophenyl)cyclohexyl]-N-methanesulphonyl]aminomethyl]-3-carboxymethyl-2-pyrrolidinone (114) (3S,5S)-5-[(trans-4-(4-amidinophenyl)cyclohexyl]oxymethyl]-3-carboxymethyl-2-pyrrolidinone (115) (3S, 6S) -6-[ (4'-amidino-4-biphenylyl)oxymethyl]-3-carboxymethyl- 2-piperidinone (116) (4R,6S)-6-[(4'-amidino-4-biphenylyl)oxymethyl]-4-carboxy- 2-piperidinone (117) (3S,5S)-5-[(4'-amidino-3-ethoxy-4-biphenylyl)oxymethyl]-3-carboxymethyl-2-pyrrolidinone (118) (3S,5S)-5-[(4'-amidino-3'-chloro-4-biphenylyl)oxymethyl]-3-carboxymethyl-2-pyrrolidinone×1.5 water Melting point: 258°–260° C. $R_f$ value: 0.66 (reversed phase silica gel; methanol/5% aqueous saline solution=6:4) Calculated: C 56.01 H 5.40 N 9.80 Found: 56.24 5.18 9.58

(119) (3S,5S)-5-[(4'-amidino-3-bromo-4-biphenylyl)oxymethyl]-3-carboxymethyl-2-pyrrolidinone $R_f$ value: 0.20 (silica gel; methylene chloride/methanol/conc. aqueous ammonia=2:1:0.25)

(120) (3S,5S)-5-[(4'-amidino-4-biphenylyl)oxymethyl]-3-carboxymethyl- 1-[2-(phenylsulphonyl)ethyl]-2-pyrrolidinone (121) (3S,5S)-5-[(4'-amidino-4-biphenylyl)oxymethyl]-3-carboxymethyl- 1-[2-(phenylsulphenyl)ethyl]-2-pyrrolidinone (122) (3S,5S)-5-[(4'-amidino-4-biphenylyl)oxymethyl]-3-carboxymethyl- 1-[2-(phenylsulphinyl)ethyl]-2-pyrrolidinone (123) (3R, 5S) -5-[ (4'-amidino-4-biphenylyl)oxymethyl]-3-[(carboxymethyl)oxy]-1-(3-phenylpropyl)-2-pyrrolidinone (124) (3R,5S)-5-[(4'-amidino-4-biphenylyl)oxymethyl]-3-[(carboxymethyl)sulphenyl]-1-(3-phenylpropyl)-2-pyrrolidinone (125) (3R,5S)-5-[(4'-amidino-4-biphenylyl)oxymethyl]-3-[(N-carboxymethyl-N-methyl)amino]-1-(3-phenylpropyl)-2-pyrrolidinone (126) (3S,5S)-5-[[[1-(4-amidinophenyl)-1-propyn-3-yl]aminocarbonyl]methyl]-3-carboxymethyl-2-pyrrolidinone (127) (3S,5S)-5-[(7-amidino-2-phenanthrenyl)oxymethyl]-3-carboxymethyl-2-pyrrolidinone (128) (3R,5S)-3-[(4'-amidino-4-biphenylyl)methyl]-5-carboxymethyl- 2-pyrrolidinone (129) (3S,5S)-3-[(4'-amidino-4-biphenylyl)oxymethyl]-5-carboxymethyl- 2-pyrrolidinone (130) 3-[(4'-amidino-4-biphenylyl)methyl]-1-(2-carboxyethyl)- 2-pyrrolidinone (131) 1-[2-(4'-amidino-4-biphenylyl)ethyl]-3-carboxymethyl- 2 -pyrrolidinone (132) (3R, 5S)-3-[2-(4'-amidino-4-biphenylyl)ethyl]-5-carboxymethyl- 2 -pyrrolidinone (133) (2S,5S)-5-[(4'-amidino-4-biphenylyl)oxymethyl]-2-carboxymethyl- 1-methanesulphonyl-pyrrolidine (134) (2S,5S)-1-acetyl-5-[(4'-amidino-4-biphenylyl)oxymethyl]-2-carboxymethyl-pyrrolidine (135) (3S, 5S) -5-[ [ (4'-amidino-3-biphenylyl)sulphonylamino]methyl]- 3-carboxymethyl -2-pyrrolidinone (136) (3S,5S)-5-[[(3'-amidino-4-biphenylyl)carbonylamino]methyl]-3-carboxymethyl-2-pyrrolidinone (137) (3S,5S)-5-[(4'-amidino-4-biphenylyl)oxymethyl]-1-( 2-aminoethyl)-3-carboxymethyl-2-pyrrolidinone (138) (3S,5S)-1-[2-(acetylamino)ethyl]-5-[(4'-amidino-4-biphenylyl)oxymethyl]-3-carboxymethyl-2-pyrrolidinone (139) (3S,5S)-5-[(4'-amidino-4-biphenylyl)oxymethyl]-3-carboxymethyl- 1-[2-(methanesulphonylamino)ethyl]-2-pyrrolidinone (140) (3S,5S)-5-[(4'-amidino-4-biphenylyl)oxymethyl]-1-[2-(benzoylamino)ethyl]-3-carboxymethyl-2-pyrrolidinone (141) (3S,5S)-5-[(4'-amidino-4-biphenylyl)oxymethyl]-3-carboxymethyl- 1-[2-(phenylsulphonylamino)ethyl]-2-pyrrolidinone
(142) (3S,5S)-1-[2-[(N-acetyl-N-methyl)amino]ethyl]-5-[(4'-amidino-4-biphenylyl)oxymethyl]-3-carboxymethyl-2-pyrrolidinone
(143) (3S,5S)-5-[[4-(4-amidinophenyl)naphthyl]oxymethyl]-3-carboxymethyl-2-pyrrolidinone
(144) (3S,5S)-5-[[[2-[ (4-amidinophenyl)oxy]phenyl]carbonylamino]methyl]- 3 -carboxymethyl -2-pyrrolidinone
(145) (3S, 5S) -5-[ (4 '-amidino-4-biphenylyl) oxymethyl]-3-( 1-carboxy-1-ethyl)-2-pyrrolidinone
(146) (3S,5S)-5-[2-[[2-(4-amidinophenyl)cyclopropyl]carbonylamino]ethyl]- 3-carboxymethyl-2-pyrrolidinone
(147) (3S,5S)-5-[(4'-amidino-4-biphenylyl)oxymethyl]-3-carboxymethyl- 1-[(N,N-dimethylamino)carbonyl]pyrrolidine ×1.3 H$_2$O R$_f$ value: 0.56 (reversed phase silica gel; methanol/5% aqueous saline solution=6:4) Calculated: C 61.67 H 6.89 N 12.51 Found: 61.70 6.66 12.50 Mass spectrum: (M+H)$^+$=425
(148) (3S,5S)-5-[ (4 '-amidino-4-biphenylyl)oxymethyl]-3-carboxymethyl- 1- (dimethylamino-oxalyl)-pyrrolidine
(149) (3S, 5S) -5-[ (4'-amidino-4-biphenylyl)oxymethyl]-3-carboxymethyl- 1-hydroxyoxalyl-pyrrolidine
(150) (3S,5S)-5-[(4'-amidino-4-biphenylyl)oxymethyl]-1-aminoacetyl- 3-carboxymethyl-pyrrolidine
(151) (3S,5S)-5-[2-[[N-(6-amidino-2-naphthylcarbonyl)-N-ethyl]amino]ethyl]-3-carboxymethyl-2-pyrrolidinone
(152 ) (3S, 5S ) -5-[(4'-amidino-4-biphenylyl)oxymethyl]-3-carboxymethyl- 1-[(4-methoxyphenyl)sulphonyl]-pyrrolidine ×0.5 H$_2$O R$_f$ value: 0.39 (reversed phase silica gel; methanol/10% aqueous saline solution=6:4) Calculated: C 60.88 H 5.68 N 7.89 Found: 61.00 5.87 7.63
(153) (3S,5S)-5-[(4'-amidino-4-biphenylyl)oxymethyl]-1-aminocarbonyl- 3-carboxymethyl-pyrrolidine
(154) (3S, 5S) -3-carboxymethyl-5-[[4'-(2-imidazolinyl)-4-biphenylyl)oxymethyl]-2-pyrrolidinone
(155) 1-[ (4 '-amidino-4-biphenylyl)acetyl]-3-carboxymethyl-pyrrolidine
(156) (2S, 4R) -4-[ (4 '-amidino-4-biphenylyl)oxymethyl]-2-carboxymethyl- 1-methanesulphonyl-pyrrolidine
(157 ) 5- [(4'-amidino-4-biphenylyl)oxymethyl]-3-(2-carboxyethyl)- 1- (3-phenylpropyl)-5H-2 -pyrrolinone
(158) (3R, 5S) -5-[ (4'-amidino-4-biphenylyl)oxymethyl]-3-carboxymethyl- 3-[(methanesulphonyl)methyl]-1-(3-phenyl-propyl)- 2-pyrrolidinone
(159) (3S,5S)-5-[[cis-5-(4-amidinophenyl)-2-octahydropentalenyl]aminomethyl]-3-carboxymethyl-2-pyrrolidinone
(160) (3S,5S)-5-[(4'-amidino-4-biphenylyl)oxymethyl]-3-carboxymethyl- 1-[(pyrrolidine-N-carbonyl)methyl]-2-pyrrolidinone R$_f$ value: 0.64 (reversed phase silica gel; methanol/10% aqueous saline solution=6:4)
(161) (3S,5S)-5-[(4'-amidino-4-biphenylyl)oxymethyl]-3-carboxymethyl- 1-[(piperidine-N-carbonyl)methyl]-2-pyrrolidinone
(162) (3S,5S)-5-[(4'-amidino-4-biphenylyl)oxymethyl]-1-[(azepine-N-carbonyl)methyl]-3-carboxymethyl-2-pyrrolidinone
(163) (3S,5S)-5-[(4'-amidino-4-biphenylyl)oxymethyl]-3-carboxymethyl- 1-[(morpholine-N-carbonyl)methyl]-2-pyrrolidinone R$_f$ value: 0.55 (reversed phase silica gel; methanol/10% aqueous saline solution=6:4)
(164) (3S,5S)-5-[(4'-amidino-4-biphenylyl)oxymethyl]-3-carboxymethyl- 1-[(N-methylpiperazine-N'-carbonyl)methyl]-2-pyrrolidinone
(165) (3S,5S)-1-[(N-acetylpiperazine-N'-carbonyl)methyl]-5-[(4'-amidino-4-biphenylyl)oxymethyl]-3-carboxymethyl- 2-pyrrolidinone
(166) (3S,5S)-5-[(4'-amidino-4-biphenylyl)oxymethyl]-3-carboxymethyl- 1-[(N-methanesulphonylpiperazine-N'-carbonyl)methyl]-2-pyrrolidinone
(167) (3S,5S)-5-[(4,-amidino-4-biphenylyl)oxymethyl]-3-carboxymethyl- 1-[(thiomorpholine-N-carbonyl)methyl]-2-pyrrolidinone
(168) (3S, 5S) -5-[ (4 '-amidino-4-biphenylyl) oxymethyl]-3-carboxymethyl -1-[[(thiomorpholine-S-oxide)-N-carbonyl]methyl]- 2-pyrrolidinone
(169) (3S,5S)-5-[(4,-amidino-4-biphenylyl)oxymethyl]-3-carboxymethyl- 1-[[(thiomorpholine-S-dioxide)-N-carbonyl]methyl]-2-pyrrolidinone
(170) (3S,5S)-5-[(4,-amidino-4-biphenylyl)oxymethyl]-3-carboxymethyl- 1-[(1-piperazinylcarbonyl)methyl]-2-pyrrolidinone
(171) (3S,5S)-5-[(4,-amidino-4-biphenylyl)oxymethyl]-1-( 4-bromobenzyl)-3-carboxymethyl-2-pyrrolidinone
(172) (3S,5S)-5-[(4,-amidino-4-biphenylyl)oxymethyl]-3-carboxymethyl- 1-(4-methylbenzyl)-2-pyrrolidinone
(173) (3S,5S)-5-[(4'-amidino-4-biphenylyl)oxymethyl]-3-carboxymethyl- 1-(4-methoxybenzyl)-2-pyrrolidinone
(174) (3S,5S)-5-[(4'-amidino-4-biphenylyl)oxymethyl]-3-carboxymethyl- 1-[3-(methylsulphenyl)propyl]-2-pyrrolidinone
(175) (3S,5S)-5-[(4'-amidino-4-biphenylyl)oxymethyl]-3-carboxymethyl- 1-[3-(methylsulphinyl)propyl]-2-pyrrolidinone
(176) (3S,5S)-5-[(4'-amidino-4-biphenylyl)oxymethyl]-3-carboxymethyl- 1-[3-(methylsulphonyl)propyl]-2-pyrrolidinone
(177) (3S, 5S) -5-[ (4'-amidino-4-biphenylyl) oxymethyl]-3-carboxymethyl- 1-phenylsulphonyl-pyrrolidine
(178) (3S, 5S) -5-[ (4 '-amidino-3-methoxy-4-biphenylyl)oxymethyl]- 3-carboxymethyl-2-pyrrolidinone
(179) (3R,5S)-5-[(4'-amidino-4-biphenylyl)oxymethyl]-3-carboxymethyl- 3-hydroxy-1-(3-phenylpropyl)-2-pyrrolidinone
(180) (3S,5S)-5-[(4,-amidino-4-biphenylyl)oxymethyl]-3-(carboxy-hydroxymethyl)- 1-(3-phenylpropyl)-2-pyrrolidinone
(181) (3S,5S)-5-[(4,-amidino-4-biphenylyl)oxymethyl]-1-[ [bis-(2-methoxyethyl)aminocarbonyl]methyl]-3-carboxymethyl- 2-pyrrolidinone
(182) (3S,5S)-5-[(4'-amidino-4-biphenylyl)oxymethyl]-3-carboxymethyl- 1-methoxyacetyl-pyrrolidine Melting point: 230°–233° C. R$_f$ value: 0.06 (silica gel; methylene chloride/methanol/conc. aqueous ammonia=10:2:0.4)
(183) 1-(4'-amidino-4-biphenylyl)-4-carboxymethyl-2-pyrrolidinone
(184) (3S,5S)-3-carboxymethyl-5-[(6-guanidinocarbonyl-2-naphthyl)oxymethyl]-2-pyrrolidinone

EXAMPLE 8

(3S,R;5S,R)-3-Carboxymethyl-5-[4-[(4-cyanobutyl)oxy]phenyl]- 1-(3-phenylpropyl)-2-pyrrolidinone
Prepared analogously to Example XI by oxidation of (3R,S;5S,R)-3-allyl-5-[4-[(4-cyanobutyl)oxy]phenyl]-1-( 3-phenylpropyl)-2-pyrrolidinone.
238 R$_f$ value: 0.78 (silica gel; methylene chloride/methanol=10:1) Calculated: C 71.86 H 6.96 N 6.45 Found: 71.62 6.68 6.42

The following are obtained analogously:

(1) (3S, 5S) -5-[[4-4-(tert.butyloxycarbonylamino)butyl] phenyl]oxymethyl]- 3-carboxymethyl-1- (4-phenylbutyl)-2-pyrrolidinone R$_f$ value: 0.47 (silica gel; methylene chloride/methanol=9:1)

(2) (3S, 5S) -3-carboxymethyl-5-[ (6-cyano-2-naphthyl)oxymethyl]- 1- (3-phenylpropyl)-2-pyrrolidinone $R_f$ value: 0.49 (silica gel; methylene chloride/methanol=9:1)

(3) (3S, 5S) -3-carboxymethyl-5-[ (4'-cyano-4-biphenylyl)oxymethyl]- 1- (3-phenylpropyl) -2 -pyrrolidinone $R_f$ value: 0.44 (silica gel; methylene chloride/methanol 9:1)

(4) (3S,5S)-5-[[4-[4-(tert.butyloxycarbonylamino)butyl]phenyl]oxymethyl]-3-carboxymethyl-1-[2-(2-naphthyl)ethyl]-2-pyrrolidinone $R_f$ value: 0.40 (silica gel; methylene chloride/methanol= 9:1)

(5) (3S, 5S) -5-[[4-[4-(tert.butyloxycarbonylamino)butyl]phenyl]oxymethyl]- 3-carboxymethyl-1- [2- (1-naphthyl)ethyl]- 2-pyrrolidinone $R_f$ value: 0.41 (silica gel; methylene chloride/methanol= 9:1)

(6) (3S,5S)-1-benzyl-5-[[4-[4-(tert.butyloxycarbonylamino)butyl]phenyl]oxymethyl]-3-carboxymethyl-2-pyrrolidinone $R_f$ value: 0.47 (silica gel; methylene chloride/methanol 9:1)

(7) (3S,5S)-5-[[4-[4-(tert.butyloxycarbonylamino)butyl]phenyl]oxymethyl]-3-carboxymethyl-1-(4-phenoxybutyl)-2-pyrrolidinone $R_f$ value: 0.48 (silica gel; methylene chloride/methanol= 9:1)

(8) (3S,5S)-5-[[4-(4-tert.butyloxycarbonylaminobutyl)phenyl]oxymethyl]-3-carboxymethyl-1-(2-phenylethyl)-2-pyrrolidinone $R_f$ value: 0.46 (silica gel; methylene chloride/methanol 9:1)

(9) (3S, 5S) -3-carboxymethyl-5-[[ (3-cyanophenyl)carbonylamino]methyl]- 1- (3-phenylpropyl)-2-pyrrolidinone $R_f$ value: 0.55 (silica gel; methylene chloride/methanol= 4:1)

(10) (3S,5S)-5-[[ [4-[2-(tert.butyloxycarbonylamino)ethyl]phenyl]carbonylamino]methyl]-3 -carboxymethyl-1-(3-phenylpropyl)- 2-pyrrolidinone $R_f$ value: 0.65 (silica gel; methylene chloride/methanol= 4:1)

(11) (3S,5S)-3-carboxymethyl-5-[[(4-cyanophenyl)carbonylamino]methyl]-1-(3-phenylpropyl)-2-pyrrolidinone Melting point: 184°–188° C. $R_f$ value: 0.67 (silica gel; methylene chloride/methanol= 4:1)

(12) (3S,5S)-5-[[[3-[2-(tert.butyloxycarbonylamino)ethyl]phenyl]carbonylamino]methyl]-3-carboxymethyl-1-(3-phenylpropyl)- 2-pyrrolidinone $R_f$ value: 0.30 (silica gel; methylene chloride/methanol= 10:1)

(13) (3S, 5S)-5-[[ [5-(tert.butyloxycarbonylamino)pentyl]carbonylamino]methyl]-3-carboxymethyl-1-(4-phenoxybutyl)- 2-pyrrolidinone $R_f$ value: 0.58 (silica gel; methylene chloride/methanol= 4:1)

(14) (3S,5S)-5-[[[5-(tert.butyloxycarbonylamino)pentyl]carbonylamino]methyl]-3-carboxymethyl-1-(2-phenylethyl)- 2-pyrrolidinone $R_f$ value: 0.53 (silica gel; methylene chloride/methanol= 4:1)

(15) (3S,5S)-1-benzyl-5-[[[5-(tert.butyloxycarbonylamino)pentyl]carbonylamino]methyl]-3-carboxymethyl-2-pyrrolidinone $R_f$ value: 0.58 (silica gel; methylene chloride/methanol= 4:1)

(16) (3S,5S)-5-[[(2-tert.butyloxycarbonylamino-5indanyl)methylcarbonyl]aminomethyl]-3-carboxymethyl-1-(3-phenylpropyl)-2-pyrrolidinone $R_f$ value: 0.65 (silica gel; methylene chloride/methanol= 4:1) Mass spectrum: (M+H)$^+$=564

(17) (3S, 5S)-5-[[ [5-(tert.butyloxycarbonylamino)pentyl]carbonylamino]methyl]-3-carboxymethyl-1-[2-(1-naphthyl)ethyl]- 2-pyrrolidinone $R_f$ value: 0.46 (silica gel; methylene chloride/methanol= 8:1)

(18) (3S,5S)-5-[[[5-(tert.butyloxycarbonylamino)pentyl]carbonylamino]methyl]-3-carboxymethyl-1-[2-(2-naphthyl)ethyl]-2-pyrrolidinone $R_f$ value: 0.50 (silica gel; methylene chloride/methanol=

(19) (3S,5S)-5-[[4-[3-(benzyloxycarbonylamino)propyl]phenyl]oxymethyl]-3-carboxymethyl-1-(3-phenylpropyl)-2-pyrrolidinone $R_f$ value: 0.44 (silica gel; methylene chloride/methanol= 8:1) Mass spectrum: M$^+$=558

(20) (3S,5S)-5-[[4-(tert.butyloxycarbonylaminomethyl)phenyl]oxymethyl]-3-carboxymethyl-1-(3-phenylpropyl)-2-pyrrolidinone $R_f$ value: 0.36 (silica gel; methylene chloride/methanol=12:1)

(21) (3S,5S)-5-[[3-(tert.butyloxycarbonylaminomethyl)phenyl]oxymethyl]-3-carboxymethyl-1-(3-phenylpropyl)-2-pyrrolidinone $R_f$ value: 0.25 (silica gel; methylene chloride/methanol= 20:1)

(22) (3S,5S)-5-[[3-[4-(tert.butyloxycarbonylamino)butyl]phenyl]oxymethyl]-3-carboxymethyl-1- (3-phenylpropyl)- 2-pyrrolidinone $R_f$ value: 0.24 (silica gel; methylene chloride/methanol= 20:1)

(23) (3S,5S)-5-[[ [5-(tert.butyloxycarbonylamino)pentyl]carbonylamino]methyl]-3-carboxymethyl-1-isobutyl-2-pyrrolidinone $R_f$ value: 0.60 (silica gel; methylene chloride/methanol= 4:1)

(24) (3S,5S)-5-[[3-[2-(tert.butyloxycarbonylamino)ethyl]phenyl]oxymethyl]-3-carboxymethyl-1-(3-phenylpropyl)- 2-pyrrolidinone $R_f$ value: 0.26 (silica gel; methylene chloride/methanol= 20:1)

(25) (3S, 5S) -5-[[4-[2-(tert.butyloxycarbonylamino)ethyl]phenyl]oxymethyl]-3-carboxymethyl-1- (3-phenylpropyl)- 2-pyrrolidinone $R_f$ value: 0.54 (silica gel; ethyl acetate/methanol=9:1) Mass spectrum: (M+H)$^+$=511

(26) (3S,5S)-3-carboxymethyl-5-[[4-[2-(tert.butyloxycarbonylamino)ethyl]phenyl]oxymethyl]-1-isobutyl-2-pyrrolidinone $R_f$ value: 0.57 (silica gel; ethyl acetate/methanol= 9:1)

(27) (3S,5S)-5-[(4'-amidino-4-biphenylyl)oxymethyl]-3-carboxymethyl- 1-(3-phenylpropyl)-2-pyrrolidinonesemihydrate Melting point: sinters above 170° C. $R_f$ value: 0.32 (silica gel; methylene chloride/methanol/conc. aqueous ammonia=2:1:0.25) Calculated: C 70.42 H 6.53 N 8.50 Found: 70.45 6.59 8.53

(28) (3S,5S)-5-[[4-[cis-4-(tert.butyloxycarbonylamino)cyclohexyl]phenyl]oxymethyl]-3-carboxymethyl-1-(3-phenylpropyl)- 2-pyrrolidinone $R_f$ value: 0.45 (silica gel; methylene chloride/methanol/conc. aqueous ammonia= 4:1:0.25)

(29) (3S,5S)-5-[[4-[trans-4-(tert.butyloxycarbonylamino)cyclohexyl]phenyl]oxymethyl]-3-carboxymethyl-1-(3-phenylpropyl)- 2-pyrrolidinone $R_f$ value: 0.40 (silica gel; methylene chloride/methanol/conc. aqueous ammonia=4:1:0.25)

(30) (3S,5S)-5-[[[3-(3-amidinophenyl)propyl]carbonylamino]methyl]-3-carboxymethyl-1-(3-phenylpropyl)-2-pyrrolidinone $R_f$ value: 0.12 (silica gel; methylene chloride/methanol/conc. aqueous ammonia=4:1:0.25)

(31) (3S,5S)-3-carboxymethyl-5-[[[3-(4-cyanophenyl)propyl]carbonylamino]methyl]-1-(3-phenylpropyl)-2-pyrrolidinone $R_f$ value: 0.50 (silica gel; methylene chloride/methanol/conc. aqueous ammonia=4:1:0.1)

(32) (3S,5S)-3-carboxymethyl-5-[[[3-(3-cyanophenyl)propyl]carbonylamino]methyl]-1-(3-phenylpropyl)-2-pyrrolidinone $R_f$ value: 0.24 (silica gel; methylene chloride/methanol/conc. aqueous ammonia=4:1:0.1)

(33) (3S,5S)-3-carboxymethyl-5-[[4-(3-cyanopropyl)phenyl]oxymethyl]-3-methyl-1-(3-phenylpropyl)-2-pyrrolidinone $R_f$ value: 0.22 (silica gel; methylene chloride/cyclohexane/methanol/conc. aqueous ammonia= 68:15:15:2)

(34) (3S,5S)-3-carboxymethyl-5-[[4-(3-cyanopropyl)phenyl]oxymethyl]-1-(3-phenylpropyl)-2-pyrrolidinone $R_f$ value: 0.25 (silica gel; methylene chloride/cyclohexane/methanol/conc. aqueous ammonia=68:15:15:2)

(35) (3S,5S)-1-[3-(4-benzyloxyphenyl)propyl]-5-[[4-[4-(tert.butyloxycarbonylaminphenyl]oxymethyl]-3-carboxymethyl- 2-pyrrolidinone $R_f$ value: 0.40 (silica gel; methylene chloride/methanol= 9:1)

(3S,5S)-1-[3-(4-benzyloxyphenyl)propyl]-5-[[4-[4-(tert.butyloxycarbonylamino)butyl]phenyl]oxymethyl]-3-( 2,3-dihydroxypropyl)-2-pyrrolidinone is obtained as a further product. $R_f$ value: 0.43 (silica gel; methylene chloride/methanol= 9:1)

(36) (3S,5S)-3-carboxymethyl-5-[(2-cyano-5-indanyl)oxymethyl]-1-(3-phenylpropyl)-2-pyrrolidinone $R_f$ value: 0.31 (silica gel; methylene chloride/cyclohexane/methanol/conc. aqueous ammonia=68:15:15:2)

(37) (3S,5S)-5-[(6-amidino-2-naphthyl)oxymethyl]-3-carboxymethyl- 1-(3-phenylpropyl)-2-pyrrolidinone $R_f$ value: 0.07 (silica gel; methylene chloride/methanol/conc. aqueous ammonia=4:1:0.25)

(38) (3S,5S)-5-[[[3-[3-(tert.butyloxycarbonylamino)phenyl]propyl]carbonylamino]methyl]-3-carboxymethyl-1-( 3-phenylpropyl)-2-pyrrolidinone $R_f$ value: 0.49 (silica gel; methylene chloride/methanol/glacial acetic acid= 19:1:0.1)

(39) (3S,5S)-5-[[[2-(tert.butyloxycarbonylamino)-5-indanyl]carbonylamino]methyl]-3-carboxymethyl-1-(3-phenylpropyl)- 2-pyrrolidinone $R_f$ value: 0.22 (silica gel; methylene chloride/cyclohexane/methanol/conc. aqueous ammonia=68:15:15:2)

(40) (3S,5S)-5-[[[2-(tert.butyloxycarbonylamino)methyl-5-indanyl]carbonylamino]methyl]-3-carboxymethyl-1-(3-phenylpropyl)- 2-pyrrolidinone $R_f$ value: 0.18 (silica gel; methylene chloride/cyclohexane/methanol/conc. aqueous ammonia=68:15:15:2)

(41) (3S,5S)-5-[[ [[2-[(tert.butyloxycarbonylamino)methyl]-5-indanyl]methyl]carbonylamino]methyl]-3-carboxymethyl- 1- (3-phenylpropyl) -2-pyrrolidinone $R_f$ value: 0.31 (silica gel; methylene chloride/cyclohexane/methanol/ conc. aqueous ammonia=68:15:15:2)

(42) (3S,5S)-5-[[[3-(tert.butyloxycarbonylamino)propyl]phenyl]oxymethyl]-3-carboxymethyl-1-(3-phenylpropyl)- 2-pyrrolidinone $R_f$ value: 0.42 (silica gel; methylene chloride/cyclohexane/methanol/conc. aqueous ammonia= 68:15:15:2)

(43) (3S,5S)-5-[[4-[5-(tert.butyloxycarbonylamino)pentyl]phenyl]oxymethyl]-3-carboxymethyl-1-(3-phenylpropyl)- 2-pyrrolidinone $R_f$ value: 0.37 (silica gel; methylene chloride/cyclohexane/methanol/conc. aqueous ammonia= 68:15:15:2)

(44) (3R,S;5S,R)-5-[[4-[(tert.butyloxycarbonylamino)methyl]phenyl]oxymethyl]-3-carboxymethyl-3-methyl-1-(3-phenylpropyl)- 2-pyrrolidinone $R_f$ value: 0.39 (silica gel; methylene chloride ethanol= 15:1)

(45) (3R,S;5S,R)-5-[[4-[2-(tert.butyloxycarbonylamino)ethyl]phenyl]oxymethyl]-3-carboxymethyl-3-methyl-1-(3-phenylpropyl)- 2-pyrrolidinone $R_f$ value: 0.42 (silica gel; methylene chloride/methanol= 15:1)

(46) (3R,S;5S,R)-5-[[4-[4-(tert.butyloxycarbonylamino)butyl]phenyl]oxymethyl]-3-carboxymethyl-3-methyl-1-(3-phenylpropyl)- 2-pyrrolidinone $R_f$ value: 0.36 (silica gel; methylene chloride/cyclohexane/methanol/conc. aqueous ammonia=68:15:15:2)

(47) (3R,5S)-5-[[[4-(tert.butyloxycarbonylamino)butyl]carbonylamino]methyl]-3-(2-carboxyethyl)-1-(3-phenylpropyl)- 2-pyrrolidinone $R_f$ value: 0.50 (silica gel; methylene chloride/methanol/acetic acid=9:1:0.1)

(48) (3R,5S)-5-[[[(5-(tert.butyloxycarbonylamino)pentyl]carbonylamino]methyl]-3-(2-carboxyethyl)-1-(3-phenylpropyl)- 2-pyrrolidinone $R_f$ value: 0.50 (silica gel; methylene chloride/methanol/acetic acid=9:1:0.1)

(49) (3S,5S)-5-[[2-[4-[(tert.butyloxycarbonylamino)methyl]phenyl]ethyl]carbonylamino]methyl]-3-carboxymethyl-1-(3-phenylpropyl)-2-pyrrolidinone $R_f$ value: 0.50 (silica gel; methylene chloride/methanol/acetic acid=9:1:0.1) Calculated: C 67.49 H 7.49 N 7.62 Found: 67.27 7.36 7.60

(50) (3S,5S)-5-[[[2-[3-(tert.butyloxycarbonylamino)phenyl]ethyl]carbonylamino]methyl]-3-carboxymethyl-1-(3-phenylpropyl)- 2-pyrrolidinone $R_f$ value: 0.55 (silica gel; methylene chloride/methanol/acetic acid=9:1:0.1)

(51) (3S,5S)-5-[[[2-[4-(tert.butyloxycarbonylamino)phenyl]ethyl]carbonylamino]methyl]-3-carboxymethyl-1-(3-phenylpropyl)- 2-pyrrolidinone $R_f$ value: 0.30 (silica gel; methylene chloride/methanol= 9:1)

(52) (3S,5S)-5-[[3-[4-(tert.butyloxycarbonylamino)phenyl]propyl]carbonylamino]methyl]-3-carboxymethyl-1-( 3-phenylpropyl) -2-pyrrolidinone $R_f$ value: 0.38 (silica gel; methylene chloride/methanol= 9:1)

(53) (3S,5S)-3-carboxymethyl-5-[[4-[(4-cyanophenyl)aminocarbonyl]phenyl]oxymethyl]-1-(3-phenylpropyl) -2-pyrrolidinone $R_f$ value: 0.50 (silica gel; methylene chloride/ethanol= 9:1)

(54) (3S,5S)-1-[(aminocarbonyl)methyl]-3-carboxymethyl-5-[(4,-cyano-4-biphenylyl)oxymethyl]-2-pyrrolidinone $R_f$ value: 0.28 (silica gel; ethyl acetate/cyclohexane/glacial acetic acid=40:5:2)

(55) (3S,5S)-3-carboxymethyl-5-[(4'-cyano-4-biphenylyl)-oxymethyl]-1-[(ethylaminocarbonyl)methyl]-2-pyrrolidinone Melting point: 194°–198° C., $R_f$ value: 0.23 (silica gel; ethyl acetate/glacial acetic acid=50:1)

(56) (3S,5S)-3-carboxymethyl-5-[(4'-cyano-4-biphenylyl)oxymethyl]-1-[(dimethylaminocarbonyl)methyl]-2-pyrrolidinone $R_f$ value: 0.16 (silica gel; ethyl acetate/glacial acetic acid=50:1)

(57) (3S,5S)-1-[(benzylaminocarbonyl)methyl]-3-carboxymethyl- 5-[(4'-cyano-4-biphenylyl)oxymethyl]-2-pyrrolidinone $R_f$ value: 0.34 (silica gel; cyclohexane/ethyl acetate=8:3)

(58) (3S,5S)-1-(tert.butyloxycarbonyl)-3-carboxymethyl-5-[(4'-cyano-4-biphenylyl)oxymethyl]-pyrrolidine Melting point: 132°–135° C. $R_f$ value: 0.52 (silica gel; cyclohexane/ethyl acetate=1:1) Calculated: C 68.79 H 6.47 N 6.42 Found: 68.72 6.58 6.47

(59) (3R,5S)-3-carboxymethyl-5-[(4'-cyano-4-biphenylyl)-oxymethyl]-2-pyrrolidinone Melting point: 223°–227° C. (decomp.), $R_f$ value: 0.41 (silica gel; toluene/dioxane/ethanol/glacial acetic acid=90:10:10:6) Calculated: C 68.56 H 5.18 N 8.00 Found: 68.30 5.19 7.89

EXAMPLE 9

(3S,5S)-5-[(4'-Amidino-4-biphenylyl)oxymethyl]-3-[(methoxycarbonyl)methyl]-1-phenyl-2-pyrrolidinone-hydrochloride-hydrate 900 mg of (3S,5S)-5-[[4'-(benzyloxycarbonyl-amidino)-4-biphenylyl]oxymethyl]-3-[(methoxycarbonyl)methyl]-1-phenyl-2-pyrrolidinone are mixed with 50 ml of methanol, 2 ml of methanolic hydrochloric acid, 5 ml of dioxane and 200 mg of palladium/charcoal catalyst and hydrogenated for 1.5 hours under 5 bar of hydrogen pressure and at ambient temperature. The catalyst is filtered off and the filtrate is evaporated down. The solid colourless evaporation residue is refluxed for 20 minutes with tert.butylmethylether. After cooling, the product is suction filtered and dried. Yield: 700 mg (93% of theory), $R_f$ value: 0.20 (silica gel; toluene/dioxane/methanol/conc. aqueous ammonia=2:5:2:1) Calculated: C 63.34 H 5.90 N 8.21 Cl 6.92 Found: 63.17 6.10 7.93 6.96

The following are obtained analogously:
(1) (3S,5S)-5-[[4-(3-aminopropyl)phenyl]oxymethyl]-3-carboxymethyl- 1-(3-phenylpropyl)-2-pyrrolidinone-hydrate Hydrogenation in methanol, column chromatography $R_f$ value: 0.29 (silica gel; methanol) Calculated: C 67.84 H 7.74 N 6.33 Found: 68.06 7.75 6.13 Mass spectrum: M$^+$=424
(2) (3R,5S)-5-[(4'-amidino-4-biphenylyl)oxymethyl]-3-hydroxy- 3-[(methoxycarbonyl)methyl]-1-(3-phenylpropyl)- 2-pyrrolidinone-hydrochloride
(3) (3S,5S)-5-[(4'-amidino-4-biphenylyl)oxymethyl]-3-hydroxy- 3- (methoxycarbonyl)methyl]-1-(3-phenylpropyl)-2-pyrrolidinone-hydrochloride

EXAMPLE 10

(3R,5S)-3-Allyl-5-[(4'-cyano-4-biphenylyl)oxymethyl]-2-pyrrolidinone 4.2 g of (3R,5S)-3-allyl-5-[(4'-cyano-4-biphenylyl)oxymethyl]-1-(4-methoxybenzyl)-2-pyrrolidinone are suspended in 30 ml of acetonitrile and 10 ml of water. A mixture of 15.3 g of powdered Ce(IV)ammonium nitrate and 15.3 g of silica gel (particle size: 0.03–0.06 mm) is added thereto. After 30 minutes stirring at ambient temperature, the mixture is diluted with methylene chloride and insoluble matter is removed by suction filtering. The filtrate is diluted with water, dried over magnesium sulphate and concentrated by evaporation on a rotary evaporator. The remaining orange oil is chromatographed with cyclohexane/ethyl acetate (4:6) over 330 g of silica gel. Yield: 1.4 g (45% of theory), Melting point: 97°–99° C. $R_f$ value: 0.24 (silica gel; cyclohexane/ethyl acetate=4:6)

The following are obtained analogously:
(1) (3R,S;4R,S)-3-allyl-4-[(4'-cyano-4-biphenylyl)oxymethyl]-2-pyrrolidinone Melting point: 101°–105° C. $R_f$ value: 0.37 (silica gel; ethyl acetate)
(2) (3R,S;4R,S)-3-allyl-4-[[(4'-cyano-4-biphenylyl)carbonylamino]methyl]-2-pyrrolidinone $R_f$ value: 0.12 (silica gel; ethyl acetate)
(3) (3R,S;4R,S)-3-allyl-4-[(4'-cyano-4-biphenylyl)oxymethyl]-3-methyl-2-pyrrolidinone Melting point: 137°–138° C. $R_f$ value: 0.46 (silica gel; ethyl acetate) Calculated: C 76.27 H 6.40 N 8.09 Found: 76.09 6.31 7.97

EXAMPLE 11

(3S, 5S)-5-[(3-Amino-4'-cyano-4-biphenylyl)oxymethyl]-3-[(methoxycarbonyl)methyl]-1-(3-phenylpropyl)-2-pyrrolidinone 4 g of (3S,5S)-5-[(4'-cyano-3-nitro-4-biphenylyl)oxymethyl]-3-[(methoxycarbonyl)methyl]-1-(3-phenylpropyl)-2-pyrrolidinone are hydrogenated in 40 ml of ethanol and 10 ml of dimethylformamide with 1.5 g of palladium (10% on activated charcoal) under a hydrogen pressure of 3 bar at ambient temperature. After 40 minutes the catalyst is removed by suction filtering and the filtrate is evaporated down. The residue is divided between water and methylene chloride, the organic phase is separated off, dried with magnesium sulphate and evaporated down. Column chromatography on silica gel with methylene chloride/ethyl acetate (4:1) yields 2.9 g (77% of theory) of the desired compound. Melting point: 111°–112° C. $R_f$ value: 0.37 (silica gel; 1,2-dichloroethane/ethyl acetate=3:1) Calculated: C 72.41 H 6.28 N 8.45 Found: 72.31 6.54 8.27

The following are obtained analogously:
(1) (3S,5S)-5-[[(3'-amino-3-biphenylyl)carbonyl]aminomethyl]-3-[(methoxycarbonyl)methyl]-1-(3-phenylpropyl)-2-pyrrolidinone Solvent: ethanol $R_f$ value: 0.41 (silica gel; ethyl acetate/methylene chloride=2:1)
(2) (3S,5S)-5-[(4-aminophenyl)oxymethyl]-3-[(methoxycarbonyl]methyl]-1-(3-phenylpropyl)-2-pyrrolidinone Solvent: methanol $R_f$ value: 0.26 (silica gel; cyclohexane/ethyl acetate=1:1)
(3) (3S,5S)-5-[2-[[(3'-amino-4-biphenylyl)carbonyl]amine]ethyl]-3-E(methoxycarbonyl)methyl]-1-(3-phenylpropyl)- 2-pyrrolidinone Raney nickel was used as catalyst and methanol as solvent. $R_f$ value: 0.52 (silica gel; methylene chloride/methanol/cont. aqueous ammonia= 19:1:0.1) (after developing twice)
(4) (3S,5S)-5-[[(3'-amino-4-biphenylyl)carbonyl]aminomethyl]-3-[(methoxycarbonyl)methyl]-1-(3-phenylpropyl)-2-pyrrolidinone Raney nickel was used as catalyst. $R_f$ value: 0.88 (silica gel; methylene chloride/methanol/conc. aqueous ammonia=4:1:0.25)

EXAMPLE 12

(3S,5S)-5-[(4'-Cyano-3-methanesulphonylamino-4-biphenylyl)oxymethyl]-3-[(methoxycarbonyl)methyl]-1-(3-phenylpropyl)- 2-pyrrolidinone 0.5 g of (3S,5S)-5-[(3-amino-4'-cyano-4-biphenylyl)oxymethyl]-3-[(methoxycarbonyl)methyl]-1-(3-phenylpropyl)- 2-pyrrolidinone and 0.09 ml of pyridine dissolved in 5 ml of dry methylene chloride are mixed with 0.09 ml of methanesulphonic acid chloride. After 2 hours stirring at ambient temperature, water and dilute hydrochloric acid are added and the organic phase is separated off. The aqueous phase is extracted with methylene chloride and the combined organic phases are dried with sodium sulphate. The evaporation residue is chromatographed over a silica gel column with methylene chloride/ethyl acetate (2:1). 0.39 g (68.4% of theory) of a white solid are obtained. Melting point: 140°–141° C., $R_f$ value: 0.55 (silica gel; 1,2-dichloroethane/ethyl acetate=3:1) Calculated: C 64.68 H 5.78 N 7.30 Found: 64.52 5.73 7.25

The following is obtained analogously:
(1) (3S,5S)-5-[[N-(4'-cyano-4-biphenylyl)-N-methanesulphonyl ]aminomethyl]-3-[(methoxycarbonyl)methyl]-1-(3-phenylpropyl)-2-pyrrolidinone $R_f$ value: 0.38 (silica gel; cyclohexane/ethyl acetate=1:3)

EXAMPLE 13

(3S,5S)-5-[(3-Acetylamino-4'-cyano-4-biphenylyl)oxymethyl]-3-[(methoxycarbonyl)methyl]-1-(3-phenylpropyl)-2-pyrrolidinone 0.5 g of (3S,5S)-5-[(3-amino-4'-cyano-4-biphenylyl)oxymethyl]-3-[(methoxycarbonyl)methyl]-1-(3-phenylpropyl)- 2-pyrrolidinone and 0.14 ml of triethylamine are dissolved in 5 ml of dry methylene chloride. 0.07 ml of acetylchloride are added thereto. After 2 hours stirring at ambient temperature, dilute hydrochloric acid is added and the organic phase is separated off. The aqueous phase is extracted with methylene chloride and the combined organic phases are dried over sodium sulphate. After evaporation of the solvent, 0.45 g (83% of theory) of the desired product are obtained. Melting point: 177°–179° C. $R_f$ value: 0.34 (silica gel; 1,2-dichloroethane/ethyl acetate=3:1) Calculated: C 71.22 H 6.16 N 7.79 Found: 70.97 6.39 7.53

The following is obtained analogously:
(1) (3S,5S)-5-[[N-(4'-cyano-4-biphenylyl)-N-acetyl]aminomethyl]- 3-[(methoxycarbonyl)methyl]-1-(3-phenylpropyl)- 2-pyrrolidinone $R_f$ value: 0.43 (silica gel; cyclohexane/ethyl acetate=1:3)

EXAMPLE 14

(3S,5S)-5-[(4'-Amidino-3'-chloro-4-biphenylyl)oxymethyl] -3-[(methoxycarbonyl)methyl]-1-(3-phenylpropyl)- 2-pyrrolidinone 1.07 g of (3S,5S)-5-[(4'-aminocarbonyl-3'-chloro-4-biphenylyl)oxymethyl]-3-[(methoxycarbonyl)methyl]-1-(3-phenylpropyl)- 2-pyrrolidinone are dissolved in 5 ml of dry methylene chloride and, under nitrogen, 2 ml of a 1M solution of triethyloxonium tetrafluoroborate in methylene chloride are added. After 18 hours stirring at ambient temperature, about ⅔ of the solvent are evaporated off in vacuo and the mixture is combined with 15 ml of dry diethylether. The solvent is decanted off and the residue is taken up in 17 ml of methanol. 0.5 g of ammonium carbonate are added thereto and the mixture is stirred for 18 hours at ambient temperature. The methanol is evaporated off and the residue is stirred with methylene chloride. After the insoluble matter has been filtered off the solvent is eliminated in vacuo and the residue is chromatographed with methylene chloride/methanol/conc. aqueous ammonia (80:20:1.25) over a silica gel column. Yield: 0.25 g (23.4% of theory), $R_f$ value: 0.57 (silica gel; methylene chloride/methanol/conc. aqueous ammonia=100:20:5)

EXAMPLE 15

(3S,5S)-5-[[(2-Aminomethyl-5-indanyl)sulphonyl]aminomethyl]-3-carboxymethyl-1-(3-phenylpropyl)-2-pyrrolidinone-hydrate Prepared analogously to Example LXXX by reacting (3S,5S)-3-carboxymethyl-1-(3-phenylpropyl)-5-[[[2-(N-phthalimidomethyl)- 5-indanyl]sulphonyl]aminomethyl]-2-pyrrolidinone with methylamine. The aqueous phase is worked up and purified by chromatography. $R_f$ value: 0.32 (silica gel; methanol/ethyl acetate/aqueous ammonia= 2:1:0.05 Calculated: C 60.33 H 6.82 N 8.12 S 6.19 Found: 60.08 6.63 8.20 6.21

The following is prepared analogously:
(1) (3S,5S)-5-[[(2-amino-5-indanyl)sulphonyl]aminomethyl]-3-carboxymethyl-1-(3-phenylpropyl)-2-pyrrolidinone-hydrate The aqueous phase is worked up and purified by chromatography. $R_f$ value: 0.39 (silica gel; methylene chloride/cyclohexane/methanol/conc. aqueous ammonia=34:7.5:57.5:1) Calculated: C 59.57 H 6.55 N 8.33 S 6.35 Found: 59.80 6.62 8.89 7.02

EXAMPLE 16

(3R,5S)-3-Allyl-5-[[[3-(3-cyanophenyl)propyl]carbonylamino]methyl]-1-(3-phenylpropyl)-2-pyrrolidinone 4.5 g of 4-(3-cyanophenyl)butyric acid and 4.6 g of carbonyldiimidazole are dissolved in 50 ml of tetrahydrofuran and stirred for one hour at ambient temperature. 7.66 g of (3R,5S)-3-allyl-5-aminomethyl-1-( 3-phenylpropyl)-2-pyrrolidinone are added and the mixture is stirred for a further 16 hours at ambient temperature. The solution is concentrated by evaporation and the residue is taken up in ethyl acetate. The ethyl acetate phase is washed with dilute hydrochloric acid, bicarbonate solution and water, then evaporated down, the crude product remaining is further processed directly. Yield: 4.5 g (40% of theory), $R_f$ value: 0.30 (silica gel; methylene chloride/methanol= 19:1)

The following are obtained analogously:
(1) (3R,5S)-3-allyl-5-[[(3-cyanophenyl)carbonyl]aminomethyl]-1-(3-phenylpropyl)-2-pyrrolidinone $R_f$ value: 0.72 (silica gel; ethyl acetate) (2) (3R,5S)-3-allyl-5-[[[4-[2-(tert.butyloxycarbonylamino)ethyl]phenyl]carbonyl]aminomethyl]-1-(3-phenylpropyl)- 2-pyrrolidinone $R_f$ value: 0.53 (silica gel; methylene chloride/methanol=10:1)

(3) (3R,5S)-3-allyl-5-[[(4-cyanophenyl)carbonyl]aminomethyl]-1-(3-phenylpropyl)-2-pyrrolidinone $R_f$ value: 0.70 (silica gel; methylene chloride/methanol= 20:1)
(4) (3R,5S)-3-allyl-5-[[[3-[2-(tert.butyloxycarbonylamino)ethyl]phenyl]carbonyl]aminomethyl]-1-(3-phenylpropyl)- 2-pyrrolidinone $R_f$ value: 0.48 (silica gel; methylene chloride/methanol= 10:1)
(5) (3R,5S)-3-allyl-5-[[[5-(tert.butyloxycarbonylamino)pentyl]carbonyl]aminomethyl]-1-(4-phenoxybutyl)-2-pyrrolidinone $R_f$ value: 0.44 (silica gel; methylene chloride/methanol= 10:1)
(6) (3R,5S)-3-allyl-5-[[[5-(tert.butyloxycarbonylamino)pentyl]carbonyl]aminomethyl]-1-(2-phenylethyl)-2-pyrrolidinone $R_f$ value: 0.68 (silica gel; methylene chloride/methanol= 9:1)
(7) (3R, 5S)-3-allyl-1-benzyl-5-[[ 5-(tert.butyloxycarbonylamino) pentyl]carbonyl]aminomethyl]-2-pyrrolidinone $R_f$ value: 0.49 (silica gel; methylene chloride/methanol 10:1)
(8) (3R,5S)-3-allyl-5-[[[2-(tert.butyloxycarbonylamino)-5-indanyl]methylcarbonyl]aminomethyl]-1-(3-phenylpropyl)- 2-pyrrolidinone $R_f$ value: 0.57 (silica gel; ethyl acetate/methanol= 20:1)
(9) (3R,5S)-3-allyl-5-[[[5-(tert.butyloxycarbonylamino)pentyl]carbonyl]aminomethyl]-1-[2-(1-naphthyl)ethyl]-2-pyrrolidinone $R_f$ value: 0.74 (silica gel; methylene chloride/methanol= 9:1) Mass spectrum: $M^+$=521
(10) (3R,5S)-3-allyl-5-[[[5-(tert.butyloxycarbonylamino)pentyl]carbonyl]aminomethyl]-1-[2-(2naphthyl)ethyl]-2-pyrrolidinone $R_f$ value: 0.61 (silica gel; ethyl acetate/methanol=9:1) Mass spectrum: $M^+$=521
(11) (3R,5S)-3-allyl-5-[[[5-(tert.butyloxycarbonylamino)pentyl]carbonyl]aminomethyl]-1-isobutyl-2-pyrrolidinone $R_f$ value: 0.44 (silica gel; ethyl acetate/methanol= 9:1)
(12) (3R,5S)-3-allyl-5-[[[3-(4-cyanophenyl)propyl]carbonylamino]methyl]-1-(3-phenylpropyl)-2-pyrrolidinone $R_f$ value: 0.30 (silica gel; methylene chloride/methanol= 19:1)
(13) (3R,5S)-3-allyl-5-[[[3-[3-(tert.butyloxycarbonylamino)phenyl]propyl]carbonylamino]methyl]-1-(3-phenylpropyl)- 2-pyrrolidinone $R_f$ value: 0.30 (silica gel; methylene chloride/methanol= 19:1)
(14) (3R,5S)-3-allyl-5-[[[2-(tert.butyloxycarbonyl-amino)-5-indanyl]carbonyl]aminomethyl]-1-(3-phenylpropyl)-2-pyrrolidinone $R_f$ value: 0.47 (silica gel; methylene chloride/methanol= 15:1)
(15) (3R, 5S) -3-allyl-5-[[ 2-[(tert.butyloxycarbonylamino) methyl]-5-indanyl]carbonyl]aminomethyl]-1-(3-phenylpropyl)- 2-pyrrolidinone $R_f$ value: 0.20 (silica gel; cyclohexane/ethyl acetate=1:1)
(16) (3R,5S)-3-allyl-5-[[[[2-[(tert.butyloxycarbonylamino)methyl]-5-indanyl]methyl]carbonyl]aminomethyl]-1-( 3-phenylpropyl)-2-pyrrolidinone $R_f$ value: 0.47 (silica gel; ethyl acetate/ethanol=40:1)
(17) (3R,5S)-3-(1-buten-4-yl)-5-[[[4-(tert.butyloxycarbonylamino)butyl]carbonylamino]methyl]-1-(3-phenylpropyl)- 2-pyrrolidinone $R_f$ value: 0.50 (silica gel; methylene chloride/methanol 9:1)
(18) (3R,5S)-3-(1-buten-4-yl)-5-[[ 5-(tert.butyloxycarbonylamino) pentyl]carbonylamino]methyl]-1-(3-phenylpropyl)- 2-pyrrolidinone $R_f$ value: 0.54 (silica gel; methylene chloride/methanol= 9:1)
(19) (3R,5S)-3-allyl-5-[[[2-(4-tert.butyloxycarbonylaminomethyl)phenyl]ethyl]carbonylamino]methyl]-1-(3-phenylpropyl)- 2-pyrrolidinone $R_f$ value: 0.50 (silica gel; methylene chloride/methanol=19:1)

(20) (3R, 5S)-3-allyl-5-[[ [2-[3-(tert.butyloxycarbonylamino) phenyl]ethyl]carbonylamino]methyl]-1-(3-phenylpropyl)- 2-pyrrolidinone $R_f$ value: 0.60 (silica gel; methylene chloride/methanol= 9:1)

(21) (3R,5S)-3-allyl-5-[(4'-cyano-4-biphenylyl)oxymethyl]-1-[(ethylaminocarbonyl)methyl]-2-pyrrolidinone $R_f$ value: 0.55 (silica gel; ethyl acetate/methanol=20:1) Calculated: C 71.92 H 6.52 N 10.06 Found: 71.75 6.64 10.26

(22) (3R,5S)-3-allyl-5-[(4'-cyano-4-biphenylyl)oxymethyl]-1-[(dimethylaminocarbonyl)methyl]-2-pyrrolidinone ×0.25 water $R_f$ value: 0.55 (silica gel; ethyl acetate/methanol= 20:1) Calculated: C 71.16 H 6.57 N 9.96 Found: 70.98 6.74 9.93

(23) (3S,5S)-5-[2-[ (4-cyanocinnamoyl)amino]ethyl]-3-[(methoxycarbonyl)methyl]-1-(3-phenylpropyl)-2-pyrrolidinone $R_f$ value: 0.43 (silica gel; methylene chloride/ methanol 15:1)

EXAMPLE 17

(3S,5S)-5-[[(4'-Cyano-4-biphenylyl)carbonyl]aminomethyl]-3-[(methoxycarbonyl)methyl]-1-(3-phenyl-propyl)- 2-pyrrolidinone 0.3 g of 4'-cyano-4-biphenylcarboxylic acid, 0.45 g of (3S,5S)-5-aminomethyl-3-[(methoxycarbonyl)methyl]-1-(3-phenylpropyl)-2-pyrrolidinone-hydrochloride, 0.18 g of 1-hydroxybenzotriazole and 0.4 ml of triethylamine are placed in 10 ml of dry dimethylformamide. Then 0.3 g of N,N'-dicyclohexylcarbodiimide are added whilst cooling with ice and the mixture is stirred for 20 hours at ambient temperature. After this time, water is added to the mixture, it is extracted with ethyl acetate, the organic phase is separated off, dried and concentrated by evaporation. The residue is purified with ethyl acetate on a silica gel column. The resulting product is taken up in a little ethyl acetate, the precipitate is filtered off and the filtrate is evaporated down. Yield: 390 mg (57% of theory), $R_f$ value: 0.46 (silica gel; ethyl acetate)

The following are obtained analogously:

(1) (3S,5S)-5-[[4-[[3-(tert.butyloxycarbonylamino)propyl]carbonylamino]phenyl]oxymethyl]-3-(methoxycarbonyl)-methyl] -1-(3-phenylpropyl)-2-pyrrolidinone-semihydrate $R_f$ value: 0.42 (silica gel; cyclohexane/ethyl acetate=1:2) Calculated: C 65.07 H 7.51 N 7.11 Found: 64.95 7.57 6.94

(2) (3S,5S)-5-[(7-cyano-2-naphthylcarbonyl)aminomethyl]-3-[(methoxycarbonyl)methyl]-1-(3-phenylpropyl)-2-pyrrolidinone $R_f$ value: 0.51 (silica gel; ethyl acetate)

(3) (3S,5S)-5-[2-[(7-cyano-2-naphthylcarbonyl)amino]ethyl]-3-[(methoxycarbonyl)methyl]-1-(3-phenylpropyl)-2-pyrrolidinone $R_f$ value: 0.31 (silica gel; ethyl acetate) Calculated: C 72.41 H 6.28 N 8.44 72.22 6.58 8.29

(4) (3S,5S)-5-[2-[(6-tert.butyloxycarbonylamino-5,6,7,8-tetrahydro- 2-naphthylcarbonyl)amino]ethyl]-3-[(methoxycarbonyl)methyl]-1-(3-phenylpropyl)-2-pyrrolidinonesemihydrate $R_f$ value: 0.39 (silica gel; ethyl acetate) Calculated: C 67.98 H 7.72 N 6.99 Found: 67.89 7.77 7.02

(5) (3S,5S)-5-[(6-tert.butyloxycarbonylamino-5,6,7,8-tetrahydro- 2-naphthylcarbonyl)aminomethyl]-3-[(methoxycarbonyl)methyl]-1-(3-phenylpropyl)-2-pyrrolidinone $R_f$ value: 0.56 (silica gel; ethyl acetate)

(6) (3S,5S)-5-[(6-cyano-5,6,7,8-tetrahydro-2-naphthylcarbonyl)aminomethyl]-3-[(methoxycarbonyl)methyl]-1-(3-phenylpropyl)- 2-pyrrolidinone $R_f$ value: 0.43 (silica gel; ethyl acetate)

(7) (3S,5S)-5-[2-[(6-cyano-5,6,7,8-tetrahydro-2-naphthylcarbonyl)amino]ethyl]-3-[(methoxycarbonyl)methyl]-1-(3-phenylpropyl)-2-pyrrolidinone $R_f$ value: 0.25 (silica gel; ethyl acetate) Calculated: C 70.57 H 7.11 N 8.23 Found: 70.61 7.33 8.33

(8) (3S,5S)-5-[[trans-3-(4-cyanophenyl)cyclobutyl]carbonylaminomethyl]-3-[(methoxycarbonyl)methyl]-1-(3-phenylpropyl)- 2-pyrrolidinone-hydrate By chromatographic separation of the cis/trans mixture $R_f$ value: 0.60 (silica gel; ethyl acetate/methanol= 15:1) Calculated: C 68.89 H 6.98 N 8.31 Found: 69.21 7.11 8.67

(9) (3S, 5S) -5-[[cis-3-(4-cyanophenyl)cyclobutyl]carbonylaminomethyl]- 3-[(methoxycarbonyl)methyl]-1-(3-phenylpropyl)- 2-pyrrolidinone-hydrate By chromatographic separation of the cis/trans mixture $R_f$ value: 0.51 (silica gel; ethyl acetate/methanol= 15:1) Calculated: C 68.89 H 6.98 N 8.31 Found: 68.85 7.26 8.41

(10) (3S,5S)-5-[2-[[cis-3-(4-cyanophenyl)cyclobutyl]carbonylamino]ethyl]-3-[(methoxycarbonyl)methyl]-1-(3-phenylpropyl)- 2-pyrrolidinone By chromatographic separation of the cis/trans mixture $R_f$ value: 0.49 (silica gel; ethyl acetate/methanol= 15:1)

(11) (3S,5S)-5-[2-[[trans-3-(4-cyanophenyl)cyclobutyl]carbonylamino]ethyl]-3-[(methoxycarbonyl)methyl]-1-(3-phenylpropyl)- 2-pyrrolidinone-hydrate By chromatographic separation of the cis/trans mixture $R_f$ value: 0.54 (silica gel; ethyl acetate/methanol= 15:1) Calculated: C 69.34 H 7.18 N 8.09 Found: 69.59 7.26 7.92

(12) (3S,5S)-5-[[4-[3-(tert.butyloxycarbonylamino)cyclobutyl]phenyl]carbonylaminomethyl]-3-[(methoxycarbonyl)methyl]-1-(3-phenylpropyl)-2-pyrrolidinonesemihydrate $R_f$ value: 0.52 (silica gel; ethyl acetate) Calculated: C 67.56 H 7.56 N 7.16 Found: 67.69 7.86 7.35

(13) (3S,5S)-5-[2-[[4-[3-(tert.butyloxycarbonylamino)cyclobutyl]phenyl]carbonylamino]ethyl]-3-[(methoxycarbonyl)methyl]-1-(3-phenylpropyl)-2-pyrrolidinonesemihydrate $R_f$ value: 0.23 (silica gel; cyclohexane/ethyl acetate=1:3) Calculated: C 67.98 H 7.72 N 7.00 Found: 68.10 8.03 6.98

(14) (3R,S;4S,R)-3-allyl-4-[[(4'-cyano-4-biphenylyl)carbonylamino]methyl]-1-(4-methoxybenzyl)-2-pyrrolidinone $R_f$ value: 0.59 (silica gel; ethyl acetate)

EXAMPLE 18

(3S,5S)-5-[2-[(6-Cyano-2-naphthylcarbonyl)amino]ethyl]- 3-[(methoxycarbonyl)methyl]-1- (3-phenylpropyl)-2-pyrrolidinone At ambient temperature, 1.35 g of 6-cyano-2-naphthylcarbonylchloride in 20 ml of chloroform are added to 2.1 g of (3S,5S)-5-(2-aminoethyl)-3-[(methoxycarbonyl)methyl]-1-(3-phenylpropyl)-2-pyrrolidinone-hydrochloride in 20 ml of chloroform. Then 4.2 ml of triethylamine are added dropwise with stirring. After 18 hours stirring at ambient temperature the mixture is evaporated down, taken up in ethyl acetate and washed with dilute hydrochloric acid, water and saline solution. The organic phase is dried with sodium sulphate, filtered and concentrated by evaporation. After purification over a silica gel column with cyclohexane/ethyl acetate (3:7) 1 g (32% of theory) of pure product are obtained. Melting point: 93°–99° C. $R_f$ value: 0.30 (silica gel; ethyl acetate)

The following are obtained analogously:

(1) (3S,5S)-5-[(6-cyano-2-naphthylcarbonyl)aminomethyl]-3-[(methoxycarbonyl)methyl]-1-(3-phenylpropyl)-2-pyrrolidinone $R_f$ value: 0.57 (silica gel; ethyl acetate)

(2) (3S,5S)-5-[[[2-[(4-cyanophenyl)amino]phenyl]carbonylamino]methyl]-3-[(methoxycarbonyl)methyl]-1-(3-phenylpropyl)- 2-pyrrolidinone Melting point: 135° C. $R_f$ value: 0.42 (silica gel; cyclohexane/ethyl acetate/methanol=6:3:0.5)

EXAMPLE 19

(3R,5S)-3-Allyl-5-[[[2-[4-(tert.butyloxycarbonylamino)phenyl]ethyl]carbonylamino]methyl]-1-(3-phenylpropyl)-2-pyrrolidinone 2 g of 3-[4-(tert.butyloxycarbonylamino)phenyl]propionic acid are dissolved in 30 ml of tetrahydrofuran and at −15° C. 0.82 ml of N-methyl-morpholine are added and 1.0 g of isobutylchloroformate are added. After 30 minutes a solution of 2.5 g of (3R,5S)-3-allyl-5-aminomethyl- 1-(3-phenylpropyl)-2-pyrrolidinone in 10 ml of dimethylformamide is added dropwise. The mixture is stirred for 2 days at ambient temperature, the precipitated N-methyl-morpholine-hydrochloride is filtered off, the filtrate is evaporated down and the residue is taken up in ethyl acetate. After washing with 2N hydrochloric acid and water and treating with activated charcoal the solution is evaporated down and the residue is purified by column chromatography over silica gel (eluant: methylene chloride/methanol=40:1). Yield: 1.7 g (47% of theory), $R_f$ value: 0.46 (silica gel; methylene chloride/methanol= 19:1)

The following are obtained analogously:

(1) (3R, 5S)-3-allyl-5-[[ [3-[4-(tert.butyloxycarbonylamino)phenyl]propyl]carbonylamino]methyl]-1-(3-phenylpropyl)- 2-pyrrolidinone $R_f$ value: 0.86 (silica gel; methylene chloride/methanol 9:1)

(2) (3R,S;4S,R)-4-[[[3-(tert.butyloxycarbonylamino)propyl]carbonylamino]methyl]-3-carboxymethyl-1-(3-phenylpropyl)- 2-pyrrolidinone The (3R,S;4S,R)-4-aminomethyl-3-carboxymethyl-1-(3-phenylpropyl)- 2-pyrrolidinone used as amino component is first of all converted with N-trimethylsilyl-imidazole in tetrahydrofuran into the trimethylsilylester. $R_f$ value: 0.16 (silica gel; methylene chloride/methanol= 9:1)

(3) (3R,S;4S,R)-4-[[[7-(tert.butyloxycarbonylamino)heptyl]carbonylamino]methyl]-3-carboxymethyl-1-(3-phenylpropyl)- 2-pyrrolidinone The (3R,S;4S,R)-4-aminomethyl-3-carboxymethyl-1-(3-phenylpropyl)- 2-pyrrolidinone used as amino component is first of all converted with N-trimethylsilyl-imidazole in tetrahydrofuran into the trimethylsilylester. $R_f$ value: 0.25 (silica gel; methylene chloride/methanol= 9:1)

(4) (3R,S;4S,R)-4-[[ [5-(tert.butyloxycarbonylamino)pentyl]carbonylamino]methyl]-3-carboxymethyl-1-(3-phenylpropyl)- 2-pyrrolidinone The (3R,S;4S,R)-4-aminomethyl-3-carboxymethyl-1-(3-phenylpropyl)- 2-pyrrolidinone used as amino component is first of all converted with N-trimethylsilyl-imidazole in tetrahydrofuran into the trimethylsilylester. $R_f$ value: 0.31 (silica gel; methylene chloride/methanol= 9:1)

(5) (3S,5S)-5-[[4-[cis/trans-4-(tert.butyloxycarbonylamino)cyclohexyl]benzoyl]aminomethyl]-3-[(methoxycarbonyl)methyl]-1-(3-phenylpropyl)-2-pyrrolidinone The corresponding amine hydrochloride was added to the mixed anhydride after two hours of pretreatment with N-trimethylsilyl-imidazole in tetrahydrofuran. $R_f$ value: 0.65 (silica gel; methylene chloride/methanol= 90:1)

(6) (3S,5S)-5-[[4-(tert.butyloxycarbonylamino)cinnamoyl]aminomethyl]-3-[(methoxycarboxy)methyl]-1-(3-phenylpropyl)- 2-pyrrolidinone $R_f$ value: 0.47 (silica gel; methylene chloride/methanol= 15:1)

(7) (3S,5S)-5-[[(4'-cyano-3-biphenylyl)carbonyl]aminomethyl]-3-[(methoxycarboxy)methyl]-1-(3-phenylpropyl)-2-pyrrolidinone $R_f$ value: 0.27 (silica gel; methylene chloride/methanol= 40:1)

(8) (3S,5S)-5-[(3-cyanobenzoyl)aminomethyl]-3-[(methoxycarbonyl)methyl]-1-(3-phenylpropyl)-2-pyrrolidinone $R_f$ value: 0.22 (silica gel; methylene chloride/methanol= 40:1) Mass spectrum: $M^+=433$ (9) (3S,5S)-5-[exo-5-(4-cyanophenyl)bicyclo[2.2.1]-heptyl-exo- 2-carbonyl]aminomethyl]-3-[(methoxycarbonyl)methyl]-1-(3-phenylpropyl)-2-pyrrolidinone $R_f$ value: 0.52 (silica gel; methylene chloride/methanol= 9:1) Mass spectrum: $M^+=527$

EXAMPLE 20

(3S,5S)-5-[[(3'-Amino-3-biphenylyl)carbonyl]aminomethyl]-3-carboxymethyl-1-(3-phenylpropyl)-2-pyrrolidinone 0.47 g of (3S,5S)-5-[[(3'-amino-3-biphenylyl)carbonyl]aminomethyl]-3-[(methoxycarbonyl)methyl]-1-(3-phenylpropyl)- 2-pyrrolidinone are combined with 10 ml of methanol and 3 ml of 1N sodium hydroxide solution and stirred for 5 hours at ambient temperature. Then 3 ml of 1N hydrochloric acid are added. The methanol fraction is removed using a rotary evaporator, the water is decanted off and the residual oil is mixed with water and stirred for 30 minutes. The crystals are suction filtered and dried in vacuo at 80° C. Yield: 0.37 g (81% of theory), Melting point: 98°–100° C. $R_f$ value: 0.47 (silica gel; ethyl acetate/methanol=4:1)

The following are obtained analogously:

(1) (3S,5S)-5-[[4-(cis-4-aminocyclohexyl)benzoyl]aminomethyl]-3-carboxymethyl-1-(3-phenylpropyl)-2-pyrrolidinone $R_f$ value: 0.16 (silica gel; methylene chloride/methanol/conc. aqueous ammonia=4:1:0.25)

(2) (3S,5S)-5-[[4-(trans-4-aminocyclohexyl)benzoyl]aminomethyl]-3-carboxymethyl-1-(3-phenylpropyl)- 2-pyrrolidinone Melting point: 232°–236° C., $R_f$ value: 0.15 (silica gel; methylene chloride/methanol/conc. aqueous ammonia=4:1:0.25) Calculated: C 70.85 H 7.59 N 8.55 Found: 70.65 7.89 8.50

(3) (3S,5S)-5-[[4-(cis-4-aminomethylcyclohexyl)phenyl]oxymethyl]-3-carboxymethyl-1-(3-phenylpropyl)-2-pyrrolidinone-hydrate $R_f$ value: 0.45 (silica gel; methylene chloride/methanol/conc. aqueous ammonia=40:1:0.25) Calculated: C 70.28 H 7.93 N 5.65 Found: 70.48 8.23 5.69

(4) (3S,5S)-5-[[4-(trans-4-aminomethylcyclohexyl)phenyl]oxymethyl]-3-carboxymethyl-1-(3-phenylpropyl)-2-pyrrolidinone-hydrate Melting point: 192°–196° C., $R_f$ value: 0.45 (silica gel; methylene chloride/methanol/ conc. aqueous ammonia=4:1:0.25) Calculated: C 70.28 H 7.93 N 5.65 Found: 70.15 8.22 5.57

(5) (3S,5S)-5-[[(3'-amino-4-biphenylyl)carbonyl]aminomethyl]-3-carboxymethyl-1-(3-phenylpropyl)-2-pyrrolidinone $R_f$ value: 0.30 (silica gel; methylene chloride/methanol/conc. aqueous ammonia=4:1:0.25) Mass spectrum: $M^+=485$ (6) (3S,5S)-5-[(4-aminocinnamoyl)aminomethyl]-3-carboxymethyl- 1-(3-phenylpropyl)-2-pyrrolidinone $R_f$ value: 0.26 (silica gel; methylene chloride/methanol/cyclohexane/conc. aqueous ammonia=68:15:15:2)

(7) (3S,5S)-3-carboxymethyl-5-[[4'-(N-ethyloxycarbonylamidino)- 4-biphenylyl]oxymethyl]-2-pyrrolidinone Melting point: 190°–192° C. (decomp.) $R_f$ value: 0.61 (reversed phase silica gel RP 8; methanol/10% aqueous saline solution=6:4)

(8) (3S,5S)-3-carboxymethyl-5-[[4'-(N-methoxyamidino)-4-biphenylyl]oxymethyl]-2-pyrrolidinone Melting point: 234°–236° C. $R_f$ value: 0.25 (silica gel; toluene/dioxane/ethanol/glacial acetic acid=90:10:10:6)

EXAMPLE 21

(3S,5S)-3-Carboxymethyl-5-[[(3'-guanidino-3-biphenylyl)-carbonyl]aminomethyl]-1-(3-phenylpropyl)-2-pyrrolidinone 10 ml of dioxane and 0.65 ml of in hydrochloric acid are added to 290 mg of (3S,5S)-5-[[(3'-amino-3-biphenylyl)carbonyl]aminomethyl]-3-carboxymethyl-1-(3-phenylpropyl)-2-pyrrolidinone and the solvent is eliminated in vacuo. The residue is evaporated in vacuo twice with dry toluene. In order to suspend the residue in 10 ml of dioxane, 38 mg of cyanamide are added and the mixture is refluxed for 2.5 hours. The mixture is cooled, the solvent decanted off and the resin obtained is purified over a silica gel column using methylene chloride/methanol/conc. aqueous ammonia (10:5:1). Yield: 136 mg (40% of theory), Melting point: above 160° C. (decomp.) $R_f$ value: 0.64 (silica gel; methylene chloride/methanol/conc. aqueous ammonia=30:20:3)

The following are obtained analogously:

(1) (3S,5S)-3-carboxymethyl-5-[[[3-(3-guanidinophenyl)propyl]carbonylamino]methyl]-1-(3-phenylpropyl)-2-pyrrolidinone-hydrochloride $R_f$ value: 0.30 (silica gel; methylene chloride/methanol/conc. aqueous ammonia= 8:2:0.2)

(2) (3S,5S)-3-carboxymethyl-5-[[[2-(3-guanidinophenyl)ethyl]carbonylamino]methyl]-1-(3-phenylpropyl)-2-pyrrolidinone-hydrochloride $R_f$ value: 0.13 (silica gel; methylene chloride/methanol/acetic acid=4:1:0.1)

(3) (3S,5S)-3-carboxymethyl-5-[[[2-(4-guanidinophenyl)ethyl]carbonylamino]methyl]-1-(3-phenylpropyl)-2-pyrrolidinone-hydrochloride $R_f$ value: 0.10 (silica gel; methylene chloride/methanol/acetic acid=4:1:0.1) Mass spectrum: (M+H$^+$)=480

(4) (3S,5S)-3-carboxymethyl-5-[[[3-(4-guanidinophenyl)propyl]carbonylamino]methyl]-1-(3-phenylpropyl)-2-pyrrolidinone-semihydrate $R_f$ value: 0.10 (silica gel; methylene chloride/methanol/acetic acid=4:1:0.1) Calculated: C 62.26 H 7.06 N 13.44 C13.40 Found: 62.08 7.06 13.18 3.42

(5) (3S,5S)-5-[2-[N-(3'-guanidino-3-biphenylyl)benzylamino]ethyl]-3-[(methoxycarbonyl)methyl]-1-(3-phenylpropyl)- 2-pyrrolidinone-dihydrochloride $R_f$ value: 0.51 (silica gel; methylene chloride/methanol 8:2)

(6) (3S,5S)-3-carboxymethyl-5-[(4-guanidinocinnamoyl)aminomethyl]-1-(3-phenylpropyl)-2-pyrrolidinone (7) (3S,5S)-3-carboxymethyl-5-[[ (3'-guanidino-4-biphenylyl)carbonyl]aminomethyl]-1-(3-phenylpropyl)-2-pyrrolidinone $R_f$ value: 0.10 (silica gel; methylene chloride/methanol/conc. aqueous ammonia=4: 1: 0.25)

(8) (3S, 5S) -3-carboxymethyl-5-[(4'-guanidino-4-biphenylyl)oxymethyl]- 2 -pyrrolidinone

EXAMPLE 22

(3R, 5S)-3-Allyl-5-[[trans-4-(4-cyanophenyl)cyclohexyl)oxymethyl]- 1- (3-phenylpropyl)-2-pyrrolidinone 0.73 g of trans-4-(4-cyanophenyl)cyclohexanol, 2.8 g of (3R,5S)-3-allyl-5-[(methanesulphonyl)oxymethyl]-1-(3-phenylpropyl)-2-pyrrolidinone, 2.5 ml of 60% aqueous potassium hydroxide solution and 0.3 g of polyethyleneglycol-750 monomethylether (bound to polystyrene-1% divinylbenzene) are stirred for 24 hours at 45° C. Ice and water are added to the mixture, it is acidified with hydrochloric acid and extracted with ethyl acetate. The organic phase is dried with sodium sulphate, concentrated by evaporation and the residue is chromatographed over a silica gel column with petroleum ether/ethyl acetate (2:1). 0.4 g (24% of theory) of product are obtained. $R_f$ value: 0.61 (silica gel; petroleum ether/ethyl acetate 12:1) Calculated: C 78.91 H 7.95 N 6.14 Found: 78.88 8.13 6.10

EXAMPLE 23

(3S,R;5S,R)-5-[4-[(5-Aminopentyl)oxy]phenyl]-3-carboxymethyl- 1-(3-phenylpropyl)-2-pyrrolidinone-hydrate 1.4 g of (3S,R;5S,R)-3-carboxymethyl-5-[4-[ (4-cyanobutyl)oxy] phenyl]-1-(3-phenylpropyl)-2-pyrrolidinone are hydrogenated in 50 ml of methanol and 50 ml of conc. aqueous ammonia with 0.5 g of Raney nickel under a hydrogen pressure of 5 bar at ambient temperature until the starting material has disappeared. After the removal of the catalyst by suction filtering, the solution is evaporated down, the residue is taken up in methanol, filtered and evaporated down once more. The remaining resin is chromatographed over a silica gel column using methylene chloride/methanol/conc. aqueous ammonia (80:20:5). Yield: 0.86 g (62% of theory), $R_f$ value: 0.45 (silica gel; methylene chloride/methanol/conc. aqueous ammonia=80:20:5) Calculated: C 68.40 H 7.95 N 6.14 Found: 68.61 7.79 6.13

The following are obtained analogously:

(1) (3S,5S)-5-[(6-aminomethyl-5,6,7,8-tetrahydro-2-naphthylcarbonyl)aminomethyl]-3-carboxymethyl-1-(3-phenylpropyl)- 2-pyrrolidinone-semihydrate Melting point: 135°–150° C., sinters above 110° C. $R_f$ value: 0.27 (silica gel; methanol) Calculated: C 69.11 H 7.46 N 8.64 Found: 68.92 7.27 8.66

(2) (3S,5S)-5-[2-[(6-aminomethyl-5,6,7,8-tetrahydro-2-naphthylcarbonyl)amino]ethyl]-3-carboxymethyl-1-(3-phenylpropyl)- 2-pyrrolidinone-semihydrate Melting point: 124°–135° C. (decomp.) $R_f$ value: 0.22 (silica gel; methanol) Calculated: C 69.57 H 7.65 N 8.39 Found: 69.39 7.60 8.12

(3) (3S,5S)-5-[(6-aminomethyl-2-naphthyl)oxymethyl]-3-carboxymethyl- 1-(3-phenylpropyl)-2-pyrrolidinone-hydrochloride Melting point: 245°–255° C. $R_f$ value: 0.25 (silica gel; methylene chloride/methanol/conc. aqueous ammonia=16:4:1) Calculated: C 67.14 H 6.47 N 5.80 Found: 66.90 6.40 5.85

(4) (3S,5S)-5-[(4'-aminomethyl-4-biphenylyl)oxymethyl]-3-carboxymethyl-1-(3-phenylpropyl)-2-pyrrolidinonehydrate Melting point: 185°–187° C. $R_f$ value: 0.47 (silica gel; methylene chloride/methanol/conc. aqueous ammonia=16:4:1) Calculated: C 71.00 H 6.99 N 5.71 Found: 71.27 6.97 5.71

(5) (3S,5S)-5-[[3-(aminomethyl)phenyl]carbonylaminomethyl]-3-carboxymethyl-1-(3-phenylpropyl)-2-pyrrolidinone $R_f$ value: 0.50 (silica gel; n-butanol/glacial acetic acid/water=4:1:1)

(6) (3S,5S)-5-[[4-(aminomethyl)phenyl]carbonylaminomethyl]-3-carboxymethyl-1-(3-phenylpropyl)-2-pyrrolidinone $R_f$ value: 0.54 (silica gel; n-butanol/glacial acetic acid/water=4:1:1)

When the mixture is worked up with ethanol and some hydrochloric acid, a small amount of ethyl ester is formed which is chromatographically separated and characterised:

(3S,5S)-5-[[4-(aminomethyl)phenyl]carbonylaminomethyl]- 3-[(ethoxycarbonyl)methyl]-1-(3-phenylpropyl)-2-pyrrolidinone $R_f$ value: 0.61 (silica gel; n-butanol/glacial acetic acid/water=4:1:1)

(7) (3S,5S)-5-[[4-(4-aminobutyl)phenyl]oxymethyl]-3-carboxymethyl- 3-methyl-1-(3-phenylpropyl)-2-pyrrolidinone-semihydrate Calculated: C 70.25 H 8.09 N 6.05 Found: 70.42 8.08 6.07

(8) (3S,5S)-5-[[4-(4-aminobutyl)phenyl]oxymethyl]-3-carboxymethyl- 1-(3-phenylpropyl)-2-pyrrolidinonesemihydrate ×1.25 HCl Calculated: C 63.29 H 7.15 N 5.68 Cl 9.00 Found: 63.25 7.77 6.07 9.15 $R_f$ value: 0.44 (silica gel; methanol)

(9) (3S,5S)-5-[(2-aminomethyl-5-indanyl)oxymethyl]-3-carboxymethyl- 1-(3-phenylpropyl)-2-pyrrolidinone-hydrate Calculated: C 68.70 H 7.54 N 6.16 Found: 69.07 7.47 6.29

(10) (3S,5S)-5-[[[3-[4-(aminomethyl)phenyl]propyl]carbonylamino]methyl]-3-carboxymethyl-1-(3-phenyl-propyl)- 2-pyrrolidinone-semihydrate Calculated: C 68.32 H 7.64 N 8.92 Found: 68.27 7.64 8.85

(11) (3R,5S)-3-(6-aminohexyl)-5-[2,2-bis-(tert.butyloxycarbonyl)ethyl]-1-isobutyl-2-pyrrolidinone $R_f$ value: 0.65 (silica gel; methylene chloride/methanol/conc. aqueous ammonia=80:20:1) Mass spectrum: $M^+$=468

(12) (3R,5S)-3-(4-aminobutyl)-5-[2,2-bis-(tert.butyloxycarbonyl)-ethyl]- 1-isobutyl-2-pyrrolidinone $R_f$ value: 0.69 (silica gel; methylene chloride/methanol= 4:1)

(13) (3S,5S)-5-[(4'-aminomethyl-4-biphenylyl)oxymethyl]-3-carboxymethyl-2-pyrrolidinone $R_f$ value: 0.82 (reversed phase silica gel; methanol/5% aqueous saline solution=6:4)

(14) (3S, 5S)-5-[(4'-aminomethyl-2'-methyl-4-biphenylyl)oxymethyl]- 3-carboxymethyl-2 -pyrrolidinone

(15) (3S,5S)-5-[(4'-aminomethyl-2,3-dimethyl-4-biphenylyl)oxymethyl]-3-carboxymethyl-2-pyrrolidinone

EXAMPLE 24

(3S,5S)-5-[[[3-[3-(Aminomethyl)phenyl]propyl]carbonylamino]methyl]-3-carboxymethyl-1-(3-phenylpropyl)-2-pyrrolidinone ×1.5 water 3.2 g of (3S,5S)-3-carboxymethyl-5-[[[3-(3-cyanophenyl)-propyl]carbonylamino]methyl]-1-(3-phenyl-propyl)-2-pyrrolidinone are dissolved in 30 ml of glacial acetic acid and hydrogenated for 15 minutes with hydrogen in the presence of 0.5 g of Raney nickel at ambient temperature under 5 bars of pressure. The solution is evaporated down, the residue is taken up in 0.2N sodium hydroxide solution and extracted with ethyl acetate. The aqueous phase is acidified with 2N hydrochloric acid and extracted once more with ethyl acetate. The aqueous phase remaining is concentrated by evaporation and the residue remaining is purified by chromatography on silica gel (eluant: methylene chloride/methanol/conc. aqueous ammonia=17:3:0.2). Yield: 0.85 g (25% of theory), Calculated: C 65.83 H 7.78 N 8.53 Found: 65.61 7.83 8.60

EXAMPLE 25

(3S,5S)-5-[[4-[3-(tert. Butyloxycarbonylamino)cyclobutyl]phenyl]carbonylaminomethyl]-3-carboxymethyl-1-(3-phenylpropyl)- 2-pyrrolidinone-hydrate 1.3 g of (3S,5S)-5-[[4-[3-(tert.butyloxycarbonylamino)cyclobutyl]phenyl]carbonylaminomethyl]-3-[(methoxycarbonyl)methyl]-1-(3-phenylpropyl)-2-pyrrolidinone are dissolved in 5 ml of methanol and mixed with 7 ml of 1N sodium hydroxide solution. After 3 hours stirring at ambient temperature the methanol is evaporated off and the residue is adjusted to about pH 2 with saturated aqueous potassium hydrogen sulphate solution whilst cooling with ice. The mixture is extracted with ethyl acetate, the ethyl acetate solution is dried over magnesium sulphate, filtered and evaporated down. Yield: 1.2 g (100% of theory) of a white foam. $R_f$ value: 0.57 (silica gel; ethyl acetate/glacial acetic acid=50:1) Calculated: C 66.08 H 7.45 N 7.22 Found: 66.29 7.54 7.25

The following are obtained analogously:

(1) (3S,5S)-5-[[4-[[3-(tert.butyloxycarbonylamino)propyl]carbonylamino]phenyl]oxymethyl]-3-carboxymethyl-1-(3-phenylpropyl)-2-pyrrolidinone-semihydrate $R_f$ value: 0.10 (silica gel; cyclohexane/ethyl acetate=1:2) Calculated: C 64.56 H 7.34 N 7.29 Found: 64.74 7.69 7.00

(2) (3S,5S)-5-[2-[[6-(tert.butyloxycarbonylamino)- 5,6,7,8-tetrahydro-2-naphthylcarbonyl]amino]ethyl]-3-carboxymethyl- 1-(3-phenylpropyl)-2-pyrrolidinone $R_f$ value: 0.38 (silica gel; toluene/dioxane/ethanol/glacial acetic acid=90:10:10:6) Calculated: C 68.61 H 7.50 N 7.27 Found: 68.59 7.66 7.33

(3) (3S,5S)-5-[[6-(tert.butyloxycarbonylamino)-5,6,7,8-tetrahydro- 2-naphthylcarbonyl]aminomethyl]-3-carboxymethyl- 1-(3-phenylpropyl)-2-pyrrolidinone $R_f$ value: 0.36 (silica gel; toluene/dioxane/ethanol/glacial acetic acid= 90:10:10:6) Calculated: C 68.18 H 7.33 N 7.45 Found: 67.99 7.55 7.26

(4) (3S,5S)-3-carboxymethyl-5-[(6-cyano-5,6,7,8-tetrahydro- 2-naphthylcarbonyl)aminomethyl]-1-(3-phenylpropyl)- 2-pyrrolidinone $R_f$ value: 0.37 (silica gel; toluene/ dioxane/ethanol/glacial acetic acid=90:10:10:6) Calculated: C 71.02 H 6.60 N 8.87 Found: 70.80 6.68 8.81

(5) (3S,5S)-3-carboxymethyl-5-[2-[(6-cyano-5,6,7,8-tetrahydro- 2-naphthylcarbonyl)amino]ethyl]-1-(3-phenylpropyl)- 2-pyrrolidinone $R_f$ value: 0.27 (silica gel; toluene/dioxane/ethanol/glacial acetic acid=90:10:10:6) Calculated: C 71.43 H 6.82 N 8.62 Found: 71.21 6.83 8.48

(6) (3S,5S)-5-[2-[[4-[3-(tert.butyloxycarbonylamino)cyclobutyl]phenyl]carbonylamino]ethyl]-3-carboxymethyl-1-(3-phenylpropyl)-2-pyrrolidinone-semihydrate $R_f$ value: 0.44 (silica gel; ethyl acetate/glacial acetic acid= 50:1) Calculated: C 67.56 H 7.56 N 7.16 Found: 67.34 7.69 7.03

(7) (3R,5S)-3-allyl-1-carboxymethyl-5-[(4'-cyano-4-biphenylyl)oxymethyl]-2-pyrrolidinone $R_f$ value: 0.62 (silica gel; ethyl acetate/cyclohexane/glacial acetic acid=40:5:1) Calculated: C 70.75 H 5.68 N 7.17 Found: 70.67 5.88 7.00

(8) (3R,5S)-3-(4-aminobutyl)-5-[(4'-carboxymethyl-4-biphenylyl)oxymethyl]-1-methyl-2-pyrrolidinone $R_f$ value: 0.50 (silica gel; methylene chloride/methanol/conc. aqueous ammonia=20:10:2)

(9) (3R, 5S) -3-[4-(tert.butyloxycarbonylamino)butyl]-5-[(4'-carboxymethyl-4-biphenylyl)oxymethyl]-1-methyl-2-pyrrolidinone $R_f$ value: 0.39 (silica gel; methylene chloride/methanol= 10:1)

EXAMPLE 26

(3S,5S)-5-[[4-(tert. Butyloxycarbonylamino)butyl]carbonylaminomethyl]-3-carboxymethyl-1-(3-phenylpropyl)- 2-pyrrolidinone 2.37 g of (3S,5S)-5-aminomethyl-3-carboxymethyl-1-( 3-phenylpropyl)-2-pyrrolidinone, 120 ml of dry tetrahydrofuran and 3 g of N-(trimethylsilyl)imidazole are subjected to acoustic irradiation for 2 hours under Argon in an ultrasound bath. A clear solution (solution A) is obtained. At −20° C. to −30° C., 0.9 ml of N-methylmorpholine and 1.05 ml of isobutylchloroformate are added dropwise to 1.77 g of N-Boc-5-aminovaleric acid in 50 ml of dry tetrahydrofuran. After one hours stirring at the same temperature, solution A is added dropwise. Stirring is continued for a further 2 hours at −20° C. and it is then heated overnight to ambient temperature. The reaction mixture is diluted with ethyl acetate and shaken vigorously with 0.5M aqueous potassium hydrogen sulphate solution. The organic phase is separated off, dried with sodium sulphate and concentrated by evaporation. The residue is chromatographed with methylene chloride/methanol (4:1) and (2:1) over a silica gel column. Yield: 2.3 g (60% of theory), $R_f$ value: 0.66 (silica gel; methylene chloride/methanol= 4:1)

The following are obtained analogously:

(1) (3S,5S)-5-[[6-(tert.butyloxycarbonylamino)hexyl]carbonylaminomethyl]-3-carboxymethyl-1-(3-phenylpropyl)- 2-pyrrolidinone $R_f$ value: 0.69 (silica gel; methylene chloride/methanol= 4:1) Mass spectrum: (M−H)=516

(2) (3S,5S)-5-[[7-(tert.butyloxycarbonylamino)heptyl]carbonylaminomethyl]-3-carboxymethyl-1-(3-phenylpropyl)- 2-pyrrolidinone $R_f$ value: 0.71 (silica gel; methylene chloride/methanol= 4:1) Mass spectrum: (M–H)=530

(3) (3S,5S)-5-[[3-(tert.butyloxycarbonylamino)propyl]carbonylaminomethyl]-3-carboxymethyl-1-(3-phenylpropyl)- 2-pyrrolidinone $R_f$ value: 0.60 (silica gel; methylene chloride/methanol= 4:1)

(4) (3S,5S)-5-[[5-(tert.butyloxycarbonylamino)pentyl]carbonylaminomethyl]-3-carboxymethyl-1-(3-phenylpropyl)- 2-pyrrolidinone $R_f$ value: 0.62 (silica gel; methylene chloride/methanol= 4:1) Mass spectrum: (M–H)=502

EXAMPLE 27

(3S,5S)-5-[2-[[2-[(tert.butyloxycarbonylamino)methyl]-5-indanyl]carbonylamino]ethyl]-3-carboxymethyl-1-(3-phenylpropyl)- 2-pyrrolidinone 1.9 g of (3S,5S)-5-(2-aminoethyl)-3-carboxymethyl 1-(3-phenylpropyl)-2-pyrrolidinone are dissolved in a mixture of 20 ml of methylene chloride and 20 ml of acetonitrile and 0.8 ml of trimethylchlorosilane are added. The mixture is stirred for one hour at ambient temperature and then for 1.5 hours at 45° C. It is evaporated to dryness in vacuo, taken up with 50 ml of tetrahydrofuran and cooled to 0° C. This solution is added dropwise at –30° C. to a reaction mixture obtained by dropwise addition of 1.0 ml of isobutylchloroformate to a solution of 2.05 g of 2-[(tert.butyloxycarbonylamino)methyl]indane-5-carboxylic acid and 0.85 ml of N-methylmorpholine in 40 ml of tetrahydrofuran at –30° C. A further 0.75 ml of N-methylmorpholine are added and the mixture is kept for 2 hours at –20° C., one hour at 0° C. and 3 hours at ambient temperature. The reaction mixture is combined with 100 ml of water and 200 ml of ether, acidified with citric acid, the organic phase is separated off, washed with 10% citric acid and evaporated down. The residue is purified by chromatography on silica gel (eluant: ether/tetrahydrofuran/water =2:1:0.05). Yield: 1.25 g (35% of theory), $R_f$ value: 0.49 (silica gel; ether/tetrahydrofuran/water=1:1:0.5)

EXAMPLE 28

(3S,5S)-5-[[4-(4-Aminobutyl)phenyl]oxymethyl]-3-carboxymethyl- 1-[3-(4-hydroxyphenyl)propyl]-2-pyrrolidinone 0.25 g Of (3S,5S)-5-[[4-(4-aminobutyl)phenyl]oxymethyl]-1-[3-(4-benzyloxyphenyl)propyl]-3-carboxymethyl-2-pyrrolidinone are dissolved in 20 ml of glacial acetic acid, 0.2 g of 10% palladium/charcoal are added and the mixture is hydrogenated for 5 hours at ambient temperature under 5 bars of hydrogen pressure. Then the catalyst is removed by suction filtering, the filtrate is evaporated down and the residue is purified by chromatography on silica gel (eluant: methylene chloride/methanol/conc. aqueous ammonia= 4:1:0.2). Yield: 0.2 g (93% of theory), $R_f$ value: 0.30 (silica gel; methylene chloride/methanol/conc. aqueous ammonia= 4:1:0.25)

The following are obtained analogously:
(1) (3S,5S)-5-[[4-(4-aminobutyl)phenyl]oxymethyl]-3-(2,3-dihydroxypropyl)-1-[3-(4-hydroxyphenyl)propyl]-2-pyrrolidinone $R_f$ value: 0.27 (silica gel; methylene chloride/methanol/conc. aqueous ammonia=4:1:0.25)

(2) (3S,5S)-3-carboxymethyl-5-[[4'-(N-methoxycarbonylamidino)- 4-biphenylyl]oxymethyl]-2-pyrrolidinone The benzylester is hydrogenated in dioxane/dimethylformamide. $R_f$ value: 0.61 (reversed phase silica gel; methanol/ 10% aqueous saline solution=6:4)

EXAMPLE 29

(3S,5S)-5-[(3-Aminopropyl)carbonylaminomethyl]-3-[(methoxycarbonyl)methyl]-1-(3-phenylpropyl)-2-pyrrolidinone-hydrochloride 1.08 g of thionylchloride are added at –10° to –20° C. to 24 ml of methanol. After 20 minutes stirring at this temperature, 2.25 g of (3S,5S)-5-[(3-aminopropyl)-carbonylaminomethyl]- 3-carboxymethyl-1-(3-phenylpropyl)-2-pyrrolidinone in 18 ml of methanol are added dropwise, the mixture is stirred for 30 minutes at –10° C. and then heated to ambient temperature. The reaction solution is evaporated using a rotary evaporator, the residue is taken up in methanol and evaporated once more. After chromatography on silica gel using methylene chloride/methanol (4:1) 1.65 g (65% of theory) are obtained. $R_f$ value: 0.21 (silica gel; methylene chloride/methanol= 8:1) Mass spectrum: M$^+$=389

The following are obtained analogously:
(1) (3S,5S)-5-[(3-guanidinopropyl)carbonylaminomethyl]-3-[(methoxycarbonyl)methyl]-1-(3-phenylpropyl)-2-pyrrolidinone-hydrochloride $R_f$ value: 0.13 (silica gel; methylene chloride/methanol/conc. aqueous ammonia= 80:20:1) Mass spectrum: (M+H)$^+$=432

(2) (3S,5S)-5-[(5-guanidinopentyl)carbonylaminomethyl]-3-[(methoxycarbonyl)methyl]-1-(3-phenylpropyl)-2-pyrrolidinone-hydrochloride $R_f$ value: 0.27 (silica gel; methylene chloride/methanol 4:1) Mass spectrum: (M+H)$^+$= 460

(3) (3S,5S)-5-[(6-guanidinohexyl)carbonylaminomethyl]-3-[(methoxycarbonyl)methyl]-1-(3-phenylpropyl)-2-pyrrolidinone-hydrochloride $R_f$ value: 0.28 (silica gel; methylene chloride/methanol= 4:1) Mass spectrum: (M+H)$^+$= 474

(4) (3S,5S)-5-[[4-(2-guanidinoethyl)phenyl]oxymethyl]-3-[(methoxycarbonyl)methyl]-1-(3-phenylpropyl)-2-pyrrolidinone-hydrochloride $R_f$ value: 0.63 (silica gel; n-butanol/glacial acetic acid/water=4:1:1)

EXAMPLE 30

(3S,5S)-3-[(Aminocarbonyl)methyl]-5-[[4-(2-guanidinoethyl)phenyl]oxymethyl]-1-isobutyl-2-pyrrolidinoneacetic acid salt 0.42 g of (3S,5S)-3-carboxymethyl-5-[[4-(2-guanidinoethyl)phenyl]oxymethyl]-1-isobutyl-2-pyrrolidinone are suspended in 5 ml of dry tetrahydrofuran and converted into the hydrochloride with isopropanolic hydrochloric acid. The suspension is evaporated down and the residue is concentrated once with isopropanol and twice with tetrahydrofuran in vacuo. The resulting foam is dried in vacuo and dissolved in 5 ml of dry dimethylformamide and 5 ml of tetrahydrofuran. 0.28 g of carbonyldiimidazole are added and the mixture is stirred for one hour at ambient temperature. Then 5 ml of methanolic ammonia are added and the mixture is left to stand for 18 hours. After the solvent has been removed in vacuo the residue is purified over a silica gel column with n-butanol/glacial acetic acid/water (4:1:1). Any inorganic salts adhering to the product are removed by dissolving in a little methanol, filtering and evaporating the filtrate. This process is repeated with isopropanol and methylene chloride/methanol. Yield: 0.35 g (74% of theory), $R_f$ value: 0.45 (silica gel; n-butanol/glacial acetic acid/water=4:1:1) Mass spectrum: (M+H)$^+$=390

The following are prepared analogously:
(1) (3S,5S)-3-[(aminocarbonyl)methyl]-5-[(3-guanidinopropyl)carbonylaminomethyl]- 1-(3-phenylpropyl)-2-pyrrolidinone-hydrochloride $R_f$ value: 0.40 (silica gel; n-butanol/glacial acetic acid/water=4:1:1) Mass spectrum: (M+H)$^+$=417

(2) (3S,5S)-3-[(aminocarbonyl)methyl]-5-[(5-guanidinopentyl)carbonylaminomethyl]-1-(3-phenylpropyl)-2-pyrrolidinone-hydrochloride $R_f$ value: 0.41 (silica gel; n-butanol/glacial acetic acid/water=4:1:1) Mass spectrum: $(M+H)^+$=445

(3) (3S,5S)-3-[(aminocarbonyl)methyl]-5-[(6-guanidinohexyl)carbonylaminomethyl]-1-(3-phenylpropyl)-2-pyrrolidinone-acetic acid salt $R_f$ value: 0.35 (silica gel; n-butanol/glacial acetic acid/water=4:1:1) Mass spectrum: $(M+H)^+$=459

(4) (3S,5S)-3-[(aminocarbonyl)methyl]-5-[[4-(2-guanidinoethyl)phenyl]oxymethyl]-1-(3-phenylpropyl)-2-pyrrolidinone-hydrochloride $R_f$ value:-0.50 (silica gel; n-butanol/glacial acetic acid/water=4:1:1) Mass spectrum: $(M+H)^+$=452

EXAMPLE 31

(3S,5S)-3-Carboxymethyl-5-[[4-(cis-4-guanidinocyclohexyl)phenyl]oxymethyl]-1-(3-phenylpropyl)-2-pyrrolidinone 0.85 g of (3S,5S)-5-[[4-(cis-4-aminocyclohexyl)phenyl]oxymethyl-3-carboxymethyl-1-(3-phenylpropyl)-2-pyrrolidinone are suspended in a mixture of 100 ml of dimethylformamide and 50 ml of water. 1.5 g of 1-amidino- 3,5-dimethylpyrazole and 1.3 ml of triethylamine are added and the mixture is stirred at ambient temperature for 11 days. It is concentrated by evaporation and triturated with acetone and ethyl acetate. The crystals thus obtained are triturated with methanol and suction filtered. A second fraction is obtained by chromatography of the ethyl acetate and acetone extracts on silica gel (eluant: methylene chloride/methanol/conc. aqueous ammonia=4:1:0.25). Yield: 0.35 g (38% of theory), Melting point: 240°–245° C.

The following are obtained analogously:

(1) (3S,R;5S,R)-3-carboxymethyl-5-[4-[(5-guanidinopentyl)oxy]phenyl]-1-(3-phenylpropyl)-2-pyrrolidinone $R_f$ value: 0.39 (silica gel; methylene chloride/methanol/conc. aqueous ammonia=80:20:5) Mass spectrum: $(M+H)^+$=481

(2) (3S,5S)-3-carboxymethyl-5-[[4-[(3-guanidinopropyl)carbonylamino]phenyl]oxymethyl]-1-(3-phenylpropyl)-2-pyrrolidinone $R_f$ value: 0.19 (silica gel; methylene chloride/methanol/conc. aqueous ammonia=40:4:1)

(3) (3S,5S)-3-carboxymethyl-5-[2-[(6-guanidino-5,6,7,8-tetrahydro- 2-naphthylcarbonyl)amino]ethyl]-1-(3-phenylpropyl)- 2-pyrrolidinone-hydrate $R_f$ value: 0.35 (silica gel; methanol/conc. aqueous ammonia=98:2) Calculated: C 64.78 H 7.31 N 13.02 Found: 64.85 7.36 13.30

(4) (3S,5S)-3-carboxymethyl-5-[(6-guanidino-5,6,7,8-tetrahydro- 2-naphthylcarbonyl)aminomethyl]-1-(3-phenylpropyl)- 2-pyrrolidinone-hydrate $R_f$ value: 0.42 (silica gel; methanol/conc. aqueous ammonia=98:2) Calculated: C 64.23 H 7.12 N 13.37 Found: 63.99 7.13 13.40

(5) (3S,5S)-3-carboxymethyl-5-[(6-guanidinomethyl- 5,6,7, 8-tetrahydro-2-naphthylcarbonyl)aminomethyl]-1-(3-phenylpropyl)- 2-pyrrolidinone-hydrate $R_f$ value: 0.27 (silica gel; methanol/conc. aqueous ammonia=98:2) Calculated: C 64.78 H 7.31 N 13.02 Found: 64.66 7.25 13.33

(6) (3S,5S)-3-carboxymethyl-5-[2-[(6-guanidinomethyl-5,6,7,8-tetrahydro-2-naphthylcarbonyl)amino]ethyl]-1-(3-phenylpropyl)- 2-pyrrolidinone-hydrate $R_f$ value: 0.29 (silica gel; methanol/conc. aqueous ammonia=99:1) Calculated: C 65.31 H 7.49 N 12.69 Found: 65.06 7.37 13.00

(7) (3S,5S)-3-carboxymethyl-5-[[4-(3-guanidinocyclobutyl)phenyl]carbonylaminomethyl]-1-(3-phenylpropyl)-2-pyrrolidinone $R_f$ value: 0.36 (silica gel; methylene chloride/methanol/conc. aqueous ammonia=35:15:4)

(8) (3S,5S)-3-carboxymethyl-5-[2-[[4-(3-guanidinocyclobutyl)phenyl]carbonylamino]ethyl]-1-(3-phenylpropyl)-2-pyrrolidinone $R_f$ value: 0.27 (silica gel; methylene chloride/methanol/conc. aqueous ammonia=35:15:4)

(9) (3S,5S)-3-carboxymethyl-5-[[6-(guanidinomethyl)-2-naphthyl]oxymethyl]-1-(3-phenylpropyl)-2-pyrrolidinone $R_f$ value: 0.28 (silica gel; methylene chloride/methanol/conc. aqueous ammonia=16:8:1)

(10) (3S,5S)-3-carboxymethyl-5-[[4'-(guanidinomethyl)-4-biphenylyl]oxymethyl]-1-(3-phenylpropyl)-2-pyrrolidinone $R_f$ value: 0.13 (silica gel; methylene chloride/methanol/conc. aqueous ammonia=16:4:1)

(11) (3S,5S)-3-carboxymethyl-5-[[3-(guanidinomethyl)phenyl]carbonylaminomethyl]-1-(3-phenylpropyl)-2-pyrrolidinone-hydrate Melting point: sinters above 120° C. $R_f$ value: 0.30 (silica gel; methylene chloride/methanol/conc. aqueous ammonia=8:4:1) Calculated: C 62.10 H 6.88 N 14.48 Found: 62.47 6.90 14.60

(12) (3S,5S)-3-carboxymethyl-5-[[4-(2-guanidinoethyl)phenyl]carbonylaminomethyl]-1-(3-phenylpropyl)-2-pyrrolidinone $R_f$ value: 0.64 (silica gel; n-butanol/glacial acetic acid/water=4:1:1)

(13) (3S,5S)-3-carboxymethyl-5-[[4-(guanidinomethyl)phenyl]carbonylaminomethyl]-1-(3-phenylpropyl)-2-pyrrolidinone Melting point: 250°–260° C. $R_f$ value: 0.54 (silica gel; n-butanol/glacial acetic acid/water=4:1:1) Calculated: C 64.50 H 6.71 N 15.04 Found: 64.44 6.95 15.06

(14) (3S,5S)-3-carboxymethyl-5-[[3-(2-guanidinoethyl)phenyl]carbonylaminomethyl]-1-(3-phenylpropyl)-2-pyrrolidinone $R_f$ value: 0.14 (silica gel; methylene chloride/methanol/conc. aqueous ammonia=20:5:1)

(15) (3S,5S)-3-carboxymethyl-5-[(5-guanidinopentyl)carbonylaminomethyl]-1-(4-phenoxybutyl)-2-pyrrolidinone $R_f$ value: 0.49 (silica gel; n-butanol/glacial acetic acid/water=4:1:1)

(16) (3S,5S)-3-carboxymethyl-5-[(5-guanidinopentyl)carbonylaminomethyl]-1-(2-phenylethyl)-2-pyrrolidinone $R_f$ value: 0.46 (silica gel; methylene chloride/methanol/conc. aqueous ammonia=8:4:1) Mass spectrum: $(M+H)^+$=432

(17) (3S,5S)-1-benzyl-3-carboxymethyl-5-[(5-guanidinopentyl)carbonylaminomethyl]-2-pyrrolidinone $R_f$ value: 0.26 (silica gel; methylene chloride/methanol/conc. aqueous ammonia=8:4:1) Mass spectrum: $(M+H)^+$=418

(18) (3S,5S)-3-carboxymethyl-5-[[(2-guanidino-5-indanyl)-methylcarbonyl]aminomethyl]-1-(3-phenylpropyl)-2-pyrrolidinone $R_f$ value: 0.64 (silica gel; n-butanol/glacial acetic acid/water=4:1:1) Mass spectrum: $(M+H)^+$=506

(19) (3S,5S)-3-carboxymethyl-5-[(5-guanidinopentyl)carbonylaminomethyl]-1-[2-(1-naphthyl)ethyl]-2-pyrrolidinone $R_f$ value: 0.41 (silica gel; n-butanol/glacial acetic acid/water=4:1:1) Mass spectrum: $(M+H)^+$=482

(20) (3S,5S)-3-carboxymethyl-5-[(5-guanidinopentyl)carbonylaminomethyl]-1-[2-(2-naphthyl)ethyl]-2-pyrrolidinone $R_f$ value: 0.43 (silica gel; n-butanol/glacial acetic acid/water=4:1:1) Mass spectrum: $(M+H)^+$=482

(21) (3S,5S)-3-carboxymethyl-5-[[4-(3-guanidinopropyl)phenyl]oxymethyl]-1-(3-phenylpropyl)-2-pyrrolidinonesemihydrate $R_f$ value: 0.58 (silica gel; n-butanol/glacial acetic acid/water=4:1:1) Calculated: C 65.66 H 7.42 N 11.78 Found: 65.69 7.39 11.69 Mass spectrum: $(M+H)^+$=467

(22) (3S,5S)-3-carboxymethyl-5-[[4-(guanidinomethyl)phenyl]oxymethyl]-1-(3-phenylpropyl)-2-pyrrolidinone $R_f$ value: 0.49 (silica gel; n-butanol/glacial acetic acid/water=4:1:1) Mass spectrum: $(M+H)^+$=439

(23) (3S,5S)-3-carboxymethyl-5-[[3-(guanidinomethyl)phenyl]oxymethyl]- 1- (3-phenylpropyl) -2-pyrrolidinone $R_f$ value: 0.54 (silica gel; n-butanol/glacial acetic acid/water=4:1:1) Mass spectrum: $(M+H)^+$=439

(24) (3S,5S)-3-carboxymethyl-5-[[3-(4-guanidinobutyl)phenyl]oxymethyl]-1-(3-phenylpropyl)-2-pyrrolidinone $R_f$ value: 0.59 (silica gel; n-butanol/glacial acetic acid/water=4:1:1) Mass spectrum: $(M+H)^+=481$

(25) (3S,5S)-3-carboxymethyl-5-[(5-guanidinopentyl)carbonylaminomethyl]-1-isobutyl-2-pyrrolidinone $R_f$ value: 0.44 (silica gel; n-butanol/glacial acetic acid/water=4:1:1) Mass spectrum: $(M+H)^+=384$

(26) (3S,5S)-3-carboxymethyl-5-[[3-(2-guanidinoethyl)phenyl]-oxymethyl]-1-(3-phenylpropyl)-2-pyrrolidinonesemihydrate $R_f$ value: 0.57 (silica gel; n-butanol/glacial acetic acid/water=4:1:1) Calculated: C 65.05 H 6.99 N 12.13 Found: 64.81 7.17 11.92 Mass spectrum: $(M+H)^+=453$

(27) (3S,5S)-3-carboxymethyl-5-[[4-(2-guanidinoethyl)phenyl]oxymethyl]-1-(3-phenylpropyl)-2-pyrrolidinone $R_f$ value: 0.51 (silica gel; n-butanol/glacial acetic acid/water=4:1:1) Mass spectrum: $(M+H)^+=453$

(28) (3S,5S)-3-carboxymethyl-5-[(4-guanidinobutyl)carbonylaminomethyl]-1-(3-phenylpropyl)-2-pyrrolidinone $R_f$ value: 0.51 (silica gel; n-butanol/glacial acetic acid/water=4:1:1) Mass spectrum: $(M+H)^+=432$

(29) (3S,5S)-3-carboxymethyl-5-[(6-guanidinohexyl)carbonylaminomethyl]-1-(3-phenylpropyl)-2-pyrrolidinone $R_f$ value: 0.56 (silica gel; n-butanol/glacial acetic acid/water=4:1:1)

(30) (3S,5S)-3-carboxymethyl-5-[(7-guanidinoheptyl)carbonylaminomethyl]-1-(3-phenylpropyl)-2-pyrrolidinone $R_f$ value: 0.47 (silica gel; methanol) Mass spectrum: $(M-H)^+=472$

(31) (3S,5S)-3-carboxymethyl-5-[(3-guanidinopropyl)carbonylaminomethyl]-1-(3-phenylpropyl)-2-pyrrolidinone $R_f$ value: 0.42 (silica gel; n-butanol/glacial acetic acid/water=4:1:1) Mass spectrum: $(M-H)^+=416$

(32) (3S,5S)-3-carboxymethyl-5-[[4-(2-guanidinoethyl)phenyl]oxymethyl]-1-isobutyl-2-pyrrolidinone $R_f$ value: 0.31 (silica gel; methanol) Mass spectrum: $(M-H)^+=389$

(33) (3S,5S)-3-carboxymethyl-B-[(B-guanidinopentyl)carbonylaminomethyl]-1-(3-phenylpropyl)-2-pyrrolidinone $R_f$ value: 0.52 (silica gel; n-butanol/glacial acetic acid/water=4:1:1) Mass spectrum: $(M-H)^+=444$

(34) (3S,5S)-3-carboxymethyl-5-[[4-(4-guanidinobutyl)phenyl]oxymethyl]-1-(3-phenylpropyl)-2-pyrrolidinone $R_f$ value: 0.61 (silica gel; n-butanol/glacial acetic acid/water=4:1:1) Mass spectrum: $(M+H)^+=481$

(35) (3S,5S)-3-carboxymethyl-5-[[4-(trans-4-guanidinocyclohexyl)phenyl]oxymethyl]-1-(3-phenylpropyl)-2-pyrrolidinone Melting point: sinters above 130° C. $R_f$ value: 0.14 (silica gel; methylene chloride/methanol/conc. aqueous ammonia=4:1:0.25)

(36) (3S,5S)-3-carboxymethyl-5-[[3-[3-(guanidinomethyl)phenyl]propyl]carbonylaminomethyl]-1-(3-phenylpropyl)-2-pyrrolidinone-semihydrate Calculated: C 65.09 H 7.41 N 13.56 Found: 64.90 7.95 13.32

(37) (3S,5S)-3-carboxymethyl-5-[(2-guanidinomethyl-5-indanyl)oxymethyl]-1-(3-phenylpropyl)-2-pyrrolidinonehydrate
The reaction is carried out without the addition of dimethylformamide and the reaction lasts one day Calculated: C 65.30 H 7.31 N 11.29 Found: 65.50 7.20 10.93

(38) (3S,5S)-3-carboxymethyl-5-[[3-[4-(guanidinomethyl)phenyl]propyl]carbonylaminomethyl]-1-(3-phenylpropyl)-2-pyrrolidinone Calculated: C 66.25 H 7.35 N 13.80 Found: 65.99 7.59 13.60

(39) (3S,5S)-3-carboxymethyl-5-[(2-guanidinomethyl-5-indanyl)sulphonylaminomethyl]-1-(3-phenylpropyl)-2-pyrrolidinone $R_f$ value: 0.27 (silica gel; methanol) Calculated: C 59.87 H 6.51 N 12.93 S 5.92 Found: 59.76 6.47 12.50 5.86

(40) (3S,5S)-3-carboxymethyl-5-[(2-guanidino-5-indanyl)-sulphonylaminomethyl]-1-(3-phenylpropyl)-2-pyrrolidinone $R_f$ value: 0.63 (silica gel; methanol) Calculated: C 57.23 H 6.47 N 12.84 S 5.88 Found: 57.45 6.49 13.00 5.93

(41) (3S,5S)-3-carboxymethyl-5-[(2-guanidino-5-indanyl)-carbonylaminomethyl]-1-(3-phenylpropyl)-2-pyrrolidinonehydrate $R_f$ value: 0.15 (silica gel; methylene chloride/cyclohexane/methanol/conc. aqueous ammonia= 34:7.5:57.5:1) Calculated: C 63.63 H 6.92 N 13.74 Found: 63.88 6.74 13.77

(42) (3S,5S)-3-carboxymethyl-5-[(2-guanidinomethyl-5-indanyl)carbonylaminomethyl]-1-(3-phenylpropyl)-2-pyrrolidinone-dihydrate $R_f$ value: 0.40 (silica gel; methanol/conc. aqueous ammonia=1:0.02) Calculated: C 62.09 H 7.26 N 12.93 Found: 62.38 7.11 12.91

(43) (3S,5S)-3-carboxymethyl-5-[[(2-guanidinomethyl-5-indanyl)methyl]carbonyl]aminomethyl]-1-(3-phenylpropyl)- 2-pyrrolidinone-hydrate $R_f$ value: 0.54 (silica gel; methanol/conc. aqueous ammonia=1:0.02) Calculated: C 64.78 H 7.31 N 13.03 Found: 64.65 7.31 13.37

(44) (3S,5S)-3-carboxymethyl-5-[[3-(3-guanidinopropyl)phenyl]oxymethyl]-1-(3-phenylpropyl)-2-pyrrolidinonehydrate $R_f$ value: 0.52 (silica gel; methanol/water=9:1) Calculated: C 64.44 H 7.49 N 11.56 Found: 64.61 7.25 11.44

(45) (3S,5S)-3-carboxymethyl-5-[[4-(5-guanidinopentyl)phenyl]oxymethyl]-1-(3-phenylpropyl)-2-pyrrolidinone $R_f$ value: 0.53 (silica gel; methanol/water=9:1)

(46) (3R,S;5S,R)-3-carboxymethyl-5-[[4-(guanidinomethyl)phenyl]oxymethyl]-3-methyl-1-(3-phenylpropyl)-2-pyrrolidinone-semihydrate $R_f$ value: 0.44 (silica gel; methanol) Calculated: C 65.05 H 7.21 N 12.14 Found: 64.85 7.41 12.18

(47) (3R,S;5S,R)-3-carboxymethyl-5-[[4-(2-guanidinoethyl)phenyl]oxymethyl]-3-methyl-1-(3-phenylpropyl)-2-pyrrolidinone-dihydrate Melting point: 119°–121° C. $R_f$ value: 0.41 (silica gel; methanol) Calculated: C 62.13 H 7.62 N 11.15 Found: 61.98 7.62 10.90

(48) (3R,5S)-3-(2-carboxyethyl)-5-[(4-guanidinobutyl)-carbonylaminomethyl]- 1-(3-phenylpropyl)-2-pyrrolidinone $R_f$ value: 0.10 (silica gel; methylene chloride/methanol/acetic acid=4:1:0.1)

(49) (3R,5S)-3-(2-carboxyethyl)-5-[(5-guanidinopentyl)-carbonylaminomethyl]- 1-(3-phenylpropyl)-2-pyrrolidinone-hydrate Calculated: C 60.30 H 8.16 N 14.66 Found: 60.63 8.32 14.65

(50) (3S,5S)-3-carboxymethyl-5-[[2-[4-(guanidinomethyl)phenyl]ethyl]carbonylaminomethyl]-1-(3-phenylpropyl)-2-pyrrolidinone-hydrate Calculated: C 63.38 H 7.29 N 13.69 Found: 63.49 7.33 13.49

(51) (3R,S;4S,R)-3-carboxymethyl-4-[(3-guanidinopropyl)-carbonylaminomethyl]-1-(3-phenylpropyl)-2-pyrrolidinone $R_f$ value: 0.42 (silica gel; methylene chloride/methanol/water=2:1:0.1)

(52) (3R,S;4S,R)-3-carboxymethyl-4-[(7-guanidinoheptyl)-carbonylaminomethyl]-1-(3-phenylpropyl)-2-pyrrolidinone $R_f$ value: 0.71 (silica gel; methylene chloride/methanol/water=2:1:0.1)

(53) (3R,S;4S,R)-3-carboxymethyl-4-[(5-guanidinopentyl)-carbonylaminomethyl]-1-(3-phenylpropyl)-2-pyrrolidinone $R_f$ value: 0.30 (silica gel; methylene chloride/methanol/water=4:1:0.1)

(54) (3R,5R)-5-(2-carboxyethyl)-3-(6-guanidinohexyl)-1-isobutyl- 2-pyrrolidinone $R_f$ value: 0.58 (silica gel; n-butanol/glacial acetic acid/water=4:1:1) Mass spectrum: $(M-H)^+=353$

(55) (3S,5S)-3-carboxymethyl-5-[[4-(cis-4-guanidinocyclohexyl)benzoyl]aminomethyl]-1-(3-phenylpropyl)-2-pyrrolidinone $R_f$ value: 0.20 (silica gel; methylene chloride/methanol/conc. aqueous ammonia=4:1:0.25)

(56) (3S,5S)-3-carboxymethyl-5-[[4-(trans-4-guanidinocyclohexyl)benzoyl]aminomethyl]-1-(3-phenylpropyl)-2-pyrrolidinone $R_f$ value: 0.20 (silica gel; methylene chloride/methanol/conc. aqueous ammonia=4:1:0.25)

(57) (3S,5S)-3-carboxymethyl-5-[[4-[cis-4-(guanidinomethyl)cyclohexyl]phenyl]oxymethyl]-1-(3-phenylpropyl)-2-pyrrolidinone $R_f$ value: 0.16 (silica gel; methylene chloride/methanol/conc. aqueous ammonia=4:1:0.25)

(58) (3S,5S)-3-carboxymethyl-5-[[[2-[(4-guanidinobutyl)oxy]phenyl]carbonylamino]methyl]-2-pyrrolidinone

(59) (3S,5S)-3-carboxymethyl-5-[[[3-[(3-guanidinopropyl)carbonylamino]phenyl]carbonylamino]methyl]-2-pyrrolidinone

EXAMPLE 32

(3S,5S)-5-[2-[(6-Amino-5,6,7,8-tetrahydro-2-naphthylcarbonyl)amino]ethyl]-3-carboxymethyl-1-(3-phenylpropyl)- 2-pyrrolidinone-semihydrate A mixture of 7 ml of trifluoroacetic acid and 7 ml of methylene chloride is added dropwise, with stirring, at ambient temperature, to a solution of 2.1 g of (3S,5S)-5-[2-[(6-tert.butyloxycarbonylamino-5,6,7,8-tetrahydro- 2-naphthylcarbonyl)amino]ethyl]-3-carboxymethyl- 1-(3-phenylpropyl)-2-pyrrolidinone in 7 ml of methylene chloride. After 30 minutes stirring at ambient temperature the reaction mixture is concentrated by evaporation, mixed with methylene chloride and with methanolic ammonia. The resulting solution is then chromatographed over silica gel with methanol chloride/methanol/conc. aqueous ammonia (70:30:2). After evaporation of the eluate, the crude product obtained is triturated with tert.butyl-methylether, suction filtered, washed with tert.butyl-methylether and dried. Yield: 1.5 g (84% of theory), Melting point: 138°–145° C. $R_f$ value: 0.12 (silica gel; methylene chloride/methanol/conc. aqueous ammonia=70:30:2) Calculated: C 69.11 H 7.46 N 8.64 Found: 68.92 7.48 8.60

The following are obtained analogously:

(1) (3S,5S)-5-[[4-[(3-aminopropyl)carbonylamino]phenyl]oxymethyl]-3-carboxymethyl-1-(3-phenylpropyl)-2-pyrrolidinone Melting point: 180°–182° C. $R_f$ value: 0.27 (silica gel; methylene chloride/methanol/conc. aqueous ammonia=40:4:1) Calculated: C 66.79 H 7.11 N 8.99 Found: 66.55 7.04 8.73

(2) (3S,5S)-5-[[4-(cis-4-aminocyclohexyl)phenyl]oxymethyl]-3-carboxymethyl-1-(3-phenylpropyl)-2-pyrrolidinone Melting point: 238°–245° C.

(3) (3S,5S)-5-[(6-amino-5,6,7,8-tetrahydro-2-naphthylcarbonyl)aminomethyl]-3-carboxymethyl-1-(3-phenylpropyl)- 2-pyrrolidinone-semihydrate Melting point: 147°–156° C. (sinters above 143° C.) $R_f$ value: 0.08 (silica gel; methylene chloride/methanol/conc. aqueous ammonia=70:30:2) Calculated: C 68.62 H 7.25 N 8.89 Found: 68.71 7.30 8.89

(4) (3S,5S)-5-[[4-(3-aminocyclobutyl)phenyl]carbonylaminomethyl]-3-carboxymethyl-1-(3-phenylpropyl)-2-pyrrolidinone $R_f$ value: 0.67 (silica gel; methylene chloride/methanol/conc. aqueous ammonia=35:15:4)

(5) (3S,5S)-5-[2-[[4-(3-aminocyclobutyl)phenyl]carbonylamino]ethyl]-3-carboxymethyl-1-(3-phenylpropyl)-2-pyrrolidinone $R_f$ value: 0.71 (silica gel; methylene chloride/methanol/conc. aqueous ammonia=35:15:4)

(6) (3S,5S)-5-[[4-(4-aminobutyl)phenyl]oxymethyl]-3-carboxymethyl- 1-(4-phenylbutyl)-2-pyrrolidinone $R_f$ value: 0.25 (silica gel; methylene chloride/methanol= 9:1)

(7) (3S,5S)-5-[[4-(4-aminobutyl)phenyl]oxymethyl]-3-carboxymethyl- 1-[2-(2-naphthyl)ethyl]-2-pyrrolidinone $R_f$ value: 0.34 (silica gel; methylene chloride/methanol/conc. aqueous ammonia=16:4:1)

(8) (3S,5S)-5-[[4-(4-aminobutyl)phenyl]oxymethyl]-3-carboxymethyl- 1-[2-(1-naphthyl)ethyl]-2-pyrrolidinone $R_f$ value: 0.43 (silica gel; methylene chloride/methanol/conc. aqueous ammonia=30:10:3)

(9) (3S,5S)-5-[[4-(4-aminobutyl)phenyl]oxymethyl]-1-benzyl- 3-carboxymethyl-2-pyrrolidinone $R_f$ value: 0.53 (silica gel; methylene chloride/methanol/conc. aqueous ammonia=30:10:3)

(10) (3S,5S)-5-[[4-(4-aminobutyl)phenyl]oxymethyl]-3-carboxymethyl- 1-(4-phenoxybutyl)-2-pyrrolidinone $R_f$ value: 0.19 (silica gel; methylene chloride/methanol/conc. aqueous ammonia=16:4:1)

(11) (3S,5S)-5-[[4-(4-aminobutyl)phenyl]oxymethyl]-3-carboxymethyl- 1-(2-phenylethyl)-2-pyrrolidinone $R_f$ value: 0.26 (silica gel; methylene chloride/methanol/conc. aqueous ammonia=30:10:3)

(12) (3S,5S)-5-[[4-(2-aminoethyl)phenyl]carbonylaminomethyl]-3-carboxymethyl-1-(3-phenylpropyl)-2-pyrrolidinone $R_f$ value: 0.38 (silica gel; n-butanol/glacial acetic acid/water=4:1:1)

(13) (3S,5S)-5-[[3-(2-aminoethyl)phenyl]carbonylaminomethyl]-3-carboxymethyl-1-(3-phenylpropyl)-2-pyrrolidinone $R_f$ value: 0.39 (silica gel; n-butanol/glacial acetic acid/water=4:1:1)

(14) (3S,5S)-5-[(5-aminopentyl)carbonylaminomethyl]-3-carboxymethyl- 1-(4-phenoxybutyl)-2-pyrrolidinone $R_f$ value: 0.25 (silica gel; n-butanol/glacial acetic acid/water=4:1:1)

(15) (3S,5S)-5-[(5-aminopentyl)carbonylaminomethyl]-3-carboxymethyl- 1-(2-phenylethyl)-2-pyrrolidinone $R_f$ value: 0.39 (silica gel; n-butanol/glacial acetic acid/water=4:1:1)

(16) (3S,5S)-5-[(5-aminopentyl)carbonylaminomethyl]-1-benzyl- 3-carboxymethyl-2-pyrrolidinone $R_f$ value: 0.38 (silica gel; n-butanol/glacial acetic acid/water=4:1:1)

(17) (3S,5S)-5-[[(2-amino-5-indanyl)methylcarbonyl]aminomethyl]-3-carboxymethyl-1-(3-phenylpropyl)-2-pyrrolidinone $R_f$ value: 0.61 (silica gel; n-butanol/glacial acetic acid/water=4:1:1)

(18) (3S,5S)-5-[(5-aminopentyl)carbonylaminomethyl]-3-carboxymethyl- 1-[2-(1-naphthyl)ethyl]-2-pyrrolidinone $R_f$ value: 0.38 (silica gel; n-butanol/glacial acetic acid/water=4:1:1) Mass spectrum: (M−H)+=438

(19) (3S,5S)-5-[(5-aminopentyl)carbonylaminomethyl]-3-carboxymethyl- 1-[2-(2-naphthyl)ethyl]-2-pyrrolidinone $R_f$ value: 0.38 (silica gel; n-butanol/glacial acetic acid/water=4:1:1) Mass spectrum: (M+H)+=440

(20) (3S,5S)-5-[[4-(aminomethyl)phenyl]oxymethyl]-3-carboxymethyl- 1-(3-phenylpropyl)-2-pyrrolidinone $R_f$ value: 0.45 (silica gel; n-butanol/glacial acetic acid/water=4:1:1) Mass spectrum: M+=396

(21) (3S,5S)-5-[[3-(aminomethyl)phenyl]oxymethyl]-3-carboxymethyl- 1-(3-phenylpropyl)-2-pyrrolidinone $R_f$ value: 0.55 (silica gel; n-butanol/glacial acetic acid/water=4:1:1) Mass spectrum: M+=396

(22) (3S,5S)-5-[[3-(4-aminobutyl)phenyl]oxymethyl]-3-carboxymethyl- 1-(3-phenylpropyl)-2-pyrrolidinone $R_f$ value: 0.58 (silica gel; n-butanol/glacial acetic acid/water=4:1:1)

(23) (3S,5S)-5-[(5-aminopentyl)carbonylaminomethyl]-3-carboxymethyl- 1-isobutyl-2-pyrrolidinone $R_f$ value: 0.40 (silica gel; n-butanol/glacial acetic acid/water=4:1:1) Mass spectrum: M+=341

(24) (3S,5S)-5-[[3-(2-aminoethyl)phenyl)oxymethyl]-3-carboxymethyl- 1-(3-phenylpropyl)-2-pyrrolidinone $R_f$ value: 0.50 (silica gel; n-butanol/glacial acetic acid/water=4:1:1) Mass spectrum: $(M+H)^+=411$

(25) (3S,5S)-5-[[4-(2-aminoethyl)phenyl]oxymethyl]-3-carboxymethyl- 1-(3-phenylpropyl)-2-pyrrolidinone $R_f$ value: 0.49 (silica gel; n-butanol/glacial acetic acid/water=4:1:1) Mass spectrum: $(M+H)^+=411$

(26) (3S,5S)-5-[(4-aminobutyl)carbonylaminomethyl]-3-carboxymethyl- 1-(3-phenylpropyl)-2-pyrrolidinone $R_f$ value: 0.38 (silica gel; n-butanol/glacial acetic acid/water=4:1:1)

(27) (3S,5S)-5-[(6-aminohexyl)carbonylaminomethyl]-3-carboxymethyl- 1-(3-phenylpropyl)-2-pyrrolidinone $R_f$ value: 0.46 (silica gel; n-butanol/glacial acetic acid/water=4:1:1)

(28) (3S,5S)-5-[ (7-aminoheptyl)carbonylaminomethyl]-3-carboxymethyl- 1-(3-phenylpropyl) -2-pyrrolidinone $R_f$ value: 0.37 (silica gel; methylene chloride/methanol= 4:1) Mass spectrum: $(M-H)^+=430$

(29) (3S,5S)-5-[(3-aminopropyl)carbonylaminomethyl]-3-carboxymethyl- 1-(3-phenylpropyl)-2-pyrrolidinone $R_f$ value: 0.38 (silica gel; n-butanol/glacial acetic acid/water=4:1:1) Mass spectrum: $(M-H)^+=374$

(30) (3S,5S)-5-[[4-(2-aminoethyl)phenyl]oxymethyl]-3-carboxymethyl- 1-isobutyl-2-pyrrolidinone cleavage in formic acid $R_f$ value: 0.28 (silica gel; methanol)

(31) (3S,5S)-5-[(5-aminopentyl)carbonylaminomethyl]-3-carboxymethyl-1-(3-phenylpropyl)-2-pyrrolidinone cleavage in formic acid $R_f$ value: 0.31 (silica gel; n-butanol/glacial acetic acid/water=4:1:1)

(32) (3S,5S)-5-[[4-(trans- 4-aminocyclohexyl)phenyl]-oxymethyl]- 3-carboxymethyl-1-(3-phenylpropyl)-2-pyrrolidinone Melting point: 230°–240° C.

(33) (3S,5S)-5-[[4-( 4-aminobutyl)phenyl]oxymethyl]-1-[3-( 4-benzyloxyphenyl)propyl]-3-carboxymethyl-2-pyrrolidinone Melting point: 190°–195 ° C.

(34) (3S,5S)-5-[[4-( 4-aminobutyl)phenyl]oxymethyl]-1-[3-( 4-benzyloxyphenyl)propyl]-3-(2,3-dihydroxypropyl)-2-pyrrolidinone $R_f$ value: 0.54 (silica gel; methylene chloride/methanol/conc. aqueous ammonia=4:1:0.2)

(35) (3S,5S)-5-[2-[(2-aminomethyl- 5-indanyl)carbonylamino]ethyl]- 3-carboxymethyl-1-(3-phenylpropyl)-2-pyrrolidinone $R_f$ value: 0.43 (silica gel; methylene chloride/methanol= 9:1) (after developing twice)

(36) (3S,5S)-5-[(2-amino- 5-indanyl)carbonylaminomethyl] -3-carboxymethyl- 1-(3-phenylpropyl)-2-pyrrolidinone×1 $CH_3COOH$×1 $H_2O$ $R_f$ value: 0.25 (silica gel; methylene chloride/cyclohexane/methanol/conc. aqueous ammonia=34:7.5:57.5:1)

Calculated: C 63.74 H 7.07 N 7.96 Found: 63.83 7.29 8.16

(37) (3S,5S)-5-[(2-aminomethyl- 5-indanyl)carbonylaminomethyl]- 3-carboxymethyl-1-(B-phenylpropyl)-2-pyrrolidinone-hydrate $R_f$ value: 0.38 (silica gel; methanol/conc. aqueous ammonia=1:0.02)

Calculated: C 67.34 H 7.33 N 8.73 Found: 67.25 7.33 8.51

(38) (3S,5S)-5-[[(2-aminomethyl-5-indanyl)methylcarbonyl]aminomethyl]-3-carboxymethyl-1-(3-phenylpropyl)-2-pyrrolidinone×2.5 $CF_3COOH$×1 $H_2O$ $R_f$ value: 0.50 (silica gel; methanol/conc. aqueous ammonia=1:0.02)

Calculated: C 55.80 H 5.78 N 6.30 Found: 56.09 6.01 6.59

(39) (3S,5S)-5-[[3-( 3-aminopropyl)phenyl]oxymethyl]-3-carboxymethyl- 1-(3-phenylpropyl)-2-pyrrolidinone-hydrate $R_f$ value: 0.32 (silica gel; methanol)

Calculated: C 67.85 H 7.74 N 6.33 Found: 67.80 8.05 5.80

(40) (3S,5S)-5-[[4-( 5-aminopentyl)phenyl]oxymethyl]-3-carboxymethyl- 1-(3-phenylpropyl)-2-pyrrolidinone×1 $CF_3COOH$×1 $CF_3COONH_4$ $R_f$ value: 0.22 (silica gel; methylene chloride/methanol= 5:1)

Calculated: C 53.33 H 5.88 N 6.02 Found: 53.52 5.97 5.58

During column chromatography with methylene chloride, methanol=40:1, large amounts of (3S,5S)- 5-[[4-(5-aminopentyl)phenyl]oxymethyl]-3-[(methoxycarbonyl)methyl]-1-(3-phenylpropyl)-2-pyrrolidinone are obtained $R_f$ value: 0.43 (silica gel; methylene chloride/methanol= 5:1)

(41) (3R,S;5S,R)-5-[[- 4-(aminomethyl)phenyl]oxymethyl]-3-carboxymethyl- 3-methyl-1-(3-phenylpropyl)-2-pyrrolidinone-dihydrate $R_f$ value: 0.41 (silica gel; methanol)

Calculated: C 64.55 H 7.67 N 6.27 Found: 64.72 7.60 5.95

(42) (3R,S;5S,R)-5-[[4-( 2-aminoethyl)phenyl]oxymethyl]-3-carboxymethyl-3-methyl-1-( 3-phenylpropyl)-2-pyrrolidinone-semihydrate $R_f$ value: 0.46 (silica gel; methanol)

Melting point: 225°–227° C.

Calculated: C 69.20 H 7.61 N 6.45 Found: 69.56 7.22 6.48

(43) (3R,S;5S,R)-5-[[- 4-(4-aminobutyl)phenyl]oxymethyl] -3-carboxymethyl- 3-methyl-1-(3-phenylpropyl)-2-pyrrolidinone-hydrate $R_f$ value: 0.40 (silica gel; methanol)

Calculated: C 68.91 H 8.14 N 5.95 Found: 68.60 8.22 5.48

(44) (3R,5S)-5-[-( 5-aminopentyl)carbonylaminomethyl]-3-( 2-carboxyethyl)-1-(3-phenylpropyl)-2-pyrrolidinone×4 $CF_3COOH$ Cleaving is carried out in pure trifluoroacetic acid.

Calculated: C 42.60 H 4.49 N 4.81 Found: 42.40 4.51 4.89

(45) (3R,S;4S,R)-4-[( 3-aminopropyl)carbonylaminomethyl]- 3-carboxymethyl-1-(3-phenylpropyl)-2-pyrrolidinone-trifluoroacetate Cleaving is carried out in pure trifluoroacetic acid.

$R_f$ value: 0.16 (silica gel; butanol/glacial acetic acid/water=4:1:1)

(46) (3S,5S)-3-carboxymethyl-5-[( 4'-cyano-4-biphenylyl)oxymethyl]pyrrolidine $R_f$ value: 0.32 (silica gel; methylene chloride/methanol= 10:1)

(47) (3R,5S)-3-(4-aminobutyl)-5-[[4'-[(ethoxycarbonyl)methyl]- 4-biphenylyl]oxymethyl]-1-methyl-2-pyrrolidinone After cleaving the Boc-protecting group the product is treated with ethanolic hydrochloric acid and the ethyl ester is isolated.

$R_f$ value: 0.51 (silica gel; butanol/glacial acetic acid/water=4:1:1)

(48) (3R,5S)-3-(4-aminobutyl)-5-[( 3-carboxy-4biphenylyl)oxymethyl]- 1-methyl-2-pyrrolidinone $R_f$ value: 0.44 (silica gel; n-butanol/glacial acetic acid/water=4:1:1)

Mass spectrum: $(M-H)^-=395$

(49) (3S,5S)-5-[[4-(cis- 4-aminocyclohexyl)benzoyl]aminomethyl]- 3-[(methoxycarbonyl)methyl]-1-(3-phenylpropyl)- 2-pyrrolidinone $R_f$ value: 0.26 (silica gel; methylene chloride/methanol/conc. aqueous ammonia=8:1:0.25)

(50) (3S,5S)-5-[[4-(trans- 4-aminocyclohexyl)benzoyl]aminomethyl]- 3-[(methoxycarbonyl)methyl]-1-(3-phenylpropyl)- 2-pyrrolidinone $R_f$ value: 0.21 (silica gel; methylene chloride/methanol/conc. aqueous ammonia=8:1:0.25)

(51) (3S,5S)-5-[[4-(cis-4-aminomethylcyclohexyl)benzoyl] aminomethyl]- 3-[(methoxycarbonyl)methyl]-1-(3-phenylpropyl)- 2-pyrrolidinone $R_f$ value: 0.36 (silica gel; methylene chloride/methanol/conc. aqueous ammonia=10:1:0.20)

(52) (3S,5S)-5-[[4-(trans-4-aminomethylcyclohexyl)benzoyl]aminomethyl]- 3-[(methoxycarbonyl)methyl]-1-(3-phenylpropyl)- 2-pyrrolidinone $R_f$ value: 0.33 (silica gel; methylene chloride/methanol/conc. aqueous ammonia=10:1:0.20)

(53) (3S,5S)-5-[(4-aminocinnamoyl)aminomethyl]-3-[(methoxycarbonyl)methyl]-1-(3-phenylpropyl)-2-pyrrolidinone $R_f$ value: 0.46 (silica gel; methylene chloride/methanol=15:1)

(54) (3S,5S)-5-[[[2-[( 4-aminobutyl)oxy]phenyl]carbonylamino]methyl]- 3-carboxymethyl -2-pyrrolidinone

(55) (3S,5S)-5-[[[3-[( 3-aminopropyl)carbonylamino]phenyl]carbonylamino]methyl]- 3-carboxymethyl-2-pyrrolidinone

(56) (3S,5S)-5-[[4'-(2-aminoethyl)- 4-biphenylyl]oxymethyl]- 3-carboxymethyl-2-pyrrolidinone

(57) (3S,5S)-5-[2-[( 6-amino-2-trans-decalinyl)carbonylamino]ethyl]- 3-carboxymethyl-2-pyrrolidinone

(58) (3S,5S)-5-[2-[( 9-amino-3-spiro[5,5]undecanyl)carbonylamino]ethyl]- 3-carboxymethyl-2-pyrrolidinone

(59) (3S,5S)-5-[2-[[(cis- 5-amino-2-octahydropentalenyl)aminocarbonyl]amino]ethyl]- 3-carboxymethyl-2-pyrrolidinone

EXAMPLE 33

(3S,5S)-5-[[3-(3-Aminophenyl)propyl]carbonyl-aminomethyl]-3-carboxymethyl-1-(3-phenylpropyl)-2-pyrrolidinone ×1.25 HCl×0.5 H$_2$O 1.9 g of (3S,5S)-5-[3-[3-(tert.butyloxycarbonylamino)phenyl]propyl]carbonylaminomethyl]- 3-carboxymethyl-1-(3-phenylpropyl)-2-pyrrolidinone are dissolved in 20 ml of dioxane and 20 ml of ethereal hydrochloric acid are added. The mixture is left to stand for one hour at ambient temperature and the solid product precipitated is filtered off.

Yield: 1.8 g (99% of theory), $R_f$ value: 0.35 (silica gel; methylene chloride/methanol/conc. aqueous ammonia=8:2:0.2)

Calculated: C 61.66 H 6.97 N 8.30 Cl8.76 Found: 61.51 7.11 7.94 8.52

The following are obtained analogously:

(1) (3R,5S)-5-[( 4-aminobutyl)carbonylaminomethyl]-3-(2-carboxyethyl)- 1-(3-phenylpropyl)-2-pyrrolidinone×1.5 HCl×1 H$_2$O Calculated: C 55.48 H 7.73 N 8.82 Cl 11.17 Found: 55.63 8.07 8.96 10.81

(2) (3S,5S)-5-[[2-[4-(aminomethyl)phenyl]ethyl]carbonylaminomethyl]- 3-carboxymethyl-1-(3-phenylpropyl)-2-pyrrolidinone ×1.2 HCl×0.5 H$_2$O Calculated: C 61.93 H 7.04 N 8.33 Cl8.43 Found: 62.16 6.78 7.97 8.31

(3) (3S,5S)-5-[[2-[3-(aminophenyl)ethyl]carbonylaminomethyl]- 3-carboxymethyl-1-(3-phenylpropyl)-2-pyrrolidinone-hydrochloride $R_f$ value: 0.60 (silica gel; methylene chloride/methanol/acetic acid=4:1:0.1)

(4) (3S,5S)-5-[[2-( 4-aminophenyl)ethyl]carbonylaminomethyl]- 3-carboxyethyl-1-(3-phenylpropyl)-2-pyrrolidinone ×1.75 HCl×1.5 H$_2$O $R_f$ value: 0.48 (silica gel; methylene chloride/methanol=5:1)

Calculated: C 56.82 H 6.82 N 7.95 Cl 11.74 Found: 56.70 6.67 7.66 11.57

(5) (3S,5S)-5-[[3-( 4-aminophenyl)propyl]carbonylaminomethyl)- 3-carboxymethyl-1-(3-phenylpropyl)-2-pyrrolidinone-hydrochloride $R_f$ value: 0.29 (silica gel; methylene chloride/methanol=9:1)

(6) (3R,S;4S,R)-4-[( 7-aminoheptyl)carbonylaminomethyl]- 3-carboxymethyl-1-(3-phenylpropyl)-2-pyrrolidinone-hydrochloride $R_f$ value: 0.53 (silica gel; methylene chloride/methanol/water=2:1:0.1)

(7) (3R,S;4S,R)-4-[(5-aminopentyl)carbonylaminomethyl]- 3-carboxymethyl-1-(3-phenylpropyl)-2-pyrrolidinone-hydrochloride (ethyl acetate is used instead of dioxane)

$R_f$ value: 0.47 (silica gel; butanol/glacial acetic acid/water=4:1:1)

EXAMPLE 34

(3S,5S)-5-[(4'-Amidino-4-biphenylyl)oxymethyl]-3-[(isopropyloxycarbonyl)-methyl]-1-(3-phenylpropyl)-2-pyrrolidinone-hydrochloride 2 g of (3S,5S)-5-[( 4'-amidino-4-biphenylyl)oxymethyl]-3-[(methoxycarbonyl)methyl]-1-(3-phenylpropyl)- 2-pyrrolidinone-hydrochloride are suspended in 300 ml of saturated isopropanolic hydrochloric acid and stirred for 6 hours at 50°–60° C. The mixture is then left to stand for 2 days at ambient temperature, the solvent is distilled off and it is purified over silica gel (eluant: methylene chloride/methanol/conc. aqueous ammonia=4:1:0.25).

Yield: 1.4 g (67% of theory), $R_f$ value: 0.27 (silica gel; methylene chloride/methanol/conc. aqueous ammonia=4:1:0.25)

The following is obtained analogously:

(1) (3S,5S)-5-[( 4'-amidino-4-biphenylyl)oxymethyl]-3 [(hexyloxycarbonyl)methyl]-1-( 3-phenylpropyl)-2-pyrrolidinone-hydrochloride Solvent: a mixture of 150 ml of n-hexanol and 100 ml of ethereal hydrochloric acid $R_f$ value: 0.64 (silica gel; methylene chloride/methanol/conc. aqueous ammonia=4:1:0.25)

EXAMPLE 35

(3S,5S)-5-[(4'-(N,N-Dimethylamidino)-4-biphenylyl)oxymethyl]-3-[(methoxycarbonyl)-methyl]-1-(3-phenylpropyl)-2-pyrrolidinone-hydrochloride 1 g of (3S,5S)-5-[(4'-amidino- 4-biphenylyl)oxymethyl]-3-[(methoxycarbonyl)methyl]-1-(3-phenylpropyl)- 2-pyrrolidinone-hydrochloride is dissolved in 70 ml of methanol. The solution is cooled in an ice bath and 5 ml of liquid dimethylamine are added. The mixture is then left to stand for 40 hours at ambient temperature and finally heated to 55° C. for a further 4 hours. The solvent is evaporated off in vacuo and the residue is chromatographed over silica gel (eluant: methylene chloride/methanol/conc. aqueous ammonia=4:1:0.25).

Yield: 0.28 g (27% of theory), $R_f$ value: 0.63 (silica gel; methylene chloride/methanol/conc. aqueous ammonia=4:1:0.25)

The following are obtained analogously:

(1) (3S,5S)-3-carboxymethyl- 5-[[4'-(2-imidazolinyl)-4-biphenylyl]oxymethyl]- 1-(3-phenylpropyl)-2-pyrrolidinone The amidine was refluxed for one hour with ethylenediamine.

$R_f$ value: 0.49 (silica gel; methylene chloride/methanol/conc. aqueous ammonia=4:1:0.25)

(2) (3S,5S)- 3-carboxymethyl-5-[[4'-( 2-imidazolinyl)-4biphenylyl)oxymethyl]- 2-pyrrolidinone Carried out with ethylenediamine.

(3) (3S,5S)-5-[[4'-(N-hydroxyamidino)-4-biphenylyl]oxymethyl]- 3-[(methoxycarbonyl)methyl]-2-pyrrolidinone Carried out with hydroxylamine-hydrochloride/ethyldiisopropylamine.

Melting point: 232° C. (decomp.)

Calculated: C 63.46 H 5.83 N 10.57 Found: 63.20 5.81 10.40

(4) (3S,5S)-5-[[4'-(N-methoxyamidino)-4-biphenylyl]oxymethyl]- 3-[(methoxycarbonyl)methyl]-2-pyrrolidinone Carried out with 0-methylhydroxylamine-hydrochloride/ethyl-diisopropylamine.

Melting point: 158°–160° C.

$R_f$ value: 0.43 (silica gel; ethyl acetate)

EXAMPLE 36

4-Carboxy-1-(4'-cyano-4-biphenylyl)-2-pyrrolidinone

Prepared analogously to Example XXII from itaconic acid and 4-amino-4'-cyanobiphenyl $R_f$ value: 0.58 (silica gel; toluene/dioxane/ethanol/glacial acetic acid=90:10:10:6)

EXAMPLE 37

(3S, 5S )-3-Carboxymethyl-5-[[4-(4-dimethylaminobutyl)phenyl]oxymethyl]-1-(3-phenylpropyl)-2-pyrrolidinone A mixture of 0.5 g of (3S,5S)-5-[[- 4-(4-aminobutyl)phenyl]oxymethyl]-3-carboxymethyl-1-(3-phenylpropyl)-2-pyrrolidinone-hydrochloride, 10 ml of water, 10 ml of tetrahydrofuran, 0.4 ml of 40% aqueous formaline solution, 0.1 ml of triethylamine and 0.5 g of 10% palladium/charcoal is shaken for 12 hours at ambient temperature under a hydrogen pressure of 3 bars. After the catalyst has been filtered off the filtrate is evaporated down and the residue is purified by chromatography (silica gel; eluant: methanol/ethyl acetate/conc. aqueous ammonia=20:10:1).

Yield: 0.2 g (41% of theory), $R_f$ value: 0.28 (silica gel; methylene chloride/methanol/conc. aqueous ammonia=4:1:0.25)

EXAMPLE 38

(3S,5S)-5-[(7-Amidino-9-hydroxy-2-fluorenyl)oxymethyl]-3-carboxymethyl-1-(3-phenylpropyl)-2-pyrrolidinone 0.77 g of (3S,5S)-5-[( 7-amidino-9-keto-2-fluorenyl)oxymethyl]- 3-carboxymethyl-1-(3-phenylpropyl)- 2-pyrrolidinone are dissolved in 15 ml of glacial acetic acid, 0.4 g of 10% palladium/charcoal are added and the mixture is hydrogenated for 24 hours at ambient temperature under 3 bars of hydrogen pressure. The catalyst is filtered off, the filtrate is evaporated down and purified by chromatography over silica gel (eluant: methylene chloride/methanol/glacial acetic acid =3:1:0.1). The crude product obtained is triturated with ether, filtered off and taken up in 50 ml of a mixture of glacial acetic acid and water (1:2). This solution is concentrated until crystallisation begins (about 5 ml). The crystals precipitated are washed with water, acetone and ether.

Yield: 0.35 g (45% of theory),

Melting point: 182°–185° C. (decomp.).

EXAMPLE 39

(3S,5S)-5-[(7-Amidino-2-fluorenyl)oxymethyl]-3-carboxymethyl-1-(3-phenylpropyl)-2-pyrrolidinone 0.3 g of (3S,5S)-5-[( 7-amidino-9-keto-2-fluorenyl)oxymethyl]- 3-carboxymethyl-1-(3-phenylpropyl)-2-pyrrolidinone are dissolved in 7 ml of glacial acetic acid, 0.05 g of 10% palladium charcoal are added and the mixture is hydrogenated for 6 hours at 70° C. under 3 bar of hydrogen pressure. The catalyst is filtered off, the filtrate is evaporated down and the product is purified by chromatography on silica gel (eluent: tetrahydrofuran/2N acetic acid=10:1)

Yield: 0.15 g (51% of theory),

Melting point: 182°–200° C. (decomp.)

EXAMPLE 40

1-(4'-Cyano- 4-biphenylyl)-4-methoxycarbonyl-2-pyrrolidinone 28 g of 4-carboxy-1-(4'-cyano- 4-biphenylyl)-2-pyrrolidinone in 100 ml of dioxane are mixed at 100° C. with 15.5 g of dimethylformamide-dimethylacetal and stirred for a further 20 minutes at this temperature. After cooling, the mixture is concentrated by evaporation, taken up in ethyl acetate, treated with activated charcoal, filtered and evaporated down. After purification over a silica gel column with cyclohexane/ethyl acetate (1:1) 19 g (65% of theory) are obtained.

Melting point: 153°–155° C.

$R_f$ value: 0.34 (silica gel; cyclohexane/ethyl acetate=1:1)

EXAMPLE 41

(3S,5S)-5-[(4'-Cyano- 4-biphenylyl)-aminomethyl]-3-[(methoxycarbonyl)methyl]-1-(3-phenylpropyl)-2-pyrrolidinone A mixture of 9.7 g of 4-amino-4'-cyanobiphenyl, 19.2 g of (3S,5S)-5-[(methanesulphonyloxy)methyl]- 3[-(methoxycarbonyl)-methyl]-1-(3-phenylpropyl)-2-pyrrolidinone and 6 g of ethyl-diisopropylamine is heated to 160° C. for 10 hours. The mixture is taken up in ethyl acetate, washed with 1N hydrochloric acid, the organic phase is concentrated and purified by chromatography on silica gel (eluant: cyclohexane/ethyl acetate=1:1).

Yield: 18 g (74% of theory), $R_f$ value: 0.26 (silica gel; cyclohexane/ethyl acetate=1:1)

The following are obtained analogously:

(1) (3S,5S)-5-[2-[( 4'-cyano-3-biphenylyl)amino]ethyl]-3-[(methoxycarbonyl)methyl]-1-(3-phenylpropyl)-2-pyrrolidinone $R_f$ value: 0.35 (silica gel; methylene chloride/methanol=100:1)

(2) (3S,5S)-3-[(methoxycarbonyl)methyl]- 5-[2-[(3'-nitro-3-biphenylyl)amino]ethyl]-1-( 3-phenylpropyl)-2-pyrrolidinone Solvent: dimethylacetamide $R_f$ value: 0.26 (silica gel; cyclohexane/ethyl acetate=1:1)

EXAMPLE 42

(3S, 5S)-5-[(4'-Amidino-4-biphenylyl)oxymethyl]-3-[(benzyloxycarbonyl)methyl]-1-(3-phenylpropyl)-2-pyrrolidinone-hydrochloride 2.1 g of (3S,5S)-5-[( 4'-amidino-4-biphenylyl)oxymethyl]- 3-carboxymethyl-1-(3-phenylpropyl)-2-pyrrolidinone are dissolved in a mixture of 250 ml of benzyl alcohol and 30 ml of ethereal hydrochloric acid. The ether is distilled off in vacuo and the remaining solution is stirred for 4 hours at 50°–60° C. The solvent is distilled off in vacuo and the residue is purified by chromatography on silica gel (eluant: methylene chloride/methanol/conc. aqueous ammonia=4:1:0.25).

Yield: 1.6 g (62% of theory),

Melting point: 170°–180° C.

The following are obtained analogously:

(1) (3S,5S)-5-[[4-( 4-aminobutyl)phenyl]oxymethyl]-3-[(ethoxycarbonyl)methyl]-1-(3-phenylpropyl)- 2-pyrrolidinone-hydrochloride Carried out with ethanol/hydrochloric acid $R_f$ value: 0.63 (silica gel; methylene chloride/ethanol/conc. aqueous ammonia=4:1:0.25)

(2) (3S,5S)-5-[( 4'-cyano-4-biphenylyl)oxymethyl]-1,3-bis [(methoxycarbonyl)methyl]-2-pyrrolidinone Carried out with methanol/hydrochloric acid Melting point: 121°–123° C., $R_f$ value: 0.60 (silica gel; ethyl acetate/cyclohexane/glacial acetic acid=20:5:1)

Calculated: C 65.40 H 5.25 N 6.63 Found: 65.54 5.56 6.40

(3) (3S,5S)-5-[(4'-cyano- 4-biphenylyl)oxymethyl]-1-[(ethylaminocarbonyl)methyl]-3-[(methoxycarbonyl)methyl]- 2-pyrrolidinone Carried out with methanol/hydrochloric acid Melting point: 171°–173° C.

$R_f$ value: 0.58 (silica gel; ethyl acetate/methanol=20:1)

Calculated: C 66.80 H 6.05 N 9.35 Found: 66.67 6.02 9.10

(4) (3S,5S)-5-[(4'-cyano- 4-biphenylyl)oxymethyl]-[(dimethylaminocarbonyl)methyl]- 3-[(methoxycarbonyl)methyl]-2-pyrrolidinone Carried out with methanol/hydrochloric acid Melting point: 139°–140° C.

$R_f$ value: 0.40 (silica gel; ethyl acetate/methanol=20:1)

Calculated: C 66.80 H 6.05 N 9.35 Found: 66.99 6.21 9.07

(5) (3S,5S)-1-[(benzylaminocarbonyl)methyl]- 5-[(4'-cyano- 4-biphenylyl)oxymethyl]-3-[(methoxycarbonyl)methyl]- 2-pyrrolidinone Carried out with methanol/hydrochloric acid Melting point: 108°–110° C.

$R_f$ value: 0.43 (silica gel; ethyl acetate)

Calculated: C 70.57 H 5.53 N 8.23 Found: 70.73 5.78 8.12

(6) (3S,5S)-5-[(4'-cyano- 4-biphenylyl)oxymethyl]-3-[(methoxycarbonyl)methyl]-pyrrolidine-hydrochloride Carried out with methanol/hydrochloric acid Melting point: 188°–190° C.

$R_f$ value: 0.76 (silica gel; methylene chloride/methanol/conc. aqueous ammonia=40:4:1)

Calculated: C 65.19 H 5.99 N 7.24 Cl 19.16 Found: 65.39 5.92 7.12 9.12

(7) (3R,5S)-5-[( 4'-cyano-4-biphenylyl)oxymethyl]-3 [(methoxycarbonyl)methyl]-2-pyrrolidinone Carried out with methanol/hydrochloric acid Melting point: 138°–140.5° C.

$R_f$ value: 0.35 (silica gel; methylene chloride/methanol/=98:2)

Calculated: C 69.22 H 5.53 N 7.69 Found: 69.09 5.46 7.67

(8) (3S,5S)-5-[(4'-amidino- 4-biphenylyl)oxymethyl]-3 [(isopropyloxycarbonyl)methyl]- 2-pyrrolidinone hydrochloride-semihydrate Carried out with isopropanol/hydrochloric acid $R_f$ value: 0.49 (reversed phase silica gel (RP8); methanol/10% aqueous saline solution=6:4)

Calculated: C 60.72 H 6.42 N 9.24 Cl 17.79 Found: 61.08 6.42 9.06 7.90

(9) (3S,5S)-5-[(4'-amidino- 4-biphenylyl)oxymethyl]-3-[(benzyloxycarbonyl)methyl]-2-pyrrolidinone-p-toluenesulphonate Carried out with benzyl alcohol/p-toluenesulphonic acid Melting point: 182°–184° C., $R_f$ value: 0.28 (reversed phase silica gel (RP8); methanol/10% aqueous saline solution=6:4)

Calculated: C 64.85 H 5.80 N 6.67 S 5.09 Found: 64.69 5.61 6.70 5.19

(10) (3S,5S)-5-[( 4'-amidino-4-biphenylyl)oxymethyl]-3-[(butyloxycarbonyl)methyl]-2-pyrrolidinone×1.25 HCl Carried out with n-butanol/hydrochloric acid $R_f$ value: 0.37 (reversed phase silica gel (RP8); methanol/10% aqueous saline solution=6:4)

Calculated: C 61.45 H 6.50 N 8.96 Cl 19.45 Found: 61.26 6.56 9.11 9.46

(11) (3S,5S)-5-[(4'-amidino- 4-biphenylyl)oxymethyl]-3-[ [(3-phenylpropyl)oxycarbonyl]methyl]-2-pyrrolidinone Carried out with 3-phenylpropanol/hydrochloric acid, isolation of the base $R_f$ value: 0.17 (reversed phase silica gel (RP8); methanol/10% aqueous saline solution=6:4)

Calculated: C 71.73 H 6.44 N 8.65 Found: 71.43 6.37 8.58

(12) (3S,5S)-5-[( 4'-amidino-4-biphenylyl)oxymethyl]-3-[[ [2-(3,4-dimethoxyphenyl)ethyl]oxycarbonyl]methyl]- 2-pyrrolidinone ×1.25 p-toluenesulphonic acid Carried out with 2-(3,4-dimethoxyphenyl)ethanol/p-toluenesulphonic acid Melting point: 183°–186° C.

$R_f$ value: 0.21 (reversed phase silica gel (RP8); methanol/10% aqueous saline solution=6:4)

Calculated: C 62.32 H 5.80 N 5.63 S 5.37 Found: 62.10 5.68 5.77 5.69

(13) (3S,5S)-5-[[[2-[( 4-aminobutyl)oxy]phenyl]carbonylamino]methyl]- 3-[(methoxycarbonyl)methyl]-2-pyrrolidinone-hydrochloride

(14) (3S,5S)-5-[[[2-[( 4-guanidinobutyl)oxy]phenyl]carbonylamino]methyl]- 3-[(methoxycarbonyl)methyl]-2pyrrolidinone-hydrochloride

(15) (3S,5S)-5-[[[3-[( 3-aminopropyl)carbonylamino]phenyl]carbonylamino]methyl]- 3-[(methoxycarbonyl)methyl]- 2-pyrrolidinone-hydrochloride

(16) (3S,5S)-5-[[[3-[( 3-guanidinopropyl)carbonylamino] phenyl]carbonylamino]methyl]- 3-[(methoxycarbonyl)methyl]- 2-pyrrolidinone-hydrochloride

(17) (3S,5S)-5-[( 4'-guanidino-4-biphenylyl)oxymethyl]-3-[(methoxycarbonyl)methyl]-2-pyrrolidinone-hydrochloride

(18) (3S,5S)-5-[[4'-( 2-aminoethyl)-4-biphenylyl]oxymethyl]- 3-[(methoxycarbonyl)methyl]-2-pyrrolidinone-hydrochloride
(19) (3S,5S)-5-[2-[( 6-amino-2-trans-decalinyl)carbonylamino]ethyl]- 3-[(methoxycarbonyl)methyl]- 2-pyrrolidinone-hydrochloride
(20) (3S,5S)-5-[2-[( 9-amino-3-spiro[5,5]undecanyl)carbonylamino]ethyl]- 3-[(methoxycarbonyl)methyl]- 2-pyrrolidinone-hydrochloride
(21) (3S,5S)-5-[[4'-( 2-imidazolinyl)- 4-biphenylyl]oxymethyl]-2-[(methoxycarbonyl)methyl]- 2 -pyrrolidinone-hydrochloride
(22) (3S,5S)-5-[2-[[(cis-5-amino- 2-octahydropentalenyl)aminocarbonyl]amino]ethyl]- 3-[(methoxycarbonyl)methyl]- 2-pyrrolidinone-hydrochloride
(23) (3S,5S)-5-[(4'-aminomethyl- 4-biphenylyl)oxymethyl]-3-[(methoxycarbonyl)methyl]-2-pyrrolidinone-hydrochloride
Carried out with methanol/hydrochloric acid
Melting point: 259°–261° C.
(24) (3S,5S)-5-[(4'-aminomethyl- 2'-methyl-4-biphenylyl)oxymethyl]- 3-[(methoxycarbonyl)methyl]-2-pyrrolidinone-hydrochloride
Carried out with methanol/hydrochloric acid
(25) (3S,5S)-5-[(4'-aminomethyl- 2,3-dimethyl-4biphenylyl)oxymethyl]- 3-[(methoxycarbonyl)methyl]-2-pyrrolidinone-hydrochloride
Carried out with methanol/hydrochloric acid

EXAMPLE 43

(3S,5S)-5-[[4-[(3-Cyanophenyl)-sulphonyl]phenyl]-oxymethyl]-3-[(methoxycarbonyl)methyl]-1-(3-phenylpropyl)-2-pyrrolidinone 3 ml of aqueous 30% hydrogen peroxide solution are added to 3 g of (3S,5S)-5-[[4-[(3-cyanophenyl)sulphenyl]phenyl]oxymethyl]-3-[(methoxycarbonyl)methyl]- 1-(3-phenylpropyl)-2-pyrrolidinone in 10 ml of acetic anhydride and 6 ml of glacial acetic acid at 90° C. with vigorous stirring. After one hours reaction at 90° C., the mixture is poured onto ice, neutralised with solid sodium hydrogen carbonate and extracted with ethyl acetate. After purification over a silica gel column (eluant: ethyl acetate/cyclohexane= 3:1) a colourless solid is obtained.

Yield: 2.0 g (46% of theory), $R_f$ value: 0.23 (silica gel; ethyl acetate/cyclohexane=1:1)

$R_f$ value: 0.37 (silica gel; ethyl acetate/cyclohexane=3:2)

The following are obtained analogously:
(1) (3S,5S) -5-[(4'-cyano- 3-methylsulphonyl-4biphenylyl)oxymethyl]- 3-[(methoxycarbonyl)methyl]-1-(3-phenylpropyl)- 2-pyrrolidinone
$R_f$ value: 0.57 (silica gel; methylene chloride/ethanol= 15:1)
(2) (3S,5S)-5-[(4'-cyano- 4-biphenylyl)oxymethyl]-3-[(methoxycarbonyl)methyl]- 1-[3-(4-methylsulphonylphenyl)propyl]-2-pyrrolidinone
$R_f$ value: 0.51 (silica gel; methylene chloride/ethanol= 15:1)
(3) (3S,5S) -5-[[(4'-cyano- 4-biphenylyl)sulphonyl]methyl]-3-[(methoxycarbonyl)methyl]-1-(3-phenylpropyl)- 2-pyrrolidinone
$R_f$ value: 0.53 (silica gel; methylene chloride/ethanol= 15:1)

EXAMPLE 44

(3S,5S)-5-[[4-[(3-Amidinophenyl)sulphinyl]-phenyl]oxymethyl]-3-[(methoxycarbonyl)methyl]-1-(3-phenylpropyl)-2-pyrrolidinone 0.2 g of m-chloroperbenzoic acid are added to 0.5 g of (3S,5S)-5-[[4-[( 3-amidinophenyl)sulphenyl]phenyl]of oxymethyl]-3-[(methoxycarbonyl)methyl]-1-(3-phenylpropyl)- 2-pyrrolidinone-hydrochloride in 30 ml of dichloromethane, with stirring and at −20° C. Then the mixture is left to stand overnight at −20° C., stirred into a sodium hydrogen carbonate solution and extracted with dichloromethane. After drying and evaporation in vacuo, the residue is purified over a silica gel column (eluant: dichloromethane/methanol/conc. aqueous ammonia =4:1:0.25).

Yield: 0.19 g (37% of theory), $R_f$ value: 0.30 (silica gel; dichloromethane/methanol/conc. aqueous ammonia=4:1:0.25)

Mass spectrum: (M +H)$^+$=562

The following are obtained analogously:
(1) (3S,5S)-5-[( 4'-amidino-3-methylsulphinyl-4-biphenylyl)oxymethyl]- 3-[(methoxycarbonyl)methyl]-1-(3-phenylpropyl)- 2-pyrrolidinone
$R_f$ value: 0.22 (silica gel; methylene chloride/cyclohexane/methanol/conc. aqueous ammonia=7:1.5:1.5:0.2)
(2) (3S,5S)-5-[(4'-amidino- 4-biphenylyl)oxymethyl]-3-[(methoxycarbonyl)methyl]-1-[2-phenylsulphinyl)ethyl]-2-pyrrolidinone-hydrochloride
(3) (3S,5S)-5-[(4'-amidino- 4-biphenylyl)oxymethyl]-3-[(methoxycarbonyl)methyl]-1-[[(thiomorpholine-S-oxide)-N-carbonyl]methyl]-2-pyrrolidinone-hydrochloride
(4) (3S,5S)-5-[( 4'-amidino-4-biphenylyl)oxymethyl]-3-[(methoxycarbonyl)methyl]-1-[3-(methylsulphinyl)propyl]- 2-pyrrolidinone

EXAMPLE 45

(3S,5S)-5-[[4-[(3-Amidinophenyl)hydroxymethyl]-phenyl]oxymethyl]-3-carboxymethyl-1-(3-phenylpropyl)-2-pyrrolidinone 0.06 g of sodium borohydride are added to 0.4 g of (3S,5S)-5-[[4-[( 3-amidinophenyl)carbonyl]phenyl]oxymethyl]- 3-[(methoxycarbonyl)methyl]-1-(3-phenylpropyl)-2-pyrrolidinone-hydrochloride, dissolved in 30 ml of methanol and 3 ml of water, with stirring and at ambient temperature. After 3 hours has elapsed, 2 ml of acetone are added and after a further 30 minutes 3 ml of 1N sodium hydroxide solution are added and the mixture is left to stand for 2 hours at ambient temperature. Then 1N hydrochloric acid is added until the neutral point is reached and the mixture is evaporated to dryness in vacuo. The solid remaining is triturated twice with water and suction filtered. The solid thus obtained is washed with dioxane/ethanol=1:1 and then with ether, then dried.

Yield: 0.23 g (56% of theory), $R_f$ value: 0.13 (silica gel; dichloromethane/ethanol/conc.aqueous ammonia=4:1:0.25)

Mass spectrum: (M+H)$^+$=516

EXAMPLE 46

(3S,5S)-5-[(4,-Amidino- 4-biphenylyl)-oxymethyl]-3-[[[2-(2-oxo-pyrrolidinyl)ethyloxy]-carbonyl]methyl]-2-pyrrolidinone-hydrochloride 1 g of (3S,5S)-5-[(4'-amidino- 4-biphenylyl)oxymethyl]-3-carboxymethyl-2-pyrrolidinone, 10 g of 1-( 2-hydroxyethyl)-2-pyrrolidinone and 1.5 ml of trimethylchlorosilane are stirred for 18 hours at 40° C., for 8 hours at 50° C. and for 18 hours at 65° C. After cooling, the mixture is made alkaline with concentrated aqueous ammonia and the reaction mixture is purified directly by chromatography on silica gel using methylene chloride/methanol/aqueous ammonia (18:2:0.25). The product obtained is stirred with methylene chloride/methanol (9:1), filtered and the filtrate is evaporated down.

Yield: 0.95 g $R_f$ value: 0.54 (reversed phase silica gel RP-8; methanol/ 5% aqueous saline solution=3:2)

Mass spectrum: $(M+H)^+=479$

The following are obtained analogously:
(1) (3S,5S)-5-[(4'-amidino- 4-biphenylyl)oxymethyl]-3-[[ [(dimethylaminocarbonyl)methyloxy]carbonyl]methyl]- 2-pyrrolidinone-hydrochloride
Carried out with glycolic acid dimethylamide
$R_f$ value: 0.61 (reversed phase silica gel RP-8; methanol/ 5% aqueous saline solution=3:2)
Mass spectrum: $(M+H)^+=453$
(2) (3S,5S)-5-[(4'-amidino- 4-biphenylyl)oxymethyl]-3-[[ [(diisopropylaminocarbonyl)methyloxy]carbonyl]methyl]- 2-pyrrolidinone
Carried out with glycolic acid diisopropylamide.

EXAMPLE 47

(3R,5S)-3-(5-Cyanopentyl)- 5-hydroxymethyl-1-isobutyl-2-pyrrolidinone

Prepared analogously to Example V from (3R,5S)-3-( 5-cyanopentyl)-1-isobutyl-5-[(trityloxy)methyl]-2-pyrrolidinone by treating with methanol/aqueous hydrochloric acid.

$R_f$ value: 0.59 (silica gel; ethyl acetate/methanol=9:1)

EXAMPLE 48

(3S, 5S)-5-[(4'-Amidino-4-biphenylyl)oxymethyl]- 3-[[[(3-pyridyl)methyloxy]carbonyl]methyl]- 2-pyrrolidinone-methanesulphohate 6 g of methanesulphonic acid are added to 5.5 g of 3-hydroxymethylpyridine in 2 ml of dry dimethylformamide, whilst cooling with ice, then 0.92 g of (3S,5S)-5-[(4'- amidino- 4-biphenylyl)oxymethyl]-3-carboxymethyl- 2-pyrrolidinone are added and the mixture is stirred for 3 days at 80° C. After cooling, 20 ml of methylene chloride/ methanol/conc. aqueous ammonia (18:2:0.25) are added, the mixture is neutralised with aqueous ammonia and purified directly by silica gel chromatography using methylene chloride/methanol/conc. aqueous ammonia (18:2:0.25). The product obtained is triturated with acetone, suction filtered and dried.

Yield: 0.50 g $R_f$ value: 0.58 (reversed phase silica gel RP-8; methanol/ 5% aqueous saline solution=3:2)

Mass spectrum: $(M+H)^+=459$

The following is obtained analogously:
(1) (3S,5S)-5-[(4'-amidino- 4-biphenylyl)oxymethyl]-3-[ [(2-morpholinoethyl)oxycarbonyl]methyl]- 2-pyrrolidinone-hydrochloride
Carried out with N-(2-hydroxyethyl)morpholine and hydrogen chloride gas $R_f$ value: 0.55 (reversed phase silica gel RP-8; methanol/ 5% aqueous saline solution=3:2)
Mass spectrum: $(M+H)^+=481$

EXAMPLE 49

(3R,5S)-3-Allyl-1-(tert.butyloxycarbonyl)- 5-[(4'-cyano- 4-biphenylyl)oxymethyl]-pyrrolidine 9.5 g of sodium hydride (55% in paraffin oil) are added in batches to 35.1 g of 4-cyano-4'-hydroxybiphenyl in 250 ml of dry dimethylformamide. After one and a half hours stirring at ambient temperature, 58.1 g of (3R,5S)-3-allyl- 1-(tert.butyloxycarbonyl)- 5-[(methanesulphonyloxy)methyl]pyrrolidine are added and the mixture is stirred for 7 days at 40° C. Then the solvent is eliminated in vacuo, the residue is divided between ethyl acetate and water, the organic phase is separated off, dried and evaporated down. The residue is purified over a silica gel column with cyclohexane/ethyl acetate=5:1.

Yield: 37.5 g (49% of theory), $R_f$ value: 0.54 (silica gel; cyclohexane/ethyl acetate=2:1)

The following is obtained analogously:
(1) (3R,5S)-3-allyl-5-[( 4'-cyano-4-biphenylyl)oxymethyl]- 3-methyl-2-pyrrolidinone
$R_f$ value: 0.39 (silica gel; cyclohexane/ethyl acetate=3:7)
Calculated: C 76.28 H 6.40 N 8.09 Found: 75.98 6.69 8.13

EXAMPLE 50

(3S,5S)-5-[2-[N-(3'-Amino- 3-biphenylyl)benzylamino]ethyl]- 3-[(methoxycarbonyl)methyl-1-(3-phenylpropyl)- 2'-pyrrolidinone 3 g of (3S,5S)-5-[2-[N-( 3'-nitro-3-biphenylyl)benzylamino]ethyl]-3-[(methoxycarbonyl)methyl]-1-(3'phenylpropyl)- 2-pyrrolidinone are refluxed in a mixture of 3.25 g of zinc powder, 0.75 g of calcium chloride, 3 ml of water and 30 ml of ethanol for 6 hours. The mixture is filtered while hot, washed several times with hot methanol and the filtrate is evaporated down. The residue is purified by chromatography on silica gel (eluant: methylene chloride/methanol/ conc. aqueous ammonia=30:1:0.1).

Yield: 1.0 g (35% of theory), $R_f$ value: 0.66 (silica gel; methylene chloride/methanol/ aqueous ammonia=8:2:0.1)

EXAMPLE 51

(3S,5S)-5-[2-[[(3'-Cyano- 4-biphenylyl)carbonyl]amino]ethyl]- 3-[(methoxycarbonyl)methyl]-1-(3-phenylpropyl)- 2-pyrrolidinone Prepared analogously to Example LXVIII by diazotisation of (3S,5S)-5-[2-[[( 3'-amino-4-biphenylyl)carbonyl] amino]ethyl]-3-[(methoxycarbonyl)methyl]-1-( 3'-phenylpropyl)-2-pyrrolidinone and reaction with potassium cyanide in the presence of copper(I)cyanide.

$R_f$ value: 0.45 (silica gel; methylene chloride/methanol= 9:1)

The following is obtained analogously:
(1) (3S,5S)-5-[[(3'-cyano- 4-biphenylyl)carbonyl]aminomethyl]- 3-[(methoxycarbonyl)methyl]-1-(3- 4phenylpropyl)-2-pyrrolidinone
$R_f$ value: 0.33 (silica gel; cyclohexane/ethyl acetate=1:2).

EXAMPLE 52

(3R, 5S) -3-Allyl-
1-[(benzylaminocarbonyl)methyl]-5-[(4'-cyano-
4-biphenylyl)oxymethyl]-2-pyrrolidinone 5 g of (3R,5S)-3-allyl-5-[( 4'-cyano-4-biphenylyl)oxymethyl]- 1-[(methoxycarbonyl)methyl]-2-pyrrolidinone, 4 ml of benzylamine and 5 ml of dry methanol are stirred for 3 days at ambient temperature. The mixture is concentrated by evaporation, the residue is taken up in ethyl acetate and extracted twice with 2N hydrochloric acid. The organic phase is washed with saline solution, dried over magnesium sulphate, filtered and evaporated down. The residue is purified over a silica gel column with ethyl acetate/cyclohexane=7:1.

Yield: 3.4 g (57% of theory), $R_f$ value: 0.60 (silica gel; ethyl acetate/cyclohexane=9:1)

Calculated: C 75.29 H 5.90 N 8.78 Found: 75.07 5.99 8.70

The following is obtained analogously:
(1) (3S,5S)-5-[( 4'-amidino-4-biphenylyl)oxymethyl]-1-[(aminocarbonyl)methyl]- 3-[(methoxycarbonyl)methyl]-2-pyrrolidinone ×0.2 HCl
Solvent: methanolic ammonia
Melting point: above 193° C. (decomp.),
$R_f$ value: 0.55 (silica gel; methylene chloride/methanol/conc. aqueous ammonia=30:10:2)
Calculated: C 61.97 H 5.92 N 12.57 Cl 1.59 Found: 62.10 5.85 12.74 1.44
Mass spectrum: (M+H)$^+$=439

EXAMPLE 53

(3S,5S)-1-Benzoyl-5-[(4'-cyano-4-biphenylyl)-
oxymethyl]-3-[(methoxycarbonyl)methyl]-pyrrolidine 1.16 g of (3S,5S)-5-[(4'-cyano- 4-biphenylyl)oxymethyl]-3-[(methoxycarbonyl)methyl]-pyrrolidine-hydrochloride in 50 ml of methylene chloride are mixed with 2 ml of triethylamine. Then 0.46 ml of benzoyl chloride are added, whilst cooling with ice, and the mixture is stirred for 3 days at ambient temperature. Then it is concentrated by evaporation, the residue is distributed between water and ethyl acetate and the organic phase is separated, dried and evaporated down. The residue is purified over a silica gel column with cyclohexane/ethyl acetate=2:1.

Yield: 1.07 g (78.7% of theory), $R_f$ value: 0.37 (silica gel; cyclohexane/ethyl acetate=1:1)

Calculated: C 73.99 H 5.77 N 6.16 Found: 74.16 5.78 6.02

The following are obtained analogously:
(1) (3S,5S)-5-[(4'-cyano- 4-biphenylyl)oxymethyl]-1-methanesulphonyl- 3-[(methoxycarbonyl)methyl]-pyrrolidine
Acylating agent: methanesulphochloride
Melting point: 146°–148° C.
$R_f$ value: 0.40 (silica gel; cyclohexane/ethyl acetate=1:1)
Calculated: C 61.66 H 5.65 N 6.54 S 7.48 Found: 61.39 5.74 6.70 7.31
(2) (3S,5S)-1-acetyl-5-[( 4'-cyano-4-biphenylyl)oxymethyl]- 3-[(methoxycarbonyl)methyl]-pyrrolidine×0.25 water
Acylating agent: acetic hydride
$R_f$ value: 0.17 (silica gel; cyclohexane/ethyl acetate= 1:1)
Calculated: C 69.59 H 6.22 N 7.06 Found: 69.38 6.48 6.95
(3) (3S,5S)-5-[( 4'-cyano-4-biphenylyl)oxymethyl]-1-(ethylaminocarbonyl)- 3-[(methoxycarbonyl)methyl]pyrrolidine
Acylating agent: ethyl isocyanate
Melting point: 134°–136° C.
$R_f$ value: 0.12 (silica gel; cyclohexane/ethyl acetate=1:1)
Calculated: C 68.39 H 6.46 N 9.97 Found: 68.11 6.47 10.00
(4) (3S,5S)-5-[(4'-cyano- 4-biphenylyl)oxymethyl]-1-(dimethylaminosulphonyl)- 3-[(methoxycarbonyl)methyl]pyrrolidine
Acylating agent: dimethylaminosulphonyl chloride
Melting point: 89°–90° C.
$R_f$ value: 0.51 (silica gel; cyclohexane/ethyl acetate=1:1)
Calculated: C 60.38 H 5.95 N 9.18 S 7.01 Found: 60.34 5.99 9.33 6.81
(5) (3S,5S)-5-[(4'-cyano- 4-biphenylyl)oxymethyl]-1-methoxyacetyl- 3-[(methoxycarbonyl)methyl]-pyrrolidine
Acylating agent: methoxyacetyl chloride
$R_f$ value: 0.13 (silica gel; cyclohexane/ethyl acetate=1:1)
Calculated: C 68.23 H 6.20 N 6.63 Found: 68.00 6.43 6.43
(6) (3S,5S)-5-[( 4'-cyano-4-biphenylyl)oxymethyl]-3 [(methoxycarbonyl)methyl]-1-[( 4-methoxyphenyl)sulphonyl]-pyrrolidine
Acylating agent: 4-methoxyphenylsulphonic acid chloride
Melting point: 105°–107° C.
$R_f$ value: 0.51 (silica gel; cyclohexane/ethyl acetate=1:1)
Calculated: C 64.60 H 5.42 N 5.38 S 6.16 Found: 64.66 5.54 5.11 6.18
(7) (3S,5S)-5-[( 4'-cyano-4-biphenylyl)oxymethyl]-1-[(N, N-dimethylamino)carbonyl]- 3-[(methoxycarbonyl)methyl]-pyrrolidine
Acylating agent: phosgene (in excess), followed by further reaction with dimethylamine
$R_f$ value: 0.55 (silica gel; ethyl acetate)

EXAMPLE 54

(3S,5S)-5-[(4'-Cyano-
4-biphenylyl)oxymethyl]-3-[(methoxycarbonyl)methyl]-
1-methyl-pyrrolidine×0.25 water 1.93 g of (3S,5S)-5-[( 4'-cyano-4-biphenylyl)oxymethyl]-3-[(methoxycarbonyl)methyl]-pyrrolidine-hydrochloride, 20 ml of tetrahydrofuran, 1.94 g of N-ethyldiisopropylamine and 0.31 ml of methyliodide are stirred for 4 hours at ambient temperature. The solvent is evaporated down in vacuo and the residue is triturated with water. The precipitate is suction filtered and purified by chromatography on silica gel using methylene chloride/methanol=10:1.

Yield: 340 mg (19% of theory),

Melting point: 80°–82° C.

$R_f$ value: 0.47 (silica gel; methylene chloride/methanol 10:1)

Calculated: C 71.62 H 6.69 N 7.59 Found: 71.48 6.59 7.36

EXAMPLE 55

(3R,5S)-3-Allyl-5-[(4'-cyano-4-biphenylyl)-
oxymethyl]-1-(2-methoxyethyl)-2-pyrrolidinone 0.42 g of sodium hydride (55–60% in paraffin oil) are added to 3 g of (3R,5S)-3-allyl- 5-[(4'-cyano-4biphenylyl)oxymethyl]- 1-(2-hydroxyethyl)-2-pyrrolidinone in 20 ml of dimethylformamide at 0° C. and the mixture is stirred for one hour. Then 1.35 g of methyliodide in 1 ml of dimethylformamide are added dropwise and the mixture is stirred for one hour at ambient temperature. Now a further 100 mg of sodium hydride followed by 0.15 ml of methyliodide are added. After another 4 hours, water and ethyl acetate are added, the mixture is neutralised with glacial acetic acid and the organic phase is separated off. The aqueous phase is extracted with ethyl acetate and the combined organic phases are washed with water, dried and concentrated by evaporation. The residue obtained is purified by chromatography over silica gel with ethyl acetate/cyclohexane =75:25.

Yield: 2.2 g (71% of theory), $R_f$ value: 0.61 (silica gel; ethyl acetate)

EXAMPLE 56

(3R,5S)-3-Allyl-5-[(4'-cyano-4-biphenylyl)-oxymethyl]-1-(2-hydroxyethyl)-2-pyrrolidinone 7 g of iodotrimethylsilane are added to 15.8 g of (3R, 5S)-3-allyl-1-[2-(benzyloxy)ethyl]- 5-[(4'-cyano-4biphenylyl)oxymethyl]- 2-pyrrolidinone in 200 ml of dry methylene chloride and the mixture is left to stand for 4 weeks under nitrogen at room temperature. Then 5 ml of methanol are added, the mixture is washed with aqueous sodium hydrogen sulphite solution and then with water. After drying and evaporation of the organic phase, the crude product obtained is purified by column chromatography over silica gel with ethyl acetate/cyclohexane =75:25.

Yield: 5.5 g (43% of theory), $R_f$ value: 0.21 (silica gel; ethyl acetate)

EXAMPLE 57

(3R,5S)-1-(2-Acetoxyethyl)-3-allyl-5-[(4'-cyano-4biphenylyl)oxymethyl]-2-pyrrolidinone 1.7 ml of acetic hydride, 1 ml of pyridine and 1 spatula tip of 4-dimethylaminopyridine are added to 3 g of (3R,5S)-3-allyl-1-(2-hydroxyethyl)- 5-[(4'-cyano-4biphenylyl)oxymethyl]- 2-pyrrolidinone in 30 ml of dioxane and the mixture is stirred for 2 hours at ambient temperature. Then methanol is added and it is evaporated down. The residue is taken up in ethyl acetate, washed with dilute hydrochloric acid, water and saturated saline solution, the organic phase is separated off, dried and evaporated down. The residue obtained is purified by chromatography over a silica gel column using ethyl acetate/cyclohexane=75:25.

Yield: 3.2 g (97% of theory), $R_f$ value: 0.66 (silica gel; ethyl acetate)

EXAMPLE 58

(3R,5S)-3-[4-(tert.Butyloxycarbonylamino)butyl]-5-[(3-carboxy-4-biphenylyl)oxymethyl]-1-methyl-2-pyrrolidinone 0.72 g of potassium permanganate are added in batches to 0.48 g of (3R,5S)-3-[4-(tert.butyloxycarbonylamino)butyl]-5-[(3-formyl-4-biphenylyl)oxymethyl]- 1-methyl-2-pyrrolidinone in 6 ml of acetone and 3 ml of water, whilst the mixture is kept acidic (pH not >3.8) by the addition of 0.5 N sulphuric acid. After the reaction has ended, it is decolorised with sodium disulphite solution, the pH is adjusted to 3.8 and the mixture is filtered. The filtrate is evaporated down, the residue is divided between water and methylene chloride and the organic phase is separated off. The aqueous phase is extracted twice more with methylene chloride and the combined organic phases are dried, filtered and evaporated down. The residue is purified by chromatography over a silica gel column with methylene chloride/methanol=8:1.

Yield: 0.3 g (63% of theory), $R_f$ value: 0.52 (silica gel; methylene chloride/methanol= 8:1)

Mass spectrum: $(M-H)^-=495$

EXAMPLE 59

(3R,5R)-3-(6-Aminohexyl)-5-(2-carboxyethyl)-1-isobutyl-2-pyrrolidinone-acetate 0.75 g of (3R,5S)-3-(6-aminohexyl)- 5-(2,2-dicarboxyethyl)- 1-isobutyl-2-pyrrolidinone-acetate in 20 ml of glacial acetic acid are refluxed for 2.5 hours. The glacial acetic acid is evaporated off, the residue is taken up in water and shaken with ethyl acetate. The aqueous phase is concentrated by evaporation and the crude product is purified over a silica gel column with n-butanol/glacial acetic acid/water=4:1:1.

Yield: 570 mg (85% of theory), $R_f$ value: 0.55 (silica gel; n-butanol/glacial acetic acid/water=4:1:1)

The following is obtained analogously:
(1) (3R,5R)-3-(4-aminobutyl)- 5-(2-carboxyethyl)-1-isobutyl- 2-pyrrolidinone-acetate $R_f$ value: 0.52 (silica gel; n-butanol/glacial acetic acid/water=4:1:1)

EXAMPLE 60

(3R,5S)-3-( 6-Aminohexyl)-5-(2,2-dicarboxyethyl)-1-isobutyl-2-pyrrolidinone-acetate 6 ml of trifluoroacetic acid are added to 1.52 g of (3R,5S)-3-(6-aminohexyl)- 5-[2,2-bis-(tert.butyloxy-carbonyl)-ethyl]- 1-isobutyl-2-pyrrolidinone in 6 ml of methylene chloride at 0° C. The mixture is then left to stand at ambient temperature for 2½ days. After this time it is evaporated down in vacuo, the residue is taken up in water and extracted twice with methylene chloride. The aqueous phase is evaporated down in vacuo and the residue is purified by column chromatography over silica gel with n-butanol/glacial acetic acid/water=4:1:1.

$R_f$ value: 0.37 (silica gel; n-butanol/glacial acetic acid/water=4:1:1)

The following is obtained analogously:
(1) (3R,5S)-3-(4-aminobutyl)- 5-(2,2-dicarboxyethyl)-1-isobutyl- 2-pyrrolidinone-acetate $R_f$ value: 0.31 (silica gel; n-butanol/glacial acetic acid/water=4:1:1)

EXAMPLE 61

(3R,5S)-5-[2,2-Bis-(tert.butyloxycarbonyl)-ethyl]-3-(5-cyanopentyl)-1-isobutyl-2-pyrrolidinone At 0° C., 2.8 g of di-tert.butylmalonate are added dropwise to 0.57 g of sodium hydride (55–60% dispersion in paraffin oil) in 35 ml of dry dimethylformamide. After 1½ hours stirring at ambient temperature, 3 g of (3R,5S)-3-(5-cyanopentyl)-1-isobutyl- 5-[(methanesulphonyloxy)methyl]- 2-pyrrolidinone in 15 ml of dimethylformamide are added and the resulting mixture is stirred for 6 hours at ambient temperature and for 21 hours at 55°–60° C.. It is then cooled, added to water and the mixture is extracted three times with ethyl acetate. The ethyl acetate extract is washed with water, dried, filtered and evaporated down. The residue is purified over a silica gel column with toluene/ acetone 4:1.

Yield: 2.1 g (52% of theory), $R_f$ value: 0.48 (silica gel; toluene/acetone=4:1)

The following is obtained analogously (1) (3R,5S)-5-[2,2-bis-(tert.butyloxycarbonyl)-ethyl]-3-( 3-cyanopropyl)-1-isobutyl-2-pyrrolidinone $R_f$ value: 0.37 (silica gel; toluene/acetone=4:1)

EXAMPLE 62

(3S,5S)-5-[2-[(3'-Guanidino-3-biphenylyl)-amino]ethyl]-3-[(methoxycarbonyl)methyl]-1-(3-phenylpropyl)-2-pyrrolidinone 1.3 g of (3S,5S)-5-[2-[N-(3'-guanidino-3-biphenylyl)benzylamino]ethyl]-3-[(methoxycarbonyl)methyl]- 1-(3-phenylpropyl)-2-pyrrolidinone-dihydrochloride are hydrogenated in 30 ml of methanol in the presence of 1.5 g of palladium hydroxide with hydrogen at 5 bars pressure at ambient temperature for 48 hours. After the solid products have been filtered off, the filtrate is evaporated down and the residue is purified by column chromatography over silica gel (eluant: methylene chloride/methanol/glacial acetic acid =9:1.5:0.1).

Yield: 0.63 g (55% of theory), $R_f$ value: 0.43 (silica gel; methylene chloride/methanol/ glacial acetic acid=9:1.5:0.1)

EXAMPLE 63

(3S,5S)-5-[[(4,-Cyano-4-biphenylyl)-sulphonyl]aminomethyl]-3-[(methoxycarbonyl)-methyl]-1-(3-phenylpropyl) 2-pyrrolidinone Prepared analogously to Example XIX from 4'-cyano-4-biphenylsulphonic acid chloride and (3S,5S)- 5-aminomethyl- 3-[(methoxycarbonyl)methyl]-1-(3-phenylpropyl)-2-pyrrolidinone-hydrochloride.

$R_f$ value: 0.25 (silica gel; cyclohexane/ethyl acetate/ methanol=63:32:5)

EXAMPLE 64

(3S,5S)-5-[(4'-Cyano-4-biphenylyl)sulphenylmethyl]-3-[(methoxycarbonyl)methyl]-1-(3-phenylpropyl)-2-pyrrolidinone A solution of 0.6 g of 4'-cyano-4-mercaptobiphenyl and 1.4 g of cesium carbonate in 5 ml of dimethylformamide is stirred for one hour at ambient temperature. It is then heated to 55° C., mixed with a solution of 1.1 g of (3S,5S)-5-[(methanesulphonyloxy)methyl]- 3-[(methoxycarbonyl)methyl]-1-( 3-phenylpropyl)-2-pyrrolidinone in 5 ml of dimethylformamide and stirred for 4 hours at this temperature. The solution is then poured into water and extracted with ethyl acetate. After the organic phase has been dried and evaporated down, a crude product is obtained which is chromatographed with cyclohexane/ethyl acetate=1:1 over silica gel.

Yield: 0.18 g (13% of theory), $R_f$ value: 0.41 (silica gel; cyclohexane/ethyl acetate=1:1)

EXAMPLE 65

(3S,5S)-5-[[[1-(4-Cyanophenyl)-1-propen-3-yl]aminocarbonyl]methyl]-3-[(methoxycarbonyl)-methyl]-1-(3-phenylpropyl)-2-pyrrolidinone Under inert gas, a solution of 2.1 g of (3S,5S)-5-(aminocarbonylmethyl)- 3-[(methoxycarbonyl)methyl]-1-(3-phenylpropyl)- 2-pyrrolidinone in 20 ml of absolute dimethylformamide is combined with batches of 275 mg of a 55% dispersion of sodium hydride in mineral oil and the resulting mixture is stirred for one hour. This solution is then added dropwise, with vigorous stirring, to a solution of 1.5 g of 3-chloro-1-( 4-cyanophenyl)-1-propene in 10 ml of absolute dimethylformamide. The reaction solution is stirred for 2 days, then poured into saturated saline solution and extracted three times with ethyl acetate. After drying and evaporation of the organic phase, 3.5 g of an oil are obtained which is chromatographed with methylene chloride/methanol=9:1 over silica gel.

Yield: 1.1 g (37% of theory), $R_f$ value: 0.50 (silica gel; methylene chloride/methanol= 9:1)

EXAMPLE 66

(3S,5S)-3-Carboxymethyl-1-(4-phenylbutyl)-5-[[4-(4-trimethylammoniobutyl)phenyl]oxymethyl]-2-pyrrolidinonechloride A solution of 480 mg of (3S,5S)- 3-carboxymethyl-5-[[4-( 4-dimethylaminobutyl)phenyl]oxymethyl]- 1-(4-phenylbutyl)- 2-pyrrolidinone and 10 ml of methyliodide in 20 ml of methylene chloride is stirred for 10 days at ambient temperature. The solution is evaporated down and the residue is chromatographed with methylene chloride/methanol/1N hydrochloric acid=4:2:0.1 over silica gel. The fractions obtained are concentrated by evaporation, dissolved in 15 ml of tetrahydrofuran and 10 ml of water, mixed with 124 mg of lithium hydroxide-hydrate and stirred for one hour at ambient temperature. The reaction solution is filtered, the filtrate is acidified with 1N hydrochloric acid and evaporated down and then chromatographed over silica gel with methylene chloride/methanol/aqueous ammonia (2:1:0.25). 130 mg (26% of theory) of product are obtained which is mixed with 1N hydrochloric acid, evaporated down and dried.

$R_f$ value: 0.14 (silica gel; methylene chloride/methanol/ 1N hydrochloric acid=4:2:0.1)

EXAMPLE 67

(3S,5S)-3-Carboxymethyl-5-[[4-(4-dimethyl-aminobutyl)phenyl]oxymethyl]-1-(4-phenylbutyl)-2-pyrrolidinone A solution of 1.13 g of (3S,5S)-5-[[4-(4aminobutyl)phenyl]oxymethyl]-3-carboxymethyl-1-(4-phenylbutyl)- 2-pyrrolidinone-trifluoroacetate and 0.9 g of paraformaldehyde in 70 ml of ethanol is mixed with 0.76 g of sodium cyanoborohydride and stirred for 16 hours at ambient temperature. Then water is added and the mixture is evaporated down. After the addition of more water, it is extracted with methylene chloride, the organic phase is washed with water, dried over sodium sulphate and concentrated by evaporation. 1.5 g of crude product are obtained which is chromatographed with methylene chloride/methanol/conc. aqueous ammonia over silica gel.

Yield: 0.55 g (57% of theory), $R_f$ value: 0.46 (silica gel; methylene chloride/methanol/conc. aqueous ammonia=4:1:0.25)

Mass spectrum: $M^+=480$

EXAMPLE 68

(3S,5S)-5-[(4'-Cyano-4-biphenylyl)-oxymethyl]-3-(2-hydroxyethyl)-2-pyrrolidinone 0.25 ml of methanol and, whilst cooling with ice, 135 mg of lithium borohydride are added to 1.5 g of (3S,5S)-5-[(4'-cyano- 4-biphenylyl)oxymethyl]-3-[(methoxycarbonyl)methyl]- 2-pyrrolidinone in 30 ml of tetrahydrofuran. After 2 hours stirring at ambient temperature, water is added, the mixture is acidified with 3N hydrochloric acid and extracted four times with methylene chloride. The organic phase is washed with water, dried over magnesium sulphate, filtered and evaporated down. The residue obtained is purified over a silica gel column with ethyl acetate/methanol (100:1).

Yield: 0.9 g (64% of theory),

Melting point: 114°–116° C.

$R_f$ value: 0.25 (silica gel; methylene chloride/methanol=100:2)

The following is obtained analogously:
(1) 1-(4'-cyano-4-biphenylyl)- 4-hydroxymethyl-2-pyrrolidinone Melting point: 159°–161° C.

$R_f$ value: 0.26 (silica gel; methylene chloride/methanol=95:5)

Calculated: C 73.96 H 5.52 N 9.58 Found: 73.70 5.67 9.72

EXAMPLE 69

(3S,5S)-5-[[4'-(N-Benzyloxycarbonylamidino)-4-biphenylyl]oxymethyl]-3-carboxymethyl-2-pyrrolidinone 1 ml of trifluoroacetic acid is added dropwise to 360 mg of (3S,5S)-5-[[- 4'-(N-benzyloxycarbonylamidino)-4-biphenyl] oxymethyl]-3-[(tert.butyloxycarbonyl)methyl]- 2-pyrrolidinone in 1 ml of methylene chloride. After 18 hours at ambient temperature, the mixture is evaporated down, mixed with ice water and extracted with ethyl acetate. The organic phase is washed with water, whereupon some of the product is precipitated, then dried and evaporated down. The residue is taken up in chloroform and together with the product precipitated during the washing it is washed five times with water. The organic phase is separated off, evaporated down and the residue obtained together with the product precipitated is stirred with a little acetone. It is then suction filtered and dried.

Yield: 170 mg (53% of theory),

Melting point: 197°–199° C.

$R_f$ value: 0.35 (reversed phase silica gel RP8; methanol/10% aqueous saline solution=6:4)

EXAMPLE 70

(3S,5S)-5-[[4'-(N-Ethyloxycarbonylamidino)-4-biphenylyl]oxymethyl]-3-[(methoxycarbonyl)methyl]-2-pyrrolidinone 50 ml of 0.1 N sodium hydroxide solution are slowly added dropwise, with vigorous stirring, to 1.0 g of (3S,5S)-5-[(4'-amidino- 4-biphenylyl)oxymethyl]-3-[(methoxycarbonyl)methyl]-2-pyrrolidinone-hydrochloride and 0.28 g of ethyl chloroformate in 100 ml of methylene chloride. Then the organic phase is separated off, washed with water, dried and concentrated by evaporation. The residue remaining is purified by chromatography over silica gel using ethyl acetate. The product obtained is boiled with ethyl acetate, cooled, suction filtered and dried.

Yield: 450 mg (43% of theory),

Melting point: 165°–167° C.

$R_f$ value: 0.29 (silica gel; ethyl acetate)

The following are obtained analogously:
(1) (3S,5S)-5-[[4'-(N-methoxycarbonylamidino)-4biphenylyl]oxymethyl]-3-[(methoxycarbonyl)methyl]-2-pyrrolidinone Melting point: 183°–184° C. (decomp.)

$R_f$ value: 0.47 (silica gel; ethyl acetate/methanol=97:3)
(2) (3S,5S)-5-[[4'-(N-cyanoamidino)- 4-biphenylyl]oxymethyl]- 3-[(methoxycarbonyl)methyl]-2-pyrrolidinone-semihydrate Carried out with bromocyanogen.

Melting point: 227°–231° C.

Calculated: C 63.60 H 5.58 N 13.48 Found: 63.71 5.51 13.52
(3) (3S,5S)-3-[(benzyloxycarbonyl)methyl]- 5-[[4,-(N-methoxycarbonylamidino)- 4-biphenylyl]oxymethyl]-2-pyrrolidinone Melting point: 203°–204° C.

Calculated: C 67.56 H 5.67 N 8.15 Found: 67.39 5.67 8.19
(4) (3S,5S)-5-[[4'-(N-isobutoxycarbonylamidino)-4-biphenylyl]oxymethyl]-3-[(methoxycarbonyl)methyl]-2-pyrrolidinone Carried out in methylene chloride/N-ethyldiisopropylamine Melting point: 161°–163° C.

Calculated: C 64.85 H 6.49 N 8.73 Found: 64.85 6.46 8.65
(5) (3S,5S)-5-[[4'-(N-isopropoxycarbonylamidino)-4-biphenylyl]oxymethyl]-3-[(methoxycarbonyl)methyl]-2-pyrrolidinone Melting point: 170°–172° C.

Calculated: C 64.23 H 6.25 N 8.99 Found: 64.26 6.35 8.95
(6) (3S,5S)-5-[[4'-(N-ethoxycarbonylamidino)-4-biphenylyl]oxymethyl]-3-[(ethoxycarbonyl)methyl]-2-pyrrolidinone Melting point: 138°–140° C.

$R_f$ value: 0.39 (silica gel; ethyl acetate)
(7) (3S,5S)-3-[(ethoxycarbonyl)methyl]- 5-[[4'-(N-methoxycarbonylamidino)- 4-biphenylyl]oxymethyl]-2-pyrrolidinone Melting point: 190°–192° C.

Calculated: C 63.56 H 6.00 N 9.27 Found: 63.29 6.05 9.27
(8) (3S,5S)-5-[[3'-fluoro-4'-(N-methoxycarbonylamidino)-4-biphenylyl]oxymethyl]-3-[(methoxycarbonyl)methyl]-2-pyrrolidinone Melting point: 156°–158° C.

Calculated: C 60.39 H 5.29 N 9.19 Found: 60.10 5.38 8.98
(9) (3S,5S)-1-acetyl-5-[[4'-(N-methoxycarbonylamidino)-4-biphenylyl]oxymethyl]-3-[(methoxycarbonyl)methyl]-2-pyrrolidinone ×0.25.water $R_f$ value: 0.23 (silica gel; ethyl acetate)

Calculated: C 63.61 H 6.25 N 8.90 Found: 63.61 6.30 8.77
(10) (3S,5S)-5-[[3'-chloro-4'-(N-methoxycarbonyl-amidino)- 4-biphenylyl]oxymethyl]-3-[(methoxycarbonyl)methyl]- 2-pyrrolidinone $R_f$ value: 0.70 (silica gel; methylene chloride/methanol=4:1)

Mass spectrum: $(M+H)^+=474$ and 476
(11) (3S,5S)-5-[[4'-(N-benzoylamidino)-4-biphenylyl] oxymethyl]- 3-[(methoxycarbonyl)methyl]-2-pyrrolidinone Melting point: 179°–181° C.

$R_f$ value: 0.38 (silica gel; ethyl acetate)

Mass spectrum: (M+H)$^+$=486

(12) (3S,5S)-3-[(isopropoxycarbonyl)methyl]- 5-[[4'-(N-methoxycarbonylamidino)- 4-biphenylyl]oxymethyl]-2-pyrrolidinone Melting point: 191° C. (decomp.)

Calculated: C 64.23 H 6.25 N 8.99 Found: 64.24 6.25 8.92

(13) (3S,5S)-3-[(ethoxycarbonyl)methyl]- 5-[[4'-(N-phenoxycarbonylamidino)- 4-biphenylyl]oxymethyl]-2-pyrrolidinone Mass spectrum: (M+H)$^+$=516

(14) (3S,5S)-5-[( 4'-methoxycarbonylaminomethyl-4biphenylyl)oxymethyl]- 3-[(methoxycarbonyl)methyl]-2-pyrrolidinone

(15) (3S,5S)-3-[(benzyloxycarbonyl)methyl]- 5-[[4'-(N-methozycarbonyl-amidino)- 4-biphenylyl]ozymethyl]-2-pyrrolidinone Melting point: 203°–205° C. (decomp.)

(16) (3S,5S)-3-[(n-butoxycarbonyl)methyl]- 5-[[4'-(N-methoxycarbonyl-amidino)- 4-biphenylyl]oxymethyl]-2-pyrrolidinone Melting point: 175°–178° C. (decomp.)

EXAMPLE 71

(3S,5S)-3-Carboxymethyl-5-[[4'-(N-hydroxyamidino)-4biphenylyl)oxymethyl]-2-pyrrolidinone 450 mg of (3S,5S)-5-[[4'-(N-hydroxyamidino)- 4-biphenylyl)oxymethyl]- 3-[(methoxycarbonyl)methyl]-2-pyrrolidinone, 10 ml of methanol and 0.42 ml of 4N sodium hydroxide solution are stirred for 18 hours at ambient temperature and refluxed for 30 minutes with stirring. After cooling, the mixture is concentrated by evaporation, 20 ml of semiconcentrated hydrochloric acid are added and the resulting mixture is stirred for 3½ hours at ambient temperature. The precipitate obtained is suction filtered, washed and dried and then stirred into 100 ml of water which has been adjusted to pH 1 with hydrochloric acid. It is then filtered and the filtrate is adjusted to pH 4. The precipitate obtained is suction filtered, washed and dried.

Yield: 200 mg (46% of theory),

Melting point: 218°–220° C. (decomp.)

$R_f$ value: 0.75 (reversed phase silica gel RP 8; methanol/10% aqueous saline solution=6:4)

Calculated: C 62.65 H 5.52 N 10.96 Found: 62.55 5.66 10.86

EXAMPLE 72

(3S,5S)-3-Carboxymethyl-5-[[4'-(N-cyanoamidino)-4-biphenylyl]oxymethyl]-2-pyrrolidinone 370 mg of (3S,5S)-5-[( 4'-amidino-4-biphenylyl)oxymethyl]- 3-carboxymethyl-2-pyrrolidinone, 520 mg of N-ethyl-diisopropylamine and 10 ml of dry dioxane are subjected to acoustic irradiation for 5 minutes in an ultrasound bath and then mixed with 280 mg of trimethylchlorosilane. The mixture is then subjected to acoustic irradiation for a few minutes, stirred for one hour at ambient temperature and then mixed with 130 mg of bromocyanogen. The mixture is acoustically irradiated for a few minutes and then left to stand for 2½ days at ambient temperature. A few drops of water, methanol and glacial acetic acid are added to the mixture, which is then evaporated down and purified by chromatography over a silica gel column using methylene chloride/methanol/glacial acetic acid/water (95:5:1:0.5) and methylene chloride/methanol/glacial acetic acid/water (90:10:1:0.5). The product is triturated with acetone, suction filtered and dried.

Yield: 75 mg (19% of theory),

Melting point: 260° C. (decomp.)

$R_f$ value: 0.61 (reversed phase silica gel; methanol/10% aqueous saline solution=6:4)

EXAMPLE 73

1-(4'-Cyano-4-biphenylyl)- 4-phosphonomethyl-2-pyrrolidinone 0.67 ml of chlorotrimethylsilane are added to 1.0 g of 1-(4'-cyano-4-biphenylyl)- 4-(O,O'-dimethyl-phosphonomethyl)- 2-pyrrolidinone and 0.78 g of sodium iodide in 5 ml of acetonitrile and the mixture is stirred for 30 minutes at 40° C. The precipitate is suction filtered and washed with acetonitrile. The filtrate is evaporated down and the residue is stirred for 1½ hours with water. The mixture is then made slightly alkaline with sodium hydroxide solution and extracted twice with methylene chloride to which some methanol has been added. The aqueous phase is evaporated down somewhat and filtered and the filtrate is acidified with 2N hydrochloric acid. The precipitate formed is suction filtered, washed with water and dried.

Yield: 720 mg (78% of theory), $R_f$ value: 0.38 (reversed phase silica gel; methanol/10% aqueous saline solution=1:1)

Calculated: C 60.68 H 4.81 N 7.86 Found: 60.41 4.60 7.98

EXAMPLE 74

1-(4'-Cyano-4-biphenylyl)- 4-(O-methyl-phosphonomethyl)-2-pyrrolidinone 500 mg of 1-(4'-cyano- 4-biphenylyl)-4-(O,O'-dimethyl-phosphonomethyl)- 2-pyrrolidinone, 195 mg of sodium iodide and 5 ml of ethyl-methylketone are refluxed for 3½ hours. The reaction mixture is cooled in an ice water bath. The crystals are isolated and washed with acetone. The crystals are dissolved in water, they are filtered and the filtrate is acidified with 2N hydrochloric acid. The precipitate is suction filtered, washed with water and dried.

Yield: 360 mg (75% of theory),

Melting point: 198°–204° C.

$R_f$ value: 0.30 (reversed phase silica gel; methanol/10% aqueous saline solution=1:1)

EXAMPLE 75

Dry ampoule containing 2.5 mg of active substance per 1 ml

| Composition: 2 | |
| --- | --- |
| Active substance | 2.5 mg |
| Mannitol | 50.0 mg |
| Water for injections ad | 1.0 ml |

Preparation:

The active substance and mannitol are dissolved in water. After packaging, the ampoules are freeze-dried.

The solution ready for use is made up with water for injections.

EXAMPLE 76

Dry ampoule containing 35 mg of active substance per 2 ml

| Composition: | |
|---|---|
| Active substance | 35.0 mg |
| Mannitol | 100.0 mg |
| Water for injections ad | 2.0 ml |

Preparation:

The active substance and mannitol are dissolved in water. After packaging, the ampoules are freeze-dried.

The solution ready for use is made up with water for injections.

EXAMPLE 77

Tablet containing 50 mg of active substance

| Composition: | |
|---|---|
| (1) Active substance | 50.0 mg |
| (2) Lactose | 98.0 mg |
| (3) Corn starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aqueous solution of (4). (5) is added to the dried granules. From this mixture, compressed tablets are made, which are biplanar, facetted on both sides and notched on one side. Diameter of tablets: 9 mm.

EXAMPLE 78

Tablet containing 350 mg of active substance

| Composition: | |
|---|---|
| (1) Active substance | 350.0 mg |
| (2) Lactose | 136.0 mg |
| (3) Corn starch | 80.0 mg |
| (4) Polyvinylpyrrolidone | 30.0 mg |
| (5) Magnesium stearate | 4.0 mg |
| | 600.0 mg |

Preparation:

(1), (2) and (3) are mixed together and granulated with an aqueous solution of (4). (5) is added to the dried granules. From this mixture, compressed tablets are made, which are biplanar, facetted on both sides and notched on one side. Diameter of tablets: 12 mm.

EXAMPLE 79

Capsules containing 50 mg of active substance

| Composition: | |
|---|---|
| (1) Active substance | 50.0 mg |
| (2) Dried corn starch | 58.0 mg |
| (3) Powdered lactose | 50.0 mg |
| (4) Magnesium stearate | 2.0 mg |
| | 160.0 mg |

Preparation:

(1) is triturated with (3). This trituration is added to the mixture of (2) and (4) with thorough mixing.

The powdered mixture is packed into hard gelatin oblong capsules, size 3, in a capsule filling machine.

EXAMPLE 80

Capsule containing 350 mg of active substance

| Composition: | |
|---|---|
| (1) Active substance | 300.0 mg |
| (2) Dried corn starch | 46.0 mg |
| (3) Powdered lactose | 30.0 mg |
| (4) Magnesium stearate | 4.0 mg |
| | 430.0 mg |

Preparation:

(1) is triturated with (3). This trituration is added to the mixture of (2) and (4) with thorough mixing.

The powdered mixture is packed into hard gelatin oblong capsules, size 0, in a capsule filling machine.

EXAMPLE 81

Ampoule containing 35 mg of active substance per 2 ml

| Composition: | |
|---|---|
| (1) Active substance | 35.00 mg |
| (2) Mannitol | 40.00 mg |
| (3) Hydroxypropyl-β-cyclodextrine | 400.00 mg |
| (4) 1N Hydrochloric acid | 0.07 ml |
| (5) Water for injection ad | 2.00 ml |

Preparation:

(1) to (3) was dissolved in (4) and (5) by shaking and ultrasonic treatment.

What is claimed is:

1. A compound of the formula Ia

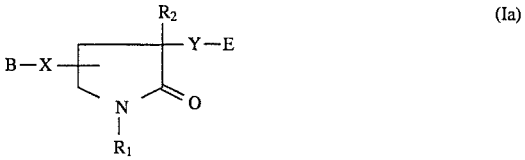

wherein $R_1$ represents a hydrogen atom, a phenyl group optionally substituted by a chlorine or bromine atom, by an $C_{1-2}$-alkyl, $C_{1-2}$-alkoxy or trifluoromethyl group, by a carboxy, alkoxycarbonyl, aminocarbonyl, aminosulphonyl, alkylaminocarbonyl, dialkylaminocarbonyl, alkylsulphonylamino or alkanoylamino group, an allyl group, a $C_{1-4}$-alkyl group which may be substituted by two phenyl groups, by a $C_{3-7}$-cycloalkyl, naphthyl or phenyl group, whilst the latter may be substituted by a fluorine, chlorine or bromine atom, by a $C_{1-4}$-alkyl group, by a $C_{1-6}$-alkoxy group, by an alkylsulphenyl, alkylsulphinyl, alkylsulphonyl, phenyl, phenylalkyl, phenylalkoxy, hydroxy or trifluoromethyl group, by two alkoxy groups or by two chlorine or bromine atoms, a $C_{2-4}$-alkyl group substituted in 2-, 3- or 4-position by an alkylsulphenyl, alkylsulphinyl, alkylsulphonyl, phenylsulphenyl, phenylsulphinyl, phenylsulphonyl, amino, alkanoylamino, benzoylamino, N-alkyl-alkanoylamino, alkanesulphonylamino, phenylsulphonylamino, hydroxy, alkoxy or phenoxy group, a methyl group substituted by a carboxy, alkoxycarbonyl, aminocarbonyl, alkylaminocarbonyl, dialkylaminocarbonyl, benzylaminocarbonyl, bis(2-methoxyethyl)aminocarbonyl or biphenylyl group, $R_2$ represents a hydrogen atom or an optionally phenyl-substituted $C_{1-4}$-alkyl group, B represents an amidino group optionally substituted by one or two $C_{1-4}$-alkyl groups, by a cyano, hydroxy, methoxy, benzyl, benzoyl, methoxybenzoyl, benzyloxycarbonyl, phenyloxycarbonyl or an $C_{1-4}$-alkyloxycarbonyl group, a cyano, aminomethyl or guanidinomethyl group;

Y represents a straight-chained or branched $C_{1-5}$-alkylene group;

E represents a carbonyl group substituted by a hydroxy, $C_{1-6}$-alkoxy, amino, $C_{1-4}$-alkylamino, dialkylaminocarbonyl-alkoxy or phenylalkoxy group wherein the phenyl nucleus may additionally be substituted by one or two methoxy groups, and X represents biphenylyloxy-$C_{1-2}$-alkylene group attached via the alkylene moiety to the pyrrolidinone ring in 4- or 5-position, wherein each phenylene moiety may be substituted by a fluorine, chlorine or bromine atom or by an alkyl, alkoxy, trifluoromethyl, alkylsulphenyl, alkylsulphinyl, alkylsulphonyl, nitro, alkanoylamino or alkanesulphonylamino group or by another alkyl group, wherein, unless otherwise stated, the above-mentioned alkyl, alkoxy and alkanoyl moieties may each contain from 1 to 3 carbon atoms, or a pharmaceutically acceptable salt thereof.

2. A compound of the formula Ia, according to claim 1, wherein $R_1$ represents a hydrogen atom, a phenyl group optionally substituted by a chlorine or bromine atom, by an $C_{1-2}$-alkyl, $C_{1-2}$-alkoxy or trifluoromethyl group, by a carboxy, alkoxycarbonyl, aminocarbonyl, aminosulphonyl, alkylaminocarbonyl, dialkylaminocarbonyl, alkylsulphonylamino or alkanoylamino group, a $C_{2-4}$-alkyl group substituted in 2-, 3- or 4-position by a hydroxy, alkoxy, phenoxy, alkylsulphenyl, alkylsulphinyl, alkylsulphonyl, phenylsulphenyl, phenylsulphinyl, phenylsulphonyl, amino, alkanoylamino, benzoylamino, N-alkyl-alkanoylamino, alkanesulphonylamino or benzenesulphonylamino group, a $C_{1-4}$-alkyl group optionally substituted by a $C_{3-7}$-cycloalkyl group, by two phenyl groups or by a phenyl group, whilst the latter may be substituted by a fluorine, chlorine or bromine atom, by a $C_{1-4}$-alkyl, $C_{1-6}$-alkoxy, phenyl, phenylalkyl, phenylalkoxy, alkylsulphenyl, alkylsulphinyl, alkylsulphonyl, hydroxy or trifluoromethyl group, by two alkoxy groups or by two chlorine or bromine atoms, a methyl group which is substituted by a carboxy, alkoxycarbonyl, aminocarbonyl, alkylaminocarbonyl, dialkylaminocarbonyl or phenylalkylaminocarbonyl group, $R_2$ represents a hydrogen atom or an optionally phenyl-substituted $C_{1-4}$-alkyl group, B represents an amidino group optionally substituted by one or two $C_{1-4}$-alkyl groups, by a benzyl, cyano, hydroxy, alkoxy, benzoyl, benzyloxycarbonyl, phenyloxycarbonyl or $C_{1-4}$-alkyloxycarbonyl group, a aminomethyl or guanidinomethyl group;

Y represents a straight-chained or branched $C_{1-5}$-alkylene group;

E represents a carbonyl group substituted by a hydroxy, $C_{1-6}$-alkoxy, dialkylaminocarbonylalkoxy or phenylalkoxy group in which the phenyl nucleus may be substituted by one or two alkoxy groups; and X represents a biphenylyloxymethylene or biphenylyloxyethylene attached via the alkylene moiety to the pyrrolidinone ring in 4- or 5-position, wherein each phenylene moiety may be substituted by a fluorine, chlorine or bromine atom, by one or two alkyl groups, by an alkoxy, trifluoromethyl, alkylsulphenyl, alkylsulphinyl, alkylsulphonyl, nitro, alkanoylamino or alkanesulphonylamino group;

wherein, unless otherwise mentioned, the above-mentioned alkyl, alkoxy and alkanoyl moieties may each contain from 1 to 3 carbon atoms.

or a pharmaceutically acceptable salt thereof.

3. A compound of the formula Ia, according to claim 1, wherein $R_1$ represents a hydrogen atom, a phenyl group optionally substituted by a chlorine or bromine atom, by an $C_{1-2}$-alkyl, $C_{1-2}$-alkoxy or trifluoromethyl group, by a carboxy, methoxycarbonyl, aminocarbonyl, methylaminocarbonyl, ethylaminocarbonyl, dimethylaminocarbonyl, methanesulphonylamino or acetylamino group, a $C_{2-4}$-alkyl group substituted in 2-, 3- or 4-position by a hydroxy, $C_{1-2}$'alkoxy, phenoxy, methylsulphenyl, methylsulphinyl, methylsulphonyl, phenylsulphenyl, phenylsulphinyl, phenylsulphonyl, amino, acetylamino, benzoylamino, N-methyl-acetylamino, methanesulphonylamino or benzenesulphonylamino group, a $C_{1-4}$-alkyl group which may by substituted by two phenyl groups, by a $C_{5-7}$-cycloalkyl group or by a phenyl group, whilst the latter may be substituted by a fluorine, chlorine or bromine atom, by a $C_{1-4}$-alkyl group, by a $C_{1-6}$-alkoxy group, by a phenyl, phenylmethyl, hydroxy, benzyloxy, methylsulphenyl, methylsulphinyl, methylsulphonyl or trifluoromethyl group, by two methoxy groups or by two chlorine atoms, a methyl group substituted by a carboxy, $C_{1-2}$-alkoxycarbonyl, aminocarbonyl, $C_{1-2}$-alkylaminocarbonyl, di-($C_{1-2}$-alkyl)-aminocarbonyl or benzylaminocarbonyl group, $R_2$ represents a hydrogen atom or a $C_{1-4}$-alkyl group optionally substituted by a phenyl group, B represents an amidino group optionally substituted by one or two $C_{1-4}$-alkyl groups, by a benzyl, cyano, hydroxy, methoxy, $C_{1-4}$-alkyloxycarbonyl, benzyloxycarbonyl, phenyloxycarbonyl or benzoyl group, a aminomethyl or guanidinomethyl group;

Y represents a straight-chained $C_{1-5}$-alkylene group; and

E represents a carbonyl group substituted by a hydroxy or $C_{1-6}$-alkoxy group or by dialkylaminocarbonylmethoxy group in which each alkyl moiety may contain 1 to 3 carbon atoms or by a phenylalkoxy group having 1 to 3 carbon atoms in the alkoxy moiety whilst the phenyl nucleus may be substituted by one or two methoxy groups, and X represents a 4-biphenylyloxymethylene group attached via the methylene moiety to the pyrrolidinone ring in 4- or 5-position, wherein the biphenyl moiety may be substituted by one or two methyl groups, by a fluorine, chlorine or bromine atom, by a methoxy, ethoxy, trifluoromethyl, methylsulphenyl, methylsulphinyl, methylsulphonyl, nitro, acetylamino or methanesulphonylamino group;

or a pharmaceutically acceptable salt thereof.

4. A compound of the formula Ia, according to claim 1 wherein $R_1$ represents a hydrogen atom, a phenyl group optionally substituted by a chlorine or bromine atom, by an $C_{1-2}$-alkyl, $C_{1-2}$-alkoxy or trifluoromethyl group, an $C_{1-4}$-alkyl group optionally substituted by two phenyl groups or by a $C_{5-7}$-cycloalkyl group, a phenyl-$C_{1-4}$-alkyl group wherein the phenyl nucleus is optionally substituted by an $C_{1-4}$-alkyl or $C_{2-6}$-alkoxy group, by one or two methoxy groups, by one or two chlorine atoms, by a bromine atom, by a trifluoromethyl, methylsulphenyl, methylsulphinyl, methylsulphonyl, phenyl or benzyl group, an $C_{2-4}$-alkyl group substituted in 2-, 3- or 4-position by a hydroxy, methoxy, ethoxy or phenoxy group, or a methyl group substituted by a carboxy, methoxycarbonyl, ethoxycarbonyl, aminocarbonyl, $C_{1-2}$-alkylaminocarbonyl, benzylaminocarbonyl or di-($C_{1-2}$-alkyl)-aminocarbonyl group;

$R_2$ represents a hydrogen atom, an $C_{1-4}$-alkyl or phenyl-$C_{1-3}$-alkyl group;

X represents a 4-biphenylyloxymethylene group attached via the methylene moiety to the pyrrolidinone ring in 4- or 5-position, whereby the biphenyl moiety is optionally substituted by one or two methyl groups, by a fluorine, chlorine or bromine atom, by a trifluoromethyl, methylsulphenyl, methylsulphinyl, methylsulphonyl, nitro, acetylamino or methanesulphonylamino group;

B represents an amidino group optionally substituted by one or two methyl groups, by an $C_{2-4}$-alkyl, benzyl, benzyloxycarbonyl, benzoyl, phenoxycarbonyl, $C_{1-4}$-alkoxycarbonyl, hydroxy, methoxy or cyano group, a aminomethyl or guanidinomethyl group;

Y represents an n-$C_{1-5}$-alkylene group; and

E represents a carbonyl group substituted by a hydroxy, $C_{1-6}$-alkoxy, phenyl-$C_{1-3}$-alkoxy, methoxyphenyl-$C_{1-3}$-alkoxy, dimethoxyphenyl-$C_{1-3}$-alkoxy or dimethylaminocarbonylmethoxy group;

or a pharmaceutically acceptable salt thereof.

5. A compound of the formula Ia, according to claim 1, wherein $R_1$ represents a hydrogen atom, a phenyl group optionally substituted by a chlorine or bromine atom, by an $C_{1-2}$-alkyl, $C_{1-2}$-alkoxy or trifluoromethyl group, an $C_{1-4}$-alkyl group optionally substituted by two phenyl groups or by a $C_{5-7}$-cycloalkyl group, a phenyl-$C_{1-4}$-alkyl group wherein the phenyl nucleus is optionally substituted by an $C_{1-4}$-alkyl or $C_{2-6}$-alkoxy group, by one or two methoxy groups, by one or two chlorine atoms, by a bromine atom, by a trifluoromethyl, methylsulphenyl, methylsulphinyl, methylsulphonyl, phenyl or benzyl group, an $C_{2-4}$-alkyl group substituted in 2-, 3- or 4-position by a hydroxy, methoxy, ethoxy or phenoxy group, or a methyl group substituted by a carboxy, methoxycarbonyl, ethoxycarbonyl, aminocarbonyl, $C_{1-2}$-alkylaminocarbonyl, benzylaminocarbonyl or di-($C_{1-2}$-alkyl)-aminocarbonyl group;

$R_2$ represents a hydrogen atom, an $C_{1-4}$-alkyl or phenyl-$C_{1-3}$-alkyl group;

X represents a 4-biphenylyloxymethylene group attached via the methylene moiety to the pyrrolidinone ring in 4- or 5-position, whereby the biphenyl moiety is optionally substituted by one or two methyl groups, by a fluorine, chlorine or bromine atom, by a trifluoromethyl, methylsulphenyl, methylsulphinyl, methylsulphonyl, nitro, acetylamino or methanesulphonylamino group;

B represents an amidino group in 4'-position optionally substituted by one or two methyl groups, by an $C_{2-4}$-alkyl, benzyl, benzyloxycarbonyl, benzoyl, phenoxycarbonyl, $C_{1-4}$-alkoxycarbonyl, hydroxy, methoxy or cyano group;

Y represents an n-$C_{1-5}$-alkylene group; and

E represents a carbonyl group substituted by a hydroxy, $C_{1-6}$-alkoxy, phenyl-$C_{1-3}$-alkoxy, methoxyphenyl-$C_{1-3}$-alkoxy, dimethoxyphenyl-$C_{1-3}$-alkoxy or dimethylaminocarbonylmethoxy group;

or a pharmaceutically acceptable salt thereof.

6. A compound selected from the group consisting of:

(3S,5S)-5-[(4'-amidino-4-biphenylyl)oxymethyl]-3-[(methoxycarbonyl)methyl]-2-pyrrolidinone, (3S,5S)-5-[(4'-amidino-4-biphenylyl)oxymethyl]- 3-carboxymethyl-1-(3-phenylpropyl)-2-pyrrolidinone.

(3S,5S)-5-[(4'-amidino-4-biphenylyl)oxymethyl]- 3-carboxymethyl-2-pyrrolidinone, (3S,5S)-5-[(4'-amidino-4-biphenylyl)oxymethyl]- 3-carboxymethyl-1-phenyl-2-pyrrolidinone, (3S,5S)-5-[(4'-amidino-2,3-dimethyl- 4-biphenylyl)oxymethyl]- 3-carboxymethyl-1-(3-phenylpropyl)-2-pyrrolidinone, (3S,5S)-5-[(4'-amidino-4-biphenylyl)oxymethyl]- 3-carboxymethyl-1-[(dimethylaminocarbonyl)methyl]-2-pyrrolidinone, (3S,5S)-5-[(4'-amidino-3'-fluoro-4-biphenylyl)oxymethyl]- 3-carboxymethyl-2-pyrrolidinone, (3R,S;4R,S)-4-[(4'-amidino-4-biphenylyl)oxymethyl]- 3-carboxymethyl-3-methyl- 2-pyrrolidinone, (3S,5S)-

5-[(4'-amidino-4-biphenylyl)oxymethyl]-3-carboxymethyl-1-methyl-2-pyrrolidinone and (3S,5S)-5-[[4'-(N-methoxycarbonylamidino)-4-biphenylyl]oxymethyl]-3-[(methoxycarbonyl)methyl]-2-pyrrolidinone and the pharmaceutically acceptable salts thereof.

7. (3S,5S)-5-[(4'-amidino-4-biphenylyl)oxymethyl]-3-(carboxymethyl)-2-pyrrolidinone or a pharmaceutically acceptable salt thereof.

8. (3S,5S)-5-[[4'-(N-methoxycarbonylamidino)-4-biphenylyl]oxymethyl]-3-[(methoxycarbonyl)methyl]-2-pyrrolidinone or a pharmaceutically acceptable salt thereof.

9. A pharmaceutical composition comprising a compound according to claim 2 and 6, 4, 5, 7 or 8 together with one or more inert carriers and/or diluents.

10. A method for treating or preventing diseases in which smaller or larger clumps of cells occur or in which cell-matrix interactions are involved, which method comprises administering a compound of formula I, according to claim 2, 3, 4, 5, 6, 7, or 8.

* * * * *